(12) United States Patent
Rothe et al.

(10) Patent No.: US 7,705,130 B2
(45) Date of Patent: Apr. 27, 2010

(54) ANTIBODIES DIRECTED TO HER-3 AND USES THEREOF

(75) Inventors: Mike Rothe, Krailling (DE); Martin Treder, Zürich (CH); Susanne Hartmann, München (DE); Eric Borges, Maria Enzersdorf (AT); Larry L. Green, San Francisco, CA (US)

(73) Assignees: U3 Pharma GmbH, Martinsried (DE); Amgen, Inc., Thousand Oaks, CA (US)

( * ) Notice: Subject to any disclaimer, the term of this patent is extended or adjusted under 35 U.S.C. 154(b) by 215 days.

(21) Appl. No.: 11/649,722

(22) Filed: Jan. 3, 2007

(65) Prior Publication Data

US 2008/0124345 A1 May 29, 2008

Related U.S. Application Data

(60) Provisional application No. 60/755,103, filed on Dec. 30, 2005.

(51) Int. Cl.
*C07K 16/00* (2006.01)
(52) U.S. Cl. .................................................. 530/387.1
(58) Field of Classification Search ........................ None
See application file for complete search history.

(56) References Cited

U.S. PATENT DOCUMENTS

| | | | |
|---|---|---|---|
| 4,399,216 A | 8/1983 | Axel et al. | |
| 4,740,461 A | 4/1988 | Kaufman et al. | |
| 4,816,397 A | 3/1989 | Boss et al. | |
| 4,816,567 A | 3/1989 | Cabilly et al. | |
| 4,912,040 A | 3/1990 | Kaufman et al. | |
| 4,959,455 A | 9/1990 | Clark et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,591,669 A | 1/1997 | Krimpenfort et al. | |
| 5,612,205 A | 3/1997 | Kay et al. | |
| 5,625,126 A | 4/1997 | Lonberg et al. | |
| 5,625,825 A | 4/1997 | Rostoker et al. | |
| 5,633,425 A | 5/1997 | Lonberg et al. | |
| 5,643,763 A | 7/1997 | Dunn et al. | |
| 5,661,016 A | 8/1997 | Lonberg et al. | |
| 5,721,367 A | 2/1998 | Kay et al. | |
| 5,770,429 A | 6/1998 | Lonberg et al. | |
| 5,789,215 A | 8/1998 | Berns et al. | |
| 5,789,650 A | 8/1998 | Lonberg et al. | |
| 5,814,318 A | 9/1998 | Lonberg et al. | |
| 5,874,299 A | 2/1999 | Lonberg et al. | |
| 5,877,397 A | 3/1999 | Lonberg et al. | |
| 5,916,771 A | 6/1999 | Hori et al. | |
| 5,939,598 A | 8/1999 | Kucherlapati et al. | |
| 5,968,511 A * | 10/1999 | Akita et al. ............. | 424/141.1 |
| 5,981,175 A | 11/1999 | Loring et al. | |
| 6,023,010 A | 2/2000 | Krimpenfort et al. | |
| 6,075,181 A | 6/2000 | Kucherlapati et al. | |
| 6,114,595 A | 9/2000 | Moore | |
| 6,150,584 A | 11/2000 | Kucherlapati et al. | |
| 6,162,963 A | 12/2000 | Kucherlapati et al. | |
| 6,207,418 B1 | 3/2001 | Hori et al. | |
| 6,255,458 B1 | 7/2001 | Lonberg et al. | |
| 6,833,268 B1 | 12/2004 | Green et al. | |
| 7,285,649 B2 | 10/2007 | Akita et al. | |
| 2002/0064805 A1 | 5/2002 | Akita et al. | |
| 2003/0217373 A1 | 11/2003 | Green et al. | |
| 2004/0050683 A1 | 3/2004 | Oliver | |
| 2004/0071696 A1 | 4/2004 | Adams et al. | |

FOREIGN PATENT DOCUMENTS

| | | |
|---|---|---|
| EP | 0463151 B1 | 7/1991 |
| EP | 546073 B1 | 3/1992 |
| JP | 3 068 180 B2 | 3/1991 |
| JP | 3 068 506 B2 | 3/1991 |
| JP | 3 068 507 B2 | 3/1991 |
| WO | WO 92/03918 | 3/1992 |
| WO | WO 92/22645 | 12/1992 |
| WO | WO 92/22647 | 12/1992 |
| WO | WO 96/34096 | 10/1996 |
| WO | WO 97/13852 | 4/1997 |
| WO | WO 98/24884 | 6/1998 |
| WO | WO 98/24893 | 6/1998 |
| WO | WO 98/50433 | 11/1998 |
| WO | WO 00/76310 | 12/2000 |
| WO | WO 00/78347 | 12/2000 |
| WO | WO 03013602 | 2/2003 |
| WO | WO 03048730 A2 | 6/2003 |

(Continued)

OTHER PUBLICATIONS

Carter (Nature Reviews; 2001; 1:118-129).*

(Continued)

*Primary Examiner*—Christopher H Yaen
(74) *Attorney, Agent, or Firm*—Fish & Richardson P.C.

(57) ABSTRACT

The present invention relates to binding proteins that bind to HER-3 and polynucleotides encoding the same. Expression vectors and host cells comprising the same for the production of the binding protein of the invention are also provided. In addition, the invention provides compositions and methods for diagnosing and treating diseases associated with HER-3 mediated signal transduction and/or its ligand heregulin.

29 Claims, 33 Drawing Sheets

FOREIGN PATENT DOCUMENTS

| WO | WO 03080835 | 10/2003 |
|---|---|---|
| WO | WO 2004011900 | 2/2004 |
| WO | WO 2004/050683 | 6/2004 |
| WO | WO 2004091384 | 10/2004 |
| WO | WO 2005003707 | 1/2005 |

OTHER PUBLICATIONS

Alberts et al.; The Receptors for Most Growth Factors Are Transmembrane Tyrosine-Specific Protein Kinases; Chapter 15.3.2; Molecular Biology of the Cell, Third Edition; Copyright 1994, Garland Publishing Co., pp. 760-761.

Alimandi et al.; "Cooperative Signaling of Erbb3 and Erbb2 in Neoplastic Transformation and Human Mammary Carcinomas"; *Oncogene*; 1995; 1813-1821; 10.

Baldrick, P.; "Pharmaceutical Excipient Development: The Need for Preclinical Guidance."; *Regulatory Toxicology and Pharmacology.*; 2000; 210-218; 32.

Binz et al.; "Engineered Proteins As Specific Binding Reagents"; *Current Opinion in Biotechnology*; 2005; 459-469; 16.

Binz et al.; "Engineering Novel Binding Proteins From Nonimmunoglobulin Domains"; *Nature Biotechnology*; 2005; 1257-1268; vol. 23.

Binz et al; "The Matrix Reloaded: Specific Binding Proteins Based on Non-immunoglobulin Domains"; Department of Biochemistry, University of Zurich; pp. 1-20.

Bowie et al..; "A Method to Identify Protein Sequences That Fold into a Known Three-Dimensional Structure"; *Science*; 1991, 164-170; vol. 253.

Carraway et al.; "A New Acquaintance for Erbb3 and Erbb4: A Role for Receptor Heterodimerization in Growth Signaling"; *Cell*; vol. 78, 1994; pp. 5-8.

Charman, W. N.; "Lipids, Lipophillic Drugs, and Oral Drug Delivery-Some Emerging Concepts;" *Journal of Pharmaceutical Sciences.*; 2000; 967-978; vol. 89, No. 8.

Chen et al.; "An Immunological Approach Reveals Biological Differences Between the Two NDF/Heregulin Receptors, Erbb-3 and Erbb-4"; *J. Bilol. Chem.*; vol. 271, No. 13, 1996; 7620-7629.

Chen et al.; "$V_H$ Gene Expression and Regulation in the Mutant Alicia Rabbit"; *Journal of Immunology*; 1993; 2783-2793; vol. 150; No. 7.

Choi et al.; "Transgenic Mice Containing a Human Heavy Chain Immunoglobulin Gene Fragment Cloned in a Yeast Artificial Chromosome"; Nature Genetics; 1993; 117-123; vol. 4.

Chothia et al.; "Canonical Structures for the Hypervariable Regions of Immunoglobulins"; *J Mol. Biol.*; Aug. 20, 1987; 901-917; 196(4).

Chothia et al.; "Conformations of Immunoglobulin Hypervariable Regions"; *Nature*; vol. 342 (Dec. 21-28, 1989), 877-883.

Clackson et al.; "Making Antibody Fragments Using Phage Display Libraries"; *Nature*; vol. 352 (Aug. 15, 1991), 624-628.

DeFazio et al.; "Expression of C-Erbb Receptors, Heregulin and Oesterogen Receptor in Human Breast Cell Lines"; *Int. J. Cancer*; (2000); 87; 487-498.

Feldhaus et al; "Yeast Display of Antibody Fragments: A Discovery and Characterization Platform"; *J. Immunol. Methods*; 290 (2004); 69-80.

Fendly et al.; "Murine Monoclonal Antibodies Defining Neutralizing Epitopes on Tumor Necrosis Factor"; *Hybridoma*; vol. 6, No. 4, 1987; 359-370.

Fishwild et al.; "High-Avidity Human Iggk Monoclonal Antibodies From a Novel Strain of Minilocus Transgenic Mice"; *Nature Biotechnology*; vol. 14 (Jul. 1996); 845-851.

Green et al.; "Regulation of B Cell Development by Variable Gene Complexity in Mice Reconstituted with Human Immunoglobulin Yeast Artificial Chromosomes"; *J. Exp. Med.*; vol. 188, No. 3 (1998), 483-495.

Groves et al.; "Applications of Ribosome Display to Antibody Drug Discovery"; *Expert Opin. Biol. Ther.*; 2005; 125-135.

Hamman et al.; "An Anti-CD33 Antibody-Calicheamicin Conjugate for Treatment of Acute Myeloid Leukemia. Choice of Linker"; *Bioconjug. Chem*; 13 (2002), 40-46.

Hazra et al.; "Linking Radiosilver to Monoclonal Antibodies Reduced by Ascorbic Acid"; *Cell Biophys.*; vols. 24-25 (1994), 1-7.

Heldin, C-H.; "Dimerization of Cell Surface Receptors in Signal Transduction"; *Cell*, 1995, vol. 80; 213-223.

Holliger et al.; "Diabodies: Small Bivalent and Bispecific Antibody Fragments"; *Proc. Natl. Acad. Sci. U.S.A.*; 90 (1993), 6444-6448.

Holt et al.; "Domain Antibodies: Proteins for Therapy"; *Trends in Biotechnology*; 21; Nov. 2003; 484-90.

Hudziak et al.; "p185$^{HER2}$ Monoclonal Antibody Has Antiproliferative Effects In Vitro and Sensitizes Human Breast Tumor Cells to Tumor Necrosis Factor"; *Molecular and Cellular Biology*; Mar. 1989; vol. 9, No. 3; 1165-1172.

Idusogie et al.; "Engineered Antibodies With Increased Activity to Recruit Complement"; *Journal of Immunology.*; 2001; 166:2571-2575.

Ishida et al.; "Production of Human Monoclonal and Polyclonal Antibodies in Transchromo Animals"; *Cloning and Stem Cells*; vol. 4 (2002), 91-102.

Jia et al.; "A Novel Method of Multiplexed Competitive Antibody Binning for the Chraracterization of Monoclonal Antibodies"; *Journal of Immunological Methods*; 288 (2004), 91-98.

Jones et al.; "Replacing the Complementarity-Determining Regions in a Human Antibody With Those From a Mouse"; *Nature*; 321 (1986), 522-525.

Jostock et al.; "Screening of Molecular Repertoires by Microbial Surface Display"; *Combinatoral Chemistry & High Throughput Screening*; 2005; 8; 127-133.

Kearney et al.; "A New Mouse Myeloma Cell Line That Has Lost Immunoglobulin Expression But Permits the Construction of Antibody-Secreting Hybrid Cell Lines"; *Journal of Immunology*; vol. 123, No. 4 (1979), 1548-1550.

Köhler et al.; "Continuous Cultures of Fused Cells Secreting Antibody of Predefined Specificity"; *Nature*; 256 (1975), 495-497.

Kraus et al.; "Isolation and Characterization of ERBB3, A Third Member of the ERBB/Epidermal Growth Receptor Family: Evidence for Overexpression in a Subset of Human Mammary Tumors"; vol. 86; Dec. 1989; 9193-9197.

Kraus et al.; "Demonstration of Ligand-Dependent Signaling by the erbB-3 Tyrosine Kinase and its Constitutive Activation in Human Breast Tumor Cells"; *Proc. Natl. Acad. Sci. U.S.A.*; vol. 90; (1993); 2900-2904.

Li et al.; "Induction of Growth Inhibition and Apoptosis in Pancreatic Cancer Cells by Auristatin-PE and Gemcitabine"; *International Journal of Molecular Medicine*; 3 (1999), 647-53.

Liu et al.; "Eradication of Large Colon Tumor Xenografts by Targeted Delivery of Maytansinoids"; *Proc. Natl. Acad. Sci. USA*; vol. 93 (1996); 8618-8623.

Lonberg et al.; "Antigen-Specific Human Antibodies From Mice Comprising Four Distinct Genetic Modifications"; *Nature*; vol. 368; (1994); 856-859.

Mandler et al.; "Immunoconjugates of Geldanamycin and Anti-HER2 Monoclonal Antibodies: Antiproliferative Activity on Human Breast Carcinoma Cell Lines"; *Journal of the National Cancer Institute*; vol. 92, No. 19; (2000); 1573-1581.

Marks et al.; "By-passing Immunization Human Antibodies from V-Gene Libraries Displayed on Phage"; *J. Mol. Biol.*; 222 (1991), 581-597.

Martin et al.; "Structural Families in Loops of Homologous Proteins: Automatic Classification, Modeling and Application to Antibodies"; *J. Mol. Biol.*; (1996); 263; 800-815.

Mendez et al.; "Functional Transplant of Megabase Human Immunoglobulin Loci Recapitulates Human Antibody Response in Mice"; *Nature Genetics*; vol. 15; (1997); 146-156.

Morrison et al.; "Chimeric Human Antibody Molecules: Mouse Antigen-Binding Domains With Human Constant Region Domains"; *Proc. Natl. Acad. Sci. U.S.A.*; vol. 81; (Nov. 1984); 6851-6855.

Muyldermans, S.; "Single Domain Camel Antibodies: Current Status"; *Reviews in Molecular Biotechnology*; 74; (2001); 277-302.

Naidu et al.; "Expression of c-erbB3 Protein in Primary Breast Carcinomas"; *British Journal of Cancer*; (1996); 78(10); 1385-1390.

Otani et al.; "TZT-1027, An Antimicrotubule Agent, Attacks Tumor Vasculature and Induces Tumor Cell Death"; *Jpn J Cancer Res.*; 91; (Aug. 2000); 837-844.

Plowman et al.; "Molecular Cloning and Expression of an Additional Epidermal Growth Factor Receptor-Related Gene"; *Proc. Natl. Acad. Sci. U.S.A.*; vol. 87; (Jul. 1990); 4905-4909.

Pluckthün, A.; "Antibodies From *Escherichia coli*" in *The Pharmacology of Monoclonal Antibodies*;, Chapter II, Rosenburg and Moore, Eds., Springer Verlag, N.Y.; 113 (1994), 269-315).

Powell et al.; "Compendium of Excipients for Parental Formulations"; *PDA Journal of Pharmaceutical Science & Technology*; vol. 52, No. 5; (Sep.-Oct. 1998), 238-311.

Presta, L. G.; "Antibody Engineering"; *Current Opinion in Structural Bioloyg*; 1992, 2:593-596.

Price et al.; "Methods for the Study of Protein-Protein Interactions in Cancer Cell Biology"; *Methods in Molecular Biology*; vol. 218; (2002); 255-267.

Rajkumar et al.; "A Monoclonal Antibody to the Human C-ERB3 Protein Stimulates the Anchorage-Independent Growth of Breast Cancer Cell Lines"; *British Journal of Cancer*, vol. 70, No. 3, 1994; 459-465.

Rajkumar et al.; "c-cerbB3 Expression in Breast Tumor Derived Cell Lines"; *The Breast* (1995), 4; 84-91.

Reichmann et al.; "Reshaping Human Antibodies for Therapy"; *Nature*; vol. 332; (Mar. 1998); 323-327.

Shields et al.; "High Resolution Mapping of the Binding Site on Human IgG1 for FcyRI, FcyRII, FcyRIII, and FcRn and Design of IgG1 Variants with Improved Binding to the FcyR*";*The Journal of Biological Chemistry*; vol. 276, No. 9; 2001; 6591-6604.

Skerra, A.; "Engineered Protein Scaffolds for Molecular Recognition"; *Journal of Molecular Recognition*; (2000); 13; 167-187.

Sliwkovsky et al; "Coexpression of erbB2 and erbB3 Proteins Reconstitutes a High Affinity Receptor for Heregulin"; *J. of Biol. Chem.*; 1994, vol. 269, No. 20; 14661-14665.

Stebbing et al.; "Herceptin (trastuzamab) in Advanced Breast Cancer"; *Cancer Treatment Reviews*; 2000; 26; 287-290.

Taylor et al.; "Human Immunoglobulin Transgenes Undergo Rearrangement, Somatic Mutation and Class Switching in Mice that Lack Endogenous IgM"; *International Immunology*; vol. 6, No. 4; (1994); 579-591.

Taylor et al.; "A Transgenic Mouse That Expresses a Diversity of Human Sequence Heavy and Light Chain Immunoglobulins"; *Nucleic Acids Research*; (1992); vol. 20, No. 23; 6287-6295.

Thornton et al.; "Prediction of Progress At Last"; *Nature*; vol. 354, (Nov. 1991); 105-106.

Tuaillon et al.; "Human Immunoglobulin Heavy-Chain Minilocus Recombination in Transgenic Mice: Gene-Segment Use in $u$ and $y$ Transcripts"; *Proc. Natl. Acad Sci.*; (Apr. 1993); vol. 90; 3720-3724.

Tuaillon et al.; "Analysis of Direct and Inverted $_{DJH}$ Rearrangments in a Human Ig Heavy Chain Transgenic Minilocus[1]"; (1995).

Ulrich et al.; "Signal Transduction by Receptors with Tyrosine Kinase Activity"; *Cell*; vol. 61, 1990; 203-212.

Wallasch et al.; "Heregulin-Dependent Regulation of HER2/Neu Oncogenic Signaling by Heterodimerization with HER3"; *The EMBO Journal*; (1995); vol. 14 No. 17; 4267-4275.

Wallasch; C.; "Bedeutung von HER3 Fur Die Signal Definition Von HER2"; Dissertation Max-Planck Institute of Biochemistry, Munich, Germany, 1996.

Wang, W.; "Lyophilization and Development of Solid Protein Pharmaceuticals"; *International Journal of Pharmaceutics.*; 203; (2000), 1-60.

Witzig, T.; "Radioimmunotherapy for Patients with Relapsed B-Cell Non-Hodgkin Lymphoma"; *Cancer Chemother. Pharmacol.*; (2001); 48 (Suppl 1); S91-S95.

Zhang et al.; "Transformation of NIH 3T3 Cells by HER3 or HER4 Receptors Requires the Presence of HER1 or HER2"; *J. of Biol. Chemistry*; 1996, vol. 271, No. 7; 3884-3890.

International Search Report in counterpart international application No. PCT/EP2006/012632 mailed Jun. 26, 2007, 4 pgs.

* cited by examiner

Fig. 1

| cell line | tissue | expression level |
|---|---|---|
| Hs578T | breast | ++ |
| T47D | breast | ++ |
| SKBr3 | breast | +++ |
| ZR 75-1 | breast | ++ |
| MDA-MB-435s | breast | +++ |
| MCF-7 | breast | ++ |
| BT474 | breast | +++ |
| MDA-MB 453 | breast | ++ |
| MDA-MB 361 | breast | ++ |
| HCT116 | colon | + |
| HT29 | colon | ++ |
| LoVo |  | + |
| CaCo-2 | colon | + |
| SW480 | colon | ++ |
| A431 | epidermoid | + |
| HT1080 | fibrosarcoma | 0/+ |
| CaKi-1 | kidney | 0 |
| CaKi-2 | kidney | 0 |
| Calu6 | lung | 0 |
| A549 | lung | ++ |
| M19 | melanoma | ++ |
| M14 | melanoma | +++ |

| cell line | tissue | expression level |
|---|---|---|
| RPMI-7951 | melanoma | 0/+ |
| MelJuso | melanoma | ++ |
| MelGerlach | melanoma | ++ |
| C32 | melanoma | +++ |
| HT144 | melanoma | +++ |
| SK-Mel2 | melanoma | +++ |
| MALME3 | melanoma | +++ |
| Hs294T | melanoma | +++ |
| A375p | melanoma | +++ |
| SK-Mel3 | melanoma | +++ |
| Sk-Mel5 | melanoma | ++ |
| KB | nasopharynx | + |
| SCC9 | Squamous cell Carcinoma | + |
| SKOV3 | ovary | + |
| Capan-1 | pancreas | + |
| Capan-2 | pancreas | + |
| Bx-PC-3 | pancreas | + |
| LNCap | prostate | ++ |
| DU145 | prostate | + |
| PC-3 | prostate | + |
| BM1604 | prostate | ++ |
| TSU | prostate | + |

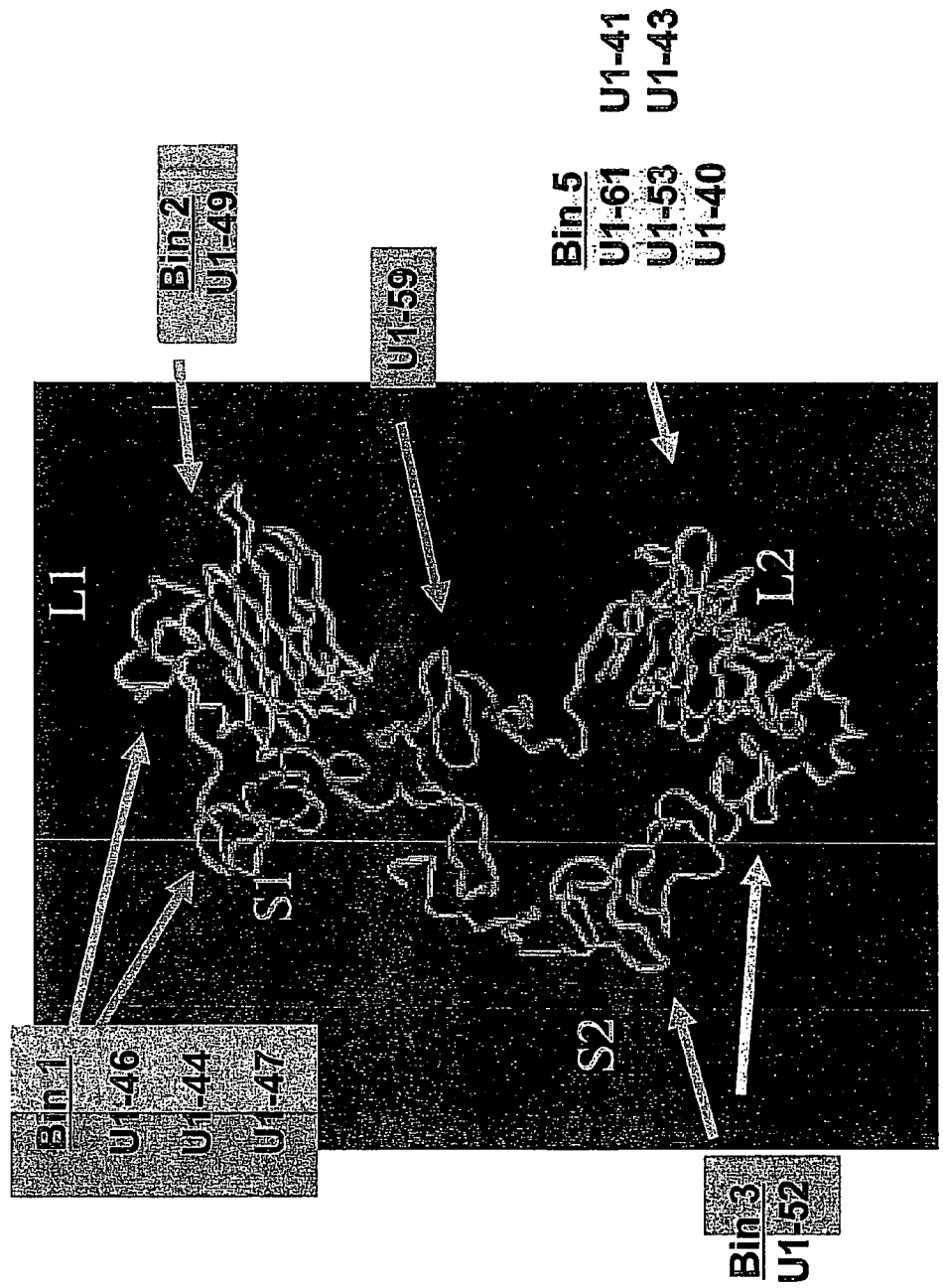
Fig. 3 antibody bins

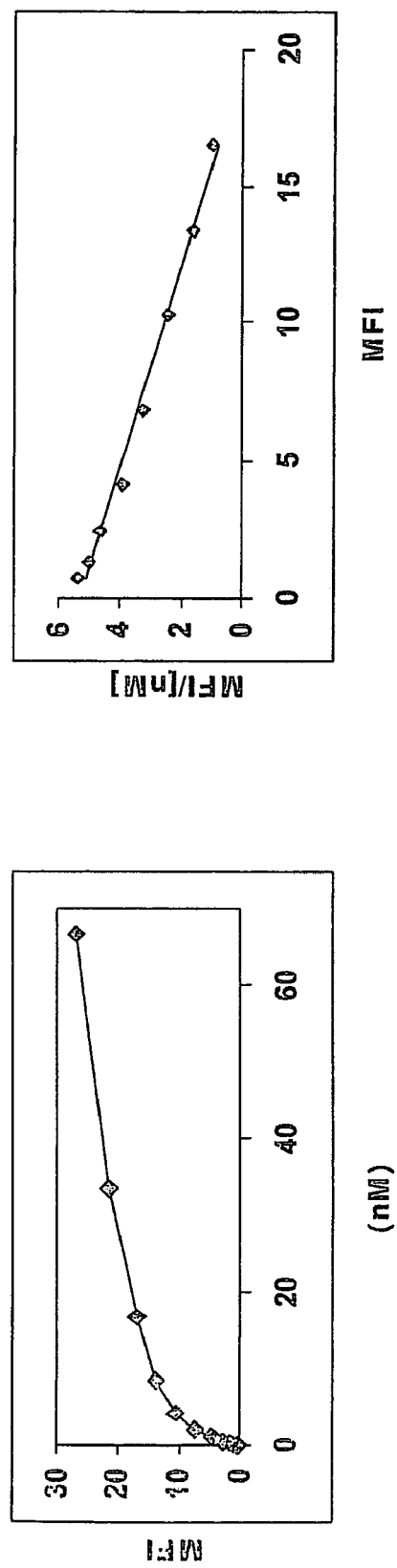
Fig. 4  FACS scatchard

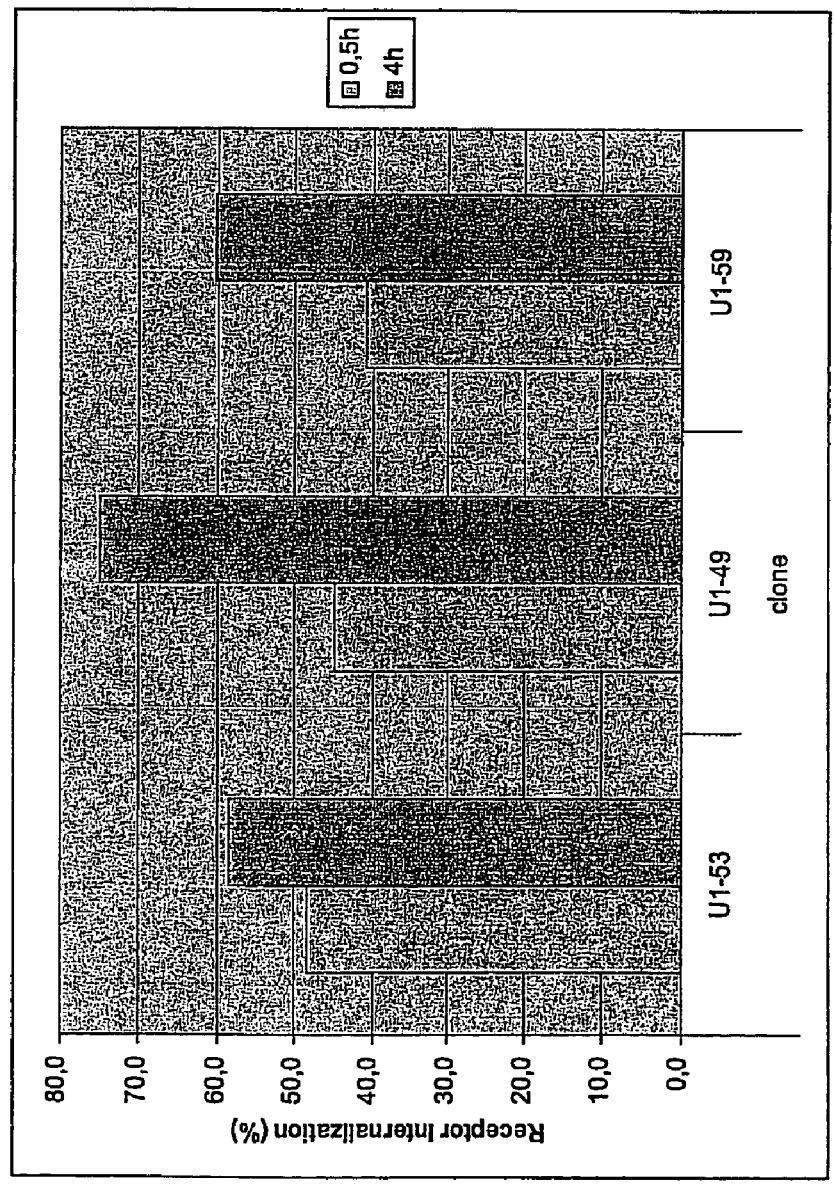

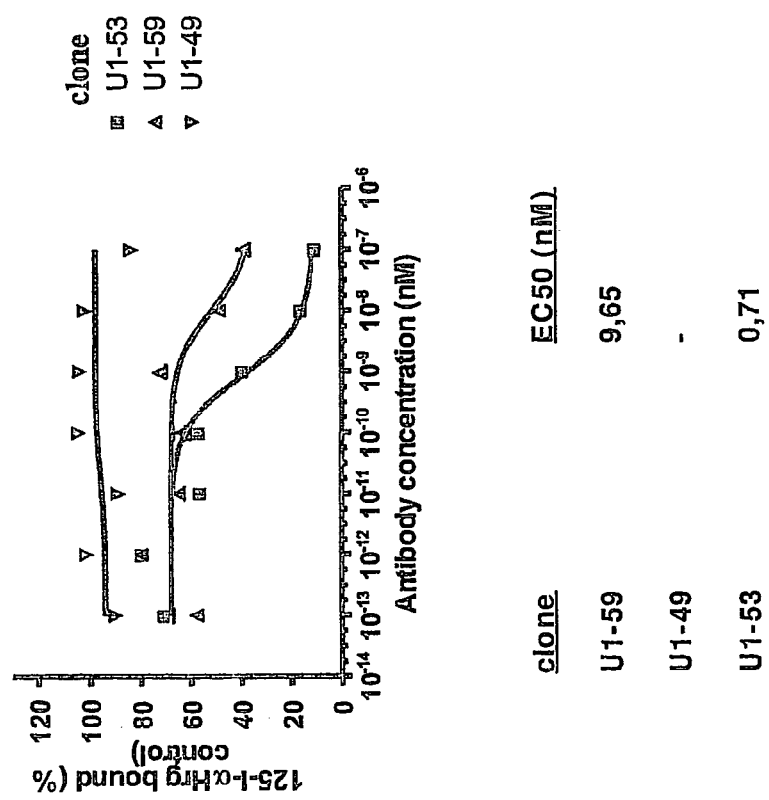

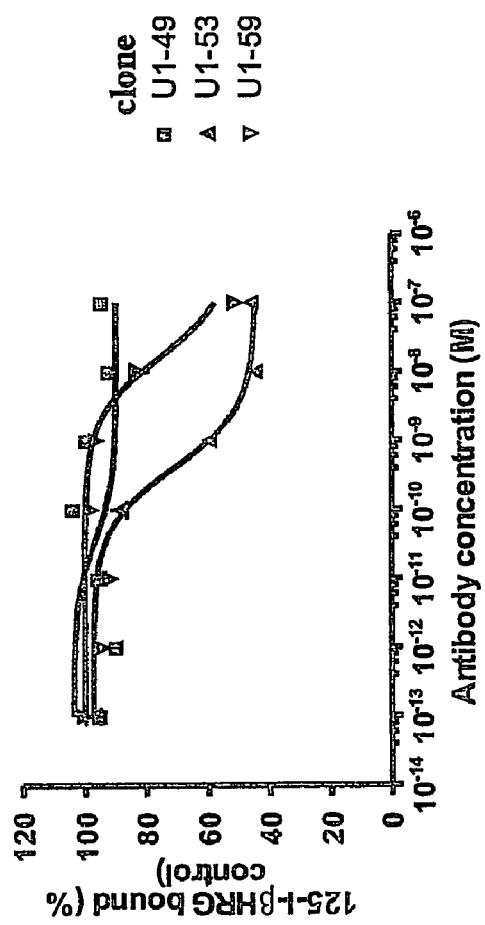
Fig. 6b HRG blocking

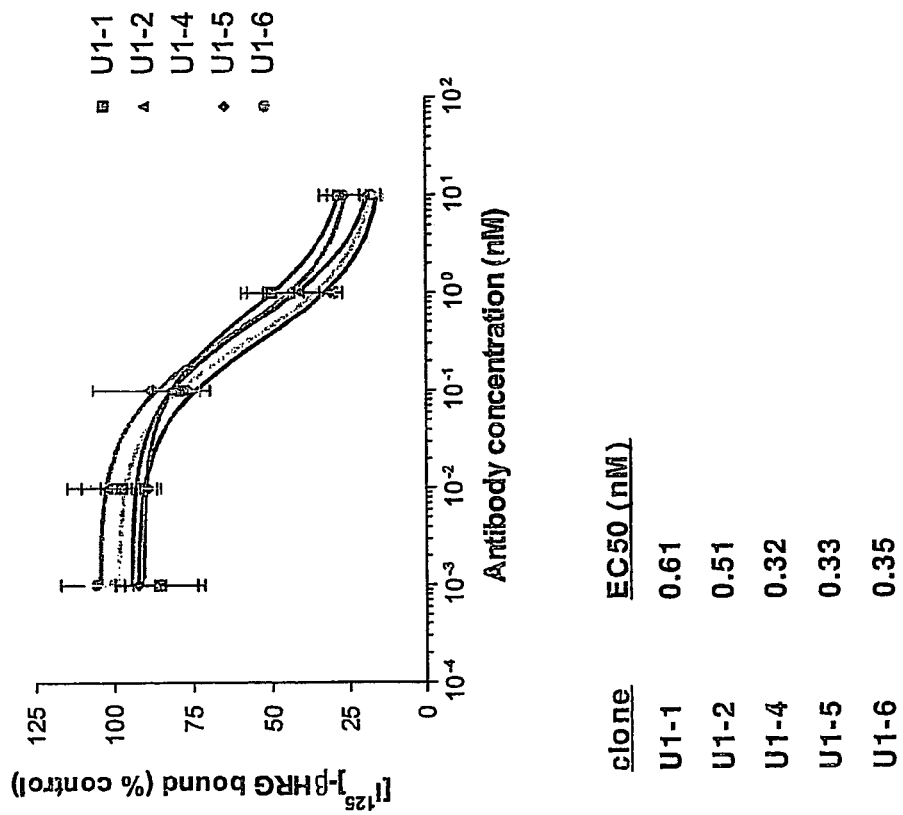

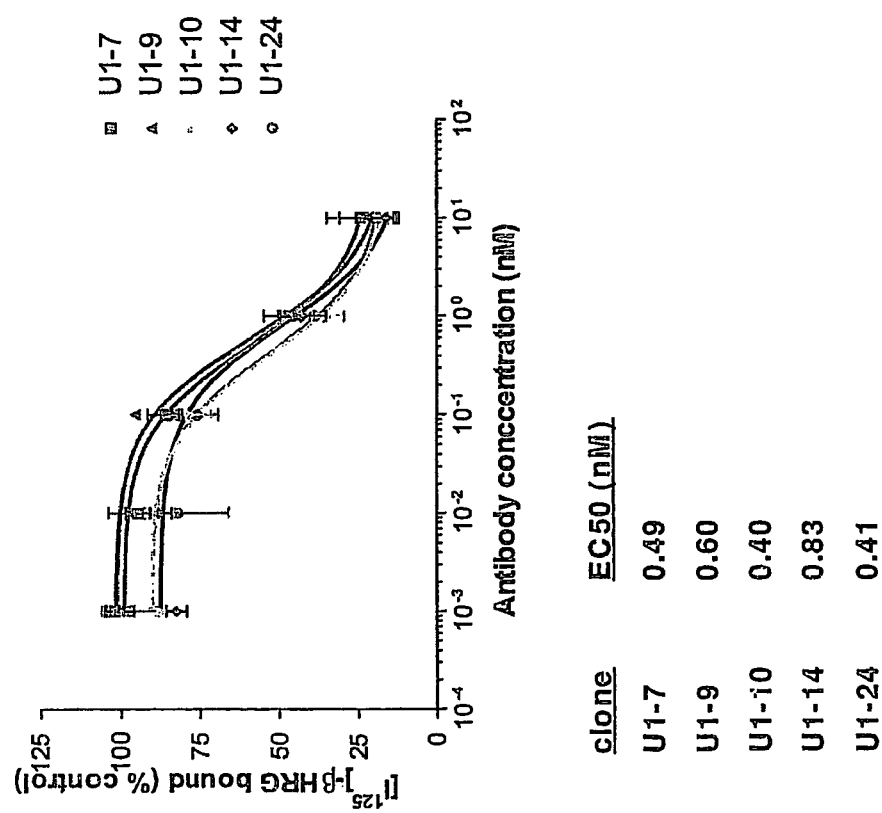

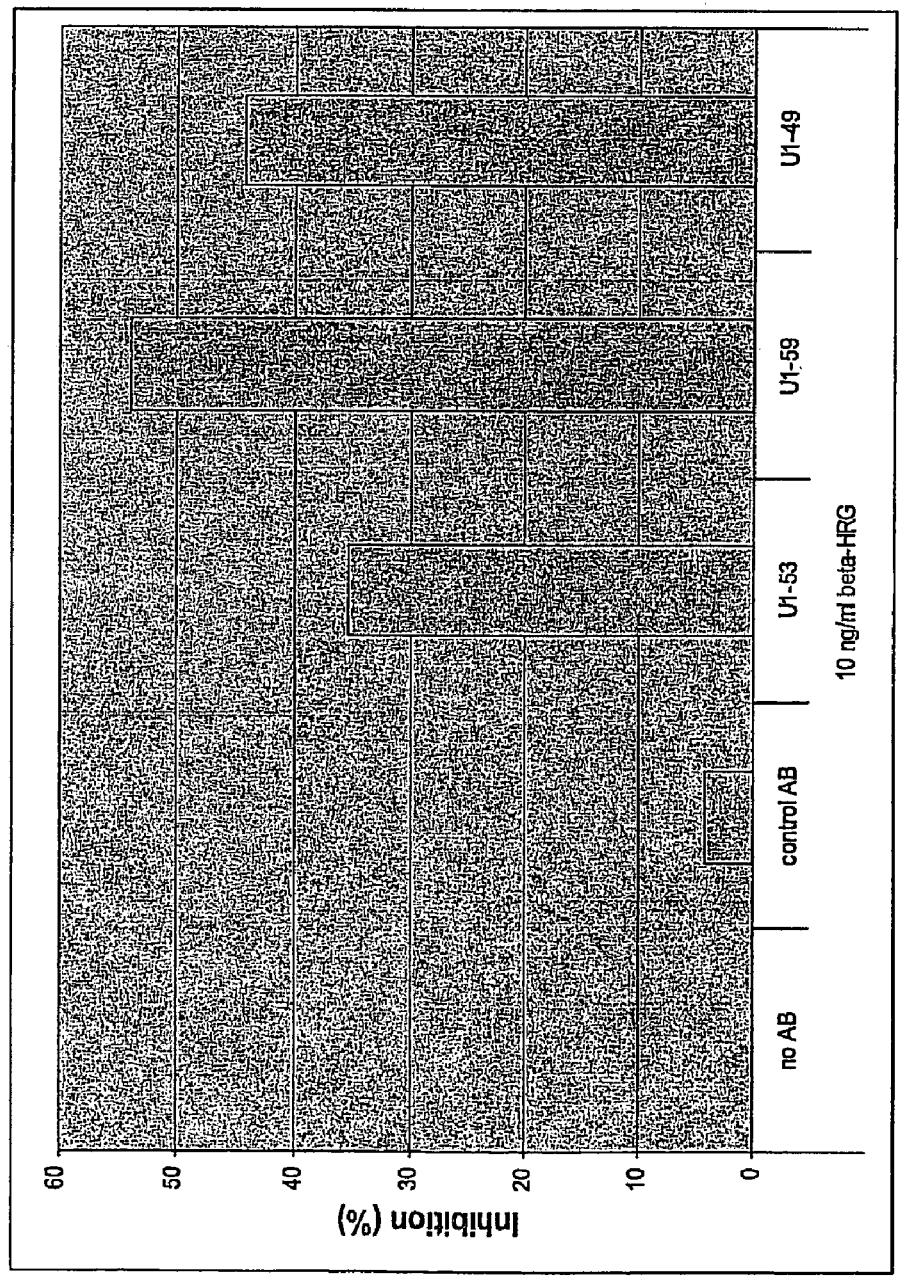

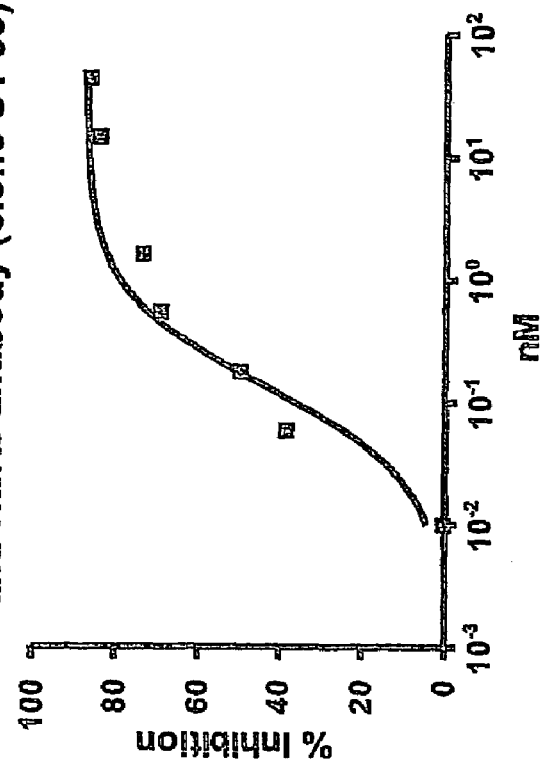

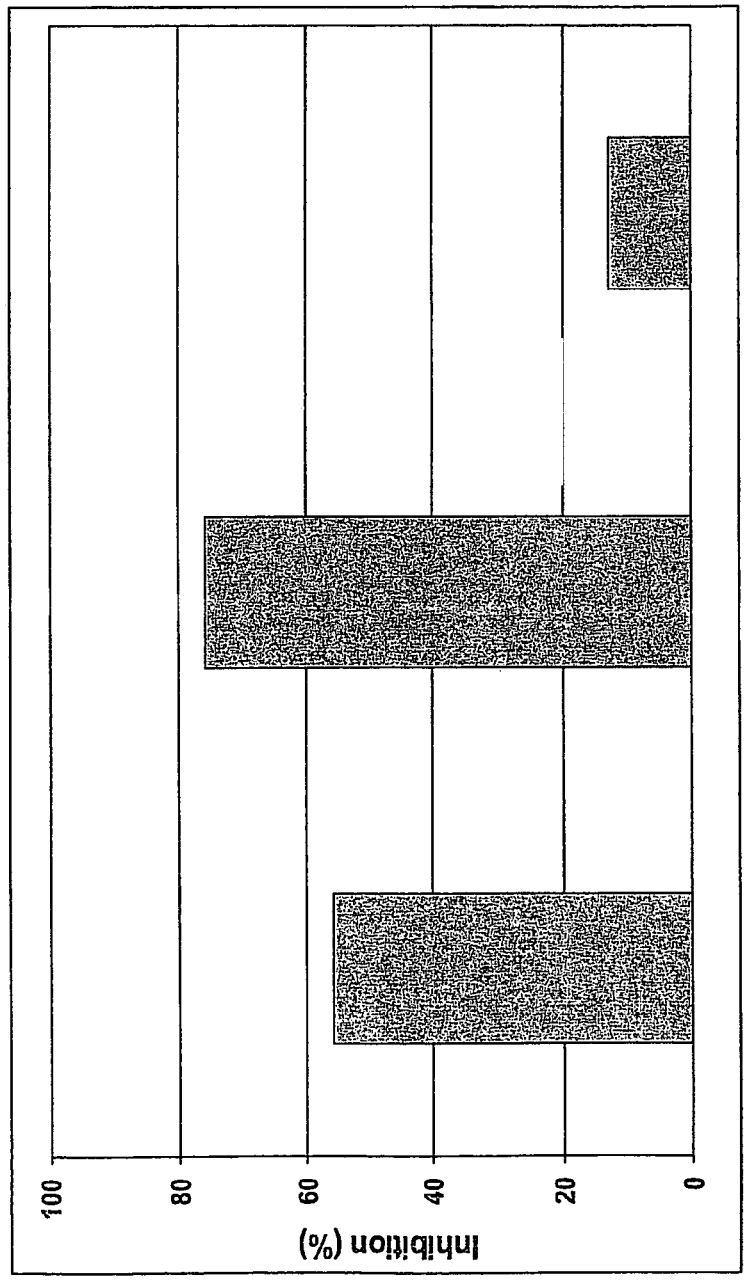
Fig. 8  MAP kinase

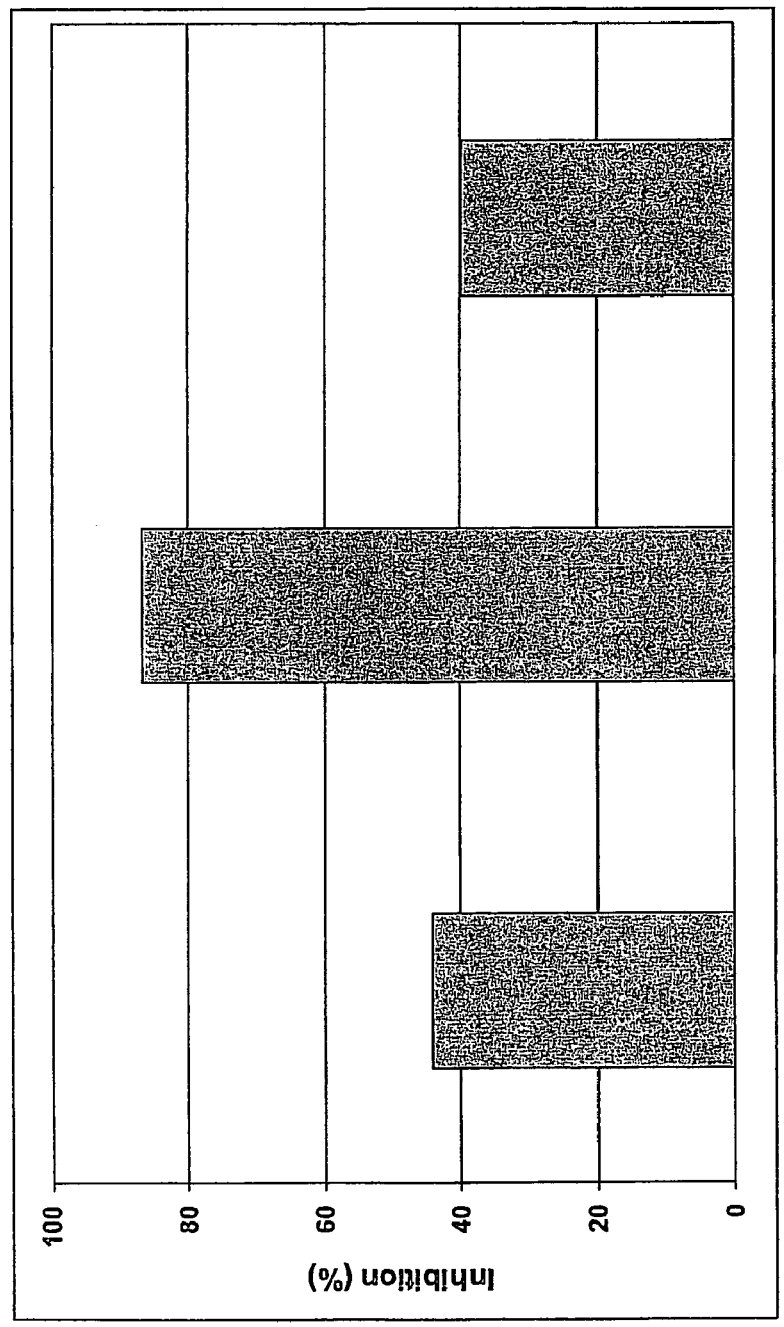
Fig. 9 AKT

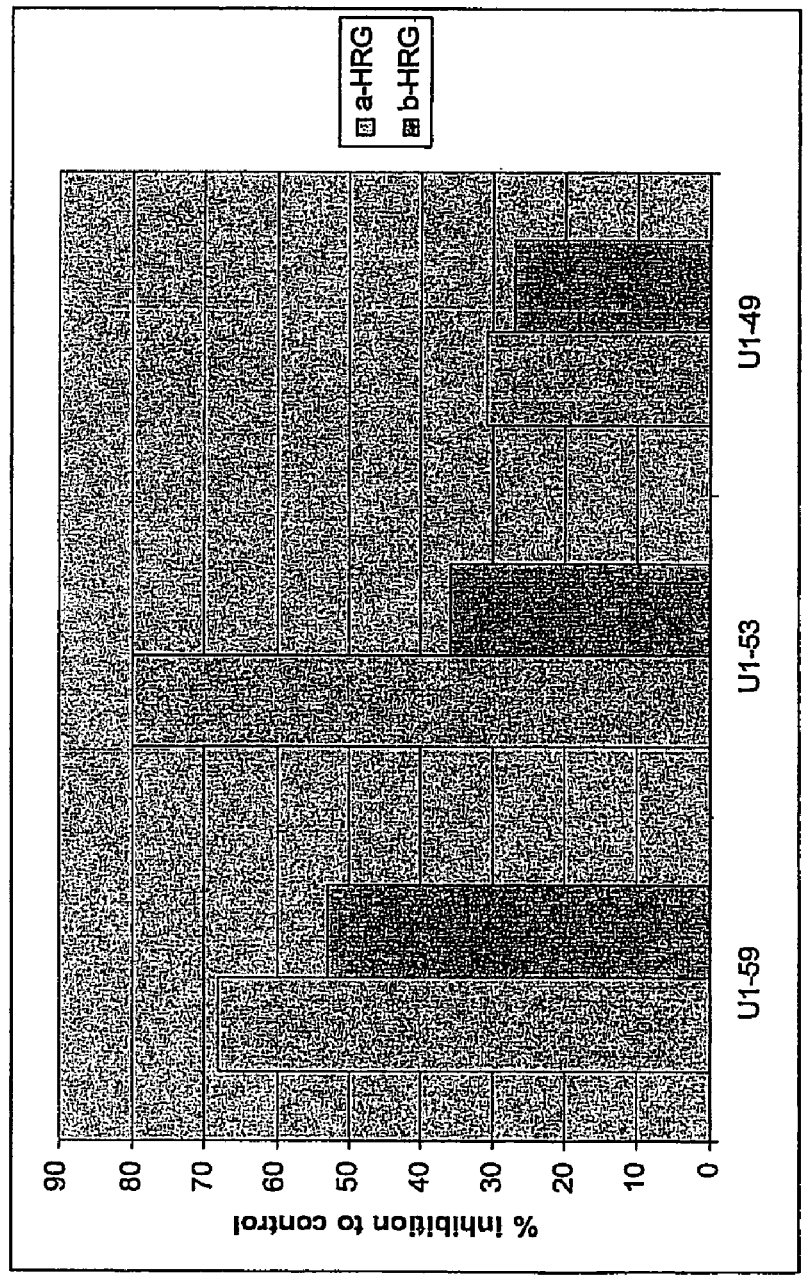
Fig. 10 proliferation

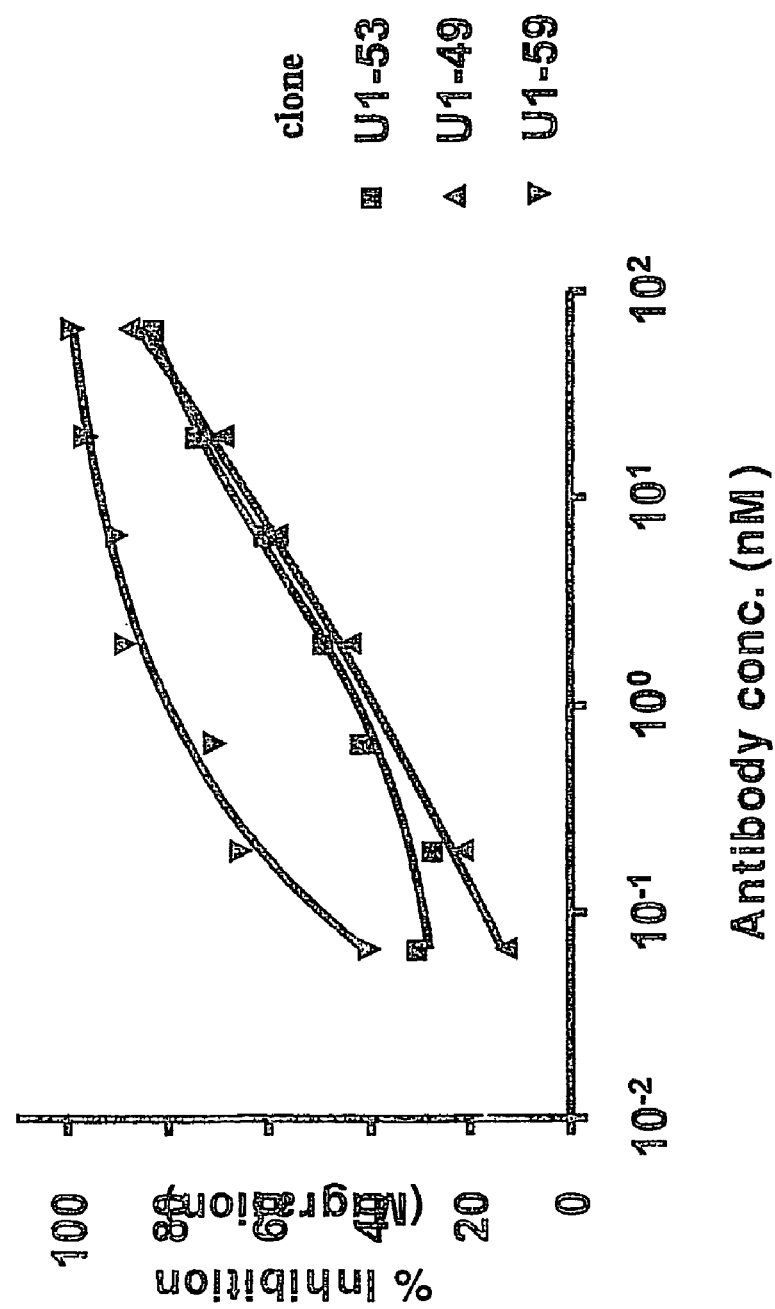
Fig. 11 migration

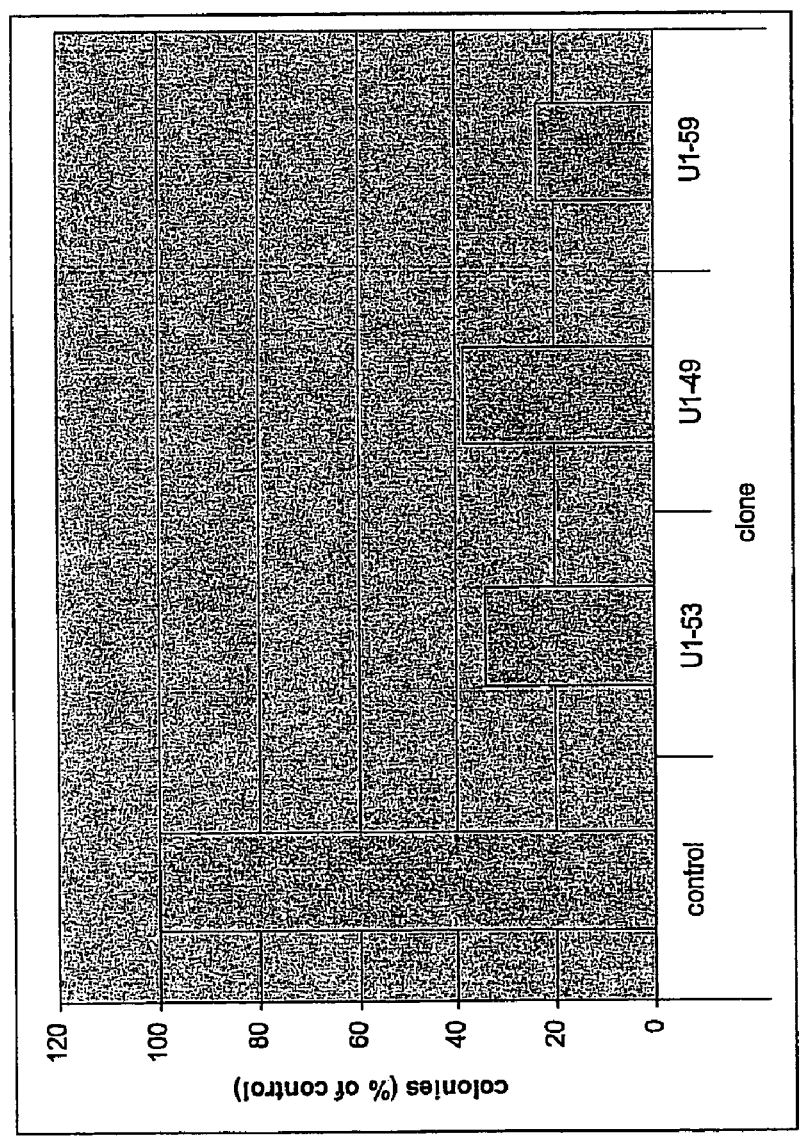
Fig. 12a Soft Agar MB361

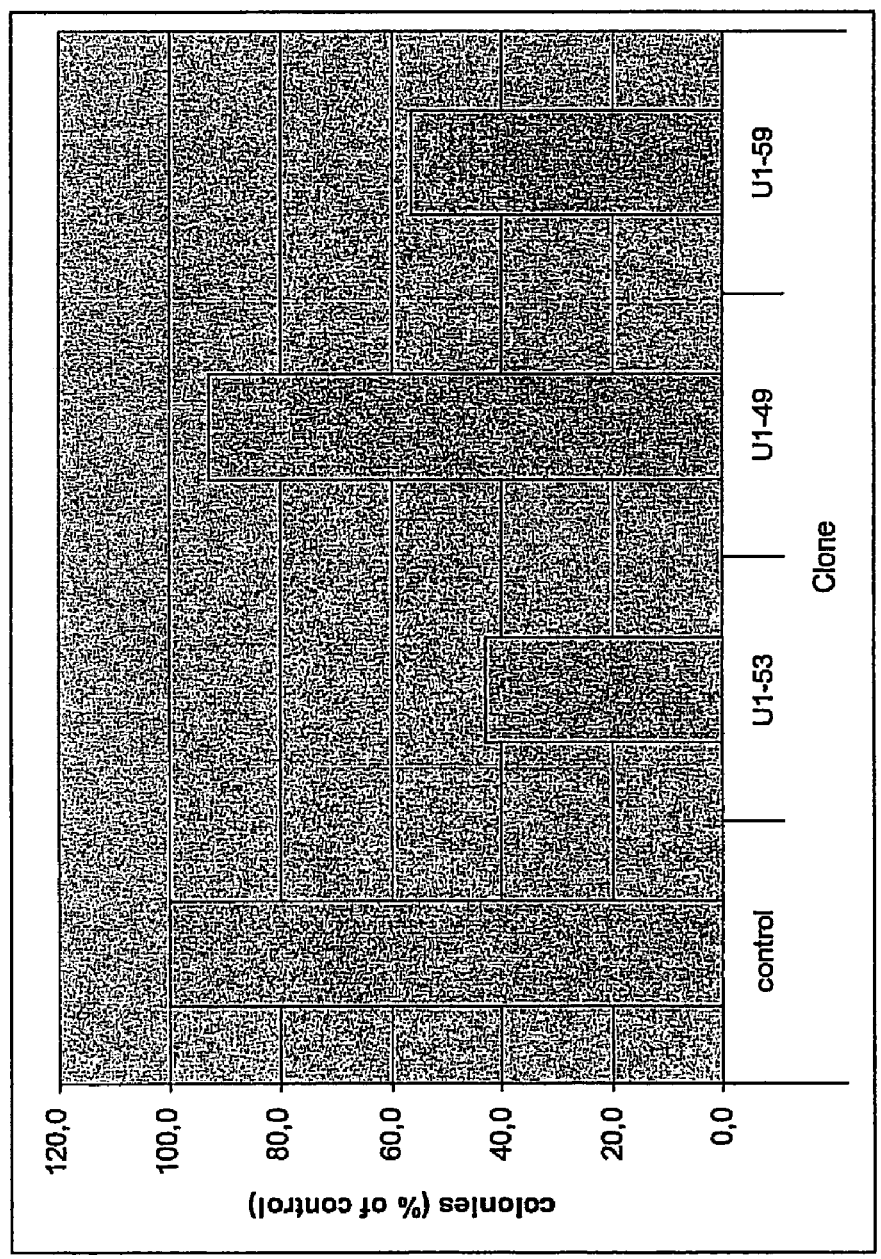
Fig. 12b Soft Agar NCI

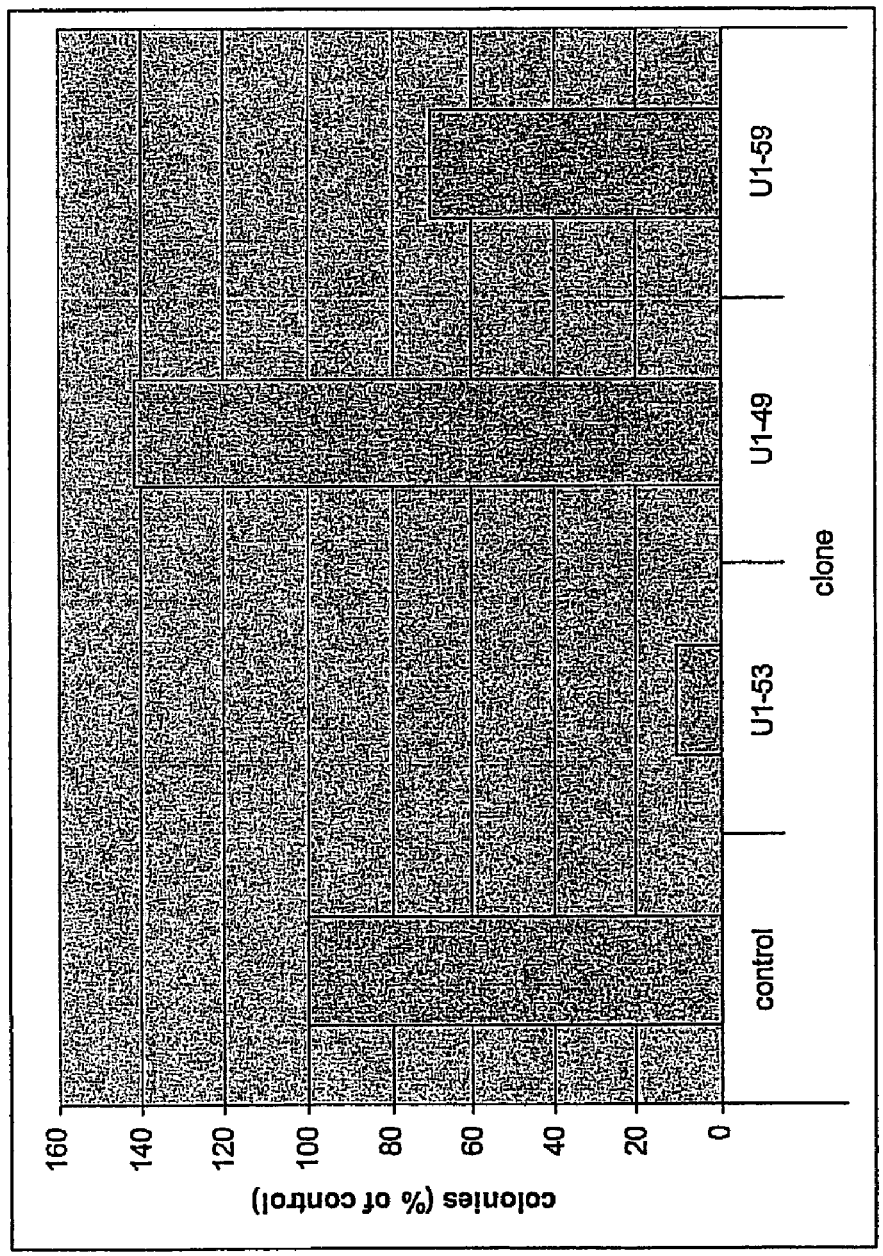

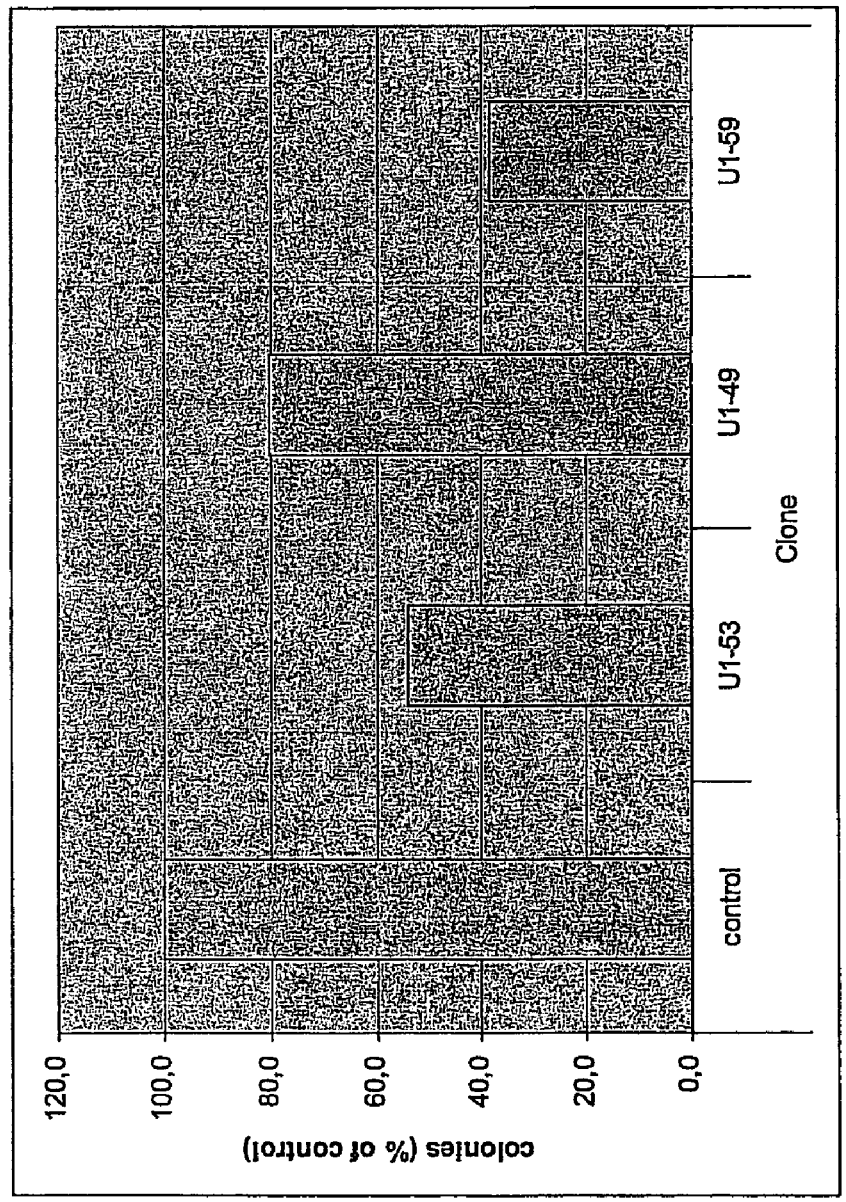

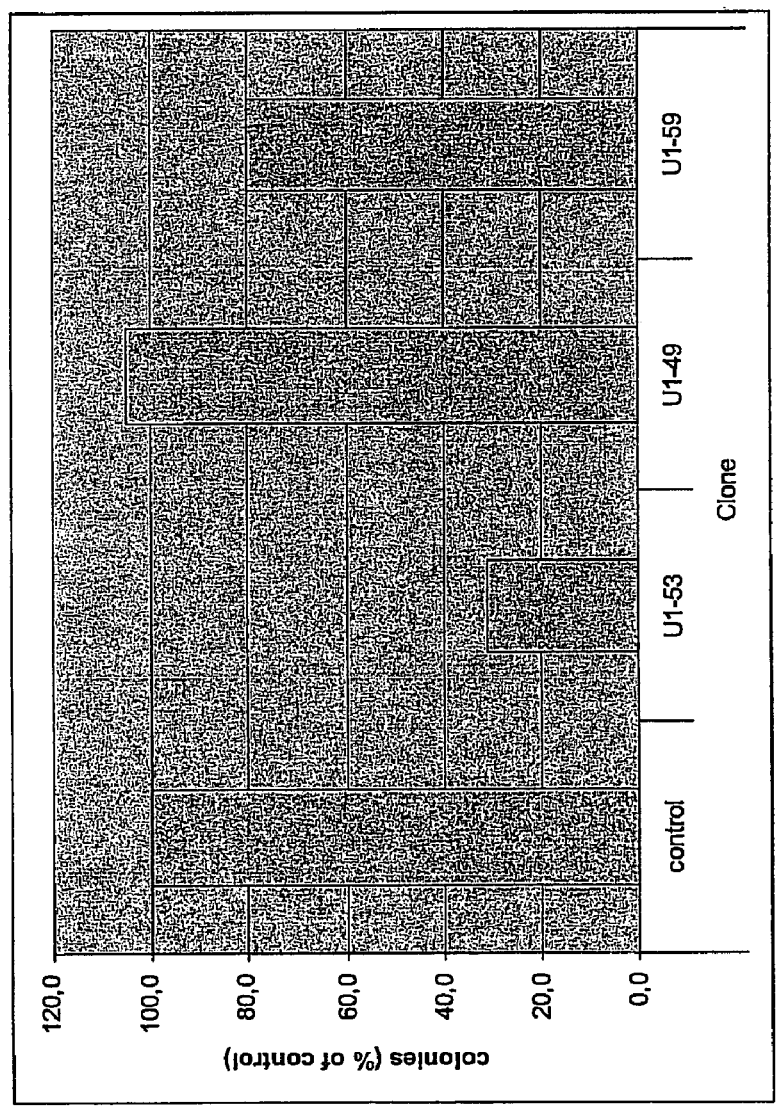
Fig. 12e  Soft Agar Skov-3

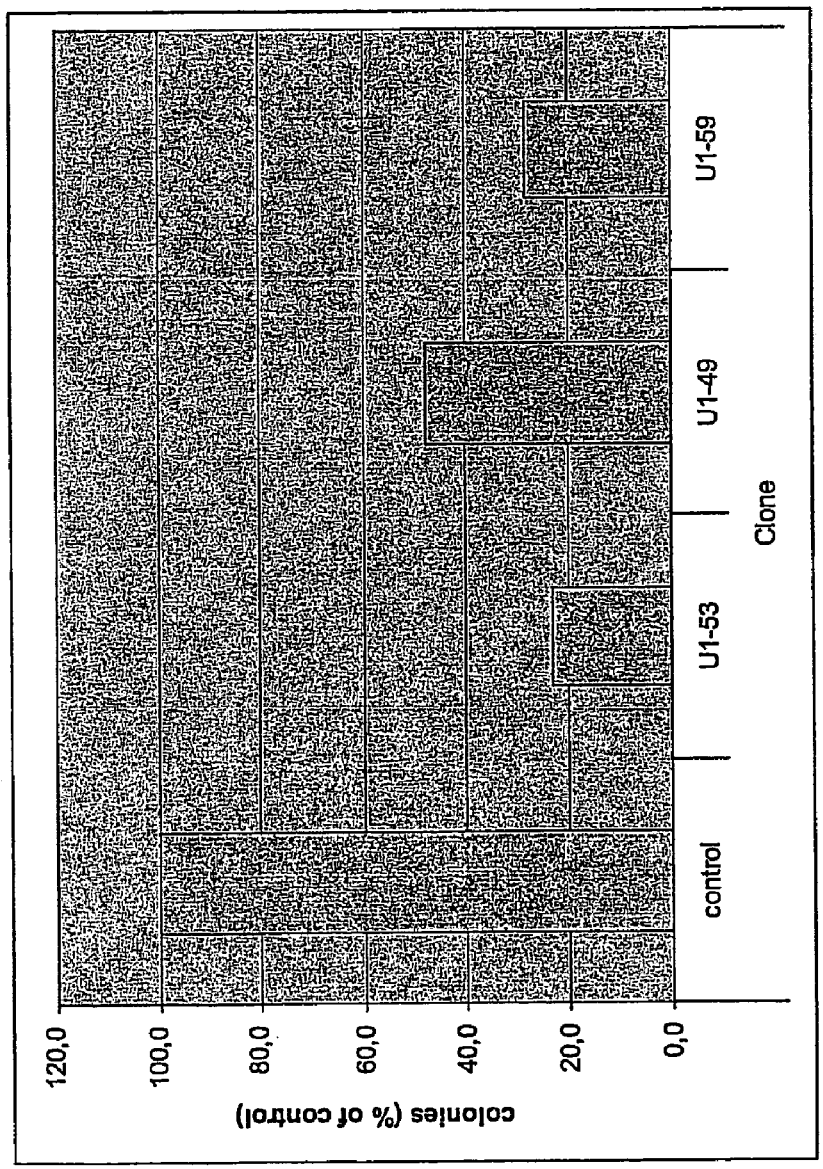
Fig. 12f Soft Agar PPC1

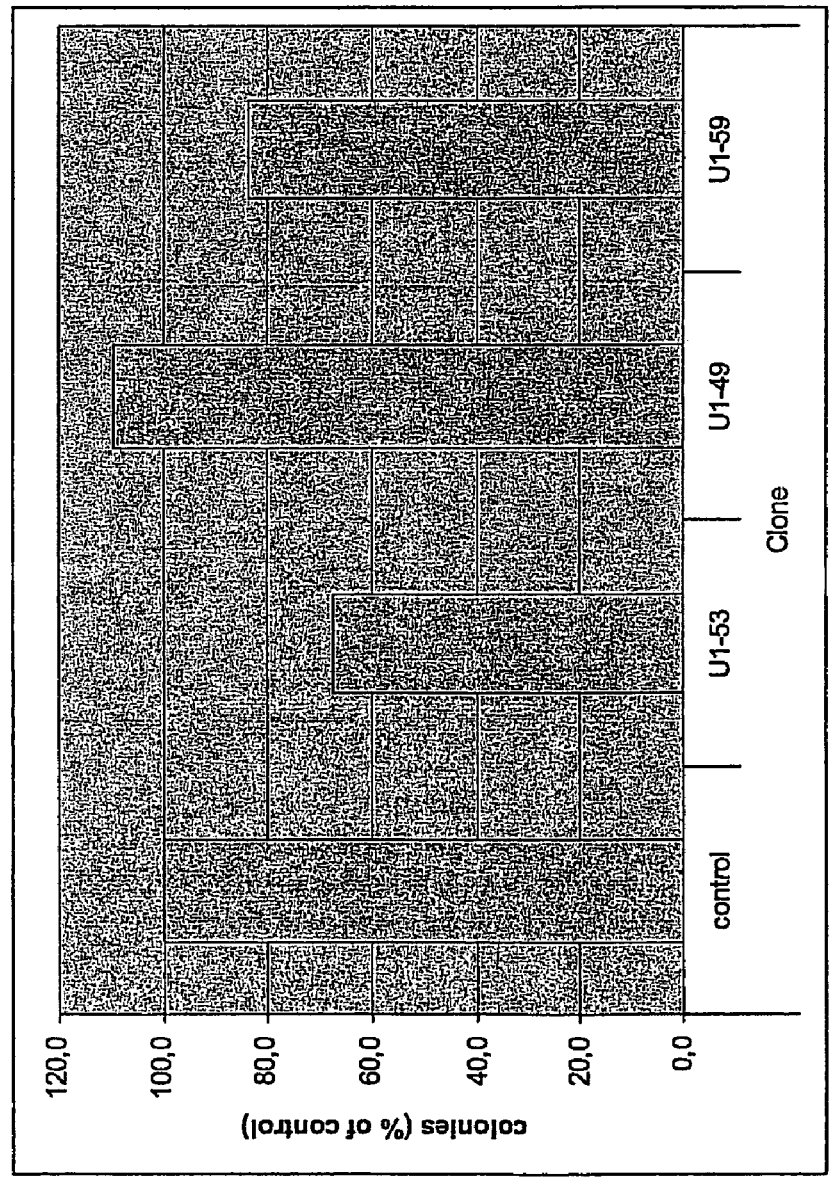
Fig. 12g  Soft Agar BX-PC3

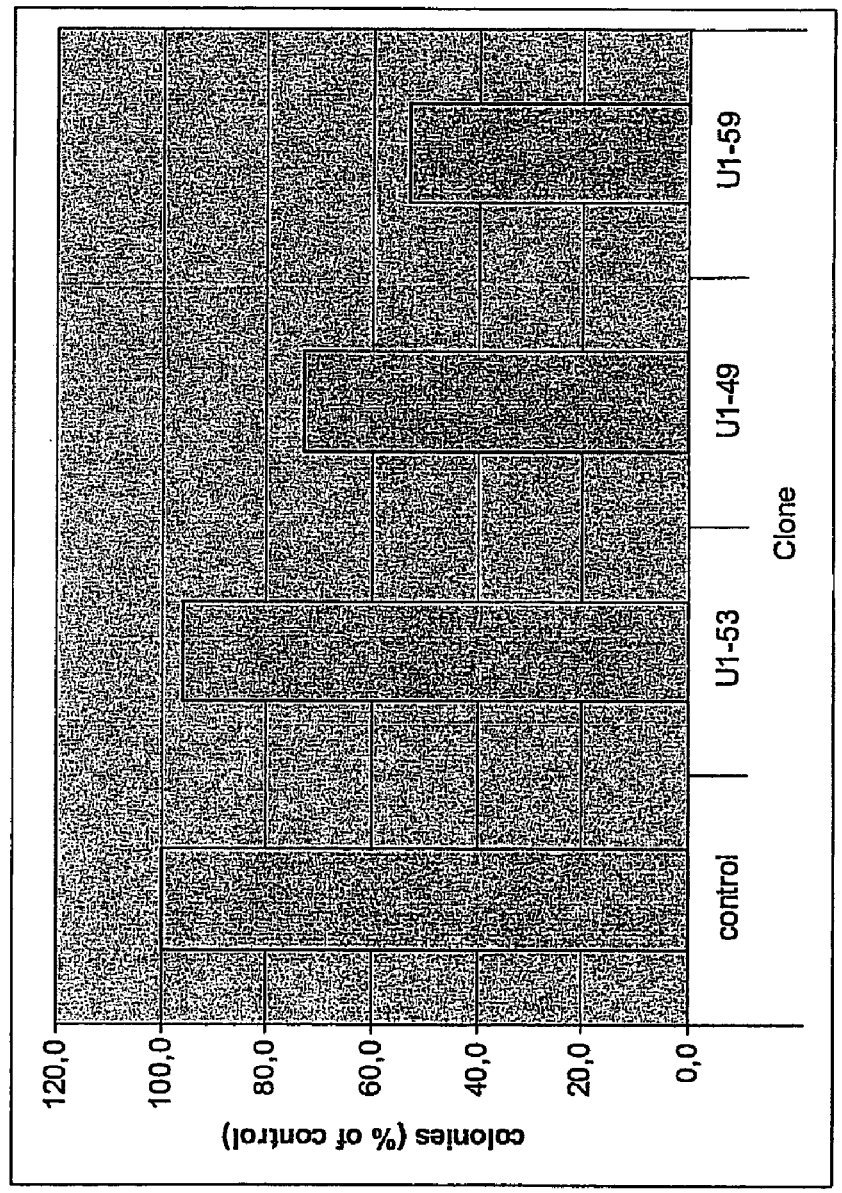
Fig. 12h Soft Agar A549

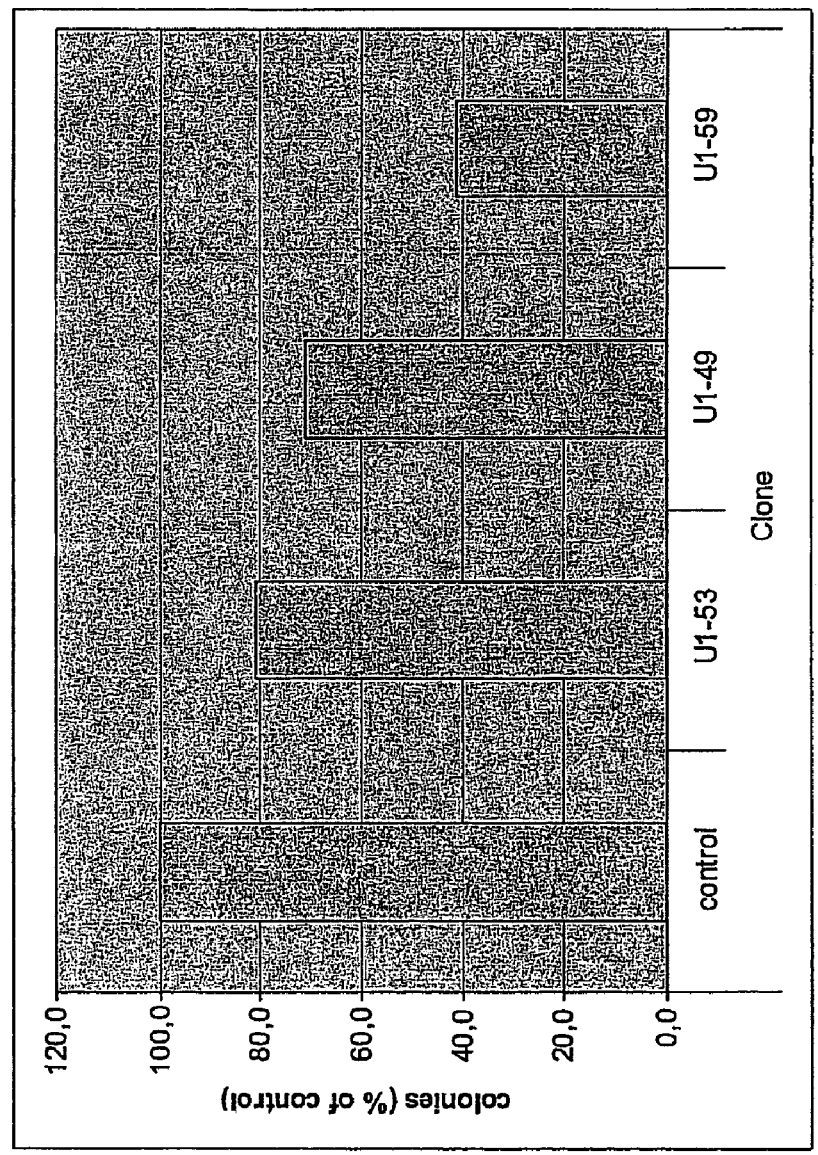
Fig. 12i Soft Agar epidermoid

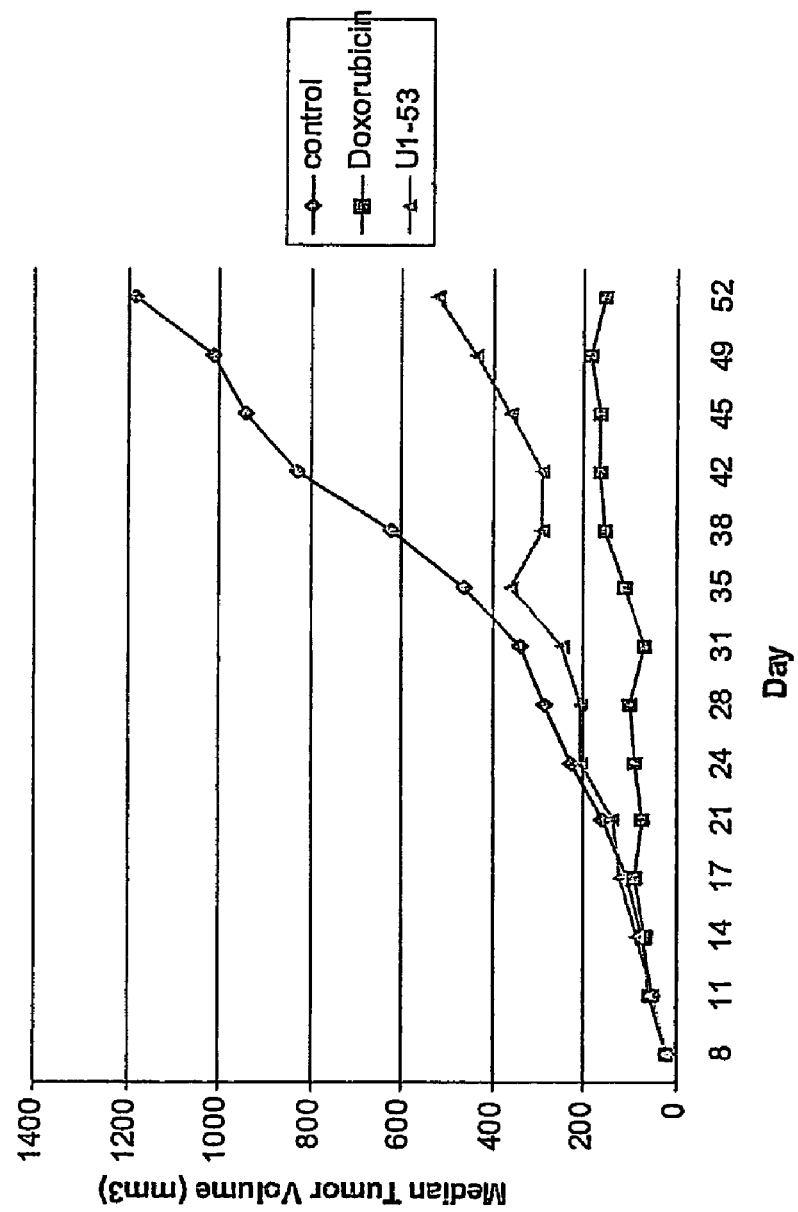
Fig. 13 in vivo T47D

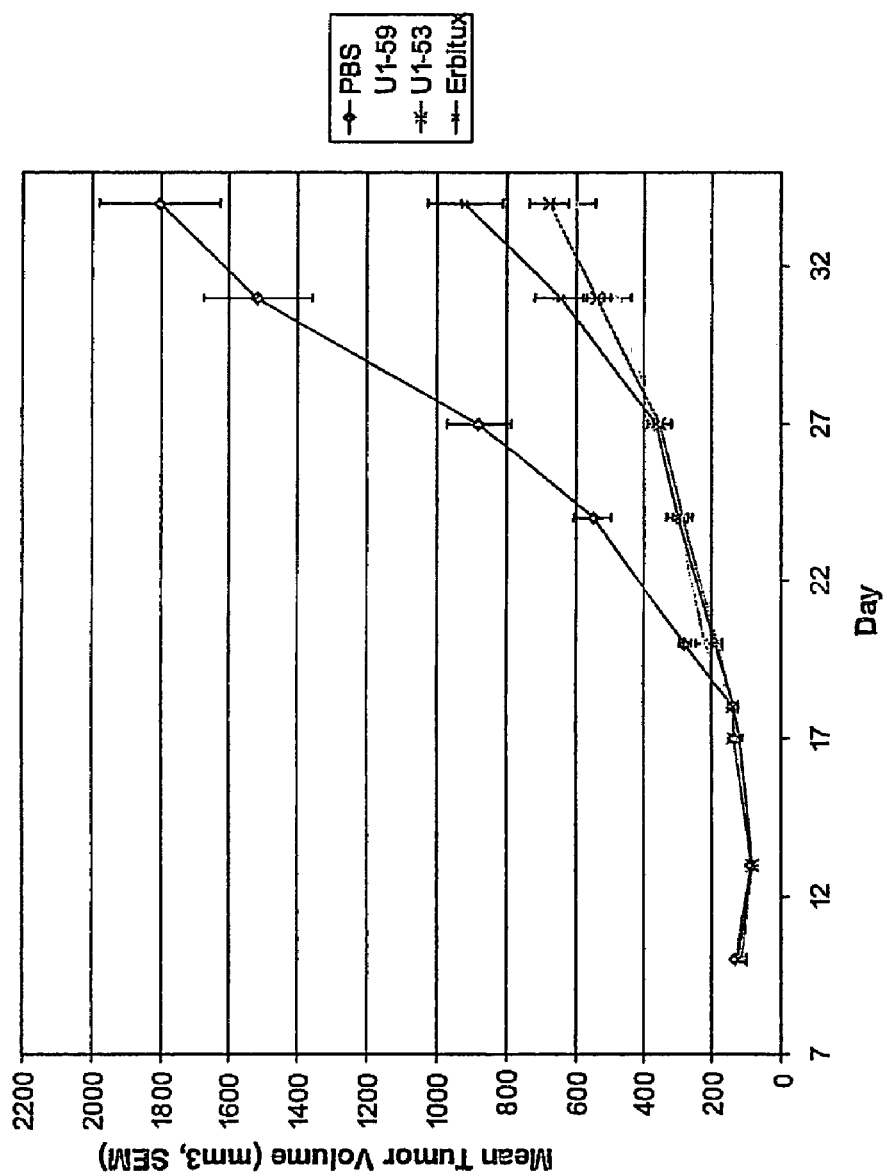

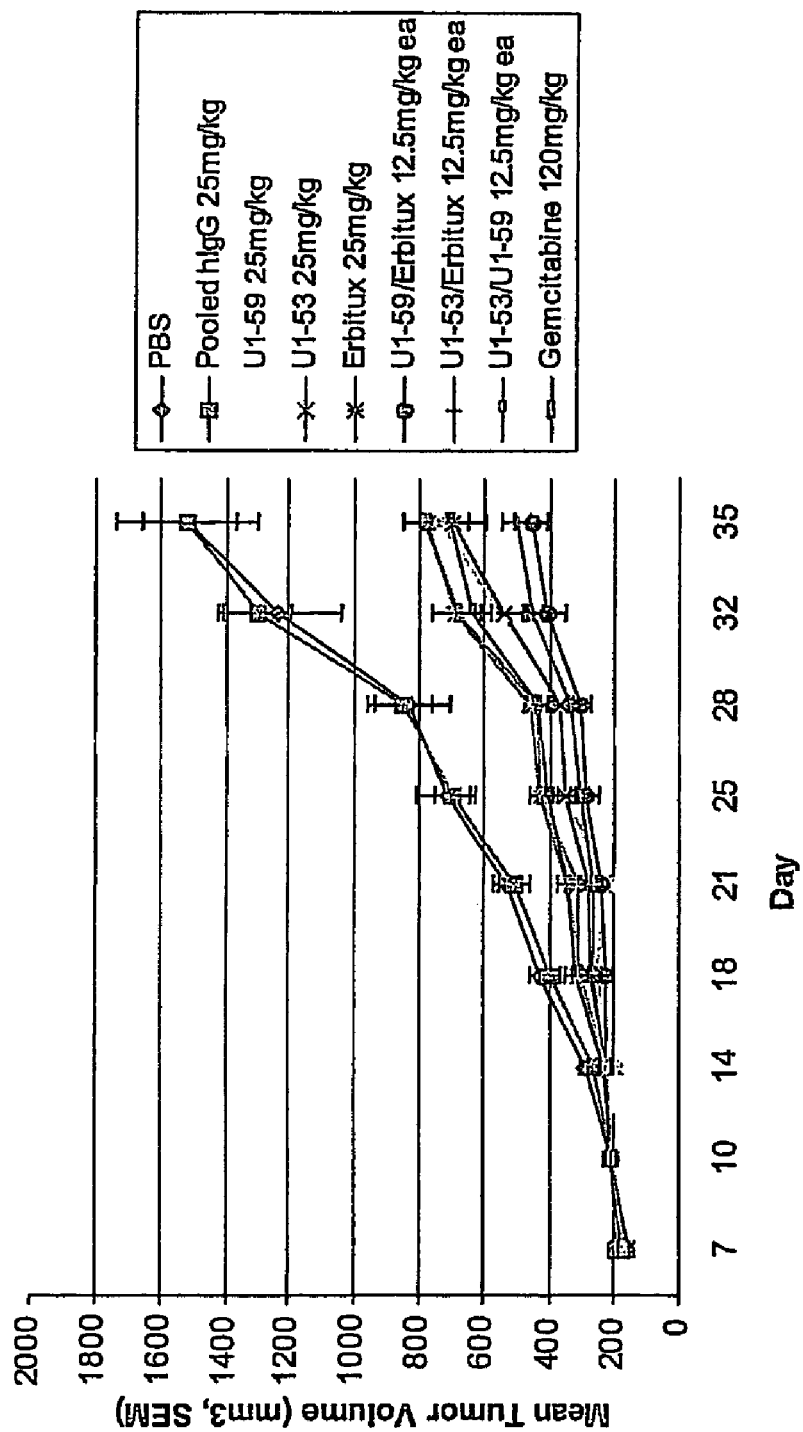

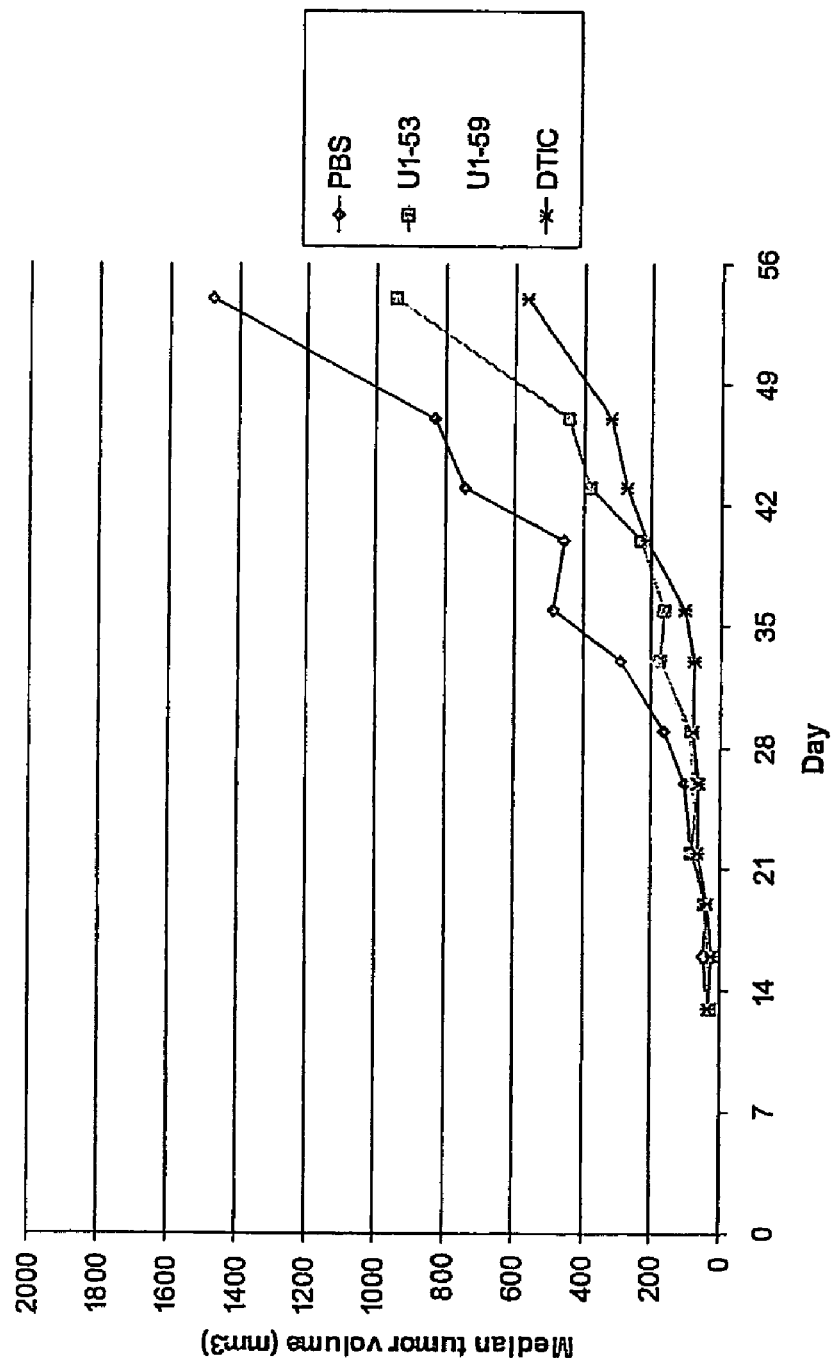
Fig. 16 HT144

ANTIBODIES DIRECTED TO HER-3 AND USES THEREOF

CROSS REFERENCE TO RELATED APPLICATIONS

This application claims the benefit of U.S. Provisional Application No. 60/755,103 filed Dec. 30, 2005, incorporated herein by reference.

BACKGROUND OF THE INVENTION

1. Field of the Invention

The present invention relates to binding proteins including antibodies and binding fragments thereof that bind to HER-3 and polynucleotides encoding the same. Expression vectors and host cells comprising the same for the production of the binding protein of the invention are also provided. In addition, the invention provides compositions and methods for diagnosing and treating diseases associated with HER-3 mediated signal transduction and/or its ligand heregulin.

2. Background of the Technology

The human epidermal growth factor receptor 3 (HER-3, also known as ErbB3) is a receptor protein tyrosine kinase and belongs to the epidermal growth factor receptor (EGFR) subfamily of receptor protein tyrosine kinases, which also includes HER-1 (also known as EGFR), HER-2, and HER-4 (Plowman et al., *Proc. Natl. Acad. Sci. U.S.A.* 87 (1990), 4905-4909; Kraus et al., *Proc. Natl. Acad. Sci. U.S.A.* 86 (1989), 9193-9197; and Kraus et al., *Proc. Natl. Acad. Sci. U.S.A.* 90 (1993), 2900-2904). Like the prototypical epidermal growth factor receptor, the transmembrane receptor HER-3 consists of an extracellular ligand-binding domain (ECD), a dimerization domain within the ECD, a transmembrane domain, an intracellular protein tyrosine kinase domain (TKD) and a C-terminal phosphorylation domain.

The ligand Heregulin (HRG) binds to the extracellular domain of HER-3 and activates the receptor-mediated signaling pathway by promoting dimerization with other human epidermal growth factor receptor (HER) family members and transphosphorylation of its intracellular domain. Dimer formation between HER family members expands the signaling potential of HER-3 and is a means not only for signal diversification but also signal amplification. For example the HER-2/HER-3 heterodimer induces one of the most important mitogenic signals among HER family members.

HER-3 has been found to be overexpressed in several types of cancer such as breast, gastrointestinal and pancreatic cancers. Interestingly a correlation between the expression of HER-2/HER-3 and the progression from a non-invasive to an invasive stage has been shown (Alimandi et al., *Oncogene* 10, 1813-1821; deFazio et al., *Cancer* 87, 487-498; Naidu et al., *Br. J. Cancer* 78, 1385-1390). Accordingly, agents that interfere with HER-3 mediated signaling are desirable. Murine or chimeric HER-3 antibodies have been reported, such as in U.S. Pat. No. 5,968,511, U.S. Pat. No. 5,480,968 and WO03013602.

A humanized monoclonal antibody against HER-2, Herceptin®, has recently been shown to interfere with HER-2 mediated signaling and is therapeutically effective in humans (Fendly et al., *Hybridoma* 6, 359-370; Hudziak et al., *Mol. Cell. Biol.* 9, 1165-1172; Stebbing et al., *Cancer Treat Rev.* 26, 287-290). Herceptin® has been shown to act through two different mechanisms, i.e. the engagement of the effector cells of the immune system as well as a direct cytotoxic, apoptosis inducing effect.

However, only patients with highly amplified HER-2 respond significantly to Herceptin® therapy, thus limiting the number of patients suitable for therapy. In addition the development of resistance to drugs or a change in the expression or epitope sequence of HER-2 on tumor cells may render even those approachable patients unreactive with the antibody and therefore abrogating its therapeutic benefits. Therefore more drugs for target based therapies approaching further members of the HER family, such as HER-3, are needed.

BRIEF DESCRIPTION OF THE DRAWING FIGURES

FIG. 1 shows the extent of HER-3 expression in a panel of human cancer cell lines and demonstrates that HER-3 is expressed in a variety of human cancers.

FIG. 3 shows antibody binding competition bins mapped to HER3 domains.

FIG. 4 show the results of the indirect FACS Scatchard antibody affinity analysis performed with anti-HER-3 antibodies of the invention. The analysis indicates that the anti-HER-3 antibodies of the invention possess high affinities and strong binding constants for HER-3 expressed on the cell surface FIG. 5 shows Anti-HER3 receptor antibody dependent HER3 receptor internalization induced by anti-HER3 antibodies of the invention.

FIGS. 6a-e show the results of a ligand competition assay performed with anti-HER-3 antibodies of the invention. The results demonstrate that the antibodies of the invention specifically reduce binding of $[^{125}I]$-α-HRG/$[^{125}I]$-β-HRG to cells expressing endogenous HER-3.

FIG. 7a shows the results of a HER-3 phosphotyrosine ELISA performed with anti-HER-3 antibodies of the invention. Antibodies according to the present invention were able to inhibit β-HRG-mediated HER-3 activation as indicated by a decrease in receptor tyrosine phosphorylation. Furthermore FIG. 7b shows representative results of this experiment with titrated antibody.

FIG. 8 shows the result of a p42/p44 MAP-Kinase ELISA performed with anti-HER-3 antibodies of the invention. Antibodies according to the present invention were able to reduce β-HRG-mediated p42/p44 MAP-Kinase activation as indicated by increased MAP-Kinase phosphorylation.

FIG. 9 shows the result of a phospho-AKT ELISA performed with anti-HER-3 antibodies of the invention. Antibodies according to the present invention were able to reduce β-HRG-mediated AKT activation as indicated by AKT phosphorylation.

FIG. 10 shows the inhibition of MCF7 cell proliferation by human anti-HER-3 antibodies of the invention. Antibodies according to the present invention inhibit HRG-induced cell growth in human cancer cells.

FIG. 11 shows the transmigration of MCF7 cells inhibited by human anti-HER-3 antibodies of the invention.

FIGS. 12a-i shows the inhibition of the anchorage independent cell growth by human HER-3 antibodies of the invention.

FIG. 13 shows the inhibition of xenograft growth of T47D human breast cancer cells by a human anti-HER-3 antibody of the invention.

FIG. 14 shows the reduction in xenograft growth of BxPC3 human pancreas cancer cells in mice after administration of anti Her3 (U1-59 and U1-53) or anti EGFR (Erbitux) antibodies.

FIG. 15 shows the reduction of xenograft growth of BxPC3 human pancreas cancer cells by a human anti-HER-3 antibody of the invention and in combination with anti EGFR (Erbitux) antibodies.

FIG. 16 demonstrates that antibodies of the invention delay xenograft growth of human melanoma (HT144) cell growth in nu/nu mice.

Figure 17:
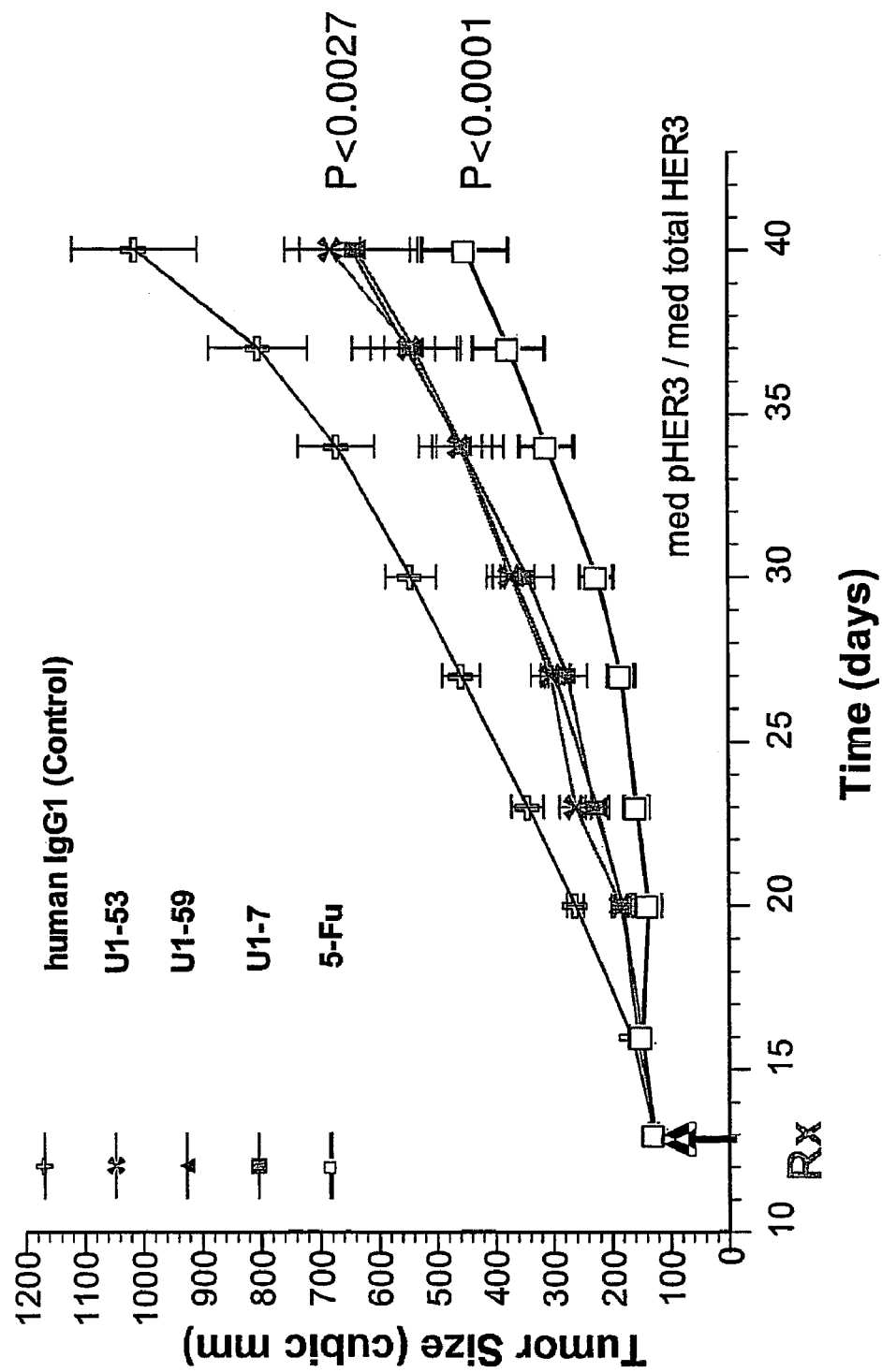

FIG. 17 shows the reduction of xenograft growth of HT-29 human colon carcinoma cells by human HER-3 antibodies of the invention (U1-53, U1-59 and U1-7).

Figure 18:
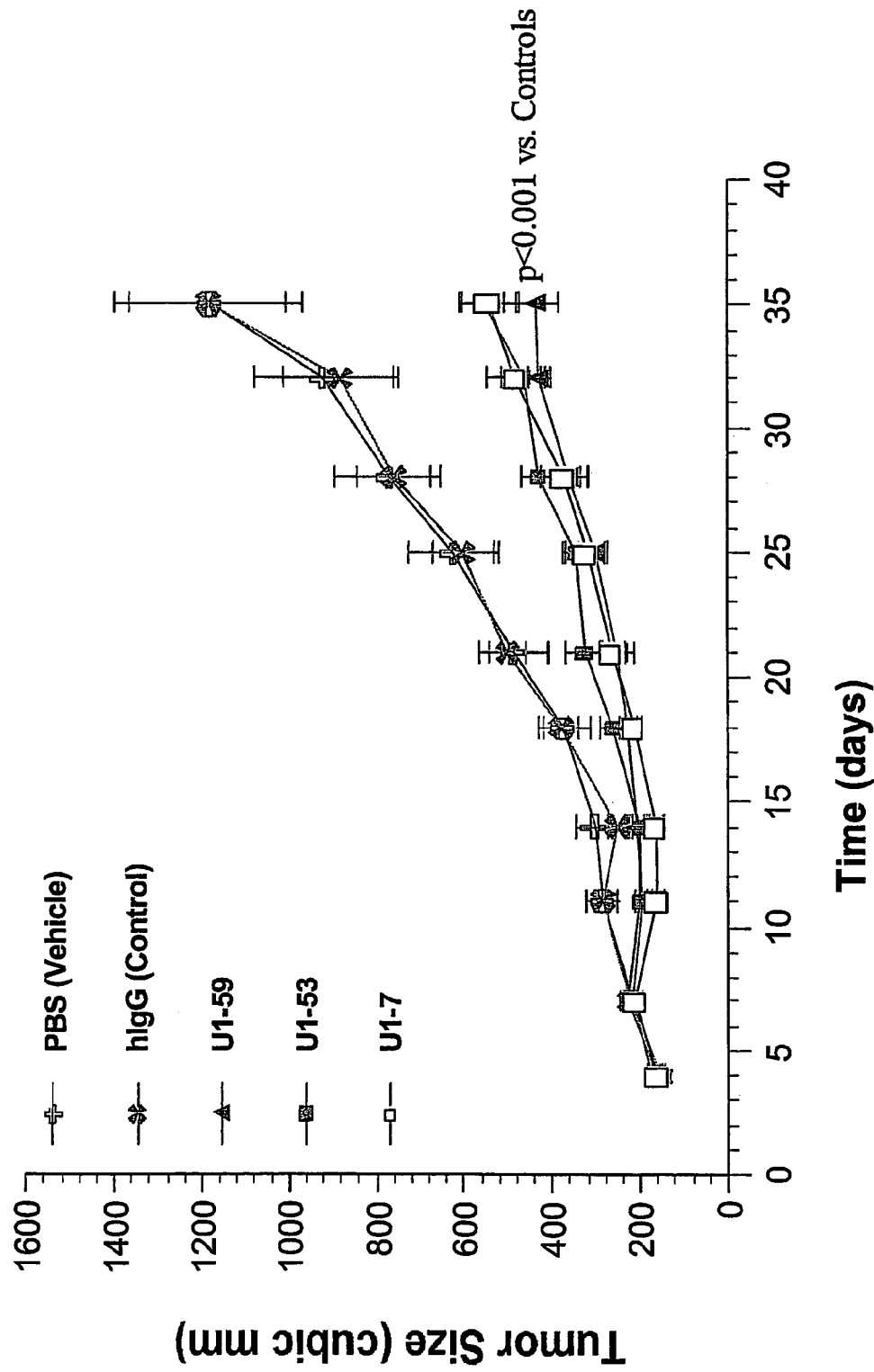

FIG. 18 shows the reduction of xenograft growth of Calu-3 human lung cancer cells by human anti-HER-3 antibodies of the invention (U1-59, U1-53 and U1-7).

Figure 19:
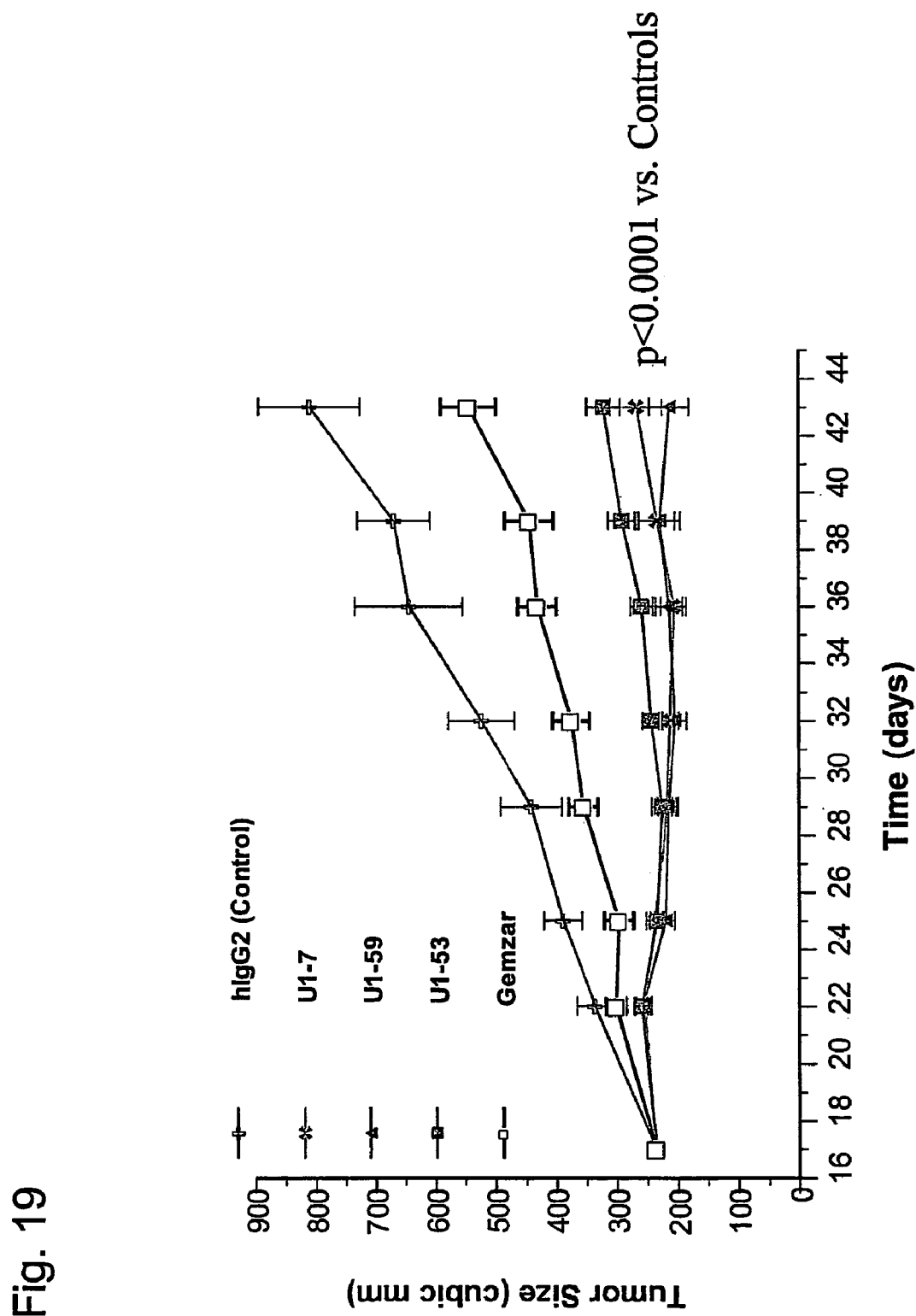

FIG. 19 shows the reduction of xenograft growth of BxPC-3 human pancreas cancer cells by human anti-HER-3 antibodies of the invention (U1-7, U1-59 and U1-53).

Figure 20:
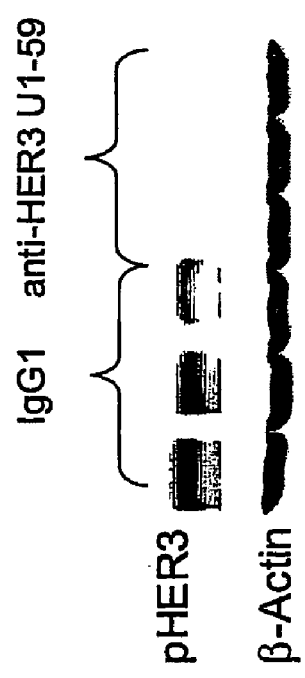

FIG. 20 demonstrates that an antibody of the invention (U1-59) causes suppression of HER-3 in BxPC3 human pancreas cancer xenografts.

SUMMARY OF THE INVENTION

A first aspect of the present invention relates to an isolated binding protein that binds to HER-3.

In one embodiment of the present invention, an isolated binding protein of the invention comprises a heavy chain amino acid sequence comprising at least one of the CDR's selected from the group consisting of: (a) CDRH1's as shown in SEQ ID NOs:235-257, (b) CDRH2's as shown in SEQ ID NOs:258-282, and (c) CDRH3's as shown in SEQ ID NOs: 283-317, and/or a light chain amino acid sequence comprising at least one of the CDR's selected from the group consisting of: (d) CDRL1's as shown in SEQ ID NOs:318-342, (e) CDRL2's as shown in SEQ ID NOs:343-359, and (f) CDRL3's as shown in SEQ ID NOs:360-388.

In another embodiment of the present invention, an isolated binding protein of the invention comprises a heavy chain amino acid sequence selected from the group consisting of SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and/or a light chain amino acid sequence selected from the group consisting of SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232.

In yet another embodiment of the present invention, an isolated binding protein of the invention comprises a heavy chain amino acid sequence and a light chain amino acid sequence as shown in SEQ ID NOs: 2 and 4, 6 and 8, 10 and 12, 14 and 16, 18 and 20, 22 and 24, 26 and 28, 30 and 32, 36 and 38, 42 and 44, 46 and 48, 50 and 52, 54 and 56, 60 and 58, 62 and 64, 66 and 68, 70 and 72, 74 and 76, 78 and 82, 80 and 82, 84 and 86, 88 and 90, 92 and 94, 96 and 98, 100 and 102, 104 and 106, 108 and 110, 112 and 114, 116 and 118, 122 and 124, 126 and 128, 130 and 132, 134 and 136, 138 and 140, 142 and 144, 146 and 148, 150 and 152, 154 and 156, 158 and 160, 162 and 164, 166 and 168, 170 and 172, 174 and 176, 178 and 180, 182 and 184, 186 and 188, 190 and 192, 194 and 196, 198 and 200, 202 and 204, 206 and 208, 210 and 212, 214 and 216, 218 and 220, 222 and 224, 226 and 228, 230 and 232, or a heavy chain amino acid sequence as shown in SEQ ID NOs: 34, 40, 60, 62 or 120, or a light chain amino acid sequence as shown in SEQ ID NOs: 58 or 64.

According to the present invention, an isolated binding protein that is capable of binding to HER-3 interacts with at least one epitope in the extracellular part of HER-3 (SEQ ID NO:390). The epitopes are preferably located in domain L1 (aa) 19-184 of SEQ ID NO:390) which is the amino terminal domain, in domain S1 (aa) 185-327 of SEQ ID NO:390) and S2 (aa) 500-632 of SEQ ID NO:390) which are the two Cysteine-rich domains, or in domain L2 (aa 328-499 of SEQ ID NO:390) which is flanked by the two Cysteine-rich domains. The epitopes may also be located in combinations of domains such as but not limited to an epitope comprised by parts of L1 and S1. Further preferred is an isolated binding protein that binds to a three-dimensional structure formed by amino acid residues 1-160, 161-358, 359-575, 1-358 and/or 359-604 of mature HER-3 (SEQ ID NO:390), particularly of mature human HER-3.

Preferably, an isolated binding protein of the invention is a scaffold protein having an antibody like binding activity or an antibody, e.g. an anti-HER-3 antibody. In particular, the anti-HER-3 antibody is selected from the group consisting of U1-1 antibody, U1-2-antibody, U1-3 antibody, U1-4 antibody, U1-5 antibody, U1-6 antibody, U1-7 antibody, U1-8 antibody, U1-9 antibody, U1-10 antibody, U1-11 antibody, U1-12 antibody, U1-13 antibody, U1-14 antibody, U1-15 antibody, U1-16 antibody, U1-17 antibody, U1-18 antibody, U1-19 antibody, U1-20 antibody, U1-21 antibody, U1-22 antibody, U1-23 antibody, U1-24 antibody, U1-25 antibody, U1-26 antibody, U1-27 antibody, U1-28 antibody, U1-29 antibody, U1-30 antibody, U1-31 antibody, U1-32 antibody, U1-33 antibody, U1-34 antibody, U1-35 antibody, U1-36 antibody, U1-37 antibody, U1-38 antibody, U1-39 antibody, U1-40 antibody, U1-41 antibody, U1-42 antibody, U1-43 antibody, U1-44 antibody, U1-45 antibody, U1-46 antibody, U1-47 antibody, U148 antibody, U1-49 antibody, U1-50 antibody, U1-51 antibody, U1-52 antibody, U1-53 antibody, U1-55.1 antibody, U1-55 antibody, U1-57.1 antibody, U1-57 antibody, U1-58 antibody, U1-59 antibody, U161.1 antibody, U1-61 antibody, U1-62 antibody or an antibody having at least one heavy or light chain of one of said antibodies. Especially preferred are the antibodies U1-49 (SEQ ID NO: 42/44), U1-53 (SEQ ID NO: 54/56) and U1-59 (SEQ ID NO: 70/72) or an antibody having at least one heavy or light chain of one of said antibodies.

In addition, further embodiments of the present invention provide an isolated binding protein coupled to a labelling group or effector group. Preferably, such an binding protein is useful for the treatment of hyperproliferative diseases, particularly oncological diseases such as breast cancer, gastrointestinal cancer, pancreatic cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, testis cancer, soft tissue sarcoma, head and neck cancer, or other HER-3 expressing or overexpressing cancers, and the formation of tumor metastases.

Other aspects of the present invention relate to an isolated nucleic acid molecule encoding a binding protein of the invention, a vector having a nucleic acid molecule encoding the binding protein of the invention, and a host cell, e.g. a CHO cell, an NS/0 myeloma cell, transformed with such nucleic acid molecule or vector.

A further aspect of the present invention relates to a method for producing a binding protein of the invention by preparing said binding protein from a host cell that secretes the binding protein. Preferably, the binding protein of the invention is prepared from a hybridoma cell line that secretes a binding protein or a CHO or other cell type transformed with a nucleic acid molecule encoding a binding protein of the invention.

Another aspect of the present invention relates to a method for producing a binding protein of the invention by preparing said binding protein from a tissue, product or secretion of an animal, plant or fungus transgenic for a nucleic acid molecule or nucleic acid molecules encoding the binding protein of the invention. Preferably, a binding protein of the invention is prepared from the tissue, product or secretion of a transgenic animal such as cow, sheep, rabbit, chicken or other mammalian or avian species, a transgenic plant such as corn, tobacco or other plant, or a transgenic fungus such as *Aspergillus*, *Pichia* or other fungal species.

Another aspect of the present invention pertains to a pharmaceutical composition comprising as an active agent at least one binding protein of the invention in admixture with pharmaceutically acceptable carriers, diluents and/or adjuvants. In another preferred embodiment of the present invention, the pharmaceutical composition of the invention additionally contains at least one other active agent, e.g. at least one antineoplastic agent. Yet another aspect of the present invention pertains to the use of at least one binding protein of the invention, and optionally at least one other active agent, e.g. at least one antineoplastic agent, in admixture with pharmaceutically acceptable carriers, diluents and/or adjuvants for the preparation of a pharmaceutical composition. The pharmaceutical composition is suitable for diagnosing, preventing or treating a hyperproliferative disease, particularly an oncological disease such as breast cancer, gastrointestinal cancer, pancreas cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma or other HER-3 expressing or overexpressing cancers, and the formation of tumor metastases.

Moreover, the present invention relates in a further aspect to a method for diagnosing diseases or conditions associated with the expression of HER-3, comprising contacting a sample with at least one binding protein of the invention, and detecting the presence of HER-3. Preferred diseases or conditions include the hyperproliferative diseases mentioned above.

Still another aspect of the present invention is a method for preventing or treating diseases or conditions associated with the expression of HER-3 in a patient in need thereof, comprising administering to the patient an effective amount of at least one binding protein of the invention and optionally at least one other active agent, e.g. at least one neoplastic agent. Preferably, the patient is a mammalian patient, more preferably a human patient. Preferred diseases or conditions associated with the expression of HER-3 are the hyperproliferative diseases mentioned above.

A further aspect of the present invention relates to a kit for the diagnosis, prevention or treatment diseases or conditions associated with the expression of HER-3, comprising at least one binding protein, and/or nucleic acid molecule and/or vector of the invention. Optionally, the kit of the invention can further comprise at least one other active agent, e.g. at least one anti neoplastic agent. Preferably, the diseases or conditions associated with the expression of HER-3 are the hyperproliferative diseases mentioned above.

DETAILED DESCRIPTION

A first aspect of the present invention relates to an isolated binding protein that binds to HER-3.

In one embodiment of the present invention, the isolated binding protein of the invention comprises a heavy chain amino acid sequence comprising at least one of the CDR's selected from the group consisting of: (a) CDRH1's as shown in SEQ ID NOs:235-257, (b) CDRH2's as shown in SEQ ID NOs:258-282, and (c) CDRH3's as shown in SEQ ID NOs: 282-317, and/or a light chain amino acid sequence comprising at least one of the CDR's selected from the group consisting of: (d) CDRL1's as shown in SEQ ID NOs:318-342, (e) CDRL2's as shown in SEQ ID NOs:343-359, and (f) CDRL3's as shown in SEQ ID NOs:360-388.

In another embodiment of the present invention, the isolated binding protein of the invention comprises a heavy chain amino acid sequence selected from the group consisting of SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and/or a light chain amino acid sequence selected from the group consisting of SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232.

In yet another embodiment of the present invention, the isolated binding protein of the invention comprises a heavy chain amino acid sequence and a light chain amino acid sequence as shown in SEQ ID NOs: 2 and 4, 6 and 8, 10 and 12, 14 and 16, 18 and 20, 22 and 24, 26 and 28, 30 and 32, 36 and 38, 42 and 44, 46 and 48, 50 and 52, 54 and 56, 60 and 58, 62 and 64, 66 and 68, 70 and 72, 74 and 76, 78 and 82, 80 and 82, 84 and 86, 88 and 90, 92 and 94, 96 and 98, 100 and 102, 104 and 106, 108 and 110, 112 and 114, 116 and 118, 122 and 124, 126 and 128, 130 and 132, 134 and 136, 138 and 140, 142 and 144, 146 and 148, 150 and 152, 154 and 156, 158 and 160, 162 and 164, 166 and 168, 170 and 172, 174 and 176, 178 and 180, 182 and 184, 186 and 188, 190 and 192, 194 and 196, 198 and 200, 202 and 204, 206 and 208, 210 and 212, 214 and 216, 218 and 220, 222 and 224, 226 and 228, 230 and 232, or a heavy chain amino acid sequence as shown in SEQ ID NOs: 34, 40, 60, 62 or 120, or a light chain amino acid sequence as shown in SEQ ID NOs: 58 or 64.

In accordance with the present invention, it is to be understood, that the amino acid sequence of the binding protein of the invention is not limited to the twenty conventional amino acids (See *Immunology—A Synthesis* (2$^{nd}$ Edition, E. S. Golub and D. R. Gren, Eds., Sinauer Associates, Sunderland, Mass. (1991)), which is incorporated herein by reference). For example, the amino acids may include stereoisomers (e.g. D-amino acids) of the twenty conventional amino acids, unnatural amino acids such as α-,α-disubstituted amino acids, N-alkyl amino acids, lactic acid, and other unconventional amino acids. Examples of unconventional amino acids, which may also be suitable components for the binding protein of the invention, include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids, e.g. 4-hydroxyproline.

Furthermore, in accordance with the present invention, minor variations in the amino acid sequences shown in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230 and 232 are contemplated as being encompassed by the present invention, providing that the variations in the amino acid sequence maintain at least 75%, more preferably at least 80%, 90%, 95%, and most preferably 99% of the sequences shown in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230 and 232. The variations may occur within the framework regions (i.e. outside the CDRs), within the CDRs, or within the framework regions and the CDRs. Preferred variations in the amino acid sequences shown in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230 and 232, i.e. deletions, insertions and/or replacements of at least one amino acid, occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other binding proteins of known structure and/or function. Methods to identify protein sequences that fold into a known three-dimensional structure are known. See e.g. Bowie et al., Science 253, 164 (1991); Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., Nature 354, 105 (1991), which are all incorporated herein by reference. Thus, those of skill in the art can recognize sequence motifs and structural conformations that may be used to define structural and functional domains in accordance with the invention.

Especially preferred variations in the amino acid sequences shown in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230 and 232, are those that lead to a reduced susceptibility to proteolysis or oxidation, alter glycosylation patterns or alter binding affinities or confer or modify other physicochemical or functional properties of the binding protein. In particular, conservative amino acid replacements are contemplated. Conservative replacements are those that take place within a family of amino acids that are related in their side chains. Preferred amino acid families are the following: acidic family=aspartate, glutamate; basic family=lysine, arginine, histidine; non-polar family=alanine, valine, leucine, isoleucine, proline, phenylalanine, methionine, tryptophan; and uncharged polar family=glycine, asparagine, glutamine, cysteine, serine, threonine, tyrosine. More preferred families are: aliphatic-hydroxy family=serine and threonine; amide-containing family=asparagine and glutamine; aliphatic family=alanine, valine, leucine and isoleucine; and aromatic family=phenylalanine, tryptophan, and tyrosine. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting binding protein, especially if the replacement does not involve an amino acid within a framework site. However, all other possible amino acid replacements are also encompassed by the present invention. Whether an amino acid change results in a functional binding protein, i.e. in a binding protein that binds to HER-3 and reduces signal transduction of HER family members, can readily be determined by assaying the specific activity of the resulting binding protein in ELISA or FACS for binding to HER-3 or in vitro or in vivo functional assay.

According to the present invention, the binding protein of the invention interacts with at least one epitope in the extracellular part of HER-3 (SEQ ID NO:390). The epitopes are preferably located in domain L1 (aa ) 19-184 of SEQ ID NO:390) which is the amino terminal domain, in domain S1 (aa) 185-327 of SEQ ID NO:390) and S2 (aa) 500-632 of SEQ ID NO:390) which are the two Cysteine-rich domains, in domain L2 (aa 328-499 of SEQ ID NO:390) which is flanked by the two Cysteine-rich domains, or in a combination of HER-3 domains. The epitopes may also be located in combinations of domains such as but not limited to an epitope comprised by parts of L1 and S1. Moreover, the binding protein of the invention is further characterized in that its binding to HER-3 reduces HER-3-mediated signal transduction. In accordance with the present invention, a reduction of HER-3-mediated signal transduction may, e.g. be caused by a downregulation of HER-3 resulting in an at least partial disappearance of HER-3 molecules from the cell surface or by a stabilization of HER-3 on the cell surface in a substantially inactive form, i.e. a form which exhibits a lower signal transduction compared to the non-stabilized form. Alternatively, a reduction of HER-3-mediated signal transduction may also be caused by influencing, e.g. decreasing or inhibiting, the binding of a ligand or another member of the HER family to HER-3, of GRB2 to HER-2 or of GRB2 to SHC, by inhibiting receptor tyrosine phosphorylation, AKT phosphorylation, PYK2 tyrosine phosphorylation or ERK2 phosphorylation, or by decreasing tumor invasiveness. Alternatively, a reduction of HER-3 mediated signal transduction may also be caused by influencing, e.g., decreasing or inhibiting, the formation of HER-3 containing dimers with other HER family members. One example among others may be the decreasing or inhibiting of the HER3-EGFR protein complex formation.

Preferably, the binding protein of the invention is a scaffold protein having an antibody like binding activity or an antibody, i.e. an anti-HER-3 antibody.

Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Plückthun, *Curr Opin Biotechnol*, 16, 459-69). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against HER-3, either purified protein or protein displayed on the cell surface, for binding agents in an artificial scaffold library displayed in vitro, skills which are known in the art (Skerra, J. Mol. Recog., 2000; Binz and Plückthun, 2005). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. Said inserted binding domains may be, for example, the complementarity determining region (CDR) of an antibody, in particular an anti-HER-3 antibody. Insertion can be accomplished by various methods known to those skilled in the art including, for example, polypeptide synthesis, nucleic acid synthesis of an encoding amino acid as well by various forms of recombinant methods well known to those skilled in the art.

Moreover, the term "antibody" or "anti-HER-3 antibody", as used herein, means a monoclonal antibody, a polyclonal antibody, a recombinant antibody, a humanized antibody (Jones et al., *Nature* 321 (1986), 522-525; Riechmann et al., *Nature* 332 (1988), 323-329; and Presta, *Curr. Op. Struct. Biol.* 2 (1992), 593-596), a chimeric antibody (Morrison et al., *Proc. Natl. Acad. Sci. U.S.A.* 81 (1984), 6851-6855), a multispecific antibody (e.g. a bispecific antibody) formed from at least two antibodies, or an antibody fragment thereof. The term "antibody fragment" comprises any portion of the afore-mentioned antibodies, preferably their antigen binding or variable regions. Examples of antibody fragments include Fab fragments, Fab' fragments, F(ab')$_2$ fragments, Fv fragments, diabodies (Hollinger et al., *Proc. Natl. Aced. Sci. U.S.A.* 90 (1993), 6444-6448), single chain antibody molecules (Pluckthun in: The Pharmacology of Monoclonal Antibodies 113, Rosenburg and Moore, EDS, Springer Verlag, N.Y. (1994), 269-315) and other fragments as long as they exhibit the desired capability of binding to HER-3.

In addition, the term "antibody" or "anti-HER-3 antibody", as used herein, may include antibody-like molecules that contain engineered sub-domains of antibodies or naturally occurring antibody variants. These antibody-like molecules may be single-domain antibodies such as VH-only or VL-only domains derived either from natural sources such as camelids (Muyldermans et al., *Reviews in Molecular Biotechnology* 74, 277-302) or through in vitro display of libraries from humans, camelids or other species (Holt et al., *Trends Biotechnol.*, 21, 484-90).

In accordance with the present invention, the "Fv fragment" is the minimum antibody fragment that contains a complete antigen-recognition and -binding site. This region consists of a dimer of one heavy- and one light-chain variable domain in tight, non-covalent association. It is in this configuration that the three CDR's of each variable domain interact to define an antigen-binding site on the surface of the $V_H$-$V_L$ dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain (CH1) of the heavy chain. The "Fab fragment" differs from the "Fab' fragment" by the addition of a few residues at the carboxy terminus of the heavy chain CH1 domain including one or more cysteines from the antibody hinge region. The "F(ab')$_2$ fragment" originally is produced as a pair of "Fab' fragments" which have hinge cysteines between them. Methods of preparing such antibody fragments, such as papain or pepsin digestion, are known to those skilled in the art.

In a preferred embodiment of the present invention, the anti-HER-3 antibody of the invention is of the IgA-, IgD-, IgE, IgG- or IgM-type, preferably of the IgG- or IgM-type including, but not limited to, the IgG1-, IgG2-, IgG3-, IgG4-, IgM1- and IgM2-type. In most preferred embodiments, the antibody is of the IgG1-, IgG2- or IgG4-type.

In another preferred embodiment of the present invention, the anti-HER-3 antibody of the invention is an anti-HER-3 antibody directed against the extracellular domain (ECD) of HER-3.

In certain respects, e.g. in connection with the generation of antibodies as therapeutic candidates against HER-3, it may be desirable that the anti-HER-3 antibody of the invention is capable of fixing complement and participating in complement-dependent cytotoxicity (CDC). There are a number of isotypes of antibodies that are capable of the same including without limitations the following: murine IgM, murine IgG2a, murine IgG2b, murine IgG3, human IgM, human IgG1, human IgG3, and human IgA. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also possess an Fc region that has been molecularly engineered to possess superior CDC over naturally occurring variants (Idusogie et al., *J Immunol.*, 166, 2571-2575) and expressed recombinantly in host cells using techniques known in the art. Such techniques include the use of direct recombinant techniques (see e.g. U.S. Pat. No. 4,816,397), cell-cell fusion techniques (see e.g. U.S. Pat. Nos. 5,916,771 and 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can, thereafter, be fused and a cell line expressing an intact antibody can be isolated. By way of example, a human anti-HER-3 IgG4 antibody, that possesses the desired binding to the HER-3 antigen, could be readily isotype switched to generate a human IgM, human IgG1 or human IgG3 isotype, while still possessing the same variable region (which defines the antibody's specificity and some of its affinity). Such molecule might then be capable of fixing complement and participating in CDC.

Moreover, it may also be desirable for the anti-HER-3 antibody of the invention to be capable of binding to Fc receptors on effector cells, such as monocytes and natural killer (NK) cells, and participate in antibody-dependent cellular cytotoxicity (ADCC). There are a number of isotypes of antibodies that are capable of the same, including without limitations the following: murine IgG2a, murine IgG2b, murine IgG3, human IgG1 and human IgG3. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also possess an Fc region that has been molecularly engineered to possess superior ADCC over naturally occurring variants (Shields et al. *J Biol Chem.*, 276, 6591-6604) and expressed recombinantly in host cells using techniques known in the art. Such techniques include the use of direct recombinant techniques (see e.g. U.S. Pat. No. 4,816,397), cell-cell fusion techniques (see e.g. U.S. Pat. Nos. 5,916,771 and 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can, thereafter, be fused and a cell line expressing an intact antibody can be isolated. By way of example, a human anti-HER-3 IgG4 antibody, that possesses the desired binding to the HER-3 antigen, could be readily isotype switched to generate a human IgG1 or human IgG3 isotype, while still possessing the same variable region (which defines the antibody's specificity and some of its affinity). Such molecule might then be capable of binding to FcγR on effectors cells and participating in ADCC.

Furthermore, according to the present invention, it is appreciated that the anti-HER-3 antibody of the invention is a fully human or humanized antibody. Human antibodies avoid certain of the problems associated with xenogeneic antibodies, for example antibodies that possess murine or rat variable and/or constant regions. The presence of xenogeneic-derived proteins such murine or rat derived proteins can lead to the generation of an immune response against the antibody by a patient, subsequently leading to the rapid clearance of the antibodies, loss of therapeutic utility through neutralization of the antibody and/or severe, even life-threatening, allergic reactions.

Preferably, the anti-HER-3 antibody of the invention is selected from the group consisting of U1-1 antibody, U1-2 antibody, U1-3 antibody, U1-4 antibody, U1-5 antibody, U1-6 antibody, U1-7 antibody, U1-8 antibody, U1-9 antibody, U1-10 antibody, U1-11 antibody, U1-12 antibody, U1-13 antibody, U1-14 antibody, U1-15 antibody, U1-16 antibody, U1-17 antibody, U1-18 antibody, U1-19 antibody, U1-20 antibody, U1-21 antibody, U1-22 antibody, U1-23 antibody, U1-24 antibody, U1-25 antibody, U1-26 antibody, U1-27 antibody, U1-28 antibody, U1-29 antibody, U1-30 antibody, U1-31 antibody, U1-32 antibody, U1-33 antibody, U1-34 antibody, U1-35 antibody, U1-36 antibody, U1-37 antibody, U1-38 antibody, U1-39 antibody, U1-40 antibody, U1-41 antibody, U1-42 antibody, U1-43 antibody, U1-44 antibody, U1-45 antibody, U1-46 antibody, U1-47 antibody, U1-48 antibody, U1-49 antibody, U1-50 antibody, U1-51 antibody, U1-52 antibody, U1-53 antibody, U1-55.1 antibody, U1-55 antibody, U1-57.1 antibody, U1-57 antibody, U1-58 antibody, U1-59 antibody, U1-61.1 antibody, U1-61 antibody, U1-62 antibody.

In a preferred embodiment of the present invention, a binding protein of the invention is coupled to a labelling group. Such a binding protein is particularly suitable for diagnostic applications. As used herein, the term "labelling group" refers to a detectable marker, e.g. a radiolabelled amino acid or biotinyl moiety that can be detected by marked avidin (e.g. streptavidin bound to a fluorescent marker or enzymatic activity that can be detected by optical or colorimetric methods). Various methods for labelling polypeptides and glycoproteins, such as antibodies, are known in the art and may be used in performing the present invention. Examples of suitable labelling groups include, but are not limited to, the following: radioisotopes or radionuclides (e.g. $^3$H, $^{14}$C, $^{15}$N, $^{35}$S, $^{90}$Y, $^{99}$Tc, $^{111}$In, $^{125}$I, $^{131}$I), fluorescent groups (e.g. FITC, rhodamine, lanthanide phosphors), enzymatic groups (e.g. horseradish peroxidase, β-galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags). In certain respects, it may be desirable that the labelling groups are attached by spacer arms of various lengths to reduce potential steric hindrance.

Alternatively, a binding protein of the invention may be coupled to an effector group in another preferred embodiment of the invention. Such a binding protein is especially suitable for therapeutic applications. As used herein, the term "effector group" refers to a cytotoxic group such as a radioisotope or radionuclide, a toxin, a therapeutic group or other effector group known in the art. Examples for suitable effector groups are radioisotopes or radionuclides (e.g. $^3$H, $^{14}$C, $^{15}$N, $^{35}$S, $^{90}$Y, $^{99}$Tc, $^{111}$In, $^{125}$I, $^{131}$I), calicheamicin, dolastatin analogs such as auristatins, and chemotherapeutic agents such as geldanamycin and maytansine derivates, including DM1. In certain respects, it may be desirable that the effector groups are attached by spacer arms of various lengths to reduce potential steric hindrance.

A second aspect of the present invention relates to a process for preparing an isolated binding protein of the invention, comprising the step of preparing the binding protein from a host cell that secretes the binding protein. Host cells, that may be used according to the present invention, are hybridomas; eukaryotic cells such as mammalian cells, e.g. hamster, rabbit, rat, pig, mouse or other animal cells, plant cells, fungal cells, e.g. *Saccharomyces cerevisiae, Pichia pastoris*; prokaryotic cells such as *E. coli*; and other cells used in the art for the production of binding proteins. Various methods for preparing and isolating binding proteins, such as scaffold proteins or antibodies, from host cells are known in the art and may be used in performing the present invention. Moreover, methods for preparing binding protein fragments, e.g. scaffold protein fragments or antibody fragments, such as papain or pepsin digestion, modern cloning techniques, techniques for preparing single chain antibody molecules (Plückthun in: The Pharmacology of Monoclonal Antibodies 113, Rosenburg and Moore, EDS, Springer Verlag, N.Y. (1994), 269-315) and diabodies (Hollinger et al., *Proc. Natl. Acad. Sci. U.S.A.* 90 (1993), 6444-6448), are also known to those skilled in the art and may be used in performing the present invention.

In a preferred embodiment of the present invention, a binding protein of the invention is prepared from a hybridoma that secretes the binding protein. See e.g. Köhler et al., *Nature* 256 (1975), 495.

In a further preferred embodiment of the present invention, a binding protein of the invention is prepared recombinantly optimizing and/or amplifying expression of the binding protein in a host cell and isolating the binding protein from said host cell. To this end, the host cells are transformed or transfected with DNA encoding a binding protein or a vector containing DNA encoding the binding protein and cultured under appropriate conditions to produce the binding protein of the invention. See e.g. U.S. Pat. No. 4,816,567. Preferred host cells may be CHO cells, NS/0 myeloma cells, human embryonic kidney 293 cells, *E. coli* and *Saccharomyces cerevisiae*.

With regard to binding proteins that are antibodies, these antibodies may be prepared from animals genetically engineered to make fully human antibodies or from an antibody display library made in bacteriophage, yeast, ribosome or *E. coli*. See e.g. Clackson et al., *Nature* 352 (1991), 624-628, Marks et al., *J. Mol. Biol.* 222 (1991), 581-597, Feldhaus and Siegel *J Immunol Methods*. 290, 69-80, Groves and Osbourn, *Expert Opin Biol Ther.,* 5, 125-135 and Jostock and Dubel, *Comb Chem High Throughput Screen.* 8, 127-133.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XENOMOUSE® strains of mice that have been engineered to contain 245 kb and 190 kb-sized germline configuration fragments of the human heavy chain locus and kappa light chain locus. Other XenoMouse strains of mice contain 980 kb and 800 kb-sized germline configuration fragments of the human heavy chain locus and kappa light chain locus. Still other XenoMouse strains of mice contain 980 kb and 800 kb-sized germline configuration fragments of the human heavy chain locus and kappa light chain locus plus a 740 kb-sized germline configured complete human lambda light chain locus. See Mendez et al. *Nature Genetics* 15:146-156 (1997) and Green and Jakobovits *J. Exp. Med.* 188:483-495 (1998). The XENOMOUSE® strains are available from Abgenix, Inc. (Fremont, Calif.).

The production of the XENOMOUSE® mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996, U.S. Patent Publication 2003/0217373, filed Nov. 20, 2002, and U.S. Pat. Nos. 6,833,268, 6,162,963, 6,150,584, 6,114,598, 6,075,181, and 5,939,598 and Japanese Patent Nos. 3 068 180 B2, 3 068 506 B2, and 3 068 507 B2. See also European Patent No. EP 0 463 151 B1, grant published Jun. 12, 1996, International Patent Application No. WO 94/02602, published Feb. 3, 1994, International Patent Application No. WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more DH genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. No. 07/574,748, filed Aug. 29, 1990, Ser. No. 07/575, 962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al, 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™-mice, which are the result of cross-breeding of Kirin's Tc mice with Medarex's minilocus (Humab) mice have been generated. These mice possess the HC transchromosome of the Kirin mice and the kappa chain transgene of the Medarex mice (Ishida et al., Cloning Stem Cells, (2002) 4:91-102).

Human antibodies can also be derived by in vitro methods. Suitable examples include, but are not limited to, phage display (as commercialized by Cambridge Antibody Technology, Morphosys, Dyax, Biosite/Medarex, Xoma, Symphogen, Alexion (formerly Proliferon), Affimed) ribosome display (as commercialized by Cambridge Antibody Technology), yeast display, and the like.

Antibodies, as described herein, were prepared through the utilization of the XENOMOUSE® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XENOMOUSE® lines of mice are immunized with an antigen of interest (e.g. HER-3), lymphatic cells (such as B-cells) are recovered from the mice that expressed antibodies, and the recovered cell lines are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to HER-3. Further, provided herein are characterization of the antibodies produced by such cell lines, including nucleotide and amino acid sequence analyses of the heavy and light chains of such antibodies.

In general, antibodies produced by the fused hybridomas were human IgG1 heavy chains with fully human kappa light chains. Antibodies described herein possess human IgG4 heavy chains as well as IgG1 heavy chains. Antibodies can also be of other human isotypes, including IgG2 or IgG3. The antibodies possessed high affinities, typically possessing a $K_D$ of from about $10^{-6}$ through about $10^{-13}$ M or below, when measured by solid phase and cell-based techniques.

Another aspect of the present invention relates to an isolated nucleic acid molecule encoding a binding protein of the invention. Within the context of the present invention, the term "isolated nucleic acid molecule", as used herein, means a polynucleotide of genomic, cDNA, or synthetic origin or some combination thereof, which by virtue of its origin, the "isolated nucleic acid molecule" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Further, the term "nucleic acid molecule", as referred to herein, means a polymeric form of nucleotides of at least 10 bases in length, either ribonucleotides or deoxynucleotides or a modified form of either type of nucleotide, such as nucleotides with modified or substituted sugar groups and the like. The term also includes single and double stranded forms of DNA.

In a one embodiment of the present invention, a nucleic acid molecule of the invention is operably linked to a control sequence. The term "control sequence", as used herein, refers to polynucleotide sequences that are necessary to effect the expression and processing of coding sequences to which they are ligated. The nature of such control sequences differs depending upon the host organism. In prokaryotes, such control sequences generally include promoters, ribosomal binding sites, and transcription termination sequences. In eukaryotes, generally, such control sequences include promoters and transcription termination sequences. In accordance with the present invention, the term "control sequence" is intended to include, at a minimum, all components whose presence is essential for expression and processing, and can also include additional components whose presence is advantageous, for example, leader sequences and fusion partner sequences. Furthermore, the term "operably linked", as used herein, refers to positions of components so described which are in a relationship permitting them to function in their intended manner. Moreover, according to the present invention, an expression control sequence operably linked to a coding sequence is ligated in such a way that expression of the coding sequence is achieved under conditions compatible with the expression control sequence.

A further aspect of the present invention is a vector comprising a nucleic acid molecule that encodes a binding protein of the invention. The nucleic acid molecule can be operably linked to a control sequence. Furthermore, the vector may additionally contain a replication origin or a selection marker gene. Examples of vectors that may be used in accordance with the present invention are e.g. plasmids, cosmids, phages, viruses, etc.

Another aspect of the present invention relates to a host cell transformed with a nucleic acid molecule or vector of the invention. Transformation could be done by any known method for introducing polynucleotides into a host cell, including for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455, which patents are hereby incorporated herein by reference. Particularly, methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. Examples of host cells that may be used according to the present invention are hybridomas eukaryotic cells such as mammalian cells, e.g. hamster, rabbit, rat, pig, mouse or other animal cells; plant cells and fungal cells, e.g. corm, tobacco, *Saccharomyces cerevisiae, Pichia pastoris*; prokaryotic cells such as *E. coli*; and other cells used in the art for the production of antibodies. Especially mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g. Hep G2), and a number of other cell lines.

Yet another aspect of the present invention is a pharmaceutical composition comprising as an active agent at least one binding protein of the invention and pharmaceutically acceptable carriers, diluents and/or adjuvants. The term "pharmaceutical composition", as used herein, refers to a chemical compound or composition capable of inducing a desired therapeutic effect when properly administered to a patient (*The McGraw-Hill Dictionary of Chemical Terms*, Parker, S., Ed., McGraw-Hill, San Francisco (1985), incorporated herein by reference). In accordance with the present invention, the potency of the pharmaceutical composition of the invention is based on the binding of the at least one binding protein to HER-3. Preferably, this binding leads to a reduction of the HER-3-mediated signal transduction.

Furthermore, the term "carriers", when used herein, includes carriers, excipients, or stabilizers that are nontoxic to the cell or mammal being exposed thereto at the dosages and concentrations employed. Often the physiologically acceptable carrier is an aqueous pH buffered solution or a liposome (a small vesicle composed of various types of lipids, phospholipids and/or surfactants which is useful for delivery of a drug to a mammal). Examples of physiologically acceptable carriers include buffers such as phosphate, citrate, and other organic acids; antioxidants including ascorbic acid; low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose or dextrins; chelating agents such as EDTA; sugar alcohols such as mannitol or sorbitol; salt-forming counterions such as sodium; and/or nonionic surfactants such as TWEEN™, polyethylene-glycol (PEG), and PLURONICS™.

In a one embodiment of the present invention, the at least one binding protein of the invention contained in the pharmaceutical composition is coupled to an effector, such as calicheamicin, Auristatin-PE, a radioisotope or a toxic chemotherapeutic agent such as geldanamycin and maytansine. In particular, these binding protein conjugates are useful in targeting cells, e.g. cancer cells, expressing HER-3 for elimination.

Moreover, linking binding proteins of the invention to radioisotopes e.g. provides advantages to tumor treatments. Unlike chemotherapy and other forms of cancer treatment, radioimmunotherapy or the administration of a radioisotope-binding protein combination directly targets the cancer cells with minimal damage to surrounding normal, healthy tissue. With this "magic bullet", the patient can be treated with much smaller quantities of radioisotopes than other forms of treatment available today. Preferred radioisotopes include yttrium$^{90}$ ($^{90}$Y), indium$^{111}$ ($^{111}$In), $^{131}$I, $^{99}$mTc, radiosilver-111, radiosilver-199, and Bismuth$^{213}$. The linkage of radioisotopes to binding proteins of the invention may e.g. be performed with conventional bifunctional chelates. Since silver is monovalent, for radiosilver-111 and radiosilver-199 linkage, sulphur-based linkers may be used (Hazra et al., *Cell Biophys.* 24-25, 1-7 (1994)). Linkage of silver radioisotopes may involve reducing the immunoglobulin with ascorbic acid. Furthermore, tiuxetan is an MX-DTPA linker chelator attached to ibritumomab to form ibritumomab tiuxetan (Zevalin) (Witzig, T. E, *Cancer Chemother. Pharmacol.* 48 Suppl 1, 91-5 (2001). Ibritumomab tiuxetan can react with radioisotypes such as indium$^{111}$ ($^{111}$In) or $^{90}$Y to form $^{111}$In-ibritumomab tiuxetan and $^{90}$Y-ibritumomab tiuxetan, respectively.

Furthermore, a binding protein of the invention, particularly when used to treat cancer, may be conjugated with toxic chemotherapeutic drugs such as calicheamicin (Hamann et al., *Bioconjug. Chem.* 13(1), 40-6 (2002), geldanamycin (Mandler et al., *J. Natl. Cancer Inst.*, 92(19), 1549-51 (2000)) and maytansine, for example, the maytansinoid drug, DM1 (Liu et al., *Proc. Natl. Acad. Sci. U.S.A.* 93:8618-8623 (1996)). Different linkers that release the drugs under acidic or reducing conditions or upon exposure to specific proteases may be employed with this technology. According to the present invention, a binding protein of the invention may be conjugated as described in the art.

Auristatin-PE, e.g. is an antimicrotubule agent that is a structural modification of the marine, shell-less mollusk peptide constituent dolastatin 10. Auristatin-PE has both anti-tumor activity and anti-tumor vascular activity (Otani et al., *Jpn. J. Cancer Res.* 91(8), 837-44 (2000)). For example, auristatin-PE inhibits cell growth and induces cell cycle arrest and apoptosis in pancreatic cancer cell lines (Li et al., *Int. J. Mol. Med.* 3(6), 647-53 (1999)). Accordingly, to specifically target the anti-tumor activity and anti-tumor vascular activities of auristatin-PE to particular tumors, auristatin-PE may be conjugated to the binding protein of the invention.

In a one embodiment of the present invention, the pharmaceutical composition comprises at least one further active agent. Examples for further active agents, which may be used in accordance with the present invention, are antibodies or low molecular weight inhibitors of other receptor protein kinases, such as EGFR, HER-2, HER4, IGFR-1, or c-met, receptor ligands such as vascular endothelial factor (VEGF), cytotoxic agents, such as doxorubicin, cis-platin or carboplatin, cytokines or antineoplatic agents. Many antineoplastic agents are presently known in the art. In one embodiment, the antineoplastic agent is selected from the group of therapeutic proteins including, but not limited to, antibodies or immunomodulatory proteins. In another embodiment the anti-neoplastic agent is selected from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and anti-angiogenesis agents. When the anti-neoplastic agent is radiation, treatment can be achieved either with an internal (brachytherapy BT) or external (external beam radiation therapy: EBRT) source.

The pharmaceutical composition of the present invention is especially suitable for the diagnosis, prevention or treatment of a hyperproliferative disease. The hyperproliferative disease may be, e.g., associated with increased HER family signal transduction. Particularly, the disease can be associated with increased HER-3 phosphorylation and/or increased complex formation between HER-3 and other members of the HER family and/or increased PI$_3$ kinase activity and/or increased c-jun terminal kinase activity and/or AKT activity and/or increased ERK2 activity and/or PYK2 activity. Preferably, the hyperproliferative disease is selected from the group consisting of breast cancer, gastrointestinal cancer, pancreatic cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma or other HER-3 expressing or overexpressing cancers, and the formation of tumor metastases.

In accordance with the present invention, the term "prevention or treatment", when used herein, refers to both therapeutic treatment and prophylactic or preventative measures, wherein the patient in need is to prevent or slow down (lessen) the targeted pathologic condition or disorder. Those in need of prevention or treatment include those already with the disorder as well as those prone to have the disorder or those in whom the disorder is to be prevented. The patient in need of prevention or treatment is a mammalian patient, i.e. any animal classified as a mammal, including humans, domestic and farm animals, and zoo, sports, or pet animals, such as dogs, cats, cattle, horses, sheep, pigs, goats, rabbits, etc. Preferably, the patient in need of treatment is a human patient.

According to the present invention, the pharmaceutical composition of the invention may be formulated by mixing the active agent(s) with physiologically acceptable carriers, diluents and/or adjuvants, and optionally other agents that are usually incorporated into formulations to provide improved transfer, delivery, tolerance, and the like. The pharmaceutical composition of the invention may be formulated e.g. in the form of lyophilized formulations, aqueous solutions, dispersions or solid preparations, such as tablets, dragees or capsules. A multitude of appropriate formulations can be found in the formulary known to all pharmaceutical chemists: Remington's Pharmaceutical Sciences (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active agent in the formulation is not inactivated by the formulation and the formulation is physiologically compatible and tolerable with the route of administration. See also Baldrick P., "Pharmaceutical excipient development: the need for preclinical guidance.", *Regul. Toxicol. Pharmacol.* 32(2), 210-218 (2000); Wang W., "Lyophilization and development of solid protein pharmaceuticals.", *Int. J. Pharm.* 203(1-2), 1-60 (2000); Charman W. N., "Lipids, lipophilic drugs, and oral drug delivery-some emerging concepts.", *J. Pharm. Sci.* 89(8), 967-978 (2000); Powell et al., "Compendium of excipients for parenteral formulations", *PDA J. Pharm. Sci. Technol.* 52, 238-311 (1998); and the citations therein for additional information related to formulations, excipients and carriers well known to pharmaceutical chemists.

Another aspect of the present invention pertains to the use of at least one isolated binding protein of the invention, and optionally at least one other active agent, e.g. at least one anti-neoplastic agent as described above, in admixture with pharmaceutically acceptable carriers, diluents and/or adjuvants, for the manufacture of a pharmaceutical composition for the diagnosis, prevention or treatment of a hyperproliferative disease. Preferably, the pharmaceutical composition is a pharmaceutical composition as described above and the hyperproliferative disease is a hyperproliferative disease as mentioned above.

Yet another aspect of the present invention is concerned with a method for diagnosing diseases or conditions associated with the expression of HER-3, comprising contacting a sample with a binding protein of the invention, and detecting the presence of HER-3 in the sample. The sample may be a cell that shows expression of HER-3, such as a tumor cell, a blood sample or another suitable sample. In a preferred embodiment of the present invention, the diseases or conditions associated with the expression of HER-3 are the hyperproliferative diseases defined above.

According to the present invention, the method may, e.g., be used for the detection of HER-3 antigen in a cell, for the determination of HER-3 antigen concentration in patients suffering from a hyperproliferative disease as mentioned above or for the staging of said hyperproliferative disease in a patient. In order to stage the progression of a hyperproliferative disease in a subject under study, or to characterize the response of the subject to a course of therapy, a sample of blood can, e.g., be taken from the subject and the concentration of the HER-3 antigen present in the sample is determined. The concentration so obtained is used to identify in which range of concentrations the value falls. The range so identified correlates with a stage of progression or a stage of therapy identified in the various populations of diagnosed subjects, thereby providing a stage in the subject under study. A biopsy of the disease, e.g. cancer, tissue obtained from the patient may also be used assess the amount of HER-3 antigen present. The amount of HER-3 antigen present in the disease tissue may be assessed by immunohistochemistry, ELISA or antibody arrays using HER3 antibodies of the invention. Other parameters of diagnostic interest are the dimerization state as well as the dimerization partners of the HER3 protein and the activation state of it and its partners. Protein analytical methods to determine those parameters are well known in the art and are among others western blot and immunoprecipitation techniques, FACS analysis, chemical crosslinking, bioluminescence resonance energy transfer (BRET), fluorescence resonance energy transfer (FRET) and the like (e.g. Price et al, Methods in Molecular Biology, 218: 255-268 (2002) or the eTag technology (WO0503707, WO04091384, WO04011900).

Furthermore, the present invention relates in another aspect to a method for preventing or treating diseases or conditions associated with the expression of HER-3 in a patient, comprising administering to a patient in need thereof an effective amount of at least one binding protein of the invention. Preferably, the diseases or conditions associated with the expression of HER-3 are the hyperproliferative diseases defined above. The patient in need of prevention or treatment is a mammalian patient, i.e. any animal classified as a mammal, including humans, domestic and farm animals, and zoo, sports, or pet animals, such as dogs, cats, cattle, horses, sheep, pigs, goats, rabbits, etc. Preferably, the patient in need is a human patient.

In a preferred embodiment of the present invention, the method for preventing or treating a hyperproliferative disease in a patient in need thereof comprises administering to the patent an effective amount of at least one binding protein of the invention and additionally at least one other active agent, e.g., at least one antineoplastic agent as mentioned above. Preferably, the method is for inhibiting abnormal cell growth, migration or invasion.

In addition to classical modes of administration of potential binding protein therapeutics, e.g. via the above mentioned formulations, newly developed modalities of administration may also be useful according to the present invention. For example, local administration of $^{131}$I-labeled monoclonal antibody for treatment of primary brain tumors after surgical resection has been reported. Additionally, direct stereotactic intracerebral injection of monoclonal antibodies and their fragments is also being studied clinically and pre-clinically. Intracarotid hyperosmolar perfusion is an experimental strategy to target primary brain malignancy with drug conjugated human monoclonal antibodies.

Depending on the type and severity of the condition to be treated, about 1 μg/kg to 15 mg/kg of the at least one binding protein of the invention may be administered to a patient in need thereof, e.g. by one or more separate administrations or by continuous infusion. A typical daily dosage might range from about 1 μg/kg to about 100 mg/kg or more, depending on the factors mentioned above. For repeated administrations over several days or longer, depending on the condition to be treated, the treatment is sustained until a desired suppression of disease symptoms occurs.

The dose of the at least one antineoplastic agent administered depends on a variety of factors. These are, for example, the nature of the agent, the tumor type or the route of administration. It should be emphasized that the present invention is not limited to any dose.

Finally, the present invention relates in a further aspect to a kit for the diagnosis, prevention or treatment of hyperproliferative diseases associated with HER-3 mediated signal transduction, comprising the at least one binding protein and/or nucleic acid molecule and/or vector of the invention. In addition, the kit of the invention can further comprise at least one other active agent, e.g. at least one other antineoplastic agent as mentioned above.

Further, the present invention shall be explained by the following Examples and the accompanying drawing figures.

EXAMPLES

The following examples, including the experiments conducted and results achieved, are provided for illustrative purposes only and are not to be construed as limiting upon the present invention.

Example 1

HER-3 Antigen and Cell Line Preparation

In the present study, recombinant HER-3 proteins were prepared. The extracellular domain of HER-3 (ECD) cDNA was cloned by polymerase chain reaction (PCR) from pcDNA3-HER-3 (expression vector with full length human HER-3, C. Wallasch et al., EMBO J. 14, 4267-4275) with primers based on the sequence of HER-3 (Genebank AccNr. NM_001982; SEQ ID NO:390).

The primers used for the amplification of HER-3 were as follows:

```
Forward primer:
                                          (SEQ ID NO: 233)
5'-CGGGATCCATGTCCTAGCCTAGGGGC-3'

Reverse primer:
                                          (SEQ ID NO: 234)
5'-GCTCTAGATTAATGATGATGATGATGATGTTGTCCTAAAC
AGTCTTG-3'
```

The PCR product was digested with BamH1 and XbaI and ligated into pcDNA3 (Invitrogen) digested with BamH1 and XbaI. Plasmids were transfected into HEK293 cells using a CaPO$_4$ method. The HER-3-HIS fusion protein was purified from harvested conditioned media via Ni-NTA affinity chromatography.

RatI HER-3 cells were generated by retroviral gene transfer. Briefly, GP+E 86 cells (3×10$^5$) were seeded on a 60 mm culture disc and transfected with 2 µg/ml pIXSN vector or pIXSN-HER-3 cDNA (C. Wallasch, PhD Thesis, Max-Planck Institute of Biochemistry, Martinsried, Germany) using the calcium phosphate method. After 24 h medium was replaced by fresh medium and the GP+E 86 cells were incubated for 4-8 hrs. Subconfluent Rat1 cells (2×10$^5$ cells per 6 cm dish) were then incubated with supernatants of GP+E 86 cells releasing high titer pLXSN or pLXSN-HER-3, p virus (>1×106 G418 c.f.u./ml; m.o.i. of 10) for 4-12 h in the presence of Polybrene (4 mg/ml; Aldrich). After changing the medium, selection of RatI cells with G418 was started. Usually, stable clones were picked after selection for 21 days.

Example 2

HER-3 Expression in Human Cancer Cell Lines

Receptor tyrosine kinases, as for example HER-3, play a crucial role in the initiation and progression of hyperproliferative diseases such as the transition from benign hyperplastic cell growth towards a malignant carcinoma. Since HER-3 expression varies between tumor cells and normal tissue an analysis of HER-3 expression is a critical factor for identification of patient subgroups that would benefit from treatment with binding proteins of the invention. Thus, HER-3 expression was quantified in a panel of human cancer cell lines to elucidate the role of HER-3 in human cancer formation. Cancer cell lines were grown as recommended by the ATCC. In detail, 10$^5$ cells were harvested with 10 mM EDTA in PBS, washed once with FACS buffer (PBS, 3% FCS, 0.4% azide) and seeded on a 96-well round bottom plate. The cells were spun for 3 min at 1000 rpm to remove supernatant and then resuspended with α-HER-3 antibody 2D1D12 (WO03013602) (3 µg/ml). Cell suspensions were incubated on ice for 1 hr, washed twice with FACS buffer and resuspended with secondary antibody (100 µl/well) donkey-anti-human-PE (Jackson) diluted 1:50 in FACS buffer. The cell suspensions were incubated on ice and in the dark for 30 min, washed twice with FACS buffer and analyzed (FACS, Beckman Coulter). FIG. 1 shows representative results of the analysis and demonstrates that HER-3 is expressed in a variety of human cancers.

Example 3

Immunization and Tittering

The HER-3 ECD protein, that was prepared as described in Example 1 and C32 cells (Human melanoma; ATCC #CRL-1585) were used as an antigen. Monoclonal antibodies against HER-3 were developed by sequentially immunizing XenoMouse® mice (XenoMouse® strains: XMG1 and XMG4, Abgenix, Inc. Fremont, Calif.). XenoMouse® animals were immunized via footpad route for all injections. The total volume of each injection was 50 µl per mouse, 25 µl per footpad.

For cohort #1 (10 XMG1 mice), the initial immunization was with 10 µg of HER-3 ECD protein admixed 1:1 (v/v) with TITERMAX GOLD® (Sigma, Oakville, ON) per mouse. The subsequent five boosts were made with 10 µg of HER-3 ECD protein admixed 1:1 (v/v) with 100 µg alum gel (Sigma, Oakville, ON) in pyrogen-free D-PBS. The sixth boost consisted of 10 µg of HER-3 ECD protein admixed 1:1 (v/v) with TITERMAX GOLD®. The seventh injection consisted of 10 µg of HER-3 ECD protein admixed 1:1 v/v with 100 µg alum gel. A final boost was made with 10 µg HER-3 ECD protein in pyrogen-free DPBS, without adjuvant. The XenoMouse® mice were immunized on days 0, 4, 7, 11, 15, 20, 24, and 29 for this protocol and fusions were performed on day 33. The two bleeds were made through Retro-Orbital Bleed procedure on day 13 after the fourth boost, on day 19 after the sixth boost. There was no cohort #2.

For Cohort #3 (10 XMG1 mice) and Cohort #4 (10 XMG4 mice), the first 15 injection was with 10$^7$ C32 cells in pyrogen-free Dulbecco's PBS (DPBS) admixed 1:1 (v/v) with TITERMAX GOLD® per mouse. The next four boosts were with 10$^7$ C32 cells in pyrogen-free DPBS, admixed with 25 µg of Adju-Phos and 10 µg CpG per mouse. The sixth boost was with 10$^7$ C32 cells in pyrogen-free DPBS, admixed 1:1 (v/v) with TITERMAX GOLD® per mouse. The seventh, eighth, ninth boosts were with 107 C32 cells in pyrogen-free DPBS, admixed with 25 µg of Adju-Phos and 10 µg CpG per mouse. From tenth to fourteen boosts were 5 µg of HER-3 ECD protein in pyrogen-free DPBS, admixed with 25 µg of Adju-Phos and 10 µg CpG per mouse. A final boost consisted of 5 µg of HER-3 ECD protein in pyrogen-free DPBS, without adjuvant. Both Cohort #3 and #4, the XenoMouse® mice were immunized on days 0, 3, 7, 11, 14, 17, 21, 24, 28, 33, 35, 38, 42 and 45 for this protocol and fusions were performed on day 49. The three bleeds were made through Retro-Orbital Bleed procedure on day 12 after the fourth boost, on day 19 after the sixth boost and on day 40 after twelfth boost.

Selection of Animals for Harvest by Titer

For cohort #1, anti-HER-3 antibody titers in the serum from immunized XenoMouse® mice were determined by ELISA against HER-3 ECD protein. The specific titer of each XenoMouse® animal was determined from the optical density at 650 nm and is shown in Table 1 below. The titer value is the reciprocal of the greatest dilution of sera with an OD reading two-fold that of background. Therefore, the higher the number, the greater was the humoral immune response to HER-3 ECD.

TABLE 1

Cohort #1, XMG1

| Mouse ID | After 4 inj. | After 6 inj. |
|---|---|---|
| P3421 | 8,000 | 11,000 |
| P3422 | 850 | 2,600 |
| P3423 | 2,700 | 5,200 |
| P3424 | 3,200 | 9,100 |
| P3425 | 5,400 | 2,500 |
| P3426 | 700 | 1,500 |
| P3427 | 5,800 | 7,000 |
| P3428 | 3,900 | 4,300 |
| P3429 | 2,200 | 2,500 |
| P34210 | 600 | 850 |
| NC | 250 | 175 |
| PC | 377,000 | 311,000 |
| NC | mAb IL-8, D39.2.1 | |
| PC | xHER-3-2D1D12 | |

For cohort #3 and #4, anti-HER-3 antibody titers in the serum from immunized XenoMouse® mice were determined by FACS using Rat1/HER-3 cells (antigen positive cell line) cells and Rat1/pLSXN cells (antigen negative cell line). Data are presented as geometric mean (GeoMean) fluorescent intensity of cell anti-HER-3 cell staining by serial dilutions of serum samples.

TABLE 2

Cohort #3, XMG1

| Mouse ID | Sample dilution | After 6 inj. | | After 12 inj. | |
|---|---|---|---|---|---|
| | | pos cells GeoMean | neg cells GeoMean | pos cells GeoMean | neg cells GeoMean |
| Q832-1 | 1:50 | 9 | 10 | 11 | 10 |
| | 1:250 | 6 | 9 | 6 | 6 |
| | 1:1250 | 6 | 7 | 4 | 4 |
| Q832-2 | 1:50 | 8 | 10 | 29 | 42 |
| | 1:250 | 7 | 8 | 11 | 11 |
| | 1:1250 | 5 | 6 | 6 | 5 |
| Q832-3 | 1:50 | 7 | 12 | 11 | 9 |
| | 1:250 | 5 | 7 | 5 | 5 |
| | 1:1250 | 5 | 5 | 4 | 4 |
| Q832-4 | 1:50 | 6 | 10 | 9 | 9 |
| | 1:250 | 6 | 6 | 5 | 5 |
| | 1:1250 | 5 | 5 | 4 | 4 |
| Q832-5 | 1:50 | 11 | 11 | 17 | 13 |
| | 1:250 | 10 | 9 | 7 | 6 |
| | 1:1250 | 6 | 8 | 5 | 4 |
| Q832-6 | 1:50 | 7 | 11 | 15 | 14 |
| | 1:250 | 7 | 7 | 7 | 6 |
| | 1:1250 | 5 | 6 | 6 | 4 |
| Q832-7 | 1:50 | 8 | 11 | 7 | 15 |
| | 1:250 | 6 | 7 | 5 | 5 |
| | 1:1250 | 5 | 5 | 4 | 4 |
| Q832-8 | 1:50 | 7 | 8 | 11 | 20 |
| | 1:250 | 6 | 6 | 7 | 8 |
| | 1:1250 | 5 | 5 | 5 | 4 |

TABLE 2-continued

Cohort #3, XMG1

| Mouse ID | Sample dilution | After 6 inj. | | After 12 inj. | |
|---|---|---|---|---|---|
| | | pos cells GeoMean | neg cells GeoMean | pos cells GeoMean | neg cells GeoMean |
| Q832-9 | 1:50 | 7 | 12 | 15 | 16 |
| | 1:250 | 6 | 8 | 6 | 5 |
| | 1:1250 | 6 | 6 | 4 | 4 |
| Q832-10 | 1:50 | 8 | 13 | 34 | 38 |
| | 1:250 | 6 | 8 | 9 | 8 |
| | 1:1250 | 6 | 6 | 5 | 4 |

TABLE 3

Cohort #4, XMG4

| Mouse ID | Sample dilution | After 6 inj. | | After 12 inj. | |
|---|---|---|---|---|---|
| | | pos cells GeoMean | neg cells GeoMean | pos cells GeoMean | neg cells GeoMean |
| Q856-1 | 1:50 | 4 | 6 | 91 | 44 |
| | 1:250 | 4 | 5 | 32 | 18 |
| | 1:1250 | 4 | 4 | 19 | 10 |
| Q856-2 | 1:50 | 4 | 8 | 148 | 54 |
| | 1:250 | 4 | 5 | 89 | 23 |
| | 1:1250 | 4 | 4 | 42 | 9 |
| Q856-3 | 1:50 | 4 | 5 | 72 | 14 |
| | 1:250 | 4 | 4 | 28 | 6 |
| | 1:1250 | 4 | 4 | 18 | 4 |
| Q856-4 | 1:50 | 4 | 5 | 11 | 49 |
| | 1:250 | 4 | 5 | 10 | 17 |
| | 1:1250 | 4 | 4 | 8 | 7 |
| Q856-5 | 1:50 | 4 | 4 | 74 | 20 |
| | 1:250 | 4 | 4 | 30 | 14 |
| | 1:1250 | 4 | 4 | 16 | 6 |
| Q856-6 | 1:50 | 4 | 5 | 86 | 21 |
| | 1:250 | 4 | 4 | 32 | 10 |
| | 1:1250 | 4 | 4 | 16 | 5 |
| Q856-7 | 1:50 | 5 | 6 | 74 | 32 |
| | 1:250 | 4 | 5 | 32 | 14 |
| | 1:1250 | 4 | 4 | 16 | 6 |
| Q856-8 | 1:50 | 4 | 5 | 106 | 14 |
| | 1:250 | 4 | 4 | 45 | 6 |
| | 1:1250 | 4 | 4 | 22 | 4 |
| Q856-9 | 1:50 | 5 | 6 | 53 | 22 |
| | 1:250 | 4 | 4 | 17 | 11 |
| | 1:1250 | 4 | 4 | 11 | 5 |
| Q856-10 | 1:50 | 4 | 5 | 72 | 53 |
| | 1:250 | 4 | 4 | 26 | 17 |
| | 1:1250 | 4 | 4 | 15 | 7 |

Example 4

Recovery of Lymphocytes, B-Cell Isolations, Fusions and Generation of Hybridomas Immunized mice were sacrificed and the lymph nodes were harvested and pooled from each cohort. The lymphoid cells were dissociated by grinding in DMEM to release the cells from the tissues, and the cells were suspended in DMEM. The cells were counted, and 0.9 ml DMEM per 100 million lymphocytes was added to the cell pellet to resuspend the cells gently but completely. Using 100 µl of CD90+ magnetic beads per 100 million cells, the cells were labeled by incubating the cells with the magnetic beads at 4° C. for 15 min. The magnetically-labeled cell suspension containing up to $10^8$, positive cells (or up to $2 \times 10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC (Cat. No. CRL 1580) (Kearney et al, J. Immunol. 123, 1979, 1548-1550) at a ratio of 1:1. The cell mixture was gently pelleted by centrifugation at 800 g. After complete removal of the supernatant, the cells were treated with 2 to 4 ml of pronase solution (CalBiochem, Cat. No. 53702; 0.5 mg/ml in PBS) for no more than 2 min. Then 3 to 5 ml of FBS was added to stop the enzyme activity and the suspension was adjusted to 40 ml total volume using electro cell fusion solution, ECFS (0.3 M sucrose, Sigma, Cat. No. S7903, 0.1 mM magnesium acetate, Sigma, Cat. No. M2545, 0.1 mM calcium acetate, Sigma, Cat. No. C4705). The supernatant was removed after centrifugation and the cells were resuspended in 40 ml ECFS. This wash step was repeated and the cells again were resuspended in ECFS to a concentration of $2 \times 10^6$ cells/ml.

Electro-cell fusion was performed using a fusion generator, model ECM2001, Genetronic, Inc., San Diego, Calif. The fusion chamber size used was 2.0 ml, using the following instrument settings: Alignment condition: voltage: 50 V, time: 50 sec; membrane breaking at: voltage: 3000 V, time: 30 μsec; post-fusion holding time: 3 sec.

After ECF, the cell suspensions were carefully removed from the fusion chamber under sterile conditions and transferred into a sterile tube containing the same volume of Hybridoma Culture Medium (DMEM (JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15 to 30 min at 37° C., and then centrifuged at 400 g for five min. The cells were gently resuspended in a small volume of Hybridoma Selection Medium (Hybridoma Culture Medium supplemented with 0.5×HA (Sigma, Cat. No. A9666)), and the volume was adjusted appropriately with more Hybridoma Selection Medium, based on a final plating of $5 \times 10^6$ B cells total per 96-well plate and 200 μl per well. The cells were mixed gently and pipetted into 96-well plates and allowed to grow. On day 7 or 10, one-half the medium was removed, and the cells were re-fed with Hybridoma Selection Medium.

Example 5

Selection of Candidate Antibodies by ELISA

After 14 days of culture, primary screening of hybridoma supernatants from the cohort #1 (mice in cohort one were split arbitrarily into fusion #1 and #2) for HER-3-specific antibodies was performed by ELISA using purified his-tagged HER-3 ECD and counter-screening against an irrelevant his-tagged protein by ELISA using goat anti-huIgGFc-HRP (Caltag Inc., Cat. No. H10507, using concentration was 1:2000 dilution) to detect human IgG binding to HER-3 ECD immobilized on ELISA plates. The old culture supernatants from the positive hybridoma cells growth wells based on primary screen were removed and the HER-3 positive hybridoma cells were suspended with fresh hybridoma culture medium and were transferred to 24-well plates. After 2 days in culture, these supernatants were ready for a secondary confirmation screen. In the secondary confirmation screen for HER-3 specific fully human IgGk antibodies, the positives in the first screening were screened by ELISA with two sets of detective antibodies: goat anti-huIgGFc-HRP (Caltag Inc., Cat. No. H10507, using concentration was 1:2000 dilution) for human gamma chain detection and goat anti-hIg kappa-HRP (Southern Biotechnology, Cat. No. 2060-05) for human kappa light chain detection. There were 91 fully human IgG/kappa HER-3 specific monoclonal antibodies that were generated from cohort #1.

Example 6

Selection of Candidate Antibodies by FMAT/FACS

After 14 days of culture, hybridoma supernatants from the cohort #3 and #4 (fusion #3 and #4) were screened for HER-3-specific monoclonal antibodies by FMAT. In the primary screen, hybridoma supernatants at 1:10 final dilution were incubated with Rat1-Her3 cells expressing human HER-3 and 400 ng/ml Cy5-conjugated Goat F(ab')2 anti-human IgG, Fc-specific antibody (Jackson ImmunoResearch, Cat. No. 109-176-098) at room temperature for 6 hr. The binding of antibodies and detection antibodies complex to cells were measured by FMAT (Applied Biosystems). Non-specific binding of antibodies to the cells was determined by their binding to parental Rat1 cells. A total of 420 hybridomas producing HER-3-specific antibodies were selected from primary screen of fusion #3. The supernatants from these expanded cultures were tested again using the same FMAT protocol and 262 of them were confirmed to bind to HER-3 expressing cells specifically. A total of 193 hybridomas producing HER-3 specific antibodies were selected from primary screen of fusion #4. The supernatants from these expanded cultures were tested by FACS and 138 of them were confirmed to bind to HER-3 expressing cells specifically. In the FACS confirmation assay, Rat1-Xher3 cells and parental Rat1 cells (as negative control) were incubated with hybridoma supernatants at 1:2 dilution for 1 hr at 40 C in PBS containing 2% FBS. Following washing with PBS, the binding of antibodies to the cells were detected by 2.5 μg/ml Cy5-conjugated Goat F(ab')2 anti-human IgG, Fc-specific antibody (JIR#109-176-098) and 5 μg/ml PE-conjugated Goat F(ab')2 anti-human kappa-specific antibody (SB#2063-09). After removing the unbound antibodies by washing with PBS, the cells were fixed by cytofix (BD#51-2090KZ) at 1:4 dilution and analyzed by FACSCalibur.

Example 7

Selection of Hybridomas for Cloning

Antibodies from cohorts 1 and 2 were selected for hybridoma cloning based on specificity for HER-3 over HER1 (EGFR), HER-2 and HER-4 in ELISA using purified recombinant extra-cellular domains available from, for example R&D Biosystems, and FACS-based analysis of human tumor cell lines expressing different HER family members, and a >5-time increase in mean fluorescent intensity in FACS staining for HER-3 positive cells over background. Based on these criteria, a total of 23 hybridoma lines were selected for cloning by limiting dilution cell plating.

Antibodies from cohorts 3 and 4 were selected for hybridoma cloning based on specificity for HER-3 over HER-1 (EGFR), HER-2 and HER-4 plus three other criteria. The first criterion was an ELISA screen for antibodies with epitopes contained within the L2 domain of HER-3 (see Example "Structural Analysis of anti-HER-3 Antibodies in the Invention).

The second criterion was neutralization of binding of biotinylated heregulin-alpha to HER-3 expressing cells in a FACS based assay. SKBR-3 cells were harvested, washed in culture medium, pelleted via centrifugation and resuspended in culture medium. Resuspended cells were aliquoted into 96-well plates. The plates were centrifuged to pellet the cells. Test antibodies in exhaust hybridoma supernatants were added at 25 μl/well and incubated for 1 hr on ice to allow antibody binding. Fifty μl of a 10 nM heregulin-alpha (R&D Biosystems, Minneapolis, Minn.) solution was added to each well for a final concentration of 5 nM and incubated on ice for 1.5 hr. Cells were washed in 150 μl PBS, pelleted by centrifugation and the supernatant removed. Cells were resuspended in 50 μl of goat anti-HRG-alpha polyclonal antibody at 10 μg/ml and incubated for 45 min of ice. Cells were washed in 200 μl PBS, pelleted by centrifugation and the supernatant removed. Fifty μl of a solution of rabbit Cy5-labeled anti-goat polyclonal antibody at 5 μg/ml plus 7AAD at 10 μg/ml was added and incubated on ice for 15 min. Cells were washed in 200 μl PBS, pelleted by centrifugation and the supernatant removed. The cells were resuspended in 100 μl of FACS buffer and read in the FACS. Test HER-3 antibodies that reduced binding of heregulin-alpha were those that had lowest fluorescence intensity. As positive controls, 1:5 serial dilutions from 10,000 ng/ml to 16 ng/ml of a mouse HER-3 mAb (105.5) or the human IgG1 HER-3 mAb, U1-49 was used. Negative controls were heregulin-alpha alone, cells alone, goat anti-heregulin-alpha polyclonal antibody alone and rabbit Cy5-labeled anti-goat polyclonal antibody alone.

The third criterion was relative ranking for affinity and/or higher relative mean fluorescence intensity in FACS using HER-3 expressing cell lines. Relative ranking for affinity was performed by normalizing HER-3-specific antibody concentrations and plotting versus data from limiting antigen ELISA as follows.

Normalization of Antigen Specific Antibody Concentrations Using High Antigen ELISA Using an ELISA method, supernatants for concentration of antigen specific antibody were normalized. Using two anti-HER-3 human IgG1 antibodies from cohort 1 of known concentration titrated in parallel, a standard curve was generated and the amount of antigen specific antibody in the test hybridoma supernatants from cohorts 3 and 4 were compared to the standard. In this way, the concentration of human HER3 IgG antibody in each hybridoma culture was estimated.

Neutravidin plates were made by coating neutravidin @ 8 μg/ml in 1×PBS/0.05% sodium azide on Costar 3368 medium binding plates at 50 ul/well with overnight incubation at 4° C. The next day the plates were blocked with 1×PBS/1% skim milk. Photobiotinylated his-tagged-HER-3 ECD @ 500 ng/ml in 1×PBS/1% skim milk was bound to the neutravidin plates by incubating for 1 hour at room temperature. Hybridoma supernatant, serially diluted 1:2.5 from a starting dilution of 1:31 to a final dilution of 1:7568 in 1×PBS/1% skim milk/0.05% azide, was added at 50 μl/well, and then incubated for 20 hours at room temperature. Serially dilutions were used to ensure obtaining OD readings for each unknown in the linear range of the assay. Next, a secondary detection antibody, goat anti human IgG Fc HRP at 400 ng/ml in 1×PBX/1% skim milk was added at 50 ul/well. After 1 hour at room temperature, the plates were again washed 5 times with water and 50 μL of one-component TMB substrate were added to each well. The reaction was stopped after 30 minutes by the addition of 50 μl of 1M hydrochloric acid to each well and the plates were read at wavelength 450 nm. A standard curve was generated from the two IgG1 HER-3 mAbs from cohort 1, serially diluted at 1:2 from 1000 ng/ml to 0.06 ng/ml and assessed in ELISA using the above protocol. For each unknown, OD readings in the linear range of the assay were used to estimate the concentration of human HER-3 IgG in each sample.

The limited antigen analysis is a method that affinity ranks the antigen-specific antibodies prepared in B-cell culture supernatants relative to all other antigen-specific antibodies. In the presence of a very low coating of antigen, only the highest affinity antibodies should be able to bind to any detectable level at equilibrium. (See, e.g., PCT Publication WO/03048730A2 entitled "IDENTIFICATION OF HIGH AFFINITY MOLECULES BY LIMITED DILUTION SCREENING" published on Jun. 12, 2003). In this instance, two mAbs from cohort 1, both of known concentration and known KD, were used as benchmarks in the assay.

Neutravidin plates were made by coating neutravidin at 8 μg/ml in 1×PBS/0.05% sodium azide on Costar 3368 medium binding plates at 50 ul/well with overnight incubation at 4° C. The next day the plates were blocked with 1×PBS/1% skim milk. Biotinylated his-tagged-HER-3 ECD (50 μl/well) was bound to 96-well neutravidin plates at five concentrations: 125, 62.5, 31.2, 15.6, and 7.8 ng/ml in 1×PBS/1% skim milk for 1 hour at room temperature. Each plate was washed 5 times with water. Hybridoma supernatants diluted 1:31 in 1×PBS/1% skim milk/0.05% azide were added at 50 ul/well. After 20 hours incubation at room temperature on a shaker, the plates were again washed 5 times with dH$_2$O, Next, a secondary detection antibody, goat anti human IgG Fc HRP (Horsh Radish Peroxidase) at 400 ng/ml in 1×PBS/1% skim milk was added at 50 μl/well. After 1 hour at room temperature, the plates were again washed 5 times with dH$_2$O and 50 μL of one-component TMB substrate were added to each well. The reaction was stopped after 30 minutes by the addition of 50 μL of 1M hydrochloric acid to each well and the plates were read at wavelength 450 nm. OD readings from an antigen concentration that yielded OD values in the linear range were used in for data analysis.

Plotting the high antigen data, which comparatively estimates specific antibody concentration (see above for details), versus the limited antigen OD illustrated the relatively higher affinity antibodies, e.g., those that bound had higher OD in the limited antigen assay while having lower amounts of IgG HER-3 antibody in the supernatant.

Hybridomas from cohorts 3 and 4 for the 33 best performing antibodies in these sets of assays were advanced to cloning by limiting dilution hybridoma plating.

Figure 2:
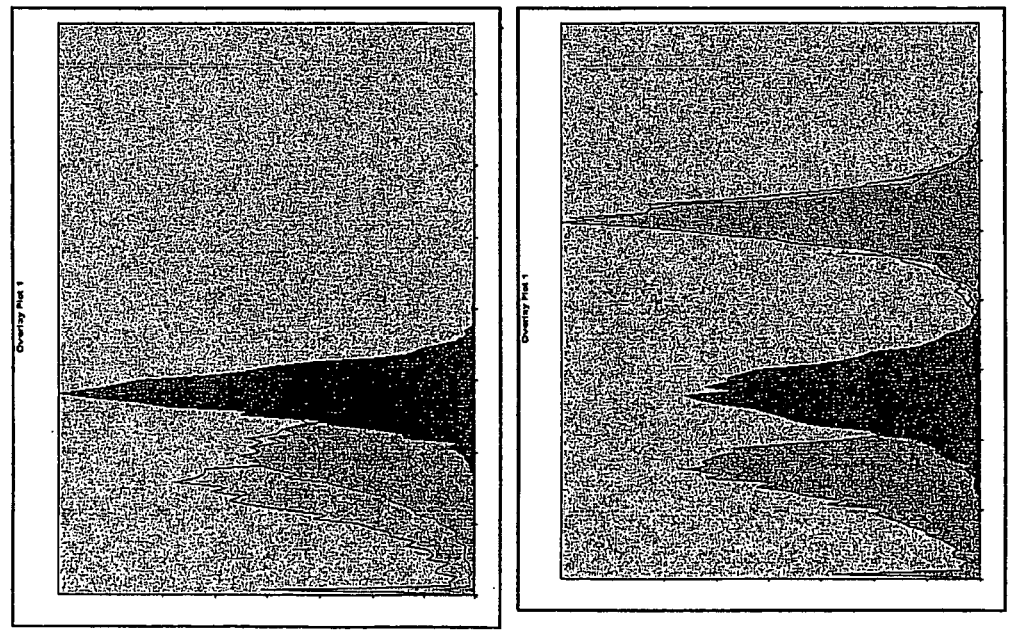
FIG. 2 shows the results of the FACS analysis of HER-3 antibody binding to either RatI cells stably expressing the different members of the HER family or only empty vector.
Figure 6E:
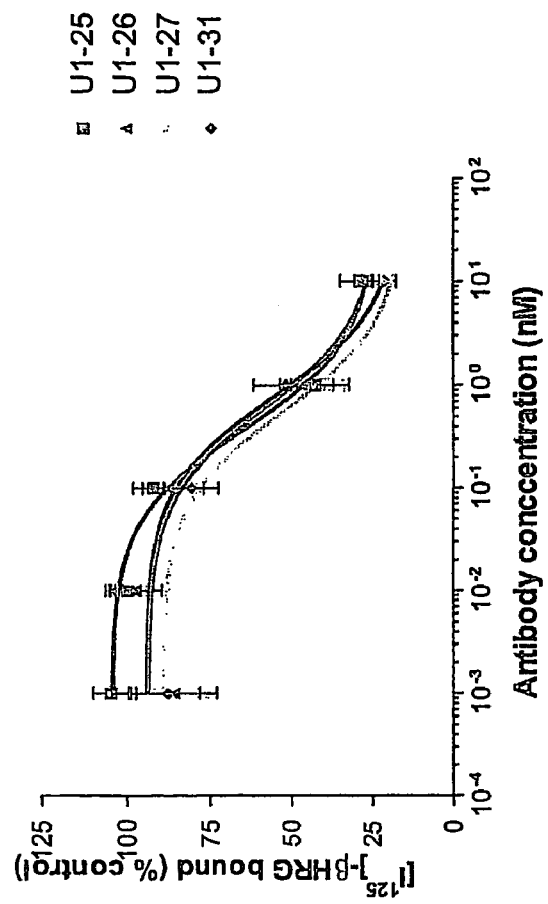

Alternatively, FACS analysis of HER-3 expression of RatI/pLXSN and RatI/HER-3 cells showed similar results (no crossreactivity with endogenous rat epitopes) (FIG. 2).

In detail 1×10$^5$ cells were harvested with 10 mM EDTA in PBS, washed once with FACS buffer (PBS, 3% FCS, 0.4% azide) and seeded on a 96-well round bottom plate. The cells were spun for 3 min at 1000 rpm to remove supernatant and then resuspended with the specific HER-family antibodies (3 μg/ml). Cell suspensions were incubated on ice for 45 min, washed twice with FACS buffer and resuspended with secondary antibody (100 μl/well) donkey-anti-human-PE (Jackson Immunoresearch, PA) diluted 1:50 in FACS buffer. The cell suspensions were incubated on ice and in the dark for 30 min, washed twice with FACS buffer and analyzed (FACS, Beckman Coulter).

Example 8

Structural Analysis of Anti-HER-3 Antibodies of the Invention

In the following discussion, structural information related to antibodies prepared in accordance with the invention is provided. In order to analyze structures of antibodies produced in accordance with the present invention, genes encoding the heavy and light chain fragments were amplified out of the particular hybridoma. Sequencing was accomplished as follows:

The VH and VL transcripts were amplified from individual hybridoma clones in 96 well plate using reverse transcriptase polymerase chain reaction (RT-PCR). Poly(A)+-mRNA was isolated from approximately $2\times10^5$ hybridoma cells using a Fast-Track kit (Invitrogen). Four PCR reactions were run for each Hybridoma: two for light chain (kappa (κ), and two for gamma heavy chain (γ). The QIAGEN OneStep room temperature-PCR kit was used for amplification (Qiagen, Catalog No. 210212). In the coupled room temperature-PCR reactions, cDNAs were synthesized with blend of room temperature enzymes (Omniscript and Sensiscript) using antisense sequence specific primer corresponded to C-κ, or to a consensus of the CH1 regions of Cγ genes. Reverse transcription was performed at 50° C. for 1 hr followed by PCR amplification of the cDNA by HotStarTaq DNA Polymerase for high specificity and sensitivity. Each PCR reaction used a mixture of 5'-sense primers; primer sequences were based on the leader sequences of VH and VK available at the Vbase website (http://vbase.mrc-cpe.cam.ac.uk/).

PCR reactions were run at 94° C. for 15 min, initial hot start followed by 40 cycles of 94° C. for 30 sec (denaturation), 60° C. for 30 sec (annealing) and 72° C. for 1 min (elongation).

PCR products were purified and directly sequenced using forward and reverse PCR primers using the ABI PRISM BigDye terminator cycle sequencing ready reaction Kit (Perkin Elmer). Both strands were sequenced using Prism dye-terminator sequencing kits and an ABI 377 sequencing machine.

Sequence Analysis

Analyses of human V heavy and V kappa cDNA sequences of the HER3 antibodies were accomplished by aligning the HER-3 sequences with human germline V heavy and V kappa sequences using Abgenix in-house software (5AS). The software identified the usage of the V gene, the D gene and the J gene as well as nucleotide insertions at the recombination junctions and somatic mutations. Amino acid sequences were also generated in silico to identify somatic mutations. Similar results could be obtained with commercially available sequence analysis software and publicly available information on the sequence of human V, D, and J genes, e.g., Vbase (http://vbase.mrc-cpe.cam.ac.uk/).

Molecular Cloning of mAb U1-59

Total RNA was extracted from the tissue culture well containing multiple hybridomas lineages, including the hybridoma lineage secreting antibody U1-59. A heavy chain variable region was amplified using 5'-leader VH family specific primers, with 3'-C-gamma primer. A major band was amplified using a VH4 primer, no other bands were visible. The VH4-34 gamma fragment was cloned into pcDNA expression vector in frame with a human gamma 1 constant region gene.

An IgM heavy chain variable region was amplified using 5' VH family specific primers with 3' mu constant region primer. A major band was amplified using VH2 primer, no other bands were visible. The VH2-5 mu fragment was cloned into pCDNA expression vector in frame with a human mu constant region gene. V kappa chains were amplified and sequenced. Four kappa chain RT-PCR products were identified. The products were sequenced and after sequence analysis via in silico translation, only three of them had open-reading frames. These three functional kappa chains were cloned out of the oligoclonal U1-59 hybridoma well identified based on V kappa gene usage as (1) VK1 A3-JK2, (2) VK1 A20-JK3 and (3) B3-JK1. All V-kappa were cloned into pCDNA expression vector in frame with a human kappa light chain constant region gene.

Transfections:

Each heavy chain was transfected with each of the kappa chains in transient transfections for a total of 6 heavy chain/kappa light chain pairs. The transfection of the gamma chain with the A20 kappa chain gave poor antibody expression, while no antibody was secreted or detected when the A20 kappa chain was co-transfected with the mu chain. A total of three IgG sups and two IgM sups were available for HER-3 binding assay.

| Chain | VH | D | J | Constant | ORF |
|---|---|---|---|---|---|
| Heavy | VH4-34 | D1-20 | JH2 | Gamma | yes |
| Heavy | VH2-5 | D6-6 | JH4b | Mu | yes |
| Light | A3 | | JK2 | Kappa | yes |
| Light | A20 | | JK3 | Kappa | yes |
| Light | B3 | | JK1 | Kappa | yes |
| Light | A27 | | JK3 | Kappa | NO |

Binding activity to HER-3+ cell lines was detected in FACS with the IgG1 mAb consisting of the VH4-34 and the B3 kappa chain. No other VH/Vk combinations gave fluorescence signal above background in FACS using HER-3+ cell lines.

Binding Competition of the Anti-HER-3 Antibodies

Multiplexed competitive antibody binning was performed as published in Jia et al. *J Immunol Methods*. 288, 91-98 (2004) to assess clusters of HER-3 antibodies that competed for binding to HER-3. Tested HER-3 antibodies from cohort 1 clustered into 5 bins based on competition for binding.

| Bin#1 | Bin#2 | Bin#3 | Bin#4 | Bin#5 |
|---|---|---|---|---|
| U1-42 | U1-48 | U1-52 | U1-38 | U1-45 |
| U1-44 | U1-50 | | U1-39 | U1-40 |
| U1-62 | U1-51 | | | U1-41 |
| U1-46 | | | | U1-43 |
| U1-47 | U1-49 | | | U1-61 |
| U1-58 | | | | U1-53 |
| | | | | U1-55 |

Epitope Characterization of Anti-HER-3 Antibodies

The epitopes of human anti-HER-3 antibodies of the invention were characterized. First a dot blot analysis of the reduced, denatured HER-3-His tagged purified ECD protein showed absence of binding by the anti-HER-3 antibodies tested (U1-59, U1-61, U1-41, U146, U1-53, U1-43, U1-44, U1-47, U1-52, U1-40, U1-49)) demonstrating that all had epitopes sensitive to reduction of disulfide bonds, suggesting that all had discontinuous epitopes. Next, the antibodies were mapped to defined domains in the HER-3 molecule by engineering various human-rat HER-3 chimeric molecules, based on the division of the HER-3 extra-cellular domain into four domains:

1) L1 (D1): the minor ligand-binding domain,

2) S1 (D2): the first cysteine-rich domain,

3) L2 (D3): the major ligand-binding domain, and

4) S2 (D4): the sec cysteine-rich domain.

The extra-cellular domain (ECD) of Human HER-3 cDNA was amplified from RAT1-HER-3 cells. The rat HER-3 cDNAs was amplified by RT-PCR from rat liver RNA and confirmed by sequencing. The cDNAs expressing the ECD of human and rat Her3 were cloned into mammalian expression vectors as V5-His fusion proteins. Domains from the human HER-3 ECD were swapped into the scaffold provided by the rat HER-3 ECD by using the Mfe1, BstX1 and DraIII internal restriction sites. By this means, various chimeric rat/human HER-3 ECD HIS fusion proteins (amino acids 1-160, 161-358, 359-575, 1-358, 359-604) were constructed and expressed via transient transfection of HEK 293T cells. Expression of the constructs was confirmed using a rat polyclonal antibody against human HER-3. The human monoclonal antibodies were tested in ELISA for binding to the secreted chimeric ECDs.

Two of the human antibodies, including antibody U1-59, cross-reacted with rat HER-3. To assign binding domains, these mAbs were tested against a truncated form of HER-3 consisting of L1-S1-V5his tagged protein purified from the supernatant of HEK 293T cells transfected with a plasmid DNA encoding the expression of the L1-S1 extra-cellular domains of HER3. mAb U1-59 bound to the L1-S1 protein in ELISA, implying that its epitope is in L1-S1. mAb 2.5.1 did not bind to the L1-S1 protein, implying that its epitope is in L2-S2. Further mapping of antibody U1-59 was accomplished using SELDI time of flight mass spectroscopy with on-chip proteolytic digests of mAb-HER-3 ECD complexes.

Mapping U1-59 Epitopes Using SELDI

Further mapping of antibody U1-59 was accomplished using a SELDI time of flight mass spectroscopy with on-chip proteolytic digests of mAb-HER-3 ECD complexes. Protein A was covalently bound to a PS20 protein chip array and used to capture mAb U1-59. Then the complex of the PS20 protein chip and the monoclonal antibody was incubated with HER-3-His purified antigen. Next the antibody-antigen complex was digested with high concentration of Asp-N. The chip was washed, resulting in retention of only the HER-3 peptide bound to the antibody on the chip. The epitope was determined by SELDI and identified by mass of the fragment. The identified 6814 D fragment corresponds to two possible expected peptides generated from a partial digest of the HER-3-his ECD. Both overlapping peptides map to the domain S1. By coupling SELDI results with binding to a HER-3 deletion construct, the epitope was mapped to residues 251 to 325 of SEQ ID NO:390.

The location of the binding domains in the extracellular part of HER-3 that are recognized by the human anti-HER-3 mAbs of the invention are summarized in Table 4. The epitope domain mapping results were consistent with results from antibody competition binding competition bins, with antibodies that cross-competed each other for binding to HER-3 also mapping to the same domains on HER-3 (FIG. 3).

TABLE 4

A summary of mAb's binding domain based on ELISA assay results

| mAb | Rat XR | Binding domain | mAb | Rat XR | Binding domain |
|---|---|---|---|---|---|
| U1-59 | Yes | S1 | U1-2 | No | L2 |
| U1-61 | No | L2 | U1-7 | No | L2 |
| U1-41 | No | L2 | U1-9 | No | L2 |
| U1-46 | No | S1 | U1-10 | No | L2 |
| U1-53 | No | L2 | U1-12 | No | L2 |
| U1-43 | No | L2 | U1-13 | No | L2 |
| U1-44 | No | S1 | U1-14 | No | L2 |
| U1-47 | No | S1 | U1-15 | No | L2 |
| U1-52 | Yes | L2S2 | U1-19 | No | L2 |
| U1-40 | No | L2 | U1-20 | No | L2 |
| U1-49 | No | L1 | U1-21 | No | L2 |
| U1-21 | No | L2 | U1-28 | No | L2 |
| U1-22 | No | L2 | (U1-31) | No | L2 |
| U1-23 | No | L2 | U1-32 | No | L2 |
| U1-24 | No | L2 | (U1-35) | No | L2 |
| U1-25 | No | L2 | U1-36 | No | L2 |
| U1-26 | No | L2 | (U1-37) | No | L2 |
| U1-27 | No | L2 | | | |

XR = cross-reactive

Example 9

Determination of Canonical Classes of Antibodies

Chothia, et al. have described antibody structure in terms of "canonical classes" for the hypervariable regions of each immunoglobulin chain (*J. Mol. Biol.,* 1987 Aug. 20, 196(4): 901-17). The atomic structures of the Fab and VL fragments of a variety of immunoglobulins were analyzed to determine the relationship between their amino acid sequences and the three-dimensional structures of their antigen binding sites. Chothia, et al. found that there were relatively few residues that, through their packing, hydrogen bonding or the ability to assume unusual phi, psi or omega conformations, were primarily responsible for the main-chain conformations of the hypervariable regions. These residues were found to occur at sites within the hypervariable regions and in the conserved β-sheet framework. By examining sequences of immunoglobulins having unknown structure, Chothia, et al. show that many immunoglobulins have hypervariable regions that are similar in size to one of the known structures and additionally contained identical residues at the sites responsible for the observed conformation.

Their discovery implied that these hypervariable regions have conformations close to those in the known structures. For five of the hypervariable regions, the repertoire of conformations appeared to be limited to a relatively small number of discrete structural classes. These commonly occurring main-chain conformations of the hypervariable regions were termed "canonical structures." Further work by Chothia, et al. (*Nature,* 1989 Dec. 21-28, 342 (6252):877-83) and others (Martin, et al. *J. Mol. Biol.,* 1996 Nov. 15, 263(5): 800-15) confirmed that there is a small repertoire of main-chain conformations for at least five of the six hypervariable regions of antibodies.

The CDRs of each antibody described above were analyzed to determine their canonical class. As is known, canonical classes have only been assigned for CDR1 and CDR2 of the antibody heavy chain, along with CDR1, CDR2 and CDR3 of the antibody light chain. The tables below summarizes the results of the analysis. The canonical class data is in the form of HCDR1-HCDR2-LCDR1-LCDR2-LCDR3, wherein "HCDR" refers to the heavy chain CDR and "LCDR" refers to the light chain CDR. Thus, for example, a canonical class of 1-3-2-1-5 refers to an antibody that has a HCDR1 that falls into canonical class 1, a HCDR2 that falls into canonical class 3, a LCDR1 that falls into canonical class 2, a LCDR2 that falls into canonical class 1, and a LCDR3 that falls into canonical class 5.

Assignments were made to a particular canonical class where there was 70% or greater identity of the amino acids in the antibody with the amino acids defined for each canonical class. The amino acids defined for each antibody can be found, for example, in the articles by Chothia, et al. referred to above. Table 5 and Table 6 report the canonical class data for each of the HER-3 antibodies. Where there was less than 70% identity, the canonical class assignment is marked with an asterisk ("*") to indicate that the best estimate of the proper canonical class was made, based on the length of each CDR and the totality of the data. Where there was no matching canonical class with the same CDR length, the canonical class assignment is marked with a letter s and a number, such as "s18", meaning the CDR is of size 18. Where there was no sequence data available for one of the heavy or light chains, the canonical class is marked with "Z".

TABLE 5

| Antibody (sorted) | H1-H2-L1-L2-L3 | H3length | Antibody (sorted) | H1-H2-L1-L2-L3 | H3length |
|---|---|---|---|---|---|
| U1-38 | 3-1-4-1-1 | 9 | U1-7 | 3-1-2-1-1 | 12 |
| U1-39 | 1-1-4-1*-1 | 6 | U1-9 | 3-1-2-1-1 | 12 |
| U1-40 | 3-1-4-1-1 | 15 | U1-10 | 3-1-2-1-1 | 12 |
| U1-41 | 3-1-2-1-1 | 15 | U1-12 | 3-1-2-1-1 | 12 |
| U1-42 | 1-2-2-1-1 | 9 | U1-13 | 3-1-4-1-1 | 7 |
| U1-43 | 3-1-2-1-1 | 17 | U1-14 | 3-1-2-1-1 | 12 |
| U1-44 | 1-2-2-1-1 | 9 | U1-15 | 3-1-8-1-1 | 14 |
| U1-45 | 1-2*-2-1-1 | 16 | U1-19 | 3-1-Z-Z-Z | 12 |
| U1-46 | 3-s18-Z-Z-Z | 17 | U1-20 | 3-1-2-1-1 | 19 |
| U1-47 | 3-s18-2-1-1 | 16 | U1-21 | 3-1-2-1-1 | 12 |
| U1-48 | 1-1-Z-Z-Z | 16 | U1-22 | 3-1-2-1-1 | 12 |
| U1-49 | 1-3-4-1-1 | 17 | U1-23 | 3-1-2-1-1 | 12 |
| U1-50 | 3-1-2-1-1 | 17 | U1-24 | 3-1-2-1-1 | 12 |
| U1-51 | 1-1-3-1-1 | 19 | U1-25 | 3-1-2-1-1 | 12 |
| U1-52 | 3-1-8-1-1 | 15 | U1-26 | 3-1-2-1-1 | 12 |
| U1-53 | 1-3-2-1-1 | 10 | U1-27 | 3-1-2-1-1 | 12 |
| U1-55 | 3-1-4-1-1 | 15 | U1-28 | 3-1-2-1-1 | 12 |
| U1-57 | 3-1-4-1-1 | 15 | U1-31 | 1-2-2-1-1 | 13 |
| U1-58 | 1-3-2-1-1 | 12 | U1-32 | 3-1-2-1-1 | 12 |
| U1-59 | 1-1-3-1-1 | 9 | U1-35 | 1-3-2-1-1 | 14 |
| U1-61.1 | 3-1*-2-1-1 | 16 | U1-36 | 3-1-2-1-1 | 12 |
| U1-62 | 1-2-8-1-1 | 12 | U1-37 | 1-2-Z-Z-Z | 13 |
| U1-2 | 3-1-2-1-1 | 12 | | | |

Table 7 is an analysis of the number of antibodies per class. The number of antibodies having the particular canonical class designated in the left column is shown in the right column. The four mAbs lacking one chain sequence data and thus having "Z" in the canonical assignment are not included in this counting.

The most commonly seen structure is 3-1-2-1-1: Twenty-one out of forty-one mAbs having both heavy and light chain sequences had this combination.

TABLE 6

| H1-H2-L1-L2-L3 | Count |
|---|---|
| 1-1-3-1-1 | 2 |
| 1-1-4-1*-1 | 1 |
| 1-2-2-1-1 | 4 |
| 1-2-8-1-1 | 1 |

TABLE 6-continued

| H1-H2-L1-L2-L3 | Count |
|---|---|
| 1-3-2-1-1 | 3 |
| 1-3-4-1-1 | 1 |
| 3-1-2-1-1 | 21 |
| 3-1-4-1-1 | 5 |
| 3-1-8-1-1 | 2 |
| 3-s18-2-1-1 | 1 |

Example 10

Determination of Antibody Affinity

Affinity measurements of anti-HER-3 antibodies of the invention were performed by indirect FACS Scatchard analysis. Therefore, $10^5$ cells of interest or SK-Br 3 cells were harvested with 10 mM EDTA in PBS, washed once with FACS buffer (PBS, 3% FCS, 0.4% azide) and seeded on a 96-well round bottom plate. The cells were spun for 3 min at 1000 rpm to remove supernatant and then resuspended with α-HER-3 antibody (3 µg/ml) or with antibody dilutions (100 µl/well) starting with 20 µg/ml human monoclonal antibody in FACS buffer, diluted in 1:2 dilution steps. Cell suspensions were incubated on ice for 1 hr, washed twice with FACS buffer and resuspended with secondary antibody (100 µl/well) donkey-anti-human-PE (Jackson) diluted 1:50 in FACS buffer. The cell suspensions were incubated on ice and in the dark for 30 min, washed twice with FACS buffer and analyzed (FACS, Beckman Coulter). According to the FACS Scatchard analysis, the fluorescence mean was calculated for each measurement. Background staining (=without $1^{st}$ antibody) was subtracted from each fluorescence mean. Scatchard plot with x-value=fluorescence mean and y-value=fluorescence mean/concentration of mAb (nM) was generated. The KD was taken as the absolute value of 1/m of linear equation. FIG. 4 shows a kinetic analysis using the U1-59 antibody of the invention. In the following table 8 affinity measurements for certain antibodies of the invention selected in this manner are provided.

TABLE 7

| clone | KD (nM) |
|---|---|
| U1-38 | n.d. |
| U1-39 | 102 |
| U1-40 | 6.7 |
| U1-41 | 0.18 |
| U1-42 | n.d. |
| U1-43 | 0.57 |
| U1-44 | 4 |
| U1-52 | 16.8 |
| U1-61 | 0.13 |
| U1-62 | 20.4 |
| U1-46 | 13.8 |
| U1-47 | 9.38 |
| U1-49 | 1 |
| U1-50 | 39.3 |
| U1-51 | 131.6 |
| U1-53 | 0.082 |
| U1-55.1 | 3.7 |
| U1-58 | 6.4 |
| U1-59 | 3.69 |
| U1-24 | 0.06 |
| U1-7 | 0.02 |

Example 11

Anti-HER-3 Antibodies of the Invention Induce HER-3 Receptor Endocytosis

HER-3 has been identified as a factor that can influence initiation and progression of hyperproliferative diseases through serving as an important gatekeeper of HER family mediated cell signaling. Thus, if HER-3 is effectively cleared from the cell surface/membrane by receptor internalization, cell signaling and therefore transformation and/or maintenance of cells in malignancy can be ultimately diminished or suppressed.

In order to investigate whether anti-HER-3 antibodies of the invention are capable of inducing accelerated endocytosis of HER-3, the relative amount of HER-3 molecules on the cell surface after 0.5 and 4 hr incubation of the cells with anti-HER-3 antibodies of the invention were compared. $3 \times 10^6$ cells were seeded in normal growth medium in 24-well dish and left to grow overnight. Cells were preincubated with 10 µg/ml anti-HER-3 mAbs in normal growth medium for the indicated times at 37° C. Cells were detached with 10 mM EDTA and incubated with 10 µg/ml anti-HER-3 mAbs in wash buffer (PBS, 3% FCS, 0.04% azide) for 45 min at 4° C. Cells were washed twice with wash buffer, incubated with donkey-anti-human-PE secondary antibody (Jackson) diluted 1:100 for 45 min at 4° C., washed twice with wash buffer and analyzed by FACS (BeckmanCoulter, EXPO).

Data shown in FIG. 5 demonstrate that treatment of cells with anti-HER-3 antibodies leads to internalization of the receptor. Data are shown as % internalization and refer to the reduction of the mean fluorescence intensity of anti-HER3 treated samples relative to control-treated samples.

Example 12

Inhibition of Ligand Binding to Human Cancer Cells SKBr3 by Human Anti-HER-3 Antibodies of the Invention Radioligand competition experiments were performed in order to quantitate the ability of the anti-HER-3 antibodies of the invention to inhibit ligand binding to HER-3 in a cell based assay. Therefore, the HER-3 receptor binding assay was performed with $4 \times 10^5$ SK-BR-3 cells which were incubated with varying concentrations of antibodies for 30 min on ice. 1.25 nM [$I^{125}$]-α-HRG/[$^{125}$I]-β-HRG were added to each well and the incubation was continued for 2 hr on ice. The plates were washed five times, air-dried and counted in a scintillation counter. FIGS. 6a-e show the results of these experiments performed with representative anti-HER-3 antibodies of the invention and demonstrate that the antibodies of the invention are capable of specifically reducing the binding of [$^{125}$I]-α-HRG/[$^{125}$I]-β-HRG to cells expressing endogenous HER-3.

Example 13

Inhibition of Ligand-Induced HER-3 Phosphorylation by Human Anti-HER-3 Antibodies of the Invention ELISA experiments were performed in order to investigate whether the antibodies of the invention are able to block ligand β-HRG-mediated activation of HER-3. Ligand-mediated HER-3 activation was detected by increased receptor tyrosine phosphorylation.

Day 1: 1×96 well dish was coated with 20 µg/ml Collagen I in 0.1 M acetic acid for 4 hr at 37° C. $2.5 \times 10^5$ cells were seeded in normal growth medium Day 2: Cells were starved in 100 µl serum free medium for 24 hr.

Day 3: Cells were preincubated with 10 µg/ml anti-HER-3 mAbs for 1 hr at 37° C. and then treated with 30 ng/ml β-HRG-EGF domain (R&D Systems) for 10 min. Medium was flicked out and cells were fixed with 4% formaldehyde solution in PBS for 1 hr at room temperature. Formaldehyde solution was removed and cells were washed with wash buffer (PBS/0.1% Tween 20). Cells were quenched with 1% $H_2O_2$, 0.1% $NaN_3$ in wash buffer and incubated for 20 min at room temperature, then blocked with NET-Gelantine for 5 hr at 4° C. Primary antibody phospho-HER-3 (Tyr1289) (polyclonal rabbit; Cell signaling #4791; 1:300) was added overnight at 4° C.

Day 4: The plate was washed 3× with wash buffer, then incubated with anti-rabbit-POD diluted 1:3000 in PBS-0.5% BSA was added to each well and incubated for 1.5 hr at room temperature. The plate was washed 3× with wash buffer and once with PBS. Tetramethylbenzidine (TMB, Calbiochem) was added and monitored at 650 nm. The reaction was stopped by addition of 100 µl 250 nM HCl and the absorbance was read at 450 nm with a reference wavelength of 650 nm using a Vmax plate reader (Thermo Lab Systems).

FIG. 7a shows representative results of this experiment, demonstrating that anti-HER-3 antibodies of the invention were able to reduce ligand-mediated HER-3 activation as indicated by decreased receptor tyrosine phosphorylation. Data are shown as percent reduction by therapeutic antibodies relative to a control antibody.

To test potency of mAb U1-53 to inhibit ligand induced HER-3 activation, MCF-7 cells were starved for 24 hr, incubated with mAb U1-53 for 1 hr at 37° C. and stimulated with 10 nM HRG-β for 10 min. Lysates were transferred to 1B4 (mouse anti-HER-3 mAb) ELISA plates and phosphorylation of HER-3 was analysed with antibody 4G10. As shown in FIG. 1b phosphorylation of HER-3 was almost completely inhibited in a dose dependent manner with an IC50 of 0.14 nM.

Example 14

Inhibition of Ligand-Induced p42/p44 MAP-Kinase Phosphorylation by Human Anti-HER-3 Antibodies of the Invention Next ELISA experiments were performed in order to investigate whether the antibodies of the invention are able to block ligand β-HRG-mediated activation of p42/p44 MAP-Kinase. Ligand-mediated HER-3 activation was detected by increased protein (Thr202/Tyr204) phosphorylation.

Day 1: 1×96 well dish was coated with 20 μg/ml Collagen I in 0.1 M acetic acid for 4 hr at 37° C. 3×10$^5$ cells were seeded in normal growth medium Day 2: Cells were starved in 100 μl serum free medium for 24 hr.

Day 3: Cells were preincubated with 5 μg/ml anti-HER-3 mAbs for 1 hr at 37° C. and then treated with 20 ng/ml β-HRG-EGF domain (R&D Systems) for 10 min. Medium was flicked out and cells were fixed with 4% formaldehyde solution in PBS for 1 hr at room temperature. Formaldehyde solution was removed and cells were washed with wash buffer (PBS/0.1% Tween 20). Cells were quenched with 1% $H_2O_2$, 0.1% $NaN_3$ in wash buffer and incubated for 20 min at room temperature, then blocked with PBS/0.5% BSA for 5 hr at 4° C. Primary antibody phospho-p44/p42 MAP Kinase (Thr202/Tyr204) (polyclonal rabbit; Cell signaling #9101; 1:3000) was added overnight at 4° C.

Day 4: The plate was washed 3× with wash buffer, then incubated with anti-rabbit-HRP diluted 1:5000 in PBS-0.5% BSA was added to each well and incubated for 1.5 hr at room temperature. The plate was washed 3× with wash buffer and once with PBS. Tetramethylbenzidine (TMB, Calbiochem) was added and monitored at 650 nm. The reaction was stopped by addition of 100 μl 250 nM HCl and The absorbance was read at 450 nm with a reference wavelength of 650 nm using a Vmax plate reader (Thermo Lab Systems).

FIG. 8 shows representative results of this experiment. The antibodies of the invention were able to reduce ligand-mediated p42/p44 MAP-Kinase activation as indicated by decreased phosphorylation. Data are shown as percent reduction by therapeutic antibodies relative to a control antibody.

Example 15

Inhibition of β-HRG-Induced Phospho-AKT Phosphorylation by Human Anti-HER-3 Antibodies of the Invention In the following ELISA experiment we investigated whether the anti-HER-3 antibodies of the invention are able to block ligand β-HRG-mediated activation of AKT-Kinase. Ligand-mediated AKT activation was detected by increased protein (Ser473) phosphorylation.

Day 1: 1×96 well dish was coated with 20 μg/ml Collagen I in 0.1 M acetic acid for 4 hr at 37° C. 3×10$^5$ cells were seeded in normal growth medium Day 2: Cells were starved in 100 μl serum free medium for 24 hr.

Day 3: Cells were preincubated with 5 μg/ml anti-HER-3 mAbs for 1 hr at 37° C. and then treated with 20 ng/ml β-HRG-EGF domain (R&D Systems) for 10 min. Medium was flicked out and cells were fixed with 4% formaldehyde solution in PBS for 1 hr at room temperature. Formaldehyde solution was removed and cells were washed with wash buffer (PBS/0.1% Tween 20). Cells were quenched with 1% $H_2O_2$, 0.1% $NaN_3$ in wash buffer and incubated for 20 min at room temperature, then blocked with PBS/0.5% BSA for 5 hr at 4° C. Primary antibody phospho-Akt (Ser473) (polyclonal rabbit; Cell signaling #9217; 1:1000) was added overnight at 4° C.

Day 4: The plate was washed 3× with wash buffer, then incubated with anti-rabbit-HRP diluted 1:5000 in PBS-0.5% BSA was added to each well and incubated for 1.5 hr at room temperature. The plate was washed 3× with wash buffer and once with PBS. Tetramethylbenzidine (TMB, Calbiochem) was added and monitored at 650 nm. The reaction was stopped by addition of 100 μl 250 nM HCl and The absorbance was read at 450 nm with a reference wavelength of 650 nm using a Vmax plate reader (Thermo Lab Systems).

FIG. 9 shows representative results of this experiment. The anti-HER-3 antibodies of the invention were able to reduce β-HRG-mediated AKT as indicated by decreased phosphorylation. Data are shown as percent reduction by therapeutic antibodies relative to a control antibody.

Example 16

Inhibition of α-HRG/β-HRG-Mediated MCF7 Cell Proliferation by Human Anti-HER-3 Antibodies of the Invention In vitro experiments were conducted in order to determine the ability of the antibodies of the invention to inhibit HRG-stimulated cell proliferation. 2000 MCF7 cells were seeded in FCS-containing medium on 96-well plates overnight. Cells were preincubated in quadruplicates with antibody diluted in medium with 0.5% FCS for 1 hr at 37° C. Cells were stimulated with 30 ng/ml α- or 20 ng/ml β-HRG (R&D Systems) by adding ligand directly to antibody solution and were then left to grow for 72 hr. AlamarBlue™ (BIOSOURCE) was added and incubated at 37° C. in the dark. Absorbance was measured at 590 nm every 30 min. The data were taken 90 min after addition of alamar blue. The results as indicated in FIG. 10 show that representative antibodies of the invention inhibit HRG-induced cell growth in human cancer cells. Data are shown as percent reduction by therapeutic antibodies relative to a control antibody.

Example 17

Inhibition of β-HRG-Induced MCF7 Cell Migration by Human Anti-HER-3 Antibodies of the Invention Transmigration experiments were performed in order to investigate whether the antibodies of the invention block cell migration. Serum-starved MCF7 cells were preincubated by adding the indicated amount of antibody to the cell suspension and incubating both for 45 min at 37° C. 500 μl cell suspension (50,000 cells) was then placed in the top chamber of collagen 1-coated transwells (BD Falcon, 8 μm pores). 750 μl medium (MEM, amino acids, Na-pyruvate, Pen.-Strept., 0.1% BSA, without fetal calf serum) alone or containing the ligands β-HRG-EGF domain (R&D Systems) were used in the bottom chamber. Cells were left to migrate for 8 hr at 37° C. and were stained with DAPI.

Stained nuclei were counted manually; percent inhibition was expressed as inhibition relative to a control antibody.

FIG. 11 shows the result of the experiment demonstrating that representative anti-HER-3 antibodies of the invention reduce HRG-induced cell migration.

Example 18

Colony Formation Assay (Soft Agar Assay)

Soft agar assays were conducted in order to investigate the ability of the anti-HER-3 antibodies of the invention to inhibit anchorage independent cell growth. The soft agar colony formation assay is a standard in vitro assay to test for transformed cells, as only such transformed cells can grow in soft agar.

750 to 2000 cells (depending on the cell line) were preincubated with indicated antibodies at 10 μg/ml in IMDM medium (Gibco) for 30 min and resuspended in 0.4% Difco noble agar. The cell suspension was plated on 0.75% agarose underlayer containing 20% FCS in quadruplicate in a 96-well plate. Colonies were allowed to form for 14 days and were then stained with 50 μl MTT (0.5 mg/ml in PBS) overnight. FIGS. 12a-i show the results of these experiments performed with three representative antibodies of the invention. These results demonstrate that anti-HER-3 antibodies of the invention reduce anchorage independent cell growth of MDA-MB361 and NCI-ADR breast cancer cells (FIG. 12a,b), MKN-28 gastric cancer (FIG. 12c), HT144 melanoma cells (FIG. 12d), Skov3 ovary carcinoma cells (FIG. 12e), PPC-1 prostate cancer cells (FIG. 12f), BX-PC3 pancreas cancer cells (FIG. 12g), A431 epidermoid carcinoma cells (FIG. 12h) and lung carcinoma cells (FIG. 12i). Colonies were counted with a Scanalyzer HTS camera system (Lemnatec, Wuerselen).

Example 19

Human Anti-HER-3 Antibodies Inhibit Human Breast Carcinoma Growth in Nude Mice

The anti-tumor efficacy of therapeutic antibodies is often evaluated in human xenograft tumor studies. In these studies, human tumors grow as xenografts in immunocompromised mice and therapeutic efficacy is measured by the degree of tumor growth inhibition. In order to determine, if the anti-HER-3 antibodies of the invention interfere with tumor growth of human breast cancer cells in nude mice, $5 \times 10^6$ T47D cells were implanted in female NMRI nude/nude mice. Tumors were subcutaneous, grown on the back of the animal. Treatments began when tumors reached a mean volume of 20 $mm^3$; eight days post implantation. Prior to first treatment, mice were randomized and statistical tests performed to assure uniformity in starting tumor volumes (mean, median and standard deviation) across treatment groups. Treatment started with a loading dose of 50 mg/kg followed by 25 mg/kg injections once a week by intraperitoneal injection. A control arm received doxorubicin (pharmaceutical grade). All animals were supplemented with 0.5 mg/kg/week oestrogen injected i.p.

Details of the treatment groups are given below.

| Gr. | N | 1st Compound | Loading (mg/kg) | Weekly dose (mg/kg) | Route | Schedule |
|---|---|---|---|---|---|---|
| 1. | 10 | PBS | | — | i.p. | once/week |
| 2. | 10 | doxorubicin | | 8 mg/kg | i.v. | once/week* |
| 3. | 10 | U1-53 | 50 mg/kg 20 ml/kg | 25 mg/kg 10 ml/kg | i.p. | once/week |

*doxorubin treatment as described by Boven et al., Cancer Research, 1992.

Data for median tumor volume (FIG. 13) demonstrated that administration of an anti-HER-3 antibody of the invention resulted in reduction of tumor growth.

Example 20

Human Anti-HER-3 Antibodies Inhibit Human Pancreatic Tumor Growth in SCID Mice

To test the therapeutic potential of anti-HER3 antibodies in other solid tumor types the anti-HER-3 antibodies, U1-53 and U1-59, were tested in mice with established tumors derived from the human pancreatic tumor cell line BxPC3. As controls sets of mice treated with either the vehicle control, PBS, or the established therapeutic antibody, Erbitux, were included. $5 \times 10^6$ BxPC3 cells were inoculated subcutaneously without Matrigel into CB17 SCiD mice. Mice bearing established tumors with a mean volume of 140 $mm^2$ received 50 mg/kg of U1-53, U1-59, Erbitux or the equivalent volume of PBS via intraperitoneal injection. Thereafter the mice received once weekly 25 mg/kg injections for the duration of the study.

The results for this experiment are shown in FIG. 14. U1-53 and U1-59 reduced the growth of the human pancreatic tumors in a cytostatic fashion. Notably, in this experiment, U1-53 and U1-59 were more effective than the EGFR-targeting antibody Erbitux at delaying tumor growth. These data demonstrated the therapeutic efficacy of anti-HER-3 antibodies of the invention in comparison to a benchmark therapeutic agent.

Example 21

Combining the Human Anti-HER-3 Antibodies with Anti-EGFR Antibodies Increases Anti-Tumor Activity The monotherapy of hyperproliferative diseases with targeted antibodies is often hampered by problems such as, on the one hand, the development of resistance to drugs, and on the other hand, a change in the antigenicity. For example, loss of antigenicity after prolonged treatment may render tumor cells insensitive to therapeutic antibodies, since those tumor cells that do not express or have lost the targeted antigen have a selective growth advantage. These problems might be evaded by using the antibodies of the invention in combination with a therapeutic antibody that targets a different receptor on the tumor cells, or another antineoplastic agent. Intervening in multiple signaling pathways or even related pathways but at multiple intervention steps might also provide therapeutic benefit. These combined treatment modalities are likely to be more efficacious, because they combine two anti-cancer agents, each operating via a different mechanism of action.

In order to demonstrate the feasibility of the anti-HER-3 antibodies of the invention, U1-53 and U1-59, as suitable combination agents, we compared monotherapeutic administrations of U1-53 or U1-59 with those in which either U1-53 or U1-59 was combined with the anti-EGR specific antibody, Erbitux. $5\times10^6$ BxPC3 cells were inoculated subcutaneously with Matrigel into CB17 SCID mice. After tumor volumes had reached 200 mm$^3$, mice were randomized into individual treatment groups. Weekly intraperitoneal administrations of U1-53, U1-59 and Erbitux as single agents or combinations of either anti-HER3 antibodies with Erbitux or as a cocktail of two anti HER-3 antibodies were performed. All antibodies were dosed at a single loading doses of 50 mg/kg/week, followed by weekly injections of 25 mg/kg for six weeks. Control arms received bi-weekly administrations of Gemcitabine (120 mg/kg), weekly pooled human IgG or weekly vehicle (PBS) injections. The regimens are detailed below.

| Gr. | N | Compound | Loading dose (mg/kg) | Weekly dose (mg/kg) | Route | Schedule |
|-----|---|----------|----------------------|---------------------|-------|----------|
| 4.  | 12 | PBS | 20 ml/kg | 10 ml/kg | q7d | i.p. |
| 5.  | 12 | Pooled human IgG | 50 mg/kg | 25 mg/kg | q7d | i.p. |
| 6.  | 12 | U1-53 | 50 mg/kg | 25 mg/kg | q7d | i.p. |
| 7.  | 12 | U1-59 | 50 mg/kg | 25 mg/kg | q7d | i.p. |
| 8.  | 12 | Erbitux | 50 mg/kg | 25 mg/kg | q7d | i.p. |
| 9.  | 12 | U1-53 + Erbitux | 25 mg/kg each | 12.5 mg/kg each | q7d | i.p. |
| 10. | 12 | U1-59 + Erbitux | 25 mg/kg each | 12.5 mg/kg each | q7d | i.p. |
| 11. | 12 | U1-53 + U1-59 | 25 mg/kg each | 12.5 mg/kg each | q7d | i.p. |
| 12. | 12 | Gemcitabine | none | 120 mg/kg | 2x weekly | ip |

The results for this experiment are shown in FIG. 15. Antibodies U1-53 and U1-59, when administered as single agents, delayed the growth of the human pancreatic tumors to the same degree as Gemcitabine, which is often used as a standard anti-pancreatic cancer chemotherapy. Co-administration of Erbitux with U1-53 or U1-59 resulted in a significantly greater reduction of tumor growth than observed with either single agent administration of U1-53, U1-59 or Erbitux. Thus, a beneficial therapeutic response can be achieved by combining the anti-HER-3 antibodies of the invention with suitable antibodies that target separate tumor antigens.

In summary, the anti-HER-3 antibodies of the invention have potent therapeutic efficacy against human tumors in vivo. They can be effectively combined with other anti-neoplastic therapeutics for increased anti-tumor activity.

Example 22

Human Anti-HER-3 Antibodies Inhibit Human Melanoma Tumor Growth in nu/nu Mice

Members of the erbB family of receptors, including Her3, are abnormally expressed in a large variety of epithelial cancers and they are known to play important roles in the growth and survival of many these solid tumors. These tumors include melanomas, head and neck squamous cell cancers, non-small cell lung cancers and prostate, glioma, gastric, breast, colorectal, pancreatic, ovarian cancers. In order to verify, that the anti-Her3 antibodies of the invention are not restricted in their anti-cancer activity to individual tumor types, e.g. pancreatic cancers (see Example 21), but can be used as therapeutics against many HER-3-dependent tumors, we tested U1-53 and U1-59 in additional xenograft studies.

One example is shown in FIG. 16. $5\times10^5$ human melanoma cells, HT144, were injected subcutaneously into CB17 SCID mice, followed by immediate subsequent intraperitoneal injection of 50 mg/kg of U1-53 and U1-59, the equivalent volume of PBS or Dacarbacin (DITC) at 200 mg/kg. Thereafter, mice received 25 mg/kg of U1-53 or U1-59 once weekly, whereas DITC was given once every two weeks at 200 mg/kg.

The median tumor volumes from each treatment group are shown in FIG. 16. Administration of the antibodies of the invention resulted in growth reduction of the human melanomas when compared to tumors that had been treated with the vehicle control. These results demonstrate that the antibodies of the invention are not restricted in their therapeutic potential and target a wide variety of HER-3 expressing cancers.

Example 23

Human Anti-HER-3 Antibodies Inhibit Growth of Colon Carcinoma Xenografts in Mice HT-29 human colon carcinoma cells were suspended in medium with 2:1 ratio of Matrigel to a final concentration of $10\times10^6$ cells/ml. 0.2 ml of cell suspension were injected s.c. into the right flank of 4-5-week-old CD1 nu/nu mice. A total of 95 mice were used.

The mice were randomly assigned to control and treatment groups. The treatment started on the same day. Duration of treatment was 29 days. Upon completion of the study, three tumours per group were collected 3 hours after administration of treatment. The tumours were fast-frozen and kept at −80° C.

The following treatment protocol was carried out:

Control group: non-specific human IgG 25 mg/kg, twice weekly, intraperitoneal

Treatment group: antibody U1-53, 25 mg/kg, twice weekly, intraperitoneal

Treatment group: antibody U1-7, 25 mg/kg, twice weekly, intraperitoneal

Treatment group: antibody U1-59, 25 mg/kg, twice weekly, intraperitoneal

Treatment group 5-FU: 5-fluorouracil, 50 mg/kg, 9 d×5, intraperitoneal

The median tumor volumes from each group are shown in FIG. 17. Administration of the antibodies of the invention resulted in growth reduction of the HT-29 colon carcinoma tumors when compared to tumors that had been treated with non-specific human IgG1.

Example 24

Human Anti-HER-3 Antibodies Inhibit Lung Cancer Growth in Mice

Calu-3 human non-small cell lung cancer cells were suspended in medium with 1:1 ratio of Matrigel to a final concentration of $5\times10^6$ cells/ml. 0.05 ml of cell suspension were injected s.c. into the right flank of 9-week-old female CB17 scid mice. A total of 60 mice were used.

The mice were randomly selected to control and treatment groups. Treatment started on the same day. The duration of treatment was 32 days.

The following treatment protocol was carried out:

PBS Vehicle Group hG control group: non-specific human IgG: 25 mg/kg, twice weekly, intraperitoneal Treatment group antibody U1-53, 25 mg/kg, twice weekly, intraperitoneal Treatment group antibody U1-7, 25 mg/kg, twice weekly, intraperitoneal Treatment group antibody U1-59, 25 mg/kg, twice weekly, intraperitoneal The median tumor volumes from each control and treatment group are shown in FIG. 18. Administration of the antibodies of the invention resulted in growth reduction of the human non-small lung cancer xenografts when compared to tumors that had been treated with the PBS vehicle control or non-specific human IgG.

Example 25

Human Anti-HER-3 Antibodies Inhibit Human Pancreatic Tumor Growth in Balb/C-Mice Human pancreatic BxPC3 tumor cells were suspended in medium with a 2:1 ratio of Matrigel to a final concentration of $5 \times 10^6$ cells per ml. 0.2 ml of cell suspension were injected s.c. into the right flank of 5-7-week-old female Balb/c nu/nu mice. A total of 100 mice were used.

The mice were randomly distributed into control and treatment groups. The treatment started on the same day. The treatment duration was 27 days.

The following treatment protocol was carried out:

hIgG control group: non-specific human IgG2, 25 mg/kg, twice weekly, intraperitoneal Treatment group antibody U1-53, 25 mg/kg, twice weekly, intraperitoneal Treatment group antibody U1-7, 25 mg/kg, twice weekly, intraperitoneal Treatment group antibody U1-59, 25 mg/kg, weekly, intraperitoneal Gemzar treatment group, gemcitabine, 80 mg/kg, weekly, intraperitoneal The median tumor volumes from each control and treatment group are shown in FIG. 19. Administration of the antibodies of the invention resulted in growth reduction of the human pancreatic tumors when compared to tumors that had been treated with non-specific human IgG or with Gemzar.

The inhibition of HER-3 in the human pancreatic tumors could also be shown in a pharmacodynamic experiment. The BxPC3 tumor xenografts were grown as described above. 3 mice were treated with 500 μg of an IgG1 control antibody and 3 mice were treated with 500 μg of the anti-HER-3 antibody U1-59. The mice were treated on day 1 and day 4 and then sacrificed on day 5 to measure the antibody-dependent inhibition of HER-3 phosphorylation (pHER-3).

The tumors were homogenized in a standard RIPA buffer with protease inhibitors. 50 μg clear lysate was separated on a 4-20% Tris-glycine gel, transferred onto a nitrocellulose membrane and blocked in 3% bovine serum albumin (BSA). Immunoblotting was performed using an anti-pHER-3 antibody (antibody 21D3, Cell Signaling technology). An anti-actin antibody (AB a-2066, Sigma) was used as a control.

The expression was detected by enhanced chemiluminescence (Amersham Biosciences, Piscataway, N.J.). The images were captured with the Versadoc 5000 Imaging System (BioRad, Hercules, Calif.).

The results are shown in FIG. 20. After administration of the human anti-HER-3-antibody U1-59 phosphorylation of HER-3 was no longer detectable. Thus, the antibodies of the invention are capable of significantly reducing HER-3 activation in human pancreatic tumor cells.

Example 26

Use of Anti-HER-3 Antibodies of the Invention as a Diagnostic Agent

Anti-HER-3 mAb can be used in the diagnostic of malignant diseases. HER-3 is expressed on tumor cells in a very distinct way compared to normal tissue and, therefore, an expression analysis of HER-3 would assist in the primary diagnosis of solid tumors, staging and grading of solid tumors, assessment of prognostic criteria for proliferative diseases and neoplasias and risk management in patients with HER-3 positive tumors.

A. Detection of HER-3 Antigen in a Sample

An Enzyme-Linked Immunosorbent Assay (ELISA) for the detection of HER-3 antigen in a sample is developed. In the assay, wells of a microtiter plate, such as a 96-well microtiter plate or a 384-well microtiter plate, are adsorbed for several hr with a first fully human monoclonal antibody directed against the HER-3 antigen. The immobilized antibody serves as a capture antibody for any of the HER-3 antigen that may be present in a test sample. The wells are rinsed and treated with a blocking agent such as milk protein or albumin to prevent nonspecific adsorption of the analyte.

Subsequently the wells are treated with a test sample suspected of containing the HER-3 antigen, or with a solution containing a standard amount of the HER-3 antigen. Such a sample is, for example, a serum sample from a subject suspected of having levels of circulating HER-3 antigen considered to be diagnostic of a pathology. After rinsing away the test sample or standard, the wells are treated with a second fully human monoclonal anti-HER-3 antibody of the invention that is labelled by conjugation with biotin. The labeled anti-HER-3 antibody serves as a detecting antibody. After rinsing away excess secondary antibody, the wells are treated with avidin-conjugated horseradish peroxidase (HRP) and a suitable chromogenic substrate. The concentration of the HER-3 antigen in the test samples is determined by comparison with a standard curve developed from the standard samples.

B. Detection of HER3-Antigen in Immunohistochemistry (IHC)

In order to determine HER3-antigen in tissue sections by IHC, Paraffin-embedded tissues are first deparaffinized in xylene for 2×5 min and then hydrated with 100% Ethanol 2×3 min, 95% Ethanol 1 min and rinsed in distilled water. Antigenic epitopes masked by formalin-fixation and paraffin-embedding are exposed by epitope unmasking, enzymatic digestion or saponin. For epitope unmasking paraffin sections are heated in a steamer, water bath or microwave oven for 2040 min in a epitope retrieval solution as for example 2N HCl solution (pH 1.0). In the case of an enzyme digestion, tissue sections are incubated at 37° C. for 10-30 minutes in different enzyme solutions such as proteinase K, trypsin, pronase, pepsin etc.

After rinsing away the epitope retrieval solution or excess enzyme, tissue sections are treated with a blocking buffer to prevent unspecific interactions. The primary antibody is incubated at appropriate dilutions in dilution buffer for 1 hour at room temperature or overnight. Excess primary antibody is rinsed away and sections are incubated in peroxidase blocking solution for 10 min at room temperature. After another washing step, tissue sections are incubated with a secondary antibody labelled with a group that might serve as an anchor for an enzyme. Examples therefore are biotin labelled secondary antibodies that are recognized by streptavidin coupled horseradish peroxidase. Detection of said antibody/enzyme complex is achieved by incubating with a suitable chromogenic substrate.

C. Determination of HER-3 Antigen Concentration in Serum of Patients

A sandwich ELISA is developed to quantify HER-3 levels in human serum. The two fully human monoclonal anti-HER-3 antibodies used in the sandwich ELISA, recognized different domains on the HER-3 molecule and do not compete for binding, for example, see Example 8. The ELISA is performed as follows: 50 µl of capture ant-HER-3 antibody in coating buffer (0.1 M $NaHCO_3$, pH 9.6) at a concentration of 2 µg/ml were coated on ELISA plates (Fisher). After incubation at 4° C. overnight, the plates are treated with 200 µl of blocking buffer (0.5% BSA, 0.1% Tween 20, 0.01% Thimerosal in PBS) for 1 hr at 25° C. The plates were washed (3×) using 0.05% Tween 20 in PBS (washing buffer, WB). Normal or patient sera (Clinomics, Bioreclaimation) are diluted in blocking buffer containing 50% human serum. The plates are incubated with serum samples overnight at 4° C., washed with WB, and then incubated with 100 µl/well of biotinylated detection anti-HER-3 antibody for 1 hr at 25° C. After washing, the plates are incubated with HRP-Streptavidin for 15 min, washed as before, and then treated with 100 µl/well of o-phenylenediamine in $H_2O_2$ (Sigma developing solution) for color generation. The reaction is stopped with 50 µl/well of $H_2SO_4$ (2 M) and analyzed using an ELISA plate reader at 492 nm. The concentration of HER-3 antigen in serum samples is calculated by comparison to dilutions of purified HER-3 antigen using a four parameter curve fitting program.

Staging of Cancer in a Patient

Based on the results set forth and discussed under items A, B and C, through use of the present invention, it is possible to stage a cancer in a subject based on expression levels of the HER-3 antigen. For a given type of cancer, samples of blood are taken from subjects diagnosed as being at various stages in the progression of the disease, and/or at various points in the therapeutic treatment of the cancer. The concentration of the HER-3 antigen present in the blood samples is determined using a method that specifically determines the amount of the antigen that is present. Such a method includes an ELISA method, such as the method described under items A. and B. Using a population of samples that provides statistically significant results for each stage of progression or therapy, a range of concentrations of the HER-3 antigen that may be considered characteristic of each stage is designated.

In order to stage the progression of the cancer in a subject under study, or to characterize the response of the subject to a course of therapy, a sample of blood is taken from the subject and the concentration of the HER-3 antigen present in the sample is determined. The concentration so obtained is used to identify in which range of concentrations the value falls. The range so identified correlates with a stage of progression or a stage of therapy identified in the various populations of diagnosed subjects, thereby providing a stage in the subject under study.

Example 27

Uses of Anti-HER-3 Antibodies and Antibody Conjugates of the Invention for Treatment or Prevention of Hyperproliferative Diseases Many solid tumors are driven by HER family mediated signalling and it has been demonstrated that HER-3 is a crucial partner through complex formation between HER-1, HER-2 and HER-4. Therefore, a reduction or elimination of HER-3 mediated signaling would impact all other HER family members and impair cell signaling leading to a wide window of therapeutic interventions and potential in combination therapy with other targeted agents, biologics and cytotoxic agents. Thus, anti-HER-3 antibodies of the invention can be used for treatment of certain hyperproliferative or HER-3 associated disorders, that are based on a number of factors as for example HER-3 expression. Tumor types as breast cancer, gastrointestinal cancer, pancreas cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, other HER-3 expressing or overexpressing cancers, appear to present preferred indications, but indications are not limited to those on the preceding list. In addition the following groups of patients will benefit from anti-HER-3 directed mAb treatment:

Patients with resistance to anti-HER-2 mAb treatment

Patients not eligible for the treatment with anti-HER-2 mAb

Patients with resistance to anti-HER-1 mAb or small molecule anti-EGFR inhibitor Patients with non-small cell lung cancer resistant to erlotinib or gefitinib.

Anti-HER-3 antibodies of the invention would be used either as a monotherapy or in combination with one or more agent in a so called "combination therapy". Said combination therapy may include, but is not limited to, agents that were specified previously in the invention. Combination therapy with anti-HER3 antibodies and other agents may extend patient survival, time to tumor progression or quality of patient life. Protocol and administration design will address therapeutic efficacy as well as the ability to reduce the usual doses of standard therapies, as for example chemo- or radiation therapy.

Treatment of Humans with Anti-HER-3 Antibodies of the Invention

To determine the in vivo effects of anti-HER-3 antibody treatment in human patients with tumors, such human patients are injected over a certain amount of time with an effective amount of anti-HER-3 antibody of the invention. At periodic times during the treatment, the human patients are monitored to determine whether their tumors progress, in particular, whether the tumors grow and metastasize.

A tumor patient treated with the anti-HER-3 antibodies of the invention has a lower level of tumor growth and/or metastasis compared to the level of tumor growth and metastasis in tumor patients treated with the current standard of care therapeutics.

Treatment with Anti-HER-3 Antibody Conjugates of the Invention

To determine the in vivo effects of anti-HER-3 antibody conjugates of the invention, human patients or animals exhibiting tumors are injected over a certain amount of time with an effective amount of anti-HER-3 antibody conjugate of the invention. For example, the anti-HER-3 antibody conjugate administered is DM1-anti-HER-3 antibody conjugate, an auristatin-anti-HER-3 antibody conjugate or radioisotope-anti-HER-3 antibody conjugate. At periodic times during the treatment, the human patients or animals are monitored to determine whether their tumors progress, in particular, whether the tumors grow and metastasize.

A human patient or animal exhibiting tumors and undergoing treatment with, for example, DM1-anti-HER-3 antibody or radioisotope-anti-HER-3 antibody conjugates has a lower level of tumor growth and metastasis when compared to a control patient or animal exhibiting tumors and undergoing treatment with an alternate therapy. Control DM1-antibodies that may be used in animals include conjugates comprising DM1 linked to antibodies of the same isotype of the anti-HER-3 antibodies of the invention, but more specifically, not having the ability to bind to HER-3 tumor antigen. Control radioisotope-antibodies that may be used in animal tests include conjugates comprising radioisotope linked to antibodies of the same isotype of the anti-HER-3 antibodies of the invention, but more specifically, not having the ability to bind to HER-3 tumor antigen. Note: the control conjugates would not be administered to humans.

General Remarks

The foregoing written specification is considered to be sufficient to enable one skilled in the art to practice the invention. The present invention is not to be limited in scope by the construct deposited, since the deposited embodiment is intended as a single illustration of certain objects of the invention and any constructs that are functionally equivalent are within the scope of this invention. The deposit of material herein does not constitute an admission that the written description herein contained is inadequate to enable the practice of any object of the invention, including the best mode thereof, nor is it to be construed as limiting the scope of the claims to the specific illustrations that it represents.

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

Furthermore, unless otherwise defined, scientific and technical terms used in connection with the present invention shall have the meanings that are commonly understood by those of ordinary skill in the art. Moreover, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g. electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g. Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

INCORPORATION BY REFERENCE

All references cited herein, including patents, patent applications, papers, text books, and the like, including the references cited therein, are hereby incorporated herein by reference in their entirety.

TABLE OF CDR SEQUENCES

| Ab chain | Pat ID: | SEQ ID NO: | CDR1 | SEQ ID NO: | CDR2 | SEQ ID NO: | CDR3 |
| --- | --- | --- | --- | --- | --- | --- | --- |
| heavy | U1-1 | 235 | GGSINSGDYYWS | 258 | YIYYSGSTYYNPSLKS | 283 | ADYDFWSGYFDY |
| light | U1-1 | 318 | RASQGIRNDLG | 343 | AASSLQS | 360 | LQHNSYPWT |
| heavy | U1-2 | 236 | GGSISSGDYYWS | 259 | YIYYSGSTYYNPSLRS | 283 | ADYDFWSGYFDY |
| light | U1-2 | 318 | RASQGIRNDLG | 343 | AASSLQS | 361 | LQHNGYPWT |
| heavy | U1-3 | 237 | GGSISSGGYYWS | 258 | YIYYSGSTYYNPSLKS | 284 | DGYDSSGYYHGYFDY |
| light | U1-3 | 319 | KSSQSVLYSSNNKNYLA | 344 | WASTRES | 362 | QQYYSTPLT |
| heavy | U1-4 | 236 | GGSISSGDYYWS | 258 | YIYYSGSTYYNPSLKS | 283 | ADYDFWSGYFDY |
| light | U1-4 | 318 | RASQGIRNDLG | 343 | AASSLQS | 363 | LQHNNYPWT |
| heavy | U1-5 | 236 | GGSISSGDYYWS | 258 | YIYYSGSTYYNPSLKS | 283 | ADYDFWSGYFDY |
| light | U1-5 | 318 | RASQGIRNDLG | 343 | AASSLQS | 364 | LQHNTYPWT |
| heavy | U1-6 | 236 | GGSISSGDYYWS | 258 | YIYYSGSTYYNPSLKS | 285 | ADYDFWNGYFDY |
| light | U1-6 | 318 | RASQGIRNDLG | 343 | AASSLQS | 364 | LQHNTYPWT |
| heavy | U1-7 | 236 | GGSISSGDYYWS | 258 | YIYYSGSTYYNPSLKS | 283 | ADYDFWSGYFDY |
| light | U1-7 | 320 | RASQDIRNDLG | 343 | AASSLQS | 360 | LQHNSYPWT |

TABLE OF CDR SEQUENCES

| Ab chain | Pat ID: | SEQ ID NO: | CDR1 | SEQ ID NO: | CDR2 | SEQ ID NO: | CDR3 |
|---|---|---|---|---|---|---|---|
| heavy | U1-8 | 238 | GYTLTELSMY | 260 | GFDPEDGETIYAQKFQG | 286 | GWNYVFDY |
| light | U1-8 | 321 | RSSQSLLHSNGYNYLD | 345 | LDSHRAS | 365 | MQALQTPLT |
| heavy | U1-9 | 236 | GGSISSGDYYWS | 258 | YIYYSGSTYYNPSLKS | 285 | ADYDFWNGYFDY |
| light | U1-9 | 320 | RASQDIRNDLG | 343 | AASSLQS | 360 | LQHNSYPWT |
| heavy | U1-10 | 236 | GGSISSGDYYWS | 258 | YIYYSGSTYYNPSLKS | 283 | ADYDFWSGYFDY |
| light | U1-10 | 318 | RASQGIRNDLG | 343 | AASSLQS | 363 | LQHNNYPWT |
| heavy | U1-11 | 236 | GGSISSGDYYWS | 258 | YIYYSGSTYYNPSLKS | 283 | ADYDFWSGYFDY |
| light | U1-11 | 318 | RASQGIRNDLG | 343 | AASSLQS | 364 | LQHNTYPWT |
| heavy | U1-12 | 236 | GGSISSGDYYWS | 258 | YIYYSGSTYYNPSLKS | 283 | ADYDFWSGYFDY |
| light | U1-12 | 318 | RASQGIRNDLG | 343 | AASSLQS | 363 | LQHNNYPWT |
| heavy | U1-13 | 237 | GGSISSGGYYWS | 258 | YIYYSGSTYYNPSLKS | 287 | EDDGMDV |
| light | U1-13 | 322 | RSSQSLLHSNGYNYLE | 346 | LGSNRAS | 366 | MQALQTPIT |
| heavy | U1-14 | 236 | GGSISSGDYYWS | 258 | YIYYSGSTYYNPSLKS | 283 | ADYDFWSGYFDY |
| light | U1-14 | 318 | RASQGIRNDLG | 343 | AASSLQS | 364 | LQHNTYPWT |
| heavy | U1-15 | 239 | GGSVSSGGYYWS | 261 | YIYYSGSTNYNPSLKS | 288 | DGDVDTAMVDAFDI |
| light | U1-15 | 323 | RASQSLSGNYLA | 347 | GASSRAT | 367 | QQYDRSPLT |
| heavy | U1-16 | 236 | GGSISSGDYYWS | 258 | YIYYSGSTYYNPSLKS | 283 | ADYDFWSGYFDY |
| light | U1-16 | 318 | RASQGIRNDLG | 343 | AASSLQS | 360 | LQHNSYPWT |
| heavy | U1-17 | 236 | GGSISSGDYYWS | 262 | YIYYSGSTYYNSSLKS | 283 | ADYDFWSGYFDY |
| light | U1-17 | 318 | RASQGIRNDLG | 343 | AASSLQS | 360 | LQHNSYPWT |
| heavy | U1-18 | 236 | GGSISSGDYYWS | 258 | YIYYSGSTYYNPSLKS | 283 | ADYDFWSGYFDY |
| light | U1-18 | 318 | RASQGIRNDLG | 343 | AASSLQS | 360 | LQHNSYPWT |
| heavy | U1-19 | 236 | GGSISSGDYYWS | 258 | YIYYSGSTYYNPSLKS | 289 | GDYDFWSGEFDY |
| light | U1-19 | | | | sequence not available | | |
| heavy | U1-20 | 237 | GGSISSGGYYWS | 263 | YIYDSGSTYYNPSLKS | 290 | DQGQDGYSYGYGYYYGMDV |
| light | U1-20 | 324 | QASQDISNYLN | 348 | VASNLET | 368 | QQCDNLPLT |
| heavy | U1-21 | 236 | GGSISSGDYYWS | 258 | YIYYSGSTYYNPSLKS | 283 | ADYDFWSGYFDY |
| light | U1-21 | 320 | RASQDIRNDLG | 349 | AASRLQS | 360 | LQHNSYPWT |
| heavy | U1-22 | 236 | GGSISSGDYYWS | 258 | YIYYSGSTYYNPSLKS | 283 | ADYDFWSGYFDY |
| light | U1-22 | 318 | RASQGIRNDLG | 350 | AASSLQN | 360 | LQHNSYPWT |
| heavy | U1-23 | 236 | GGSISSGDYYWS | 258 | YIYYSGSTYYNPSLKS | 283 | ADYDFWSGYFDY |
| light | U1-23 | 318 | RASQGIRNDLG | 343 | AASSLQS | 360 | LQHNSYPWT |
| heavy | U1-24 | 236 | GGSISSGDYYWS | 258 | YIYYSGSTYYNPSLKS | 285 | ADYDFWNGYFDY |
| light | U1-24 | 318 | RASQGIRNDLG | 343 | AASSLQS | 363 | LQHNNYPWT |
| heavy | U1-25 | 236 | GGSISSGDYYWS | 258 | YIYYSGSTYYNPSLKS | 283 | ADYDFWSGYFDY |
| light | U1-25 | 318 | RASQGIRNDLG | 350 | AASSLQN | 360 | LQHNSYPWT |
| heavy | U1-26 | 236 | GGSISSGDYYWS | 258 | YIYYSGSTYYNPSLKS | 291 | ADYDFWSGYFDF |
| light | U1-26 | 318 | RASQGIRNDLG | 343 | AASSLQS | 361 | LQHNGYPWT |
| heavy | U1-27 | 236 | GGSISSGDYYWS | 258 | YIYYSGSTYYNPSLKS | 291 | ADYDFWSGYFDF |
| light | U1-27 | 318 | RASQGIRNDLG | 343 | AASSLQS | 361 | LQHNGYPWT |
| heavy | U1-28 | 236 | GGSISSGDYYWS | 258 | YIYYSGSTYYNPSLKS | 292 | ADYDFWSGYFDS |
| light | U1-28 | 318 | RASQGIRNDLG | 343 | AASSLQS | 361 | LQHNGYPWT |
| heavy | U1-29 | 240 | GFTFNSYDMH | 264 | VIWYDGSNKYYADSVKG | 293 | DRLCTNGVCYEDYGMDV |
| light | U1-29 | 324 | QASQDISNYLN | 351 | DASNLET | 369 | QHYDTLPLT |
| heavy | U1-30 | 236 | GGSISSGDYYWS | 265 | YIYYSGTTYYNPSLKS | 283 | ADYDFWSGYFDY |
| light | U1-30 | 325 | RAGQGIRNDLG | 343 | AASSLQS | 360 | LQHNSYPWT |
| heavy | U1-31 | 241 | GYTFTNYGIS | 266 | WISAYDGYRNYAQKLQG | 294 | DVQDYGDYDFDY |
| light | U1-31 | 326 | RASQSISSYLN | 343 | AASSLQS | 370 | QQSYSTPIT |
| heavy | U1-32 | 236 | GGSISSGDYYWS | 265 | YIYYSGTTYYNPSLKS | 283 | ADYDFWSGYFDY |
| light | U1-32 | 325 | RAGQGIRNDLG | 343 | AASSLQS | 360 | LQHNSYPWT |
| heavy | U1-33 | 236 | GGSISSGDYYWS | 258 | YIYYSGSTYYNPSLKS | 295 | ADYDFWSGHFDC |
| light | U1-33 | 327 | RASQGIRDDLG | 352 | AESSLQS | 371 | LQHHSYPWT |
| heavy | U1-34 | 241 | GYTFTNYGIS | 266 | WISAYDGYRNYAQKLQG | 294 | DVQDYGDYDFDY |
| light | U1-34 | 326 | RASQSISSYLN | 343 | AASSLQS | 370 | QQSYSTPIT |
| heavy | U1-35 | 242 | GFTFSDYYMS | 267 | YISSSGNNIYHADSVKG | 296 | ERYSGYDDPDGFDI |
| light | U1-35 | 328 | QASQDISNYLS | 351 | DASNLET | 372 | QQYDNPPCS |
| heavy | U1-36 | 243 | GGSISSGYYYWS | 268 | YIYYSGTTYYNPSFKS | 297 | ADYDFWSGHFDY |
| light | U1-36 | 318 | RASQGIRNDLG | 343 | AASSLQS | 360 | LQHNSYPWT |
| heavy | U1-37 | 244 | GYTFTSYGIS | 269 | WISAYDGHTNYAQKLQG | 298 | DPHDYSNYEAFDF |
| light | U1-37 | 326 | RASQSISSYLN | 343 | AASSLQS | 370 | QQSYSTPIT |
| heavy | U1-38 | 245 | GFSLSTSGVGVG | 270 | LIYWNDDKRYSPSLKS | 299 | RDEVRGFDY |
| light | U1-38 | 329 | RSSQSLVYSDGYTYLH | 353 | KVSNWDS | 373 | MQGAHWPIT |

-continued

TABLE OF CDR SEQUENCES

| Ab chain | Pat ID: | SEQ ID NO: | CDR1 | SEQ ID NO: | CDR2 | SEQ ID NO: | CDR3 |
|---|---|---|---|---|---|---|---|
| heavy | U1-39 | 246 | GFTVSSNYMS | 271 | VIYSGGSTYYADSVKG | 300 | GQWLDV |
| light | U1-39 | 321 | RSSQSLLHSNGYNYLD | 354 | LGFHRAS | 374 | RQALQTPLT |
| heavy | U1-40 | 237 | GGSISSGGYYWS | 272 | YIYSSGSTYYNPSLKS | 301 | DRELELYYYYGMDV |
| light | U1-40 | 330 | RSSQSLLYSNGYNYLD | 346 | LGSNRAS | 365 | MQALQTPLT |
| heavy | U1-41 | 237 | GGSISSGGYYWS | 258 | YIYYSGSTYYNPSLKS | 302 | DRELEGYSNYYGVDV |
| light | U1-41 | 331 | RASQAISNYLN | 343 | AASSLQS | 375 | QQNNSLPIT |
| heavy | U1-42 | 247 | GYSFTSYWIG | 273 | IIYPGDSDTRYSPSFQG | 303 | HENYGDYNY |
| light | U1-42 | 332 | RASQSIRSYLN | 343 | AASSLQS | 376 | QQSNGSPLT |
| heavy | U1-43 | 237 | GGSISSGGYYWS | 259 | YIYYSGSTYYNPSLRS | 304 | DREREWDDYGDPQGMDV |
| light | U1-43 | 333 | RASQSISSYLH | 343 | AASSLQS | 377 | QQSYSNPLT |
| heavy | U1-44 | 247 | GYSFTSYWIG | 274 | IIWPGDSDTIYSPSFQG | 303 | HENYGDYNY |
| light | U1-44 | 332 | RASQSIRSYLN | 343 | AASSLQS | 378 | QQSISSPLT |
| heavy | U1-45 | 248 | GYTFTSYDIN | 275 | WMNPNSGDTGYAQVFQG | 305 | FGDLPYDYSYYEWFDP |
| light | U1-45 | 326 | RASQSISSYLN | 343 | AASSLQS | 379 | QQSYSTPLT |
| heavy | U1-46 | 249 | GDSVSSNSAAWN | 276 | RTYYRSKWYNDYAVSVKS | 306 | DLYDFWSGYPYYYGMDV |
| light | U1-46 | | | | sequence not available | | |
| heavy | U1-47 | 249 | GDSVSSNSAAWN | 276 | RTYYRSKWYNDYAVSVKS | 307 | DYYGSGSFYYYYGMDV |
| light | U1-47 | 326 | RASQSISSYLN | 355 | AASNLQS | 380 | QQSYSTPRT |
| heavy | U1-48 | 250 | GGSISSYYWS | 277 | HIYTSGSTNYNPSLKS | 308 | EAIFGVGPYYYYGMDV |
| light | U1-48 | | | | sequence not available | | |
| heavy | U1-49 | 251 | GYTFTGYYMH | 278 | WINPNIGGTNCAQKFQG | 309 | GGRYSSSWSYYYYGMDV |
| light | U1-49 | 334 | KSSQSLLLSDGGTYLY | 356 | EVSNRFS | 381 | MQSMQLPIT |
| heavy | U1-50 | 239 | GGSVSSGGYYWS | 261 | YIYYSGSTNYNPSLKS | 310 | GGDSNYEDYYYYGMDV |
| light | U1-50 | 335 | RASQSISIYLH | 343 | AASSLQS | 382 | QQSYTSPIT |
| heavy | U1-51 | 250 | GGSISSYYWS | 261 | YIYYSGSTNYNPSLKS | 311 | DSSYYDSSGYYLYYYAMDV |
| light | U1-51 | 319 | KSSQSVLYSSNNKNYLA | 344 | WASTRES | 383 | QQYYTTPLT |
| heavy | U1-52 | 237 | GGSISSGGYYWS | 279 | NIYYSGSTYYNPSLKS | 312 | GGTGTNYYYYGMDV |
| light | U1-52 | 336 | RASQSVSSSYLA | 357 | GASSWAT | 384 | QQYGSSPLT |
| heavy | U1-53 | 252 | GFTFSIYSMN | 280 | YISSSSSTIYYADSVKG | 313 | DRGDFDAFDI |
| light | U1-53 | 337 | QASQDITNYLN | 351 | DASNLET | 385 | QQCENFPIT |
| heavy | U1-55.1 | 253 | GGSVSSGGYYWN | 281 | YINYSGSTNYNPSLKS | 301 | DRELELYYYYGMDV |
| light | U1-55.1 | | | | will be same as U1-55 | | |
| heavy | U1-55 | | | | will be same as U1-55.1 | | |
| light | U1-55 | 338 | RSSQSLLYSNGYKYLD | 346 | LGSNRAS | 366 | MQALQTPIT |
| heavy | U1-57.1 | | | | will be same as U1-57 | | |
| light | U1-57.1 | 338 | RSSQSLLYSNGYKYLD | 346 | LGSNRAS | 366 | MQALQTPIT |
| heavy | U1-57 | 254 | GGSVSSGGYYWN | 281 | YINYSGSTNYNPSLKS | 301 | DRELELYYYYGMDV |
| light | U1-57 | | | | will be same as U1-57.1 | | |
| heavy | U1-58 | 255 | GFTFSSYGMH | 264 | VIWYDGSNKYYADSVKG | 314 | AARLDYYYGMDV |
| light | U1-58 | 339 | RASQSINSYLN | 358 | GASGLQS | 386 | QQSYSSPLT |
| heavy | U1-59 | 256 | GGSFSGYYWS | 282 | EINHSGSTNYNPSLKS | 315 | DKWTWYFDL |
| light | U1-59 | 340 | RSSQSVLYSSSNRNYLA | 344 | WASTRES | 387 | QQYYSTPRT |
| heavy | U1-61.1 | 257 | GVSISSGGYYWS | 258 | YIYYSGSTYYNPSLKS | 316 | DSESEYSSSSNYGMDV |
| light | U1-61.1 | | | | will be the same as U1-61.1 | | |
| heavy | U1-61 | 257 | GVSISSGGYYWS | 258 | YIYYSGSTYYNPSLKS | 316 | DSESEYSSSSNYGMDV |
| light | U1-61 | 341 | RASQTISSYLN | 359 | AASSLQG | 377 | QQSYSNPLT |
| heavy | U1-62 | 247 | GYSFTSYWIG | 273 | IIYPGDSDTRYSPSFQG | 317 | QMAGNYYYGMDV |
| light | U1-62 | 342 | RASQSVISIYLA | 347 | GASSRAT | 388 | QQYGSSPCS |

The invention claimed is:

1. An isolated binding protein that binds to HER-3, wherein said binding protein comprises a heavy chain amino acid sequence that comprises a CDRH1 selected from the group consisting of SEQ ID NOs:236, 251, 252, and 256, a CDRH2 selected from the group consisting of SEQ ID NOs: 258, 278, 280, and 282, and a CDRH3 selected from the group consisting of SEQ ID NOs:283, 285, 309, 313, and 315, and a light chain amino acid sequence that comprises a CDRL1 selected from the group consisting of SEQ ID NOs:320, 334, 337, and 340, a CDRL2 selected from the group consisting of SEQ ID NOs: 343, 356, 351, and 344, and a CDRL3 selected from the group consisting of SEQ ID NOs:360, 381, 385, and 387.

2. An isolated binding protein that binds to HER3-, comprising:
a heavy chain amino acid sequence selected from the group consisting of SEQ ID NOs: 42, 70, 92, and 96.

3. The isolated binding protein of claim 2 comprising:
a light chain amino acid sequence selected from the group consisting of SEQ ID NOs: 44, 56, 72, 94, and 98.

4. An isolated binding protein that binds HER-3, comprising:
a heavy chain amino acid sequence selected from the group consisting of SEQ ID NOs: 42, 54, 70, 92, and 96; and
a light chain amino acid sequence selected from the group consisting of SEQ ID NOs: 44, 56, 72, 94, and 98.

5. An isolated binding protein that binds to HER-3, comprising the heavy chain amino acid sequence of SEQ ID NO:42 and the light chain amino acid sequence of SEQ ID NO:44.

6. An isolated binding protein that binds to HER-3, comprising the heavy chain amino acid sequence of SEQ ID NO:54 and the light chain amino acid sequence of SEQ ID NO:56.

7. The isolated binding protein that binds to HER-3, comprising the heavy chain amino acid sequence of SEQ ID NO:70 and the light chain amino acid sequence of SEQ ID NO:72.

8. The isolated binding protein of any of claims 1-4, or 5-7, wherein the binding protein is directed against the extracellular domain of HER-3.

9. The isolated binding protein of any one of claims 1-4, or 5-7, wherein the binding of the binding protein to HER-3 reduces HER-3-mediated signal transduction.

10. The isolated binding protein of any one of claims 1-4, or 5-7, wherein the binding of the binding protein to HER-3 reduces HER-3 phosphorylation.

11. The isolated binding protein of any one of claims 1-4, or 5-7, wherein the binding of the binding protein to HER-3 reduces cell proliferation.

12. The isolated binding protein of any one of claims 1-4, or 5-7, wherein the binding of the binding protein to HER-3 reduces cell migration.

13. The isolated binding protein of any one of claims 1-4, or 5-7, wherein the binding of the binding protein to HER-3 increases the downregulation of HER-3.

14. The isolated binding protein of any one of claims 1-4, or 5-7, which is an antibody.

15. The isolated binding protein of claim 14, wherein the antibody is a monoclonal antibody, a polyclonal antibody, a recombinant antibody, a humanized antibody, a human antibody, a chimeric antibody, a multispecific antibody, or an antibody fragment thereof.

16. The isolated binding protein of claim 15, wherein the antibody fragment is a Fab fragment, a Fab' fragment, a F(ab')2 fragment, a Fv fragment, a diabody, or a single chain antibody molecule.

17. The isolated binding protein of claim 14, wherein said isolated binding protein is of the IgG1-, IgG2-, IgG3- or IgG4-type.

18. The isolated binding protein of claim 14, wherein the binding protein is coupled to a labelling group.

19. The isolated binding protein of claim 18, wherein the labelling group is a radioisotope or radionuclide, a fluorescent group, an enzymatic group, a chemiluminescent group, a biotinyl group, or a predetermined polypeptide epitope.

20. The isolated binding protein of claim 14, wherein the binding protein is coupled to an effector group.

21. The isolated binding protein of claim 20, wherein the effector group is a radioisotope or radionuclide, a toxin, or a therapeutic or chemotherapeutic group.

22. The isolated binding protein of claim 21, wherein the therapeutic or chemotherapeutic group is selected from the group consisting of calicheamicin, auristatin-PE, geldanamycin, maytansine and derivatives thereof.

23. A pharmaceutical composition comprising as an active agent at least one isolated binding protein of any one of claims 2-4, or 5-7, and a pharmaceutically acceptable carrier, diluent or adjuvant.

24. The composition of claim 23 for therapeutic use.

25. The composition of claim 23 for diagnostic use.

26. A kit comprising the isolated binding protein of any one of claims 1-4 or 5-7.

27. The kit of claim 26, comprising a further therapeutic agent.

28. The kit of claim 27 wherein the further therapeutic agent is an antineoplastic agent.

29. The kit of claim 28, wherein the anti-neoplastic agent is an anti-tumor antibody or a chemotherapeutic agent.

* * * * *

UNITED STATES PATENT AND TRADEMARK OFFICE
CERTIFICATE OF CORRECTION

| | | |
|---|---|---|
| PATENT NO. | : 7,705,130 B2 | Page 1 of 1 |
| APPLICATION NO. | : 11/649722 | |
| DATED | : April 27, 2010 | |
| INVENTOR(S) | : Rothe et al. | |

It is certified that error appears in the above-identified patent and that said Letters Patent is hereby corrected as shown below:

In column 287, line 54, in Claim 2, delete "HER3-," and insert -- HER-3, --, therefor.

In column 288, line 49, in Claim 8, delete "any of" and insert -- any one of --, therefor.

In column 289, line 10, in Claim 16, delete "F(ab')2" and insert -- $F(ab')_2$ --, therefor.

Signed and Sealed this
Eighteenth Day of January, 2011

David J. Kappos
*Director of the United States Patent and Trademark Office*

SEQUENCE LISTING

<160> NUMBER OF SEQ ID NOS: 390

<210> SEQ ID NO 1
<211> LENGTH: 342
<212> TYPE: DNA
<213> ORGANISM: Artificial Sequence
<220> FEATURE:
<223> OTHER INFORMATION: Artificially synthesized sequence.

<400> SEQUENCE: 1

```
gaggtgcagc tggtggagtc tggaggaggc ttgatccagc ctgggggtc cctgagactc        60 tcctgtgcag cctctgggtt caccgtcagt agcaactaca tgagctgggt ccgccaggct      120
ccagggaagg ggctggattg ggtctcagtt atttatagcg gtggtagcac atactacgca      180
gactccgtga agggccgatt caccatctcc agagacaatt ccaagaacac gctgtatctt      240
caaatgaaca gcctgagagc cgaggacacg gccgtgtatt actgtgcgag agggcagtgg      300
ctggacgtct ggggccaagg gaccacggtc accgtctcct ca                         342
```

<210> SEQ ID NO 2
<211> LENGTH: 114
<212> TYPE: PRT
<213> ORGANISM: Artificial Sequence
<220> FEATURE:
<223> OTHER INFORMATION: Artificially synthesized sequence.

<400> SEQUENCE: 2

```
Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Asp Trp Val
         35                  40                  45

Ser Val Ile Tyr Ser Gly Gly Ser Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gln Trp Leu Asp Val Trp Gly Gln Gly Thr Thr Val Thr Val
            100                 105                 110

Ser Ser
```

<210> SEQ ID NO 3
<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 3

```
gatattgtga tgactcagtc tccactctcc ctgcccgtca cccctggaga gccggcctcc       60
atctcctgca ggtcaagtca gagcctcctg catagtaatg gatacaacta tttggattgg     120
tacctgcaga ggccagggca gtctccacaa ctcctgttct atttgggttt tcatcgggcc     180
tccggggtcc ctgacaggtt cagtggcagt ggatcaggca cagatttac actgaaaatc     240 agcagagtgg aggctgagga tgttggggtt tattactgca ggcaagctct acaaactccg     300
```

```
ctcactttcg gcggagggac caaggtggag atcaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 4

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Arg Pro Gly Gln Ser
        35                  40                  45

Pro Gln Leu Leu Phe Tyr Leu Gly Phe His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Arg Gln Ala
                85                  90                  95

Leu Gln Thr Pro Leu Thr Phe Gly Gly Gly Thr Lys Val Glu Ile Lys
            100                 105                 110
```

<210> SEQ ID NO 5
<211> LENGTH: 374
<212> TYPE: DNA
<213> ORGANISM: Artificial Sequence
<220> FEATURE:
<223> OTHER INFORMATION: Artificially synthesized sequence.

<400> SEQUENCE: 5

```
caggtgcagc tgcaggagtc gggcccagga ctggtgaagc cttcacagac cctgtccctc     60
acctgtactg tctctggtgg ctccatcagc agtggtggtt actactggag ctggatccgc    120
cagcacccag ggaagggcct ggagtggatt gggtacatct attccagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagat    300
agggaactgg aactttacta ctactactac ggtatggacg tctggggcca agggaccacg    360
gtcaccgtct cctc                                                     374
```

<210> SEQ ID NO 6
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 6

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Ser Ser Gly Ser Thr Tyr Tyr Asn Pro Ser
    50                  55                  60
```

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120

<210> SEQ ID NO 7
<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 7
gatattgtga tgactcagtc tccactctcc ctgcccgtca cccctggaga gccggcctcc      60
atctcctgca ggtctagtca gagcctcctg tatagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagatttac actgaaaatc     240 agcagagtgg aggctgagga tgttgggatt tattactgca tgcaagctct acaaactccg    300
ctcactttcg gcggagggac caaggtggag atcaaa                              336

<210> SEQ ID NO 8
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 9
<211> LENGTH: 357
<212> TYPE: DNA
<213> ORGANISM: Artificial Sequence
<220> FEATURE:
<223> OTHER INFORMATION: Artificially synthesized sequence.

<400> SEQUENCE: 9
cagatcacct tgaaggagtc tggtcctacg ctggtgaaac ccacacagac cctcacgctg      60
acctgcacct tctctgggtt ctcactcagc actagtggag tgggtgtggg ctggatccgt    120

```
cagcccccag gaaaggccct ggactggctt gcactcattt attggaatga tgataagcgc    180
tacagcccat ctctgaagag caggctcacc atcaccaagg acacctccaa aaaccaggtg    240
gtccttacaa tgaccaacat ggatcttgtg gacacagcca catattactg tgtacacaga    300
gacgaagttc gagggtttga ctactggggc caggaaccc tggtcaccgt ctcctca       357
```

<210> SEQ ID NO 10
<211> LENGTH: 119
<212> TYPE: PRT
<213> ORGANISM: Artificial Sequence
<220> FEATURE:
<223> OTHER INFORMATION: Artificially synthesized sequence.

<400> SEQUENCE: 10

```
Gln Ile Thr Leu Lys Glu Ser Gly Pro Thr Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Asp
         35                  40                  45

Trp Leu Ala Leu Ile Tyr Trp Asn Asp Asp Lys Arg Tyr Ser Pro Ser
     50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Leu Val Asp Thr Ala Thr Tyr Tyr
                 85                  90                  95

Cys Val His Arg Asp Glu Val Arg Gly Phe Asp Tyr Trp Gly Gln Gly
            100                 105                 110

Thr Leu Val Thr Val Ser Ser
        115
```

<210> SEQ ID NO 11
<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 11

```
gatgttgtga tgactcagtc tccactctcc ctgcccgtca cccttggaca gccggcctcc     60
atctcctgca ggtctagtca aagcctcgta tacagtgatg gatacaccta cttgcattgg    120
tttcagcaga ggccaggcca atctccaagg cgccttattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtgc acactggccg    300
atcaccttcg gccaagggac acgactggag attaaa                              336
```

<210> SEQ ID NO 12
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 12

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30
```

Asp Gly Tyr Thr Tyr Leu His Trp Phe Gln Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ala His Trp Pro Ile Thr Phe Gly Gln Gly Thr Arg Leu Glu Ile Lys
            100                 105                 110

<210> SEQ ID NO 13
<211> LENGTH: 374
<212> TYPE: DNA
<213> ORGANISM: Artificial Sequence
<220> FEATURE:
<223> OTHER INFORMATION: Artificially synthesized sequence.

<400> SEQUENCE: 13
caggtgcagc tgcaggagtc gggcccagga ctggtgaagc cttcacagac cctgtccctc      60
acctgcactg tctctggtgg ctccatcagc agtggtgggt actactggag ctggatccgc     120
cagcacccag ggaagggcct ggagtggatt gggtacatct attacagtgg agcacctac     180 tacaacccgt ccctcaagag tcgagttacc atatcagtag acacgtctaa gaaccagttc     240
tccctgaagc tgagctctgt gactgccgcg gacacggccg tgtatttctg tgcgagagat     300
cgggaacttg agggttactc caactactac ggtgtggacg tctggggcca agggaccacg     360
gtcaccgtct cctc                                                       374

<210> SEQ ID NO 14
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 14

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Asp Arg Glu Leu Glu Gly Tyr Ser Asn Tyr Tyr Gly Val
            100                 105                 110

Asp Val Trp Gly Gln Gly Thr Thr Val Thr Val Ser
        115                 120

<210> SEQ ID NO 15
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 15

```
gacatccaga tgacccagtc tccatcctcc ctgtctgcat ctgtaggaga cagagtcacc    60
atcacttgcc gggcaagtca ggccattagc aactatttaa attggtatca gcagaaacca   120
gggaaagccc ctaagctcct gatctatgct gcatccagtt tgcaaagtgg ggtcccatca   180
aggttcagtg gcagtggatc tgggacagat tcactctca ccatcagcag cctgcagcct   240
gaagattttg caacttatta ctgtcaacag aataatagtc tcccgatcac cttcggccaa   300
gggacacgac tggagattaa a                                              321
```

<210> SEQ ID NO 16
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 16

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Ala Ile Ser Asn Tyr
             20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Asn Asn Ser Leu Pro Ile
                 85                  90                  95
Thr Phe Gly Gln Gly Thr Arg Leu Glu Ile Lys
            100                 105
```

<210> SEQ ID NO 17
<211> LENGTH: 354
<212> TYPE: DNA
<213> ORGANISM: Artificial Sequence
<220> FEATURE:
<223> OTHER INFORMATION: Artificially synthesized sequence.

<400> SEQUENCE: 17

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct ccaaggcca ggtcaccatc tcagccgaca gtccatcag caccgcctac   240
ctgcagtgga gcagcctgaa ggcctcggac accgccatgt attactgtgc gagacatgaa   300
aactacggtg actacaacta ctggggccag ggaaccctgg tcaccgtctc ctca         354
```

<210> SEQ ID NO 18
<211> LENGTH: 118
<212> TYPE: PRT
<213> ORGANISM: Artificial Sequence
<220> FEATURE:
<223> OTHER INFORMATION: Artificially synthesized sequence.

<400> SEQUENCE: 18

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Asn Tyr Gly Asp Tyr Asn Tyr Trp Gly Gln Gly Thr
            100                 105                 110

Leu Val Thr Val Ser Ser
            115

<210> SEQ ID NO 19
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 19
gacatccaga tgacccagtc tccatcctcc ctgtctgcat ctgtcggaga cagagtcacc    60
atcacttgcc gggcaagtca gagcattcgc agctatttaa attggtatca gcagaaacca   120
gggaaagccc ctaagctcct gatctatgct gcttccagtt tgcaaagtgg ggtcccatca   180
aggttcagtg gcagtggatc tgggacagat ttcactctca ccatcagcag tctgcaacct   240
gaagattttg cactttactg ctgtcaacag agtaacggtt ccccgctcac tttcggcgga   300
gggaccaagg tggagatcaa a                                             321

<210> SEQ ID NO 20
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Cys Cys Gln Gln Ser Asn Gly Ser Pro Leu
                85                  90                  95

Thr Phe Gly Gly Gly Thr Lys Val Glu Ile Lys
            100                 105

<210> SEQ ID NO 21
<211> LENGTH: 380
<212> TYPE: DNA
<213> ORGANISM: Artificial Sequence
<220> FEATURE:
<223> OTHER INFORMATION: Artificially synthesized sequence.

<400> SEQUENCE: 21

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag gaagggcct ggagtggatt gggtacatct attacagtgg agcacctac       180
tacaacccgt ccctcaggag tcgagttacc atatcagtag acacgtctaa gaaccagttc     240
tccctgaagc tgagctctgt gactgccgcg gacacggccg tgtattactg tgcgagagat     300
agagagagag agtgggatga ttacggtgac ccccaaggta tggacgtctg gggccaaggg     360
accacggtca ccgtctcctc                                                  380
```

<210> SEQ ID NO 22
<211> LENGTH: 126
<212> TYPE: PRT
<213> ORGANISM: Artificial Sequence
<220> FEATURE:
<223> OTHER INFORMATION: Artificially synthesized sequence.

<400> SEQUENCE: 22

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                 85                  90                  95

Cys Ala Arg Asp Arg Glu Arg Glu Trp Asp Asp Tyr Gly Asp Pro Gln
            100                 105                 110

Gly Met Asp Val Trp Gly Gln Gly Thr Thr Val Thr Val Ser
        115                 120                 125
```

<210> SEQ ID NO 23
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 23

```
gacatccaga tgacccagtc tccatcctcc ctgtctgcat ctgtaggaga cagagtcacc      60
atcacttgcc gggcaagtca gagcattagc agctatttac attggtatca gcagaaacca    120
gggaaagccc ctaagctcct gatccatgct gcatccagtt tacaaagtgg ggtcccatca    180
aggttcagtg gcagtggatc tgggacagat ttcactctca ccatcagtag tctgcaacct    240
gaagattttg caacttacta ctgtcaacag agttacagta acccgctcac tttcggcgga    300
gggaccaagg tggagatcca a                                               321
```

<210> SEQ ID NO 24
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Leu
                85                  90                  95

Thr Phe Gly Gly Gly Thr Lys Val Glu Ile Gln
            100                 105

<210> SEQ ID NO 25
<211> LENGTH: 354
<212> TYPE: DNA
<213> ORGANISM: Artificial Sequence
<220> FEATURE:
<223> OTHER INFORMATION: Artificially synthesized sequence.

<400> SEQUENCE: 25
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctggcctg gtgactctga taccatatac    180
agcccgtcct tccaaggcca ggtcaccatc tcagccgaca gtccatcag caccgcctac     240
ctgcagtgga gcagcctgaa ggcctcggac accgccatgt attactgtgc gagacatgaa    300
aactacggtg actacaacta ctgggggccag ggaaccctgg tcaccgtctc ctca         354

<210> SEQ ID NO 26
<211> LENGTH: 118
<212> TYPE: PRT
<213> ORGANISM: Artificial Sequence
<220> FEATURE:
<223> OTHER INFORMATION: Artificially synthesized sequence.

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Trp Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys 85                  90                  95
Ala Arg His Glu Asn Tyr Gly Asp Tyr Asn Tyr Trp Gly Gln Gly Thr
                100                 105                 110

Leu Val Thr Val Ser Ser
        115

<210> SEQ ID NO 27
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 27
gacatccaga tgacccagtc tccatcctcc ctgtctgcat ctgtgggaga cagagtcacc      60
atcacttgcc gggcaagtca gagcattcga agttatttaa attggtatca gcagaaaccg    120
gggaatgccc ctaaactcct gatctatgct gcatccagtt tgcaaagtgg ggtcccatca    180
aggttcagtg gcagtggatc tgggacagat ttcactctca ccatcagcag tctgcaacct    240
gaagattttg cactttacta ctgtcaacag agtatcagtt ccccgctcac tttcggcgga    300
gggaccaagg tggagatcaa a                                              321

<210> SEQ ID NO 28
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 28

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Arg Ser Tyr
             20                  25                  30

Leu Asn Trp Tyr Gln Gln Lys Pro Gly Asn Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Leu Tyr Tyr Cys Gln Gln Ser Ile Ser Ser Pro Leu
                 85                  90                  95

Thr Phe Gly Gly Gly Thr Lys Val Glu Ile Lys
            100                 105

<210> SEQ ID NO 29
<211> LENGTH: 374
<212> TYPE: DNA
<213> ORGANISM: Artificial Sequence
<220> FEATURE:
<223> OTHER INFORMATION: Artificially synthesized sequence.

<400> SEQUENCE: 29
caggtgcagc tggtgcagtc tggggctgag gtgaagaagc ctggggcctc agtgaaggtc      60
tcctgcaagg cttctggata caccttcacc agttatgata tcaactgggt gcgacaggcc    120
actggacaag gcttgagtg gatgggatgg atgaaccota acagtggtga cactggctat    180
gcacaggtgt tccagggcag agtcaccatg acctggaaca cctccataag cacagcctac    240

```
atggaactga gcagcctgag atctgaggac acggccgtgt attactgtgc gagatttggg      300
gatctcccgt atgactacag ttactacgaa tggttcgacc cctggggcca gggaaccctg      360
gtcaccgtct cctc                                                         374
```

<210> SEQ ID NO 30
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 30

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asp Thr Gly Tyr Ala Gln Val Phe
    50                  55                  60

Gln Gly Arg Val Thr Met Thr Trp Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gly Asp Leu Pro Tyr Asp Tyr Ser Tyr Tyr Glu Trp Phe
            100                 105                 110

Asp Pro Trp Gly Gln Gly Thr Leu Val Thr Val Ser
        115                 120
```

<210> SEQ ID NO 31
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 31

```
gacatccaga tgacccagtc tccatcctcc ctgtctgcat ctgtaggaga cagagtcacc       60
atcacttgcc gggcaagcca gagcattagc agctatttaa attggtatca gcagagacca      120
gggaaagccc ctaagctcct gatctatgca catccagtt tgcaaagtgg ggtcccatca       180
aggttcagtg gcagtggatc tgggacagat ttcactctca ccatcagcag tctgcaacct      240
gaagattttg caacttacta ctgtcaacag agttacagta ccccgctcac tttcggcgga      300
gggaccaagg tggagatcaa a                                                 321
```

<210> SEQ ID NO 32
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 32

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Arg Pro Gly Lys Ala Pro Lys Leu Leu Ile
```

-continued

```
                    35                  40                  45
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105
```

<210> SEQ ID NO 33
<211> LENGTH: 386
<212> TYPE: DNA
<213> ORGANISM: Artificial Sequence
<220> FEATURE:
<223> OTHER INFORMATION: Artificially synthesized sequence.

<400> SEQUENCE: 33

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc aagtggtat   180 aatgattatg cagtatctgt gaaaagtcga ataaccatca cccagacac atccaagaac   240 cagttctccc tgcagctgaa ctctgtgact cccgaggaca cggctgtgta ttactgtgca   300
agagatctct acgattttg gagtggttat ccctactact acggtatgga cgtctggggc   360
caagggacca cggtcaccgt ctcctc                                        386
```

<210> SEQ ID NO 34
<211> LENGTH: 128
<212> TYPE: PRT
<213> ORGANISM: Artificial Sequence
<220> FEATURE:
<223> OTHER INFORMATION: Artificially synthesized sequence.

<400> SEQUENCE: 34

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Leu Tyr Asp Phe Trp Ser Gly Tyr Pro Tyr
            100                 105                 110

Tyr Tyr Gly Met Asp Val Trp Gly Gln Gly Thr Thr Val Thr Val Ser
        115                 120                 125
```

<210> SEQ ID NO 35
<211> LENGTH: 383
<212> TYPE: DNA
<213> ORGANISM: Artificial Sequence
<220> FEATURE:
<223> OTHER INFORMATION: Artificially synthesized sequence.

<400> SEQUENCE: 35

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct gagtggctg ggaaggacat actacaggtc caagtggtat    180
aatgattatg cagtatctgt gaaaagtcga ataaccatca acccagacac atccaagaac   240
cagttctccc tgcagctgaa ctctgtgact cccgaggaca cggctgtgta ttactgtgca   300
agagattact atggttcggg gagtttctac tactactacg gtatggacgt ctggggccaa   360
gggaccacgg tcaccgtctc ctc                                           383
```

<210> SEQ ID NO 36
<211> LENGTH: 127
<212> TYPE: PRT
<213> ORGANISM: Artificial Sequence
<220> FEATURE:
<223> OTHER INFORMATION: Artificially synthesized sequence.

<400> SEQUENCE: 36

```
Gln Val Gln Leu Gln Gln Ser Gly Pro Gly Leu Val Lys Pro Ser Gln
  1               5                  10                  15
Thr Leu Ser Leu Thr Cys Ala Ile Ser Gly Asp Ser Val Ser Ser Asn
             20                  25                  30
Ser Ala Ala Trp Asn Trp Ile Arg Gln Ser Pro Ser Arg Gly Leu Glu
         35                  40                  45
Trp Leu Gly Arg Thr Tyr Tyr Arg Ser Lys Trp Tyr Asn Asp Tyr Ala
     50                  55                  60
Val Ser Val Lys Ser Arg Ile Thr Ile Asn Pro Asp Thr Ser Lys Asn
 65                  70                  75                  80
Gln Phe Ser Leu Gln Leu Asn Ser Val Thr Pro Glu Asp Thr Ala Val
                 85                  90                  95
Tyr Tyr Cys Ala Arg Asp Tyr Tyr Gly Ser Gly Ser Phe Tyr Tyr Tyr
            100                 105                 110
Tyr Gly Met Asp Val Trp Gly Gln Gly Thr Thr Val Thr Val Ser
        115                 120                 125
```

<210> SEQ ID NO 37
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 37

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaaggtcct gatctatgct gcatccaatt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcggac gttcggccaa   300
gggaccaagg tggaaatcaa a                                             321
```

<210> SEQ ID NO 38
<211> LENGTH: 107
<212> TYPE: PRT
<213> ORGANISM: Artificial Sequence
<220> FEATURE:

-continued

<223> OTHER INFORMATION: Artificially synthesized sequence.

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

<210> SEQ ID NO 39
<211> LENGTH: 371
<212> TYPE: DNA
<213> ORGANISM: Artificial Sequence
<220> FEATURE:
<223> OTHER INFORMATION: Artificially synthesized sequence.

<400> SEQUENCE: 39
caggtgcagc tgcaggagtc gggcccagga ctggtgaagc cttcggagac cctgtccctc     60
acctgcactg tctctggtgg ctccatcagt agttactact ggagctggat ccggcagccc    120
gccgggaagg gactggagtg gattgggcat atctatacca gtgggagcac caactacaac    180
ccctccctca gagtcgagt caccatgtca gtagacacgt ccaagaacca gttctccctg    240
aagctgagct ctgtgaccgc cgcggacacg gccgtgtatt actgtgcgag agaagcgatt    300
tttggagtgg cccctactac tactacggt atggacgtct ggggccaagg gaccacggtc    360
accgtctcct c                                                         371

<210> SEQ ID NO 40
<211> LENGTH: 123
<212> TYPE: PRT
<213> ORGANISM: Artificial Sequence
<220> FEATURE:
<223> OTHER INFORMATION: Artificially synthesized sequence.

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly His Ile Tyr Thr Ser Gly Ser Thr Asn Tyr Asn Pro Ser Leu Lys
50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Ile Phe Gly Val Gly Pro Tyr Tyr Tyr Tyr Gly Met Asp
            100                 105                 110

Val Trp Gly Gln Gly Thr Thr Val Thr Val Ser
        115                 120

<210> SEQ ID NO 41
<211> LENGTH: 377
<212> TYPE: DNA
<213> ORGANISM: Artificial Sequence
<220> FEATURE:
<223> OTHER INFORMATION: Artificially synthesized sequence.

<400> SEQUENCE: 41
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccca atattggtgg cacaaactgt     180
gcacagaagt tcagggcag gtcaccatg accagggaca cgtccatcag cacagcctac     240
atggagctga gcaggctgag atctgacgac acggccgtgt attactgtgc gagaggggga     300
cggtatagca gcagctggtc ctactactac tacggtatgg acgtctgggg ccaagggacc     360
acggtcaccg tctcctc                                                    377

<210> SEQ ID NO 42
<211> LENGTH: 125
<212> TYPE: PRT
<213> ORGANISM: Artificial Sequence
<220> FEATURE:
<223> OTHER INFORMATION: Artificially synthesized sequence.

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ile Gly Gly Thr Asn Cys Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Arg Tyr Ser Ser Ser Trp Ser Tyr Tyr Tyr Tyr Gly
            100                 105                 110

Met Asp Val Trp Gly Gln Gly Thr Thr Val Thr Val Ser
        115                 120                 125

<210> SEQ ID NO 43
<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 43
gatattctga tgacccagac tccactctct ctgtccgtca cccctggaca gccggcctcc      60
atctcctgca agtctagtca gagcctcctg cttagtgatg gagggaccta tttgtattgg     120
tacctgcaga agccaggcca gcctccacag ctcctgatct atgaagtttc caaccgttc     180 tctggagtgc cagataggtt cagtggcagc gggtcaggga cagatttcac actgaaaatc     240
agccgggtgg aggctgagga tgttggggtt tattactgca tgcaaagtat gcagcttccg    300
atcaccttcg gccaagggac acgactggaa attaaa                              336

<210> SEQ ID NO 44
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 44

Asp Ile Leu Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Leu Ser
            20                  25                  30

Asp Gly Gly Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Met Gln Leu Pro Ile Thr Phe Gly Gln Gly Thr Arg Leu Glu Ile Lys
            100                 105                 110

<210> SEQ ID NO 45
<211> LENGTH: 380
<212> TYPE: DNA
<213> ORGANISM: Artificial Sequence
<220> FEATURE:
<223> OTHER INFORMATION: Artificially synthesized sequence.

<400> SEQUENCE: 45
caggtgcagc tgcaggagtc gggcccagga ctggtgaagc cttcggagac cctgtccctc    60
acctgcactg tctctggtgg ctccgtcagc agtggtggtt actactggag ctggatccgg   120
cagcccccag ggaagggact ggagtggatt gggtatatct attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg tgcgagaggg   300
ggggacagta actacgagga ttactactac tactacggta tggacgtctg gggccaaggg   360
accacggtca ccgtctcctc                                                380

<210> SEQ ID NO 46
<211> LENGTH: 126
<212> TYPE: PRT
<213> ORGANISM: Artificial Sequence
<220> FEATURE:
<223> OTHER INFORMATION: Artificially synthesized sequence.

<400> SEQUENCE: 46

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

```
Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Gly Asp Ser Asn Tyr Glu Asp Tyr Tyr Tyr Tyr Tyr
            100                 105                 110

Gly Met Asp Val Trp Gly Gln Gly Thr Thr Val Thr Val Ser
            115                 120                 125

<210> SEQ ID NO 47
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 47
gacatccaga tgacccagtc tccatcctcc ctgtctgcat ctgtaggaga cagagtcacc     60
atcacttgcc gggcaagtca gagcattagc atctatttac attggtatca gcagaaacca    120
gggaaagccc ctaagctctt gatctctgct gcatccagtt tgcaaagtgg ggtcccgtca    180
aggttcagtg gcagtggatc tgggacagat ttcactctca ccatcagaag tctgcaacct    240
gaagattttg caacttacta ctgtcaacag agttacactt ccccgatcac cttcggccaa    300
gggacacgac tggagattaa a                                              321

<210> SEQ ID NO 48
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 48

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ile Tyr
                 20                  25                  30

Leu His Trp Tyr Gln Gln Lys Pro Gly Lys Ala Pro Lys Leu Leu Ile
             35                  40                  45

Ser Ala Ala Ser Ser Leu Gln Ser Gly Val Pro Ser Arg Phe Ser Gly
 50                  55                  60

Ser Gly Ser Gly Thr Asp Phe Thr Leu Thr Ile Arg Ser Leu Gln Pro
 65                  70                  75                  80

Glu Asp Phe Ala Thr Tyr Tyr Cys Gln Gln Ser Tyr Thr Ser Pro Ile
                 85                  90                  95

Thr Phe Gly Gln Gly Thr Arg Leu Glu Ile Lys
            100                 105

<210> SEQ ID NO 49
<211> LENGTH: 380
<212> TYPE: DNA
<213> ORGANISM: Artificial Sequence
<220> FEATURE:
<223> OTHER INFORMATION: Artificially synthesized sequence.

<400> SEQUENCE: 49
caggtgcagc tgcaggagtc gggcccagga ctggtgaagc cttcggagac cctgtccctc     60
```

-continued

```
acctgcactg tctctggtgg ctccatcagt agttactact ggagctggat ccggcagccc    120
ccagggaagg gactggagtg gattgggtat atctattaca gtgggagcac caactacaac    180
ccctccctca agagtcgagt caccatatca gtagacacgt ccaagcacca gttctccctg    240
aagctgagct ctgtgaccgc tgcggacacg gccgtgtatt actgtgcgag agattcgagt    300
tactatgata gtagtggtta ttacttatac tactacgcta tggacgtctg gggccaaggg    360
accacggtca ccgtctcctc                                                380
```

<210> SEQ ID NO 50
<211> LENGTH: 126
<212> TYPE: PRT
<213> ORGANISM: Artificial Sequence
<220> FEATURE:
<223> OTHER INFORMATION: Artificially synthesized sequence.

<400> SEQUENCE: 50

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Ser Tyr Tyr Asp Ser Ser Gly Tyr Tyr Leu Tyr Tyr Tyr
            100                 105                 110

Ala Met Asp Val Trp Gly Gln Gly Thr Thr Val Thr Val Ser
        115                 120                 125

<210> SEQ ID NO 51
<211> LENGTH: 339
<212> TYPE: DNA
<213> ORGANISM: Artificial Sequence
<220> FEATURE:
<223> OTHER INFORMATION: Artificially synthesized sequence.

<400> SEQUENCE: 51

```
gacatcgtga tgacccagtc tccagactcc ctggctgtgt ctctgggcga gagggccacc    60
atcaactgca gtccagcca gagtgtttta tacagctcca acaataagaa ctacttagct    120
tggtaccagc agaaaccagg acagcctcct aagctgctca tttcctgggc atctacccgg    180
gaatccgggg tccctgaccg attcagtggc agcgggtctg ggacagattt cactctcacc    240
atcagcagcc tgcaggctga agatgtggca gtttattact gtcagcaata ttatactact    300
cctctcactt tcggccctgg gaccaaagtg gatatcaaa                           339
```

<210> SEQ ID NO 52
<211> LENGTH: 113
<212> TYPE: PRT
<213> ORGANISM: Artificial Sequence
<220> FEATURE:
<223> OTHER INFORMATION: Artificially synthesized sequence.

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Ser Trp Ala Ser Thr Arg Glu Ser Gly Val
50                      55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Pro Gly Thr Lys Val Asp Ile
            100                 105                 110

Lys

<210> SEQ ID NO 53
<211> LENGTH: 357
<212> TYPE: DNA
<213> ORGANISM: Artificial Sequence
<220> FEATURE:
<223> OTHER INFORMATION: Artificially synthesized sequence.

<400> SEQUENCE: 53
gaggtgcaac tggtggagtc tgggggaggc ttggtacagc ctggggggtc cctgagactc      60
tcctgtgcag cctctggatt caccttcagt atctatagca tgaactgggt ccgccaggct     120
ccagggaagg ggctggagtg ggtttcatac attagtagta gtagtagtac catatactac     180
gcagactctg tgaagggccg attcaccatc tccagagaca atgccaagaa ctcactgtat     240
ctgcaaatga acagcctgag agacgaggac acggctgtgt attactgtgc gagagatagg     300
ggtgacttcg atgctttga tatctggggc caagggacaa tggtcaccgt ctcttca         357

<210> SEQ ID NO 54
<211> LENGTH: 119
<212> TYPE: PRT
<213> ORGANISM: Artificial Sequence
<220> FEATURE:
<223> OTHER INFORMATION: Artificially synthesized sequence.

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Arg Gly Asp Phe Asp Ala Phe Asp Ile Trp Gly Gln Gly
            100                 105                 110

Thr Met Val Thr Val Ser Ser
        115

<210> SEQ ID NO 55
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 55

```
gacatccaga tgacccagtc tccatcctcc ctgtctgcat ctgtaggaga cagagtcacc      60
atcacttgcc aggcgagtca ggacattacc aactatttga attggtatca gcagaaacca     120
gggaaagccc ctaagctcct gatctacgat gcatccaatt tggaaacagg gtcccatca     180 aggttcagtg aagtggatc tgggacagat tttactttca ccatcagcag cctgcagcct     240
gaagatattg caacatataa ctgtcaacag tgtgaaaatt tccgatcac cttcggccaa     300 gggacacgac tggagattaa a                                               321
```

<210> SEQ ID NO 56
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Asn Cys Gln Gln Cys Glu Asn Phe Pro Ile
                85                  90                  95

Thr Phe Gly Gln Gly Thr Arg Leu Glu Ile Lys
            100                 105
```

<210> SEQ ID NO 57
<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 57

```
gatattgtga tgactcagtc tccactctcc ctgcccgtca cccctggaga gccggcctcc      60
atctcctgca ggtctagtca gagcctcctg tatagtaatg gatacaagta tttggattgg     120
tacctgcaga agccagggca gtctccacag ctcctgatct atttgggttc taatcgggcc     180
tccggggtcc ctgacaggtt cagtggcagt ggatcaggca cagatttac actgaaaatc     240 agcagagtgg aggctgagga tgttggggtt tattattgca tgcaggctct acaaactccg     300
atcaccttcg gccaagggac acgactggag attaaa                                336
```

<210> SEQ ID NO 58
<211> LENGTH: 112
<212> TYPE: PRT

<213> ORGANISM: Artificial Sequence
<220> FEATURE:
<223> OTHER INFORMATION: Artificially synthesized sequence.

<400> SEQUENCE: 58

| Asp | Ile | Val | Met | Thr | Gln | Ser | Pro | Leu | Ser | Leu | Pro | Val | Thr | Pro | Gly |
|---|---|---|---|---|---|---|---|---|---|---|---|---|---|---|---|
| 1 | | | | 5 | | | | | 10 | | | | | 15 | |

| Glu | Pro | Ala | Ser | Ile | Ser | Cys | Arg | Ser | Ser | Gln | Ser | Leu | Leu | Tyr | Ser |
|---|---|---|---|---|---|---|---|---|---|---|---|---|---|---|---|
| | | | 20 | | | | | 25 | | | | | 30 | | |

| Asn | Gly | Tyr | Lys | Tyr | Leu | Asp | Trp | Tyr | Leu | Gln | Lys | Pro | Gly | Gln | Ser |
|---|---|---|---|---|---|---|---|---|---|---|---|---|---|---|---|
| | | | 35 | | | | | 40 | | | | | 45 | | |

| Pro | Gln | Leu | Leu | Ile | Tyr | Leu | Gly | Ser | Asn | Arg | Ala | Ser | Gly | Val | Pro |
|---|---|---|---|---|---|---|---|---|---|---|---|---|---|---|---|
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Val | Gly | Val | Tyr | Tyr | Cys | Met | Gln | Ala |
|---|---|---|---|---|---|---|---|---|---|---|---|---|---|---|---|
| | | | | 85 | | | | | 90 | | | | | 95 | |

| Leu | Gln | Thr | Pro | Ile | Thr | Phe | Gly | Gln | Gly | Thr | Arg | Leu | Glu | Ile | Lys |
|---|---|---|---|---|---|---|---|---|---|---|---|---|---|---|---|
| | | | 100 | | | | | 105 | | | | | 110 | | |

<210> SEQ ID NO 59
<211> LENGTH: 374
<212> TYPE: DNA
<213> ORGANISM: Artificial Sequence
<220> FEATURE:
<223> OTHER INFORMATION: Artificially synthesized sequence.

<400> SEQUENCE: 59

```
caggtgcagc tgcaggagtc gggcccagga ctggtgaagc cttcggagac cctgtccctc      60
acctgcactg tctctggtgg ctccgtcagc agtggtggtt actactggaa ctggatccgg     120
cagcccccag ggaagggact ggagtggatt gggtatatca attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagat     300
cgagaactgg aactttacta ctactactac ggtatggacg tctggggcca agggaccacg     360
gtcaccgtct cctc                                                       374
```

<210> SEQ ID NO 60
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 60

| Gln | Val | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Val | Ser | Ser | Gly |
|---|---|---|---|---|---|---|---|---|---|---|---|---|---|---|---|
| | | | 20 | | | | | 25 | | | | | 30 | | |

| Gly | Tyr | Tyr | Trp | Asn | Trp | Ile | Arg | Gln | Pro | Pro | Gly | Lys | Gly | Leu | Glu |
|---|---|---|---|---|---|---|---|---|---|---|---|---|---|---|---|
| | | | 35 | | | | | 40 | | | | | 45 | | |

| Trp | Ile | Gly | Tyr | Ile | Asn | Tyr | Ser | Gly | Ser | Thr | Asn | Tyr | Asn | Pro | Ser |
|---|---|---|---|---|---|---|---|---|---|---|---|---|---|---|---|
| | 50 | | | | | 55 | | | | | 60 | | | | |

| Leu | Lys | Ser | Arg | Val | Thr | Ile | Ser | Val | Asp | Thr | Ser | Lys | Asn | Gln | Phe |
|---|---|---|---|---|---|---|---|---|---|---|---|---|---|---|---|
| 65 | | | | | 70 | | | | | 75 | | | | | 80 |

| Ser | Leu | Lys | Leu | Ser | Ser | Val | Thr | Ala | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

```
Cys Ala Arg Asp Arg Glu Leu Glu Leu Tyr Tyr Tyr Tyr Gly Met
            100                 105                 110
Asp Val Trp Gly Gln Gly Thr Thr Val Thr Val Ser
        115                 120
```

<210> SEQ ID NO 61
<211> LENGTH: 374
<212> TYPE: DNA
<213> ORGANISM: Artificial Sequence
<220> FEATURE:
<223> OTHER INFORMATION: Artificially synthesized sequence.

<400> SEQUENCE: 61

```
caggtgcagc tgcaggagtc gggcccagga ctggtgaagc cttctgagac cctgtccctc      60
acctgcactg tctctggtgg ctccgtcagc agtggtggtt actactggaa ctggatccgg     120
cagcccccag ggaagggact ggagtggatt gggtatatca attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagat     300
cgagaactgg aactttacta ctactactac ggtatggacg tctggggcca agggaccacg     360
gtcaccgtct cctc                                                      374
```

<210> SEQ ID NO 62
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 62

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Val Ser Ser Gly
             20                  25                  30
Gly Tyr Tyr Trp Asn Trp Ile Arg Gln Pro Pro Gly Lys Gly Leu Glu
         35                  40                  45
Trp Ile Gly Tyr Ile Asn Tyr Ser Gly Ser Thr Asn Tyr Asn Pro Ser
 50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
             85                  90                  95
Cys Ala Arg Asp Arg Glu Leu Glu Leu Tyr Tyr Tyr Tyr Gly Met
            100                 105                 110
Asp Val Trp Gly Gln Gly Thr Thr Val Thr Val Ser
        115                 120
```

<210> SEQ ID NO 63
<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 63

```
gatattgtga tgactcagtc tccactctcc ctgcccgtca cccctggaga gccggcctcc      60
atctcctgca ggtctagtca gagcctcctg tatagtaatg gatacaagta tttggattgg     120
tacctgcaga agccagggca gtctccacag ctcatgatct atttgggttc taatcgggcc     180
```

```
tccggggtcc ctgacaggtt cagtggcagt ggatcaggca cagattttac actgaaaatc    240
agcagagtgg aggctgagga tgttggggtt tattattgca tgcaggctct acaaactccg    300
atcaccttcg gccaagggac acgactggag attaaa                              336
```

<210> SEQ ID NO 64
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 64

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Met Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110
```

<210> SEQ ID NO 65
<211> LENGTH: 363
<212> TYPE: DNA
<213> ORGANISM: Artificial Sequence
<220> FEATURE:
<223> OTHER INFORMATION: Artificially synthesized sequence.

<400> SEQUENCE: 65

```
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatggtatg atggaagtaa taatactat    180 gcagactccg tgaagggccg attcaccatc tccagagaca attccaagaa cacgctgtat    240
ctgcaaatga acagcctgag agccgaggac acggctgtgt attactgtgc gagagcagct    300
cgccttgact actactacgg tatggacgtc tggggccaag ggaccacggt caccgtctcc    360
tca                                                                  363
```

<210> SEQ ID NO 66
<211> LENGTH: 121
<212> TYPE: PRT
<213> ORGANISM: Artificial Sequence
<220> FEATURE:
<223> OTHER INFORMATION: Artificially synthesized sequence.

<400> SEQUENCE: 66

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
                    35                  40                  45
Ala Val Ile Trp Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Arg Leu Asp Tyr Tyr Tyr Gly Met Asp Val Trp Gly
             100                 105                 110

Gln Gly Thr Thr Val Thr Val Ser Ser
         115                 120

<210> SEQ ID NO 67
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 67
gacatccaga tgacccagtc tccatcctcc ctgtctgcat ctgtaggaga cagagtctcc      60
atcacttgcc gggcaagtca gagcattaac agctatttaa attggtttca gcagaagcca    120
gggaaagccc ctcagctcct gatctttggt gcatccggtt tgcaaagtgg ggtcccatca    180
aggttcagtg gcagtggatc tgggacagat ttcactctca ccatcaacag tctgcaacct    240
gaagattttg caacttacta ctgtcaacag agttacagtt ccccgctcac cttcggccaa    300
gggacacgac tggagattaa a                                              321

<210> SEQ ID NO 68
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 68

Asp Ile Gln Met Thr Gln Ser Pro Ser Ser Leu Ser Ala Ser Val Gly
 1               5                  10                  15

Asp Arg Val Ser Ile Thr Cys Arg Ala Ser Gln Ser Ile Asn Ser Tyr
             20                  25                  30

Leu Asn Trp Phe Gln Gln Lys Pro Gly Lys Ala Pro Gln Leu Leu Ile
         35                  40                  45

Phe Gly Ala Ser Gly Leu Gln Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Ser Tyr Ser Ser Pro Leu
                 85                  90                  95

Thr Phe Gly Gln Gly Thr Arg Leu Glu Ile Lys
             100                 105

<210> SEQ ID NO 69
<211> LENGTH: 351
<212> TYPE: DNA
<213> ORGANISM: Artificial Sequence
<220> FEATURE:
<223> OTHER INFORMATION: Artificially synthesized sequence.

<400> SEQUENCE: 69
```

-continued

```
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagaaacgt ccaagaacca gttctccctg     240
aagctgagct ctgtgaccgc cgcggacacg gctgtgtatt actgtgcgag agataagtgg     300
acctggtact cgatctctg gggccgtggc accctggtca ctgtctcctc a               351
```

<210> SEQ ID NO 70
<211> LENGTH: 117
<212> TYPE: PRT
<213> ORGANISM: Artificial Sequence
<220> FEATURE:
<223> OTHER INFORMATION: Artificially synthesized sequence.

<400> SEQUENCE: 70

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Glu Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Lys Trp Thr Trp Tyr Phe Asp Leu Trp Gly Arg Gly Thr Leu
            100                 105                 110

Val Thr Val Ser Ser
        115
```

<210> SEQ ID NO 71
<211> LENGTH: 339
<212> TYPE: DNA
<213> ORGANISM: Artificial Sequence
<220> FEATURE:
<223> OTHER INFORMATION: Artificially synthesized sequence.

<400> SEQUENCE: 71

```
gacatcgaga tgacccagtc tccagactcc ctggctgtgt ctctgggcga gagggccacc      60
atcaactgca ggtccagcca gagtgtttta tacagctcca gcataggaa ctacttagct     120 tggtaccagc agaaacccag gacagcctcct aagctgctca tttactgggc ttctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cctcggacgt tcggccaagg gaccaaggtg gaaatcaaa                            339
```

<210> SEQ ID NO 72
<211> LENGTH: 113
<212> TYPE: PRT
<213> ORGANISM: Artificial Sequence
<220> FEATURE:
<223> OTHER INFORMATION: Artificially synthesized sequence.

<400> SEQUENCE: 72

```
Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys
```

<210> SEQ ID NO 73
<211> LENGTH: 374
<212> TYPE: DNA
<213> ORGANISM: Artificial Sequence
<220> FEATURE:
<223> OTHER INFORMATION: Artificially synthesized sequence.

<400> SEQUENCE: 73

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatg ggaacatct attacagtgg gagcacctac   180
tacaacccgt ccctcaagag tcgagttacc atatcagtag acacgtctga gaaccagttc   240
tccctgaagc tgaactctgt gactgccgcg gacacggccg tatattactg tgcgagaggg   300
ggaactggaa ccaattacta ctactactac ggtatggacg tctggggcca agggaccacg   360
gtcaccgtct cctc                                                    374
```

<210> SEQ ID NO 74
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 74

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Met Gly Asn Ile Tyr Tyr Ser Gly Ser Thr Tyr Tyr Asn Pro Ser
50                  55                  60

Leu Lys Ser Arg Val Thr Ile Ser Val Asp Thr Ser Glu Asn Gln Phe
65                  70                  75                  80

Ser Leu Lys Leu Asn Ser Val Thr Ala Ala Asp Thr Ala Val Tyr Tyr
                85                  90                  95

Cys Ala Arg Gly Gly Thr Gly Thr Asn Tyr Tyr Tyr Tyr Gly Met
            100                 105                 110

Asp Val Trp Gly Gln Gly Thr Thr Val Thr Val Ser
```

<210> SEQ ID NO 75
<211> LENGTH: 324
<212> TYPE: DNA
<213> ORGANISM: Artificial Sequence
<220> FEATURE:
<223> OTHER INFORMATION: Artificially synthesized sequence.

<400> SEQUENCE: 75

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gctgggccac tggcatccca     180
aacaggttca gtggcagtgg gtctgggaca gacttcactc tcaccatcag cagactggag     240
cctgaagatt ttgcagtgta ttactgtcag cagtatggta gctcaccgct cactttcggc     300
ggagggacca aggtggagat caaa                                             324
```

<210> SEQ ID NO 76
<211> LENGTH: 108
<212> TYPE: PRT
<213> ORGANISM: Artificial Sequence
<220> FEATURE:
<223> OTHER INFORMATION: Artificially synthesized sequence.

<400> SEQUENCE: 76

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Trp Ala Thr Gly Ile Pro Asn Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Leu Thr Phe Gly Gly Gly Thr Lys Val Glu Ile Lys
            100                 105
```

<210> SEQ ID NO 77
<211> LENGTH: 377
<212> TYPE: DNA
<213> ORGANISM: Artificial Sequence
<220> FEATURE:
<223> OTHER INFORMATION: Artificially synthesized sequence.

<400> SEQUENCE: 77

```
caggtgcagc tgcaggagtc gggcccagga ctggtgaagc cttcacagac cctgtccctc      60
acctgcactg tctctggtgt ctccatcagc agtggtggtt actactggag ctggatccgc     120
cagcacccag ggatgggcct ggagtggatt gggtacatct attacagtgg gagcacctac     180
tacaacccgt ccctcaagag tcgagtcacc atatcagaag acacgtctaa gaaccagttc     240
tccctgaagc tgagctctgt gactgccgcg gacacggccg tgtattactg tgcgagagat     300
tccgagtccg agtatagcag ctcgtcgaac tacggtatgg acgtctgggg ccaagggacc     360
acggtcaccg tctcctc                                                    377
```

<210> SEQ ID NO 78
<211> LENGTH: 125
<212> TYPE: PRT
<213> ORGANISM: Artificial Sequence
<220> FEATURE:
<223> OTHER INFORMATION: Artificially synthesized sequence.

<400> SEQUENCE: 78

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Glu Ser Glu Tyr Ser Ser Ser Asn Tyr Gly
            100                 105                 110

Met Asp Val Trp Gly Gln Gly Thr Thr Val Thr Val Ser
        115                 120                 125

<210> SEQ ID NO 79
<211> LENGTH: 377
<212> TYPE: DNA
<213> ORGANISM: Artificial Sequence
<220> FEATURE:
<223> OTHER INFORMATION: Artificially synthesized sequence.

<400> SEQUENCE: 79
caggtgcagc tgcaggagtc gggcccagga ctggtgaagc cttcacagac cctgtccctc      60
acctgcactg tctctggtgt ctccatcagc agtggtggtt actactggag ctggatccgc     120
cagcacccag ggatgggcct ggagtggatt gggtacatct attacagtgg gagcacctac     180
tacaacccgt ccctcaagag tcgagtcacc atatcagaag acacgtctaa gaaccagttc     240
tccctgaagc tgagctctgt gactgccgcg gacacggccg tgtattactg tgcgagagat     300
tccgagtccg agtatagcag ctcgtcgaac tacggtatgg acgtctgggg ccaagggacc     360
acggtcaccg tctcctc                                                    377

<210> SEQ ID NO 80
<211> LENGTH: 125
<212> TYPE: PRT
<213> ORGANISM: Artificial Sequence
<220> FEATURE:
<223> OTHER INFORMATION: Artificially synthesized sequence.

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
    50                  55                  60

```
Leu Lys Ser Arg Val Thr Ile Ser Glu Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Ser Glu Ser Glu Tyr Ser Ser Ser Asn Tyr Gly
            100                 105                 110

Met Asp Val Trp Gly Gln Gly Thr Thr Val Thr Val Ser
            115                 120                 125

<210> SEQ ID NO 81
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 81
gacatccaga tgacccagtc tccatcctcc ctgtctgcat ctgtaggaga cagaatcacc      60
atcacttgcc gggcaagtca gaccattagc agctatttaa attggtatca gcagaaacca    120
gggaaagccc ctaagctcct gatctatgct gcatccagtt tgcaaggtgg ggtcccatca    180
aggttcagtg gcagtgtatc tgggacagat ttcaccctca ccgtcagcag tctgcaacct    240
gaagattttg caacttacta ctgtcaacag agttacagta accgctcac tttcggcgga     300 gggaccaagg tggagatcaa a                                              321

<210> SEQ ID NO 82
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 82

Asp Ile Gln Met Thr Gln Ser Pro Ser Ser Leu Ser Ala Ser Val Gly
  1               5                  10                  15

Asp Arg Ile Thr Ile Thr Cys Arg Ala Ser Gln Thr Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Gly Gly Val Pro Ser Arg Phe Ser Gly
 50                  55                  60

Ser Val Ser Gly Thr Asp Phe Thr Leu Thr Val Ser Ser Leu Gln Pro
 65                  70                  75                  80

Glu Asp Phe Ala Thr Tyr Tyr Cys Gln Gln Ser Tyr Ser Asn Pro Leu
                 85                  90                  95

Thr Phe Gly Gly Gly Thr Lys Val Glu Ile Lys
            100                 105

<210> SEQ ID NO 83
<211> LENGTH: 371
<212> TYPE: DNA
<213> ORGANISM: Artificial Sequence
<220> FEATURE:
<223> OTHER INFORMATION: Artificially synthesized sequence.

<400> SEQUENCE: 83
gaggtgcagc tggtgcagtc tggagcagag gtgaaaaagc ccggggagtc tctgaagatc      60
tcctgtaagg gttctggata cagttttacc agctactgga tcggctgggt gcgccagatg    120
```

```
cccgggaaag gcctggagtg gatggggatc atctatcctg gtgactctga taccagatac    180
agcccgtcct tccaaggcca ggtcaccatg tcagccgaca agtccatcag taccgcctac    240
ctgcagctga gcagccatga aggcctcgga caccgccatg tattactgtg cgagacagat    300
ggctggaaac tacgtacatc acgggtgatc gagacgtcct ggggccaagg gaccacggtc    360
accgtctcct c                                                         371
```

<210> SEQ ID NO 84
<211> LENGTH: 123
<212> TYPE: PRT
<213> ORGANISM: Artificial Sequence
<220> FEATURE:
<223> OTHER INFORMATION: Artificially synthesized sequence.

<400> SEQUENCE: 84

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Met Ser Ala Asp Lys Ser Ile Ser Thr Ala Tyr
 65                  70                  75                  80

Leu Gln Leu Ser Ser His Glu Gly Leu Gly His Arg His Val Leu Leu
                 85                  90                  95

Cys Glu Thr Asp Gly Trp Lys Leu Arg Thr Ser Arg Val Ile Glu Thr
            100                 105                 110

Ser Trp Gly Gln Gly Thr Thr Val Thr Val Ser
        115                 120
```

<210> SEQ ID NO 85
<211> LENGTH: 324
<212> TYPE: DNA
<213> ORGANISM: Artificial Sequence
<220> FEATURE:
<223> OTHER INFORMATION: Artificially synthesized sequence.

<400> SEQUENCE: 85

```
gaaattgtgt tgacgcagtc tccaggcacc ctgtctttgt ctccagggga aagagccacc    60
ctctcctgca gggccagtca gagtgttatc agcatctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgtg cagttttggc   300
caggggacca aactggagat caaa                                           324
```

<210> SEQ ID NO 86
<211> LENGTH: 108
<212> TYPE: PRT
<213> ORGANISM: Artificial Sequence
<220> FEATURE:
<223> OTHER INFORMATION: Artificially synthesized sequence.

<400> SEQUENCE: 86

```
Glu Ile Val Leu Thr Gln Ser Pro Gly Thr Leu Ser Leu Ser Pro Gly
  1               5                  10                  15
```

Glu Arg Ala Thr Leu Ser Cys Arg Ala Ser Gln Ser Val Ile Ser Ile
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Ser Phe Gly Gln Gly Thr Lys Leu Glu Ile Lys
                100                 105

<210> SEQ ID NO 87
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 87
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaggag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaaccct ggtcaccgtc     360
tcctca                                                                366

<210> SEQ ID NO 88
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 88

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
            115                 120

<210> SEQ ID NO 89

<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 89

```
gacatccaga tgacccagtc tccatcctcc ctgtctgcat ctgtaggaga cagagtcacc      60
atcacttgcc gggcaagtca gggcattaga aatgatttag gctggtatca gcagataccc     120
gggaaagccc ctaagcgcct gatctatgct gcatccagtt tgcaaagtgg ggtcccatca     180
aggttcagcg gcagtggatc tgggacagaa ttcactctca caatcaacag cctgcagcct     240
gaagattttg caacttatta ctgtctacag cataatggtt acccgtggac gttcggccaa     300
gggaccaagg tggaaatcaa ac                                              322
```

<210> SEQ ID NO 90
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 90

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Ile Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Asn Ser Leu Gln Pro
 65                  70                  75                  80

Glu Asp Phe Ala Thr Tyr Tyr Cys Leu Gln His Asn Gly Tyr Pro Trp
                 85                  90                  95

Thr Phe Gly Gln Gly Thr Lys Val Glu Ile Lys
            100                 105
```

<210> SEQ ID NO 91
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 91

```
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt ggatacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaaccct ggtcaccgtc     360
tcctca                                                               366
```

<210> SEQ ID NO 92
<211> LENGTH: 122
<212> TYPE: PRT

<213> ORGANISM: Artificial Sequence
<220> FEATURE:
<223> OTHER INFORMATION: Artificially synthesized sequence.

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 93
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 93
gacttccaga tgacccagtc tccatcctcc ctgtctgcat ctgtaggaga cagagtcacc      60
atcacttgcc gggcaagtca ggacattcga aatgatttag ctggtatcg gcagaaacct     120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgtggac gttcggccaa     300
gggaccaagg tggaaatcaa ac                                              322

<210> SEQ ID NO 94
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 94

Asp Phe Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 95
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 95
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt ggatacatct attacagtgg gagcacctac     180
tacaacccgt ccctcaagag tcgagttacc atatcaatag acacgtctaa gaaccagttc     240
tccctgaagc tgagctctgt gactgccgcg gacacggccg tgtattactg tgcgagagcg     300
gattacgatt tttggaatgg ttattttgac tactggggcc agggaaccct ggtcaccgtc     360
tcctca                                                                366

<210> SEQ ID NO 96
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 96

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120

<210> SEQ ID NO 97
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 97
gacatccaga tgacccagtc tccatcctcc ctgtctgcat ctgtaggaga cagagtcacc      60
atcacttgcc gggcaagtca ggacattaga aatgatttag ctggtatcg gcagaaacct     120 gggaaagccc ctaagcgcct gatctatgct gcatccagtt tgcaaagtgg ggtcccatca     180
aggttcagcg gcagtggatc tgggacagaa ttcactctca caatcagcag cctgcagcct     240

```
gaagattttg caacttatta ctgtctacag cataatagtt acccgtggac gttcggccaa      300
gggaccaagg tggaaatcaa a                                               321
```

<210> SEQ ID NO 98
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 98

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 99
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 99

```
caggtgcagc tgcaggagtc gggcccagga ctggtgaagc ctacacagac cctgtccctc       60
acctgcactg tctctggtgg ctccatcagc agtggtgatt actactggag ctggatccgc      120
cagcacccag ggaagggcct ggagtggatt gggtacatct attacagtgg gagcacctac      180
tacaacccgt ccctcaagag tcgacttacc atatcagtag acacgtctaa gaaccagttc      240
tccctgaagc tgagctctgt gactgccgcg gacacggccg tgtattactg tgcgagagca      300
gattacgatt tttggagtgg ttactttgac tactggggcc agggaaccct ggtcaccgtc      360
tcctca                                                                366
```

<210> SEQ ID NO 100
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 100

```
Gln Val Gln Leu Gln Glu Ser Gly Pro Gly Leu Val Lys Pro Thr Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45
```

```
Trp Ile Gly Tyr Ile Tyr Tyr Ser Gly Ser Thr Tyr Tyr Asn Pro Ser
 50                  55                  60

Leu Lys Ser Arg Leu Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
            115                 120

<210> SEQ ID NO 101
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 101
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataataatt acccgtggac gttcggccaa     300
gggaccaagg tggaaatcaa a                                               321

<210> SEQ ID NO 102
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 102

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
                100                 105

<210> SEQ ID NO 103
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 103
caggtgcagc tgcaggagtc gggcccagga ctggtgaagc cttcacagac cctgtccctc      60
```

```
acctgcactg tctctggtgg ctccatcagt agtggtgatt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagt tgagctctgt gactgccgcg gacacggccg tgtattactg tgcgagagcc    300
gattacgatt tttggagtgg ttattttgac tactggggcc agggaaccct ggtcaccgtc    360
tcctca                                                                366
```

<210> SEQ ID NO 104
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 104

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 105
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 105

```
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a                                              321
```

<210> SEQ ID NO 106
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 106

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
                100                 105
```

<210> SEQ ID NO 107
<211> LENGTH: 351
<212> TYPE: DNA
<213> ORGANISM: Artificial Sequence
<220> FEATURE:
<223> OTHER INFORMATION: Artificially synthesized sequence.

<400> SEQUENCE: 107

```
caggtgcagc tgcaggagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagag    300
gacgacggta tggacgtctg gggccaaggg accacggtca ccgtctcctc a              351
```

<210> SEQ ID NO 108
<211> LENGTH: 117
<212> TYPE: PRT
<213> ORGANISM: Artificial Sequence
<220> FEATURE:
<223> OTHER INFORMATION: Artificially synthesized sequence.

<400> SEQUENCE: 108

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Asp Asp Gly Met Asp Val Trp Gly Gln Gly Thr Thr
                100                 105                 110

Val Thr Val Ser Ser
        115
```

<210> SEQ ID NO 109

<211> LENGTH: 336
<212> TYPE: DNA
<213> ORGANISM: Artificial Sequence
<220> FEATURE:
<223> OTHER INFORMATION: Artificially synthesized sequence.

<400> SEQUENCE: 109

```
gatattgtga tgactcagtc tccactctcc ctgcccgtca cccctggaga gccggcctcc    60
atttcctgca ggtctagtca gagcctcctg catagtaatg gatacaacta tttggaatgg   120
tacctgcaga agccagggca gtccccacag ttcatgattt atttggggtc taatcgggcc   180
tccgggtcc  ctgacaggtt cagtggcagt ggatcaggca cagatttac  actgaaaatc   240
agcagagtgg aggctgagga tgttggggtt tattactgca tgcaagctct acaaactccg   300
atcaccttcg gccagggac  acgactggag attaaa                              336
```

<210> SEQ ID NO 110
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 110

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Glu Trp Tyr Leu Gln Lys Pro Gly Gln Ser
         35                  40                  45

Pro Gln Phe Met Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Ile Thr Phe Gly Gln Gly Thr Arg Leu Glu Ile Lys
            100                 105                 110
```

<210> SEQ ID NO 111
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 111

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagtacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgaggtctgt gactgccgcg gacacggccg tgtattactg tgcgagagcg   300
gattacgatt tttggagtgg ttattttgac tactggggcc agggaaccct ggtcaccgtc   360
tcctca                                                               366
```

<210> SEQ ID NO 112
<211> LENGTH: 122
<212> TYPE: PRT

<213> ORGANISM: Artificial Sequence
<220> FEATURE:
<223> OTHER INFORMATION: Artificially synthesized sequence.

<400> SEQUENCE: 112

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 113
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 113
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatactt acccgtggac gttcggccaa    300
gggaccaagg tggaaatcaa ac                                             322

<210> SEQ ID NO 114
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105

<210> SEQ ID NO 115
<211> LENGTH: 372
<212> TYPE: DNA
<213> ORGANISM: Artificial Sequence
<220> FEATURE:
<223> OTHER INFORMATION: Artificially synthesized sequence.

<400> SEQUENCE: 115
caggtgcagc tgcaggagtc gggcccagga ctggtgaagc cttcggagac cctgtccctc      60
acctgcactg tctctggtgg ctccgtcagc agtggtggtt actactggag ctggatccgg     120
cagcccccag ggaagggact ggagtggatt gggtatatct attacagtgg agcaccaac     180 tacaacccct ccctcaagag tcgagtcacc atatcagtag acacgtccaa gaaccagttc     240
tccctgaagc tgagctctgt gaccgctgcg gacacggccg tgtattactg tgcgagagat     300
ggggacgtgg atacagctat ggtcgatgct tttgatatct ggggccaagg gacaatggtc     360
accgtctcct ca                                                         372

<210> SEQ ID NO 116
<211> LENGTH: 124
<212> TYPE: PRT
<213> ORGANISM: Artificial Sequence
<220> FEATURE:
<223> OTHER INFORMATION: Artificially synthesized sequence.

<400> SEQUENCE: 116

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Gly Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Asn Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Gly Asp Val Asp Thr Ala Met Val Asp Ala Phe Asp
            100                 105                 110

Ile Trp Gly Gln Gly Thr Met Val Thr Val Ser Ser
        115                 120

<210> SEQ ID NO 117
<211> LENGTH: 324
<212> TYPE: DNA
<213> ORGANISM: Artificial Sequence
<220> FEATURE:
<223> OTHER INFORMATION: Artificially synthesized sequence.

<400> SEQUENCE: 117
gaaattgtat tgacgcagtc tccaggcacc ctgtctttgt ctccagggga aagagccacc      60
ctctcctgca gggccagtca gagtttaagc ggcaactact tagcctggta ccagcagaag     120
cctggccagg ctcccaggct catcatctgt ggtgcatcca gcagggccac tggcatccca     180
gacaggttca gtggcagtgg gtctgggaca gacttcactc tcaccatcac aagactggag     240

```
cctgaagatt ttgcagtgta ttactgtcag cagtatgata ggtcaccgct cactttcggc    300
ggagggacca aggtggagat caaa                                           324
```

<210> SEQ ID NO 118
<211> LENGTH: 108
<212> TYPE: PRT
<213> ORGANISM: Artificial Sequence
<220> FEATURE:
<223> OTHER INFORMATION: Artificially synthesized sequence.

<400> SEQUENCE: 118

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Leu Ser Gly Asn
             20                  25                  30

Tyr Leu Ala Trp Tyr Gln Gln Lys Pro Gly Gln Ala Pro Arg Leu Ile
         35                  40                  45

Ile Cys Gly Ala Ser Ser Arg Ala Thr Gly Ile Pro Asp Arg Phe Ser
     50                  55                  60

Gly Ser Gly Ser Gly Thr Asp Phe Thr Leu Thr Ile Thr Arg Leu Glu
 65                  70                  75                  80

Pro Glu Asp Phe Ala Val Tyr Tyr Cys Gln Gln Tyr Asp Arg Ser Pro
                 85                  90                  95

Leu Thr Phe Gly Gly Gly Thr Lys Val Glu Ile Lys
            100                 105
```

<210> SEQ ID NO 119
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 119

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagga   300
gattacgatt tttggagtgg agagtttgac tactggggcc agggaaccct ggtcaccgtc   360
tcctca                                                              366
```

<210> SEQ ID NO 120
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 120

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln His Pro Gly Lys Gly Leu Glu
         35                  40                  45
```

```
Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Asp Tyr Asp Phe Trp Ser Gly Glu Phe Asp Tyr Trp
            100                 105                 110

Gly Gln Gly Thr Leu Val Thr Val Ser Ser
            115                 120
```

<210> SEQ ID NO 121
<211> LENGTH: 386
<212> TYPE: DNA
<213> ORGANISM: Artificial Sequence
<220> FEATURE:
<223> OTHER INFORMATION: Artificially synthesized sequence.

<400> SEQUENCE: 121

```
caggtgcagc tgcaggagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt gggtacatct atgacagtgg gagcacctac    180
tacaacccgt ccctcaagag tcgagttacc atatcagtag acacgtctaa gaaccagttc    240
tccctgaagc tgaggtctgt gactgccgcg gacacggccg tgtattactg tgcgagagat    300
caggggcagg acggatacag ctatggttac ggctactact acggtatgga cgtctggggc    360
caagggacca cggtcaccgt ctcctc                                         386
```

<210> SEQ ID NO 122
<211> LENGTH: 128
<212> TYPE: PRT
<213> ORGANISM: Artificial Sequence
<220> FEATURE:
<223> OTHER INFORMATION: Artificially synthesized sequence.

<400> SEQUENCE: 122

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Asp Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Arg Ser Val Thr Ala Ala Asp Thr Ala Val Tyr Tyr
                 85                  90                  95

Cys Ala Arg Asp Gln Gly Gln Asp Gly Tyr Ser Tyr Gly Tyr Gly Tyr
            100                 105                 110

Tyr Tyr Gly Met Asp Val Trp Gly Gln Gly Thr Thr Val Thr Val Ser
            115                 120                 125
```

<210> SEQ ID NO 123
<211> LENGTH: 321
<212> TYPE: DNA
<213> ORGANISM: Artificial Sequence
<220> FEATURE:

<223> OTHER INFORMATION: Artificially synthesized sequence.

<400> SEQUENCE: 123

```
gacatccaga tgacccagtc tccatcctcc ctgtctgcat ctgtaggaga cagagtcacc    60
atcacttgcc aggcgagtca ggacattagc aattatttaa attggtatca gcagaaacca   120
gggaaagccc ctaaactcct gatctacgtt gcatccaatt tggaaacagg ggtcccatca   180
aggttcagtg gaagtggatc tgggacagat tttactttca ccatcagcag cctgcagcct   240
gaagatattg caacatatta ctgtcaacag tgtgataatc tccctctcac tttcggcgga   300
gggaccaagg tggagatcaa a                                             321
```

<210> SEQ ID NO 124
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 124

```
Asp Ile Gln Met Thr Gln Ser Pro Ser Ser Leu Ser Ala Ser Val Gly
 1               5                  10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Val Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Cys Asp Asn Leu Pro Leu
                85                  90                  95
Thr Phe Gly Gly Gly Thr Lys Val Glu Ile Lys
            100                 105
```

<210> SEQ ID NO 125
<211> LENGTH: 365
<212> TYPE: DNA
<213> ORGANISM: Artificial Sequence
<220> FEATURE:
<223> OTHER INFORMATION: Artificially synthesized sequence.

<400> SEQUENCE: 125

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt ggatacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcg   300
gattacgatt ttggagtggg ttattttgac tactggggcc agggaaccct ggtcaccgtc   360
tcctc                                                               365
```

<210> SEQ ID NO 126
<211> LENGTH: 121
<212> TYPE: PRT
<213> ORGANISM: Artificial Sequence
<220> FEATURE:
<223> OTHER INFORMATION: Artificially synthesized sequence.

<400> SEQUENCE: 126

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser
            115                 120

<210> SEQ ID NO 127
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 127
gacatccaga tgacccagtc tccatcctcc ctgtctgcat ctgtaggaga cagagtcacc        60
atcacttgcc gggcaagtca ggacattaga aatgatttag ctggtatcg gcagaaacct       120 gggaaagccc ctaagcgcct gatctatgct gcatcccgtt tgcaaagtgg ggtcccatca       180
aggttcagcg gcagtggatc tgggacagaa ttcactctca caatcagcag cctgcagcct       240
gaagattttg caacttatta ctgtctacag cataatagtt acccgtggac gttcggccaa       300
gggaccaagg tggaaatcaa ac                                                322

<210> SEQ ID NO 128
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 129
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 129

```
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag gaagggcct ggagtggatt gggtacatct attacagtgg gagcacctac      180
tacaacccgt ccctcaagag tcgagttacc atatcagtag acacgtctaa gaaccagttc     240
tccctgaagc tgagctctgt gactgccgcg gacacggccg tgtattactg tgcgagagcc     300
gattacgatt tttggagtgg ttattttgac tactggggcc agggaaccct ggtcaccgtc     360
tcctca                                                                 366
```

<210> SEQ ID NO 130
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 130

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 131
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 131

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagcgcct gatctatgct gcatccagtt tgcaaaatgg ggtcccatca     180
aggttcagcg gcagtggatc tgggacagaa ttcactctca caatcagcag cctgcagcct     240
gaagattttg caacttatta ctgtctacag cataatagtt acccgtggac gttcggccaa     300
gggaccaagg tggaaatcaa ac                                               322
```

<210> SEQ ID NO 132
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 133
<211> LENGTH: 365
<212> TYPE: DNA
<213> ORGANISM: Artificial Sequence
<220> FEATURE:
<223> OTHER INFORMATION: Artificially synthesized sequence.

<400> SEQUENCE: 133
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaatcct ggtcaccgtc     360
tcctc                                                                 365

<210> SEQ ID NO 134
<211> LENGTH: 121
<212> TYPE: PRT
<213> ORGANISM: Artificial Sequence
<220> FEATURE:
<223> OTHER INFORMATION: Artificially synthesized sequence.

<400> SEQUENCE: 134

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe

```
                65                  70                  75                  80
        Ser Leu Lys Leu Ser Ser Val Thr Ala Ala Asp Thr Ala Val Tyr Tyr
                            85                  90                  95

Cys Ala Arg Ala Asp Tyr Asp Phe Trp Ser Gly Tyr Phe Asp Tyr Trp
                        100                 105                 110

Gly Gln Gly Ile Leu Val Thr Val Ser
                    115                 120

<210> SEQ ID NO 135
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 135
gacatccaga tgacccagtc tccatcctcc ctgtctgcat ctgtaggaga cagagtcacc        60
atcacttgcc gggcaagtca gggcattaga aatgatttag gctggtatca gcagaaacca      120
gggaaagccc ctaagcgcct gatttatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt acccgtggac gttcggccaa      300
gggaccaagg tggaaatcaa ac                                                322

<210> SEQ ID NO 136
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 137
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 137
caggtgcagc tgcaggagtc gggcccagga ctggtgaagc cttcacagac cctgtccctc        60
acctgcactg tctctggtgg ctccatcagt agtggtgatt actactggag ctggatccgc      120
cagcacccag ggaagggcct ggagtggatt gggtacatct attacagtgg gagcacctac      180
```

```
tacaacccgt ccctcaagag tcgagttacc atatcagtag acacgtctaa gaaccagttc    240
tccctgaagt tgagctctgt gactgccgcg gacacggccg tgtattactg tgcgagagcc    300
gattacgatt tttggaatgg ttattttgac tactggggcc agggaaccct ggtcaccgtc    360
tcctca                                                               366
```

<210> SEQ ID NO 138
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 138

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120
```

<210> SEQ ID NO 139
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 139

```
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a                                              321
```

<210> SEQ ID NO 140
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 140

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
```

-continued

```
                    20                  25                  30
Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                    85                  90                  95

Thr Phe Gly Gln Gly Thr Lys Val Glu Ile Lys
                100                 105
```

<210> SEQ ID NO 141
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 141

```
caggtgcagc tgcaggagtc gggcccagga ctggtgaagc cttcacagac cctgtccctc     60
acctgcactg tctctggtgg ctccatcagc agtggtgatt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagcc    300
gattacgatt tttggagtgg ttattttgac tactggggcc agggaaccct ggtcaccgtc    360
tcctca                                                               366
```

<210> SEQ ID NO 142
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 142

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
            115                 120
```

<210> SEQ ID NO 143
<211> LENGTH: 322
<212> TYPE: DNA

<213> ORGANISM: Artificial Sequence
<220> FEATURE:
<223> OTHER INFORMATION: Artificially synthesized sequence.

<400> SEQUENCE: 143

```
gacatccagc tgacccagtc tccatcctcc ctgtctgcat ctgtaggaga cagagtcacc      60
atcacttgcc gggcaagtca gggcattaga aatgatttag ctggtatca  gcagaaacca     120
gggaaagccc ctaagcgcct gatctatgct gcatccagtt tgcaaaatgg ggtcccatca     180
aggttcagcg gcagtggatc tgggacagaa ttcactctca caatcagcag cctgcagcct     240
gaagattttg caacttatta ctgtctacag cataatagtt acccgtggac gttcggccaa     300
gggaccaagg tggaaatcaa ac                                              322
```

<210> SEQ ID NO 144
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 144

```
Asp Ile Gln Leu Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Asp
             20                  25                  30
Leu Gly Trp Tyr Gln Gln Lys Pro Gly Lys Ala Pro Lys Arg Leu Ile
         35                  40                  45
Tyr Ala Ala Ser Ser Leu Gln Asn Gly Val Pro Ser Arg Phe Ser Gly
     50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln His Asn Ser Tyr Pro Trp
                 85                  90                  95
Thr Phe Gly Gln Gly Thr Lys Val Glu Ile Lys
            100                 105
```

<210> SEQ ID NO 145
<211> LENGTH: 365
<212> TYPE: DNA
<213> ORGANISM: Artificial Sequence
<220> FEATURE:
<223> OTHER INFORMATION: Artificially synthesized sequence.

<400> SEQUENCE: 145

```
caggtgcagc tgcaggagtc gggcccagga ctggtgaagc cttcacagac cctgtccctc      60
acctgcactg tctctggtgg ctccatcagc agtggtgatt actactggag ctggatccgc     120
cagtacccag gaagggcct ggagtggatt gggtacatct attacagtgg gagcacctac     180
tacaacccgt ccctcaagag tcgagttacc atatcagtag acacgtctaa gaaccagttc     240
tccctgaagc tgggctctgt gactgccgcg gacacggccg tgtatttctg tgcgagagcc     300
gattacgatt tttggagtgg ttattttgac ttctggggcc agggaaccct ggtcaccgtc     360
tcctc                                                                365
```

<210> SEQ ID NO 146
<211> LENGTH: 121
<212> TYPE: PRT
<213> ORGANISM: Artificial Sequence
<220> FEATURE:

-continued

<223> OTHER INFORMATION: Artificially synthesized sequence.

<400> SEQUENCE: 146

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120

<210> SEQ ID NO 147
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 147
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatggtt acccgtggac gttcggccaa     300
gggaccaagg tggaaatcaa ac                                              322

<210> SEQ ID NO 148
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys

<210> SEQ ID NO 149
<211> LENGTH: 365
<212> TYPE: DNA
<213> ORGANISM: Artificial Sequence
<220> FEATURE:
<223> OTHER INFORMATION: Artificially synthesized sequence.

<400> SEQUENCE: 149

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagtacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgggctctgt gactgccgcg gacacggccg tgtatttctg tgcgagagcc   300
gattacgatt tttggagtgg ttattttgac ttctggggcc agggaaccct ggtcaccgtc   360
tcctc                                                              365
```

<210> SEQ ID NO 150
<211> LENGTH: 121
<212> TYPE: PRT
<213> ORGANISM: Artificial Sequence
<220> FEATURE:
<223> OTHER INFORMATION: Artificially synthesized sequence.

<400> SEQUENCE: 150

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln Tyr Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Gly Ser Val Thr Ala Ala Asp Thr Ala Val Tyr Phe
                 85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120
```

<210> SEQ ID NO 151
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 151

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatggtt acccgtggac gttcggccaa   300
```

```
gggaccaagg tggaaatcaa ac                                              322
```

<210> SEQ ID NO 152
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 152

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105
```

<210> SEQ ID NO 153
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 153

```
caggtgcagc tgcaggagtc gggcccagga ctggtgaagc cttcacagac cctgtccctc    60
acctgcactg tctctggtgg ctccatcagt agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcg   300
gattacgatt tttggagtgg ttattttgac tcctggggcc agggaaccct ggtcaccgtc   360
tcctca                                                              366
```

<210> SEQ ID NO 154
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 154

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60
```

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Ser Trp
            100                 105                 110

Gly Gln Gly Thr Leu Val Thr Val Ser Ser
        115                 120

<210> SEQ ID NO 155
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 155
gacatccaga tgacccagtc tccatcctcc ctgtctgcat ctgtaggaga cagagtcacc      60
atcacttgcc gggcaagtca gggcattaga aatgatttag ctggtatca gcagatacct     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatggtt acccgtggac gttcggccaa    300
gggaccaagg tggaaatcaa a                                              321

<210> SEQ ID NO 156
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105

<210> SEQ ID NO 157
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 157
caggttcagc tggtgcagtc tggagctgag gtgaagaagc ctggggcctc agtgaaggtc      60
tcctgcaagg cttctggtta cacctttacc aactatggta tcagctgggt gcggcaggcc    120

```
cctggacaag ggcttgagtg gatgggatgg atcagcgctt acgatggtta cagaaactat    180
gcacagaagc tccagggcag agtcaccatg accacagaca catccacgac cactgcctac    240
atggagctga ggagcctgag atctgacgac acggccgtgt attactgtgc gagagatgtt    300
caagactacg gtgactacga ctactttgac tactggggcc agggaaccct ggtcaccgtc    360
tcctca                                                                366
```

<210> SEQ ID NO 158
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 158

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Tyr Arg Asn Tyr Ala Gln Lys Leu
    50                  55                  60

Gln Gly Arg Val Thr Met Thr Thr Asp Thr Ser Thr Thr Ala Tyr
 65                  70                  75                  80

Met Glu Leu Arg Ser Leu Arg Ser Asp Asp Thr Ala Val Tyr Tyr Cys
                85                  90                  95

Ala Arg Asp Val Gln Asp Tyr Gly Asp Tyr Asp Tyr Phe Asp Tyr Trp
               100                 105                 110

Gly Gln Gly Thr Leu Val Thr Val Ser Ser
           115                 120
```

<210> SEQ ID NO 159
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 159

```
gacatccaga tgacccagtc tccatcctcc ctgtctgcat ctgtaggaga cagagtcacc     60
atcacttgcc gggcaagtca gagcattagc agttatttaa attggtatca gcagaaacca    120
gggaaagccc ctaacctcct gatctatgct gcatccagtt tgcaaagtgg ggtcccatca    180
agattcaggg gcagtggatc tgggacagat ttcactctca ccatcagcag tctgcaacct    240
gaagattttg caacttacta ctgtcaacag agttacagta ccccccatca cttcggccaa    300
gggacacgac tggagattaa a                                              321
```

<210> SEQ ID NO 160
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 160

```
Asp Ile Gln Met Thr Gln Ser Pro Ser Ser Leu Ser Ala Ser Val Gly
 1               5                  10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Arg Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 161
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 161
caggtgcagc tgcaggagtc gggcccagga ctggtgaagc ctttacagac cctgtccctc      60
acctgcactg tctctggtgg ctccatcagc agtggtgatt actactggag ctggatccgc     120
cagcacccag ggaagggcct ggagtggatt gggtacatct attacagtgg gaccacctac     180
tacaacccgt ccctcaagag tcgagttacc atatcagtag acacgtctaa gaaccagttc     240
gccctgaagc tgaactctgt gactgccgcg gacacggccg tgtattactg tgcgagagcc     300
gattacgatt tttggagtgg ttattttgac tactggggcc agggaaccct ggtcaccgtc     360
tcctca                                                                366

<210> SEQ ID NO 162
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 162

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 163

```
<211> LENGTH: 322
<212> TYPE: DNA
<213> ORGANISM: Artificial Sequence
<220> FEATURE:
<223> OTHER INFORMATION: Artificially synthesized sequence.

<400> SEQUENCE: 163
gacatccaga tgacccagtc tccatcctcc ctgtctgcat ctgtaggaga cagagtcacc      60
atcacttgcc gggcaggtca gggcattaga aatgatttag ctggtatca gcagaaacca     120 gggaaagccc ctcagcgcct gatctatgct gcatccagtt tgcaaagtgg ggtcccatca    180
aggttcagcg gcagtggatc tgggacagaa ttctctctca caatctccag cctgcagcct    240
gaagattttg caacttatta ctgtctacag cataatagtt acccgtggac gttcggccaa    300
gggaccaagg tggaaatcaa ac                                             322

<210> SEQ ID NO 164
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 164

Asp Ile Gln Met Thr Gln Ser Pro Ser Ser Leu Ser Ala Ser Val Gly
 1               5                  10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 165
<211> LENGTH: 369
<212> TYPE: DNA
<213> ORGANISM: Artificial Sequence
<220> FEATURE:
<223> OTHER INFORMATION: Artificially synthesized sequence.

<400> SEQUENCE: 165
caggtgcagc tggtggagtc tgggggaggc ttggtcaagc ctggagggtc cctgagactc      60
tcctgtgcag cctctggatt caccttcagt gactactaca tgagctggat ccgccaggct    120
ccagggaagg ggctggagtg ggtttcatat attagtagta gtggtaataa catataccac    180
gcagactctg tgaagggccg attcaccatc tccagggaca acgccaagaa ctcactgtat    240
ctgcaaatga acagcctgag agccgaggac acggccgtgt attactgtgc gagagagaga    300
tatagtggct acgacgaccc tgatggtttt gatatctggg gccaagggac aatggtcacc    360
gtctcttca                                                            369

<210> SEQ ID NO 166
<211> LENGTH: 123
<212> TYPE: PRT
```

<213> ORGANISM: Artificial Sequence
<220> FEATURE:
<223> OTHER INFORMATION: Artificially synthesized sequence.

<400> SEQUENCE: 166

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Asn Ile Tyr His Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Ser Gly Tyr Asp Asp Pro Asp Gly Phe Asp Ile
            100                 105                 110

Trp Gly Gln Gly Thr Met Val Thr Val Ser Ser
        115                 120

<210> SEQ ID NO 167
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 167
gacatccaga tgacccagtc tccatcctcc ctgtctgcat ctgtaggaga cagagtcacc      60
atcacttgcc aggcgagtca ggacattagc aactatttaa gttggtttca gcagaaacca     120
gggaaagccc ctaagctcct gatccacgat gcatccaatt tggaaacagg ggtcccttca     180
aggttcagtg aagtggatc tgggacagat tttactttca ccatcagcag cctgcagcct     240
gaagatattg caacatatta ctgtcaacag tatgataatc ccccgtgcag ttttggccag     300
gggaccaagc tggagatcaa a                                               321

<210> SEQ ID NO 168
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Ser Trp Phe Gln Gln Lys Pro Gly Lys Ala Pro Lys Leu Leu Ile
        35                  40                  45

His Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Pro Pro Cys
                85                  90                  95

<210> SEQ ID NO 169
<211> LENGTH: 366
<212> TYPE: DNA
<213> ORGANISM: Artificial Sequence
<220> FEATURE:
<223> OTHER INFORMATION: Artificially synthesized sequence.

<400> SEQUENCE: 169

```
caggtgcagc tgcaggagtc gggcccagga ctggtgaagc cttcacagac cctgtccctc    60
acctgcactg tctctggtgg ctccatcagc agtggttatt actactggag ctggatccgc   120
cagcacccag ggaagggcct ggagtggatt gggtacatct attacagtgg gaccacctac   180
tacaatccgt ccttcaagag tcgagttacc atatcagtag acacgtctaa gaaccagttc   240
tccctgaaac tgagctctgt gactgccgcg gacacggccg tgtattactg tgcgagagcc   300
gattacgatt tttggagtgg tcactttgac tactggggcc agggaaccct ggtcaccgtc   360
tcctca                                                              366
```

<210> SEQ ID NO 170
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 170

Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
            20                  25                  30
Tyr Tyr Tyr Trp Ser Trp Ile Arg Gln His Pro Gly Lys Gly Leu Glu
        35                  40                  45
Trp Ile Gly Tyr Ile Tyr Tyr Ser Gly Thr Thr Tyr Tyr Asn Pro Ser
    50                  55                  60
Phe Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Ala Asp Tyr Asp Phe Trp Ser Gly His Phe Asp Tyr Trp
            100                 105                 110
Gly Gln Gly Thr Leu Val Thr Val Ser Ser
        115                 120

<210> SEQ ID NO 171
<211> LENGTH: 321
<212> TYPE: DNA
<213> ORGANISM: Artificial Sequence
<220> FEATURE:
<223> OTHER INFORMATION: Artificially synthesized sequence.

<400> SEQUENCE: 171

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
```

```
gaagattttg caacttatta ctgtctacag cataatagtt acccgtggac gttcggccaa    300
gggaccaagg tggaaatcaa a                                              321
```

<210> SEQ ID NO 172
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 172

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105
```

<210> SEQ ID NO 173
<211> LENGTH: 365
<212> TYPE: DNA
<213> ORGANISM: Artificial Sequence
<220> FEATURE:
<223> OTHER INFORMATION: Artificially synthesized sequence.

<400> SEQUENCE: 173

```
caggttcagc tggtgcagtc tggagctgag gtgaagaagc ctggggcctc agtgaaggtc     60
tcctgcaagg cttctggtta cacctttacc agctatggta tcagctgggt gcgacaggcc    120
cctggacaag gacttgagtg gatgggatgg atcagcgctt acgatggtca cacaaactat    180
gcacagaagc tccagggcag agtcaccatg accacagaca tccacgaa cacagcctac     240 atggagctga ggagcctgag atctgacgac acggccgttt attactgtgc gagagacccc    300
catgactaca gtaactacga ggcttttgac ttctggggcc agggaaccct ggtcaccgtc    360
tcctc                                                                365
```

<210> SEQ ID NO 174
<211> LENGTH: 121
<212> TYPE: PRT
<213> ORGANISM: Artificial Sequence
<220> FEATURE:
<223> OTHER INFORMATION: Artificially synthesized sequence.

<400> SEQUENCE: 174

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45
```

```
Gly Trp Ile Ser Ala Tyr Asp Gly His Thr Asn Tyr Ala Gln Lys Leu
 50                  55                  60
Gln Gly Arg Val Thr Met Thr Thr Asp Thr Ser Thr Asn Thr Ala Tyr
 65                  70                  75                  80
Met Glu Leu Arg Ser Leu Arg Ser Asp Asp Thr Ala Val Tyr Tyr Cys
                 85                  90                  95
Ala Arg Asp Pro His Asp Tyr Ser Asn Tyr Glu Ala Phe Asp Phe Trp
            100                 105                 110
Gly Gln Gly Thr Leu Val Thr Val Ser
            115                 120
```

<210> SEQ ID NO 175
<211> LENGTH: 519
<212> TYPE: DNA
<213> ORGANISM: Artificial Sequence
<220> FEATURE:
<223> OTHER INFORMATION: Artificially synthesized sequence.

<400> SEQUENCE: 175

```
atgaggtccc ctgctcagct cctggggctc ctgctactct ggctccgagg tgccagatgt    60
gacatccaga tgacccagtc tccatcctcc ctgtctgcat ctgtaggaga cagagtcacc   120
atcacttgcc gggcaagtca gagcattagc agttatttaa attggtatca gcagaaacca   180
gggaaagccc ctaacctcct gatctatgct gcatccagtt tgcaaagtgg ggtcccatca   240
agattcagtg gcagtggatc tgggacagat ttcactctca ccatcagcag tctgcaacct   300
gaagattttg caacttacta ctgtcaacag agttacagta cccccatcac cttcggccaa   360
gggacacgac tggagattaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgcc                          519
```

<210> SEQ ID NO 176
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 176

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Ser Ile Ser Ser Tyr
             20                  25                  30
Leu Asn Trp Tyr Gln Gln Lys Pro Gly Lys Ala Pro Asn Leu Leu Ile
         35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Ile
                 85                  90                  95
Thr Phe Gly Gln Gly Thr Arg Leu Glu Ile Lys
            100                 105
```

<210> SEQ ID NO 177
<211> LENGTH: 534
<212> TYPE: DNA
<213> ORGANISM: Artificial Sequence
<220> FEATURE:
<223> OTHER INFORMATION: Artificially synthesized sequence.

<400> SEQUENCE: 177

| | | | | | |
|---|---|---|---|---|---|
| accatggact | ggacctggag | ggtccttttc | ttggtggcag | cagcaacagg | tgcccactcc | 60 |
| caggttcagc | tggtgcagtc | tggagctgag | gtgaagaagc | ctggggcctc | agtgaaggtc | 120 |
| tcctgcaagg | cttctggtta | cacctttacc | aactatggta | tcagctgggt | gcggcaggcc | 180 |
| cctggacaag | ggcttgagtg | gatgggatgg | atcagcgctt | acgatggtta | cagaaactat | 240 |
| gcacagaagc | tccagggcag | agtcaccatg | accacagaca | catccacgac | cactgcctac | 300 |
| atggagctga | ggagcctgag | atctgacgac | acggccgtgt | attactgtgc | gagagatgtt | 360 |
| caagactacg | gtgactacga | ctactttgac | tactggggcc | agggaaccct | ggtcaccgtc | 420 |
| tcctcagctt | ccaccaaggg | cccatccgtc | ttccccctgg | tgccctgctc | caggagcacc | 480 |
| tccgagagca | cagccgccct | gggctgcctg | gtcaaggact | acttccccga | accg | 534 |

<210> SEQ ID NO 178
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Tyr Arg Asn Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Gln Asp Tyr Gly Asp Tyr Asp Tyr Phe Asp Tyr Trp
            100                 105                 110

Gly Gln Gly Thr Leu Val Thr Val Ser Ser
        115                 120

<210> SEQ ID NO 179
<211> LENGTH: 504
<212> TYPE: DNA
<213> ORGANISM: Artificial Sequence
<220> FEATURE:
<223> OTHER INFORMATION: Artificially synthesized sequence.

<400> SEQUENCE: 179

| | | | | | |
|---|---|---|---|---|---|
| cagctcctgg | ggctcctgct | actctggctc | cgaggtgcca | gatgtgacat | ccagatgacc | 60 |
| cagtctccat | cctccctgtc | tgcatctgta | ggagacagag | tcaccatcac | ttgccgggca | 120 |
| agtcagagca | ttagcagtta | tttaaattgg | tatcagcaga | aaccagggaa | agcccctaac | 180 |
| ctcctgatct | atgctgcatc | cagtttgcaa | agtggggtcc | catcaagatt | cagtggcagt | 240 |
| ggatctggga | cagatttcac | tctcaccatc | agcagtctgc | aacctgaaga | ttttgcaact | 300 |
| tactactgtc | aacagagtta | cagtaccccc | atcaccttcg | gccaagggac | acgactggag | 360 |

```
attaaacgaa ctgtggctgc accatctgtc ttcatcttcc cgccatctga tgagcagttg    420
aaatctggaa ctgcctctgt tgtgtgcctg ctgaataact tctatcccag agaggccaaa    480
gtacagtgga aggtggataa cgcc                                          504
```

<210> SEQ ID NO 180
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 180

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105
```

<210> SEQ ID NO 181
<211> LENGTH: 493
<212> TYPE: DNA
<213> ORGANISM: Artificial Sequence
<220> FEATURE:
<223> OTHER INFORMATION: Artificially synthesized sequence.

<400> SEQUENCE: 181

```
catctgtggt tcttcctcct gctggtggca gctcccagat gggtcctgtc ccaggtgcag    60
ctgcaggagt cgggcccagg actggtgaag ccttcacaga ccctgtccct cacctgcact    120
gtctctggtg gctccatcaa cagtggtgat tactactgga gctggatccg ccagcaccca    180
gggaagggcc tggagtggat tgggtacatc tattacagtg ggagcaccta ctacaacccg    240
tccctcaaga gtcgagttac catatcagta gacacgtcta agaaccagtt ctccctgaag    300
ctgagctctg tgactgccgc ggacacggcc gtgtattact gtgcgagagc agattacgat    360
ttttggagtg gttactttga ctactggggc cagggaaccc tggtcaccgt ctcctcagcc    420
tccaccaagg gcccatcggt cttccccctg gcaccctcct ccaagagcac ctctgggggc    480
acaacggccc tgg                                                      493
```

<210> SEQ ID NO 182
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 182

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Asn Ser Gly
```

```
            20                  25                  30
Asp Tyr Tyr Trp Ser Trp Ile Arg Gln His Pro Gly Lys Gly Leu Glu
    35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 183
<211> LENGTH: 518
<212> TYPE: DNA
<213> ORGANISM: Artificial Sequence
<220> FEATURE:
<223> OTHER INFORMATION: Artificially synthesized sequence.

<400> SEQUENCE: 183
atgagggtcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatca gcagaaacca   180 gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgc                           518

<210> SEQ ID NO 184
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 185
<211> LENGTH: 436
<212> TYPE: DNA
<213> ORGANISM: Artificial Sequence
<220> FEATURE:
<223> OTHER INFORMATION: Artificially synthesized sequence.

<400> SEQUENCE: 185

```
tggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tggttactac tggagctgga tccgccagca cccagggaag     180
ggcctggagt ggattgggta catctattac agtgggagca cctactacaa cccgtccctc     240
aagagtcgag ttaccatatc agtagacacg tctaagaacc agttctccct gaagctgagc     300
tctgtgactg ccgcggacac ggccgtgtat tactgtgcga gagatggcta tgatagtagt     360
ggttattacc acggctactt tgactactgg ggccagggaa ccctggtcac cgtctcctca     420
gcctccacca agggcc                                                    436
```

<210> SEQ ID NO 186
<211> LENGTH: 125
<212> TYPE: PRT
<213> ORGANISM: Artificial Sequence
<220> FEATURE:
<223> OTHER INFORMATION: Artificially synthesized sequence.

<400> SEQUENCE: 186

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Tyr Asp Ser Ser Gly Tyr Tyr His Gly Tyr Phe
            100                 105                 110

Asp Tyr Trp Gly Gln Gly Thr Leu Val Thr Val Ser Ser
        115                 120                 125
```

<210> SEQ ID NO 187
<211> LENGTH: 521
<212> TYPE: DNA
<213> ORGANISM: Artificial Sequence
<220> FEATURE:
<223> OTHER INFORMATION: Artificially synthesized sequence.

<400> SEQUENCE: 187

```
caggtcttca tttctctgtt gctctggatc tctggtgcct acggggacat cgtgatgacc      60
cagtctccag actccctggc tgtgtctctg ggcgagaggg ccaccatcaa ctgcaagtcc     120
agccagagtg tttttataca gctccaacat aagaactact tagcttggta ccagcagaaa     180
ccaggacagc ctcctaagct gctcatttac tgggcatcta cccgggaatc cggggtccct     240
gaccgattca gtggcagcgg gtctgggaca gatttcactc tcaccatcag cagcctgcag     300
```

```
gctgaagatg tggcagttta ttactgtcag caatattata gtactccgct cactttcggc    360
ggagggacca aggtggagat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg c                       521
```

<210> SEQ ID NO 188
<211> LENGTH: 113
<212> TYPE: PRT
<213> ORGANISM: Artificial Sequence
<220> FEATURE:
<223> OTHER INFORMATION: Artificially synthesized sequence.

<400> SEQUENCE: 188

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

<210> SEQ ID NO 189
<211> LENGTH: 455
<212> TYPE: DNA
<213> ORGANISM: Artificial Sequence
<220> FEATURE:
<223> OTHER INFORMATION: Artificially synthesized sequence.

<400> SEQUENCE: 189

```
ctgtggttct tcctcctgct ggtggcagct cccagatggg tcctgtccca ggtgcagctg     60
caggagtcgg gcccaggact ggtgaagcct tcacagaccc tgtccctcac ctgcactgtc    120
tctggtggct ccatcagtag tggtgattac tactggagct ggatccgcca gcacccaggg    180
aagggcctgg agtggattgg gtacatctat tacagtggga gcacctacta caacccgtcc    240
ctcaagagtc gagttaccat atcagtagac acgtctaaga accagttctc cctgaagttg    300
agctctgtga ctgccgcgga cacggccgtg tattactgtg cgagagccga ttacgatttt    360
tggagtggtt attttgacta ctggggccag ggaaccctgg tcaccgtctc ctcagcctcc    420
accaagggcc catcggtctt ccccctggca ccctc                              455
```

<210> SEQ ID NO 190
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 190

```
Gln Val Gln Leu Gln Glu Ser Gly Pro Gly Leu Val Lys Pro Ser Gln
```

```
                 1               5                  10                 15
Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
                35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
                115                 120

<210> SEQ ID NO 191
<211> LENGTH: 442
<212> TYPE: DNA
<213> ORGANISM: Artificial Sequence
<220> FEATURE:
<223> OTHER INFORMATION: Artificially synthesized sequence.

<400> SEQUENCE: 191
gtgcccgctc agcgcctggg gctcctgctg ctctggttcc caggtgccag gtgtgacatc      60
cagatgaccc agtctccatc ctccctgtct gcatctgtag agacagagt caccatcact     120 tgccgggcaa gtcagggcat tagaaatgat ttaggctggt atcagcagaa accagggaaa    180
gcccctaagc gcctgatcta tgctgcatcc agtttgcaaa gtggggtccc atcaaggttc    240
agcggcagtg gatctgggac agaattcact ctcacaatca gcagcctgca gcctgaagat    300
tttgcaactt attactgtct acagcataat aattacccgt ggacgttcgg ccaagggacc    360
aaggtggaaa tcaaacgaac tgtggctgca ccatctgtct tcatcttccc gccatctgat    420
gagcagttga aatctggaac tg                                              442

<210> SEQ ID NO 192
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
                100                 105
```

<210> SEQ ID NO 193
<211> LENGTH: 427
<212> TYPE: DNA
<213> ORGANISM: Artificial Sequence
<220> FEATURE:
<223> OTHER INFORMATION: Artificially synthesized sequence.

<400> SEQUENCE: 193

```
tggttcttcc ttctgctggt ggcagctccc agatgggtcc tgtcccaggt gcagctgcag    60
gagtcgggcc caggactggt gaagccttca cagaccctgt ccctcacctg cactgtctct   120
ggtggctcca tcagcagtgg tgattactac tggagctgga tccgccagca cccagggaag   180
ggcctggagt ggattgggta catctattac agtgggagca cctactacaa cccgtccctc   240
aagagtcgag ttaccatatc agtagacacg tctaagaacc agttctccct gaagctgagc   300
tctgtgactg ccgcggacac ggccgtgtat ttctgtgcga gagccgatta cgattttggg   360
agtggttatt ttgactactg gggccaggga accctggtca ccgtctcctc agcctccacc   420
aagggcc                                                             427
```

<210> SEQ ID NO 194
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 194

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Asp Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Phe
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 195
<211> LENGTH: 518
<212> TYPE: DNA
<213> ORGANISM: Artificial Sequence
<220> FEATURE:
<223> OTHER INFORMATION: Artificially synthesized sequence.

<400> SEQUENCE: 195

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatcag cagaaaccca   180
gggaaagccc ctaagcgcct gatctatgct gcatccagtt tgcaaagtgg ggtcccatca   240
```

```
aggttcagcg gcagtggatc tgggacagaa ttcactctca caatcagcag cctgcagcct        300
gaagattttg caacttatta ctgtctacag cataatactt acccgtggac gttcggccaa        360
gggaccaagg tggaaatcaa acgaactgtg gctgcaccat ctgtcttcat cttcccgcca        420
tctgatgagc agttgaaatc tggaactgcc tctgttgtgt gcctgctgaa taacttctat        480
cccagagagg ccaaagtaca gtggaaggtg gataacgc                                518
```

```
<210> SEQ ID NO 196
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 196
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Thr Tyr Pro Trp
                 85                  90                  95

Thr Phe Gly Gln Gly Thr Lys Val Glu Ile Lys
            100                 105
```

```
<210> SEQ ID NO 197
<211> LENGTH: 428
<212> TYPE: DNA
<213> ORGANISM: Artificial Sequence
<220> FEATURE:
<223> OTHER INFORMATION: Artificially synthesized sequence.

<400> SEQUENCE: 197
```

```
tggttcttcc ttctgctggt ggcagctccc agatgggtcc tgtcccaggt gcagctgcag        60
gagtcgggcc caggactggt gaagccttca cagaccctgt ccctcacctg cactgtctct        120
ggtggctcca tcagcagtgg tgattactac tggagctgga tccgccagca cccagggaag       180
ggcctggagt ggattgggta catctattac agtgggagca cctactacaa cccgtccctc        240
aagagtcgag ttaccatatc agtagacacg tctaagaacc agttctccct gaagctgagc        300
tctgtgactg ccgcggacac ggccgtgtat ttctgtgcga gagccgatta cgattttgg       360 aatggttatt ttgactactg gggccaggga accctggtca ccgtctcctc agcctccacc        420
aagggccc                                                                 428
```

```
<210> SEQ ID NO 198
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 198
```

```
Gln Val Gln Leu Gln Glu Ser Gly Pro Gly Leu Val Lys Pro Ser Gln
  1               5                  10                  15
```

-continued

```
Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120
```

<210> SEQ ID NO 199
<211> LENGTH: 519
<212> TYPE: DNA
<213> ORGANISM: Artificial Sequence
<220> FEATURE:
<223> OTHER INFORMATION: Artificially synthesized sequence.

<400> SEQUENCE: 199

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatca gcagaaacca   180 gggaaagccc ctaagcgcct gatctatgct gcttccagtt tgcaaagtgg ggtcccatca   240
aggttcagcg gcagtggatc tgggacagaa ttcactctca caatcagcag cctgcagcct   300
gaagattttg caacttatta ctgtctacag cataatactt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgcc                          519
```

<210> SEQ ID NO 200
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 200

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
```

<210> SEQ ID NO 201
<211> LENGTH: 398
<212> TYPE: DNA
<213> ORGANISM: Artificial Sequence
<220> FEATURE:
<223> OTHER INFORMATION: Artificially synthesized sequence.

<400> SEQUENCE: 201

```
ttggtggcag cagctacagg cacccacgcc caggtccagc tggtacagtc tggggctgag    60
gtgaagaagc ctggggcctc agtgaaggtc tcctgcaagg tttccggata cccctcact   120
gaattatcca tgtactgggt gcgacaggct cctggaaaag gcttgagtg atgggaggt    180
tttgatcctg aagatggtga acaatctac gcacagaagt tccagggcag agtcaccatg   240
accgaggaca catctacaga cacagcctac atggagctga gcagcctgag atctgaggac   300
acggccgtgt attactgtgc aactgggtgg aactacgtct ttgactactg gggccaggga   360
accctggtca ccgtctcctc agcctccacc aagggccc                           398
```

<210> SEQ ID NO 202
<211> LENGTH: 117
<212> TYPE: PRT
<213> ORGANISM: Artificial Sequence
<220> FEATURE:
<223> OTHER INFORMATION: Artificially synthesized sequence.

<400> SEQUENCE: 202

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met Tyr Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Trp Asn Tyr Val Phe Asp Tyr Trp Gly Gln Gly Thr Leu
            100                 105                 110

Val Thr Val Ser Ser
        115
```

<210> SEQ ID NO 203
<211> LENGTH: 388
<212> TYPE: DNA
<213> ORGANISM: Artificial Sequence
<220> FEATURE:
<223> OTHER INFORMATION: Artificially synthesized sequence.

<400> SEQUENCE: 203

```
ggatccagtg gggatattgt gatgactcag tctccactct ccctgcccgt cacccctgga    60
gagccggcct ccatctcctg caggtccagt cagagcctcc tgcatagtaa tggatacaac   120
tatttggatt ggtacctgca gaagccaggg cagtctccac agctcctgat ctatttggat   180
tctcatcggg cctccggggt ccctgacagg ttcagtggca gtggatcagg cacagatttt   240
acactgaaaa tcagcagagt ggaggctgag gatgttgggg tttattactg catgcaagct   300
```

-continued

```
ctacaaactc cgctcactttt cggcggaggg accaaggtgg agatcaaacg aactgtggct    360
gcaccatctg tcttcatctt cccgccat                                        388
```

<210> SEQ ID NO 204
<211> LENGTH: 112
<212> TYPE: PRT
<213> ORGANISM: Artificial Sequence
<220> FEATURE:
<223> OTHER INFORMATION: Artificially synthesized sequence.

<400> SEQUENCE: 204

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Asp Ser His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 205
<211> LENGTH: 446
<212> TYPE: DNA
<213> ORGANISM: Artificial Sequence
<220> FEATURE:
<223> OTHER INFORMATION: Artificially synthesized sequence.

<400> SEQUENCE: 205

```
tggttcttcc ttctgctggt ggcagctccc agatgggtcc tgtcccaggt gcagctgcag    60
gagtcgggcc caggactggt gaagccttca cagaccctgt ccctcacctg cactgtctct   120
ggtggctcca tcagcagtgg tgattactac tggagctgga tccgccagca cccagggaag   180
ggcctggagt ggattgggta catctattac agtgggagca cctactacaa cccgtccctc   240
aagagtcgag ttaccatatc agtagacacg tctaagaacc agttctccct gaagctgagc   300
tctgtgactg ccgcggacac ggccgtgtat ttctgtgcga gagccgatta cgattttttgg   360 agtggttatt ttgactactg gggccaggga accctggtca ccgtctcctc agcctccacc   420
aagggcccat cgagtcttcc ccctgg                                         446
```

<210> SEQ ID NO 206
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 206

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu

```
                35                  40                  45
Trp Ile Gly Tyr Ile Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
            115                 120

<210> SEQ ID NO 207
<211> LENGTH: 519
<212> TYPE: DNA
<213> ORGANISM: Artificial Sequence
<220> FEATURE:
<223> OTHER INFORMATION: Artificially synthesized sequence.

<400> SEQUENCE: 207
atgagggtcc ccgctcagct cctggggctc ctgctgctct ggttcccagg tgccaggtgt     60
gacatccaga tgacccagtc tccatcctcc ctgtctgcat ctgtaggaga cagagtcacc    120
atcacttgcc gggcaagtca gggcattaga aatgatttag ctggtatca gcagaaacca    180 gggaaagccc ctaagcgcct gatctatgct gcatccagtt tgcaaagtgg ggtcccatca    240
aggttcagcg gcagtggatc tgggacaaaa ttcactctca ctatcagcag cctgcagcct    300
gaagattttg caacttatta ctgtctacag cataatactt acccgtggac gttcggccaa    360
gggaccaagg tggaaatcag acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                           519

<210> SEQ ID NO 208
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Lys Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Arg
            100                 105

<210> SEQ ID NO 209
<211> LENGTH: 564
```

-continued

<212> TYPE: DNA
<213> ORGANISM: Artificial Sequence
<220> FEATURE:
<223> OTHER INFORMATION: Artificially synthesized sequence.

<400> SEQUENCE: 209

```
accatgaaac atctgtggtt cttcctcctg ctggtggcag ctcccagatg ggtcctgtcc      60
caggtgcagc tgcaggagtc gggcccagga ctggtgaagc cttcacagac cctgtccctc     120
acctgcactg tctctggtgg ctccatcagc agtggtgatt actactggag ctggatccgc     180
cagcacccag ggaagggcct ggagtggatt gggtacatct attacagtgg gagcacctac     240
tacaacccgt ccctcaagag tcgagttacc atatcagtag acacgtctaa gaaccagttc     300
tccctgaagc tgagctctgt gactgccgcg gacacggccg tgtattactg tgcgagagcg     360
gattacgatt tttggagtgg ttattttgac tactggggcc agggaatcct ggtcaccgtc     420
tcctcagcct ccaccaaggg cccatcggtc ttccccctgg cacccctcct caagaacacc     480
tctgggggca cagcggccct gggctgcctg gtcaaggact acttccccga accggtgacg     540
gtgtcctgga actcaggcgc cctg                                             564
```

<210> SEQ ID NO 210
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 210

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser Ser
        115                 120
```

<210> SEQ ID NO 211
<211> LENGTH: 519
<212> TYPE: DNA
<213> ORGANISM: Artificial Sequence
<220> FEATURE:
<223> OTHER INFORMATION: Artificially synthesized sequence.

<400> SEQUENCE: 211

```
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag gctggtatca gcagaaacca     180
gggaaagccc ctaagcgcct gatctatgct gcatccagtt tgcaaagtgg ggtcccatca     240
```

```
aggttcagcg gcagtggatc tgggacagaa ttcactctca caatcagcag cctgcagcct    300
gaagattttg caacttatta ctgtctacag cataatagtt acccgtggac gttcggccaa    360
gggaccaagg tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                           519
```

<210> SEQ ID NO 212
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 212

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 213
<211> LENGTH: 432
<212> TYPE: DNA
<213> ORGANISM: Artificial Sequence
<220> FEATURE:
<223> OTHER INFORMATION: Artificially synthesized sequence.

<400> SEQUENCE: 213

```
tggttcttcc ttctgctggt ggcagctccc agatgggtcc tgtcccaggt gcagctgcag    60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattggata catctattac agtgggagca cctactacaa ttcgtccctc    240
aagagtcgag ttaccatatc agtagacacg tctaagaacc agttctccct gaagctgagc    300
tctgtgactg ccgcggacac ggccgtgtat tactgtgcga gagcggatta cgattttttgg    360 agtggttatt ttgactactg gggccaggga accctggtca ccgtctcctc agcctccacc    420
aagggcccat cg                                                        432
```

<210> SEQ ID NO 214
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 214

```
Gln Val Gln Leu Gln Glu Ser Gly Pro Gly Leu Val Lys Pro Ser Gln
 1               5                  10                  15
```

```
Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Ser Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
            115                 120

<210> SEQ ID NO 215
<211> LENGTH: 372
<212> TYPE: DNA
<213> ORGANISM: Artificial Sequence
<220> FEATURE:
<223> OTHER INFORMATION: Artificially synthesized sequence.

<400> SEQUENCE: 215
ggtgccaggt gtgacatcca gatgacccag tctccatcct ccctgtctgc atctgtagga    60
gacagagtca ccatcacttg ccgggcaagt cagggcatta gaaatgattt aggctggtat   120
cagcagaaac ctgggaaagc ccctaagcgc ctgatctatg ctgcatccag tttgcaaagt   180
ggggtcccat caaggttcag cggcagtgga tctgggacag aattcactct cacaatcagc   240
agcctgcagc ctgaagattt tgcaacttat tactgtctac agcacaatag ttacccgtgg   300
acgttcggcc aagggaccaa ggtggaaatc aaacgaactg tggctgcacc atctgtcttc   360
atcttcccgc ca                                                       372

<210> SEQ ID NO 216
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 216

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
            85                  90                  95

Thr Phe Gly Gln Gly Thr Lys Val Glu Ile Lys
            100                 105

<210> SEQ ID NO 217
```

<211> LENGTH: 548
<212> TYPE: DNA
<213> ORGANISM: Artificial Sequence
<220> FEATURE:
<223> OTHER INFORMATION: Artificially synthesized sequence.

<400> SEQUENCE: 217

| | | |
|---|---|---|
| aggttcttcc ttctgctggt ggcagctccc agatgggtcc tgtcccaggt gcagctgcag | 60 |
| gagtcgggcc caggactggt gaagccttca cagaccctgt ccctcacctg cactgtctct | 120 |
| ggtggctcca tcagcagtgg tgattactac tggagctgga tccgccagca cccagggaag | 180 |
| ggcctggagt ggattggata catctattac agtgggagca cctactacaa cccgtccctc | 240 |
| aagagtcgag ttaccatatc agtagacacg tctaagaacc agttctccct gaagctgagc | 300 |
| tctgtgactg ccgcggacac ggccgtgtat tactgtgcga gagccgatta cgattttggg | 360 |
| agtggttatt ttgactactg gggccaggga accctggtca ccgtctcctc agcctccacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccct | 548 |

<210> SEQ ID NO 218
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 218

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 219
<211> LENGTH: 517
<212> TYPE: DNA
<213> ORGANISM: Artificial Sequence
<220> FEATURE:
<223> OTHER INFORMATION: Artificially synthesized sequence.

<400> SEQUENCE: 219

| | | |
|---|---|---|
| atgagggtcc ccgctcagct cctggggctc ctgctgctct ggttcccagg tgccaggtgt | 60 |
| gacatccaga tgacccagtc tccatcctcc ctgtctgcat ctgtaggaga cagagtcacc | 120 |
| atcacttgcc gggcaagtca gggcattaga aatgatttag ctggtatca gcagaaacca | 180 |
| gggaaagccc ctaagcgcct gatctatgct gcatccagtt tgcaaagtgg ggtcccatca | 240 |

```
aggttcagcg gcagtggatc tgggacagaa ttcactctca caatcagcag cctgcagcct    300
gaagattttg caacttatta ctgtctacag cataatagtt acccgtggac gttcggccaa    360
gggaccaagg tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacg                             517
```

<210> SEQ ID NO 220
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 220

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 221
<211> LENGTH: 446
<212> TYPE: DNA
<213> ORGANISM: Artificial Sequence
<220> FEATURE:
<223> OTHER INFORMATION: Artificially synthesized sequence.

<400> SEQUENCE: 221

```
ctgtggttct tccttctgct ggtggcagct cccagatggg tcctgtccca ggtgcagctg     60
caggagtcgg gcccaggact ggtgaagcct tcacagaccc tgtccctcac ctgcactgtc    120
tctggtggct ccatcagcag tggtgattac tactggagct ggatccgcca gcacccaggg    180
aagggcctgg agtggattgg gtacatctat tacagtggga gcacctacta caacccgtcc    240
ctcaagagtc gagttaccat gtcagtagac acgtctaaga accagttctc cctgaagctg    300
agctctgtga ctgccgcgga cacggccgtg tattactgtg cgagagccga ttacgatttt    360
tggagtggtc actttgactg ctggggccag ggaaccctgg tcaccgtctc ctcagcttcc    420
accaagggcc catccgtctt ccccc                                         446
```

<210> SEQ ID NO 222
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 222

Gln Val Gln Leu Gln Glu Ser Gly Pro Gly Leu Val Lys Pro Ser Gln

```
              1               5                  10                 15
Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
                35                  40                  45

Trp Ile Gly Tyr Ile Tyr Tyr Ser Gly Ser Thr Tyr Tyr Asn Pro Ser
        50                  55                  60

Leu Lys Ser Arg Val Thr Met Ser Val Asp Thr Ser Lys Asn Gln Phe
 65                 70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly His Phe Asp Cys Trp
                100                 105                 110

Gly Gln Gly Thr Leu Val Thr Val Ser Ser
                115                 120
```

<210> SEQ ID NO 223
<211> LENGTH: 419
<212> TYPE: DNA
<213> ORGANISM: Artificial Sequence
<220> FEATURE:
<223> OTHER INFORMATION: Artificially synthesized sequence.

<400> SEQUENCE: 223

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga gatgatttag ctggtatca gcagaaacca   180
gggaaagccc ctaagcgcct gatctatgct gaatccagtt tgcaaagtgg ggtcccatca   240
aggttcagcg gcagtggatc tgggacagaa ttcactctca caatcagcag cctgcagcct   300
gaagattttg caacttatta ctgtctacag catcatagtt acccgtggac gttcggccaa   360
gggaccaagg tggaaatcaa acgaactgtg gctgcaccat ctgtcttcat cttcccgcc    419
```

<210> SEQ ID NO 224
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 224

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asp Asp
                20                  25                  30

Leu Gly Trp Tyr Gln Gln Lys Pro Gly Lys Ala Pro Lys Arg Leu Ile
                35                  40                  45

Tyr Ala Glu Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
 65                 70                  75                  80

Glu Asp Phe Ala Thr Tyr Tyr Cys Leu Gln His His Ser Tyr Pro Trp
                85                  90                  95

Thr Phe Gly Gln Gly Thr Lys Val Glu Ile Lys
                100                 105
```

<210> SEQ ID NO 225
<211> LENGTH: 504
<212> TYPE: DNA
<213> ORGANISM: Artificial Sequence
<220> FEATURE:
<223> OTHER INFORMATION: Artificially synthesized sequence.

<400> SEQUENCE: 225

```
tggctgagct gggttttcct cgttgctctt ttaagaggtg tccagtgtca ggtgcagctg      60
gtggagtctg ggggaggcgt ggtccagcct gggaggtccc tgagactctc ctgtgcagcg     120
tctggattca ccttcaatag ctatgacatg cactgggtcc gccaggctcc aggcaagggg     180
ctggagtggg tggcagttat atggtatgat ggaagtaata atactatgc agactccgtg      240
aagggccgat tcaccatctc tagagacaat tccaagaaca cgctgtatct gcaaatgaac     300
agcctgagag ccgaggacac ggctgtgtat tactgtgcga gaccgcttt gtgtactaat      360
ggtgtatgct atgaagacta cggtatggac gtctggggcc aagggaccac ggtcaccgtc     420
tcctcagctt ccaccaaggg cccatccgtc ttccccctgg cgccctgctc caggagcacc     480
tccgagagca cagccgccct gggc                                            504
```

<210> SEQ ID NO 226
<211> LENGTH: 126
<212> TYPE: PRT
<213> ORGANISM: Artificial Sequence
<220> FEATURE:
<223> OTHER INFORMATION: Artificially synthesized sequence.

<400> SEQUENCE: 226

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Asn Ser Tyr
            20                  25                  30
Asp Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Leu Cys Thr Asn Gly Val Cys Tyr Glu Asp Tyr Gly
            100                 105                 110
Met Asp Val Trp Gly Gln Gly Thr Thr Val Thr Val Ser Ser
        115                 120                 125
```

<210> SEQ ID NO 227
<211> LENGTH: 504
<212> TYPE: DNA
<213> ORGANISM: Artificial Sequence
<220> FEATURE:
<223> OTHER INFORMATION: Artificially synthesized sequence.

<400> SEQUENCE: 227

```
atgagggtcc ctgctcagct cctggggctc ctgctgctct ggctctcagg tgccagatgt      60
gacatccaga tgacccagtc tccatcctcc ctgtctgcat ctgtaggaga cagagtcacc     120
atcacttgcc aggcgagtca ggacattagc aactatttaa attggtatca gcagaaacca     180
gggaaagccc ctaaggtcct gatctacgat gcatccaatt tggaaacagg ggtcccatca     240
```

```
aggttcagtg gaagtggatc tgggacagat tttactttca ccatcagcag cctgcagcct        300
gaagatgttg caacatatta ctgtcaacac tatgatactc tcccgctcac tttcggcgga        360
gggaccaagg tggagatcaa acgaactgtg gctgcaccat ctgtcttcat cttcccgcca        420
tctgatgagc agttgaaatc tggaactgcc tctgttgtgt gcctgctgaa taacttctat        480
cccagagagg ccaaagtaca gtgg                                               504
```

<210> SEQ ID NO 228
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 228

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Tyr Cys Gln His Tyr Asp Thr Leu Pro Leu
                85                  90                  95

Thr Phe Gly Gly Gly Thr Lys Val Glu Ile Lys
            100                 105
```

<210> SEQ ID NO 229
<211> LENGTH: 472
<212> TYPE: DNA
<213> ORGANISM: Artificial Sequence
<220> FEATURE:
<223> OTHER INFORMATION: Artificially synthesized sequence.

<400> SEQUENCE: 229

```
ggactgtgca agaacatgaa acacctgtgg ttcttcctcc tgctggtggc agctcccaga         60
tgggtcctgt cccaggtgca gctgcaggag tcgggcccag gactggtgaa gccttacag        120 accctgtccc tcacctgcac tgtctctggt ggctccatca gcagtggtga ttactactgg        180
agctggatcc gccagcaccc agggaagggc ctggagtgga ttgggtacat ctattacagt        240
gggaccacct actacaaccc gtccctcaag agtcgagtta ccatatcagt agacacgtct        300
aagaaccagt tcgccctgaa gctgaactct gtgactgccg cggacacggc cgtgtattac        360
tgtgcgagag ccgattacga ttttggagt ggttattttg actactgggg ccagggaacc        420
ctggtcaccg tctcctcagc ttccaccaag ggcccatccg tcttccccct gg               472
```

<210> SEQ ID NO 230
<211> LENGTH: 122
<212> TYPE: PRT
<213> ORGANISM: Artificial Sequence
<220> FEATURE:
<223> OTHER INFORMATION: Artificially synthesized sequence.

<400> SEQUENCE: 230

```
Gln Val Gln Leu Gln Glu Ser Gly Pro Gly Leu Val Lys Pro Leu Gln
 1               5                  10                  15
```

```
Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
            115                 120
```

<210> SEQ ID NO 231
<211> LENGTH: 531
<212> TYPE: DNA
<213> ORGANISM: Artificial Sequence
<220> FEATURE:
<223> OTHER INFORMATION: Artificially synthesized sequence.

<400> SEQUENCE: 231

```
atgagggtcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaggtca gggcattaga aatgatttag ctggtatca gcagaaacca    180
gggaaagccc ctcagcgcct gatctatgct gcatccagtt tgcaaagtgg ggtcccatca   240
aggttcagcg gcagtggatc tgggacagaa ttctctctca caatctccag cctgcagcct   300
gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc ttccaatcgg g           531
```

<210> SEQ ID NO 232
<211> LENGTH: 107
<212> TYPE: PRT
<213> ORGANISM: Artificial Sequence
<220> FEATURE:
<223> OTHER INFORMATION: Artificially synthesized sequence.

<400> SEQUENCE: 232

```
Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
                100                 105
```

-continued

```
<210> SEQ ID NO 233
<211> LENGTH: 26
<212> TYPE: DNA
<213> ORGANISM: Artificial Sequence
<220> FEATURE:
<223> OTHER INFORMATION: Primer

<400> SEQUENCE: 233
cgggatccat gtcctagcct aggggc                                           26

<210> SEQ ID NO 234
<211> LENGTH: 39
<212> TYPE: DNA
<213> ORGANISM: Artificial Sequence
<220> FEATURE:
<223> OTHER INFORMATION: Primer

<400> SEQUENCE: 234
gctctagatt aatgatgatg atgatgatgt tgtcctaaa                             39

<210> SEQ ID NO 235
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 235

Gly Gly Ser Ile Asn Ser Gly Asp Tyr Tyr Trp Ser
  1               5                  10

<210> SEQ ID NO 236
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 236

Gly Gly Ser Ile Ser Ser Gly Asp Tyr Tyr Trp Ser
  1               5                  10

<210> SEQ ID NO 237
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 237

Gly Gly Ser Ile Ser Ser Gly Gly Tyr Tyr Trp Ser
  1               5                  10

<210> SEQ ID NO 238
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 238

Gly Tyr Thr Leu Thr Glu Leu Ser Met Tyr
  1               5                  10
```

```
<210> SEQ ID NO 239
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 239

Gly Gly Ser Val Ser Ser Gly Gly Tyr Tyr Trp Ser
 1               5                  10

<210> SEQ ID NO 240
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 240

Gly Phe Thr Phe Asn Ser Tyr Asp Met His
 1               5                  10

<210> SEQ ID NO 241
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 241

Gly Tyr Thr Phe Thr Asn Tyr Gly Ile Ser
 1               5                  10

<210> SEQ ID NO 242
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 242

Gly Phe Thr Phe Ser Asp Tyr Tyr Met Ser
 1               5                  10

<210> SEQ ID NO 243
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 243

Gly Gly Ser Ile Ser Ser Gly Tyr Tyr Tyr Trp Ser
 1               5                  10

<210> SEQ ID NO 244
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 244

Gly Tyr Thr Phe Thr Ser Tyr Gly Ile Ser
 1               5                  10

<210> SEQ ID NO 245
```

```
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 245

Gly Phe Ser Leu Ser Thr Ser Gly Val Gly Val Gly
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 246

Gly Phe Thr Val Ser Ser Asn Tyr Met Ser
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 247

Gly Tyr Ser Phe Thr Ser Tyr Trp Ile Gly
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 248

Gly Tyr Thr Phe Thr Ser Tyr Asp Ile Asn
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 249

Gly Asp Ser Val Ser Ser Asn Ser Ala Ala Trp Asn
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 250

Gly Gly Ser Ile Ser Ser Tyr Tyr Trp Ser
1               5                   10

<210> SEQ ID NO 251
<211> LENGTH: 10
```

```
<212> TYPE: PRT
<213> ORGANISM: Artificial Sequence
<220> FEATURE:
<223> OTHER INFORMATION: Artificially synthesized protein sequence.

<400> SEQUENCE: 251

Gly Tyr Thr Phe Thr Gly Tyr Tyr Met His
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 252

Gly Phe Thr Phe Ser Ile Tyr Ser Met Asn
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 253

Gly Gly Ser Val Ser Ser Gly Gly Tyr Tyr Trp Asn
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 254

Gly Gly Ser Val Ser Ser Gly Gly Tyr Tyr Trp Asn
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 255

Gly Phe Thr Phe Ser Ser Tyr Gly Met His
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 256

Gly Gly Ser Phe Ser Gly Tyr Tyr Trp Ser
1               5                   10

<210> SEQ ID NO 257
<211> LENGTH: 12
<212> TYPE: PRT
```

```
<213> ORGANISM: Artificial Sequence
<220> FEATURE:
<223> OTHER INFORMATION: Artificially synthesized protein sequence.

<400> SEQUENCE: 257

Gly Val Ser Ile Ser Ser Gly Gly Tyr Tyr Trp Ser
1               5                   10

<210> SEQ ID NO 258
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 258

Tyr Ile Tyr Tyr Ser Gly Ser Thr Tyr Tyr Asn Pro Ser Leu Lys Ser
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 259

Tyr Ile Tyr Tyr Ser Gly Ser Thr Tyr Tyr Asn Pro Ser Leu Arg Ser
1               5                   10                  15

<210> SEQ ID NO 260
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 260

Gly Phe Asp Pro Glu Asp Gly Glu Thr Ile Tyr Ala Gln Lys Phe Gln
1               5                   10                  15

Gly

<210> SEQ ID NO 261
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 261

Tyr Ile Tyr Tyr Ser Gly Ser Thr Asn Tyr Asn Pro Ser Leu Lys Ser
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 262

Tyr Ile Tyr Tyr Ser Gly Ser Thr Tyr Tyr Asn Ser Ser Leu Lys Ser
1               5                   10                  15

<210> SEQ ID NO 263
<211> LENGTH: 16
```

<212> TYPE: PRT
<213> ORGANISM: Artificial Sequence
<220> FEATURE:
<223> OTHER INFORMATION: Artificially synthesized protein sequence.

<400> SEQUENCE: 263

Tyr Ile Tyr Asp Ser Gly Ser Thr Tyr Tyr Asn Pro Ser Leu Lys Ser
1               5                   10                  15

<210> SEQ ID NO 264
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 264

Val Ile Trp Tyr Asp Gly Ser Asn Lys Tyr Tyr Ala Asp Ser Val Lys
1               5                   10                  15

Gly

<210> SEQ ID NO 265
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 265

Tyr Ile Tyr Tyr Ser Gly Thr Thr Tyr Tyr Asn Pro Ser Leu Lys Ser
1               5                   10                  15

<210> SEQ ID NO 266
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 266

Trp Ile Ser Ala Tyr Asp Gly Tyr Arg Asn Tyr Ala Gln Lys Leu Gln
1               5                   10                  15

Gly

<210> SEQ ID NO 267
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 267

Tyr Ile Ser Ser Ser Gly Asn Asn Ile Tyr His Ala Asp Ser Val Lys
1               5                   10                  15

Gly

<210> SEQ ID NO 268
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 268

Tyr Ile Tyr Tyr Ser Gly Thr Thr Tyr Tyr Asn Pro Ser Phe Lys Ser

<210> SEQ ID NO 269
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 269

Trp Ile Ser Ala Tyr Asp Gly His Thr Asn Tyr Ala Gln Lys Leu Gln
1               5                   10                  15
Gly

<210> SEQ ID NO 270
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 270

Leu Ile Tyr Trp Asn Asp Asp Lys Arg Tyr Ser Pro Ser Leu Lys Ser
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 271

Val Ile Tyr Ser Gly Gly Ser Thr Tyr Tyr Ala Asp Ser Val Lys Gly
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 272

Tyr Ile Tyr Ser Ser Gly Ser Thr Tyr Tyr Asn Pro Ser Leu Lys Ser
1               5                   10                  15

<210> SEQ ID NO 273
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 273

Ile Ile Tyr Pro Gly Asp Ser Asp Thr Arg Tyr Ser Pro Ser Phe Gln
1               5                   10                  15
Gly

<210> SEQ ID NO 274
<211> LENGTH: 17
<212> TYPE: PRT
<213> ORGANISM: Artificial Sequence
<220> FEATURE:
<223> OTHER INFORMATION: Artificially synthesized protein sequence.

-continued

```
<400> SEQUENCE: 274

Ile Ile Trp Pro Gly Asp Ser Asp Thr Ile Tyr Ser Pro Ser Phe Gln
1               5                   10                  15
Gly

<210> SEQ ID NO 275
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 275

Trp Met Asn Pro Asn Ser Gly Asp Thr Gly Tyr Ala Gln Val Phe Gln
1               5                   10                  15
Gly

<210> SEQ ID NO 276
<211> LENGTH: 18
<212> TYPE: PRT
<213> ORGANISM: Artificial Sequence
<220> FEATURE:
<223> OTHER INFORMATION: Artificially synthesized protein sequence.

<400> SEQUENCE: 276

Arg Thr Tyr Tyr Arg Ser Lys Trp Tyr Asn Asp Tyr Ala Val Ser Val
1               5                   10                  15
Lys Ser

<210> SEQ ID NO 277
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 277

His Ile Tyr Thr Ser Gly Ser Thr Asn Tyr Asn Pro Ser Leu Lys Ser
1               5                   10                  15

<210> SEQ ID NO 278
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 278

Trp Ile Asn Pro Asn Ile Gly Gly Thr Asn Cys Ala Gln Lys Phe Gln
1               5                   10                  15
Gly

<210> SEQ ID NO 279
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 279

Asn Ile Tyr Tyr Ser Gly Ser Thr Tyr Tyr Asn Pro Ser Leu Lys Ser
1               5                   10                  15
```

```
<210> SEQ ID NO 280
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 280

Tyr Ile Ser Ser Ser Ser Ser Thr Ile Tyr Tyr Ala Asp Ser Val Lys
1               5                   10                  15
Gly

<210> SEQ ID NO 281
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 281

Tyr Ile Asn Tyr Ser Gly Ser Thr Asn Tyr Asn Pro Ser Leu Lys Ser
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 282

Glu Ile Asn His Ser Gly Ser Thr Asn Tyr Asn Pro Ser Leu Lys Ser
1               5                   10                  15

<210> SEQ ID NO 283
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 283

Ala Asp Tyr Asp Phe Trp Ser Gly Tyr Phe Asp Tyr
1               5                   10

<210> SEQ ID NO 284
<211> LENGTH: 15
<212> TYPE: PRT
<213> ORGANISM: Artificial Sequence
<220> FEATURE:
<223> OTHER INFORMATION: Artificially synthesized protein sequence.

<400> SEQUENCE: 284

Asp Gly Tyr Asp Ser Ser Gly Tyr Tyr His Gly Tyr Phe Asp Tyr
1               5                   10                  15

<210> SEQ ID NO 285
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 285

Ala Asp Tyr Asp Phe Trp Asn Gly Tyr Phe Asp Tyr
1               5                   10
```

```
<210> SEQ ID NO 286
<211> LENGTH: 8
<212> TYPE: PRT
<213> ORGANISM: Artificial Sequence
<220> FEATURE:
<223> OTHER INFORMATION: Artificially synthesized protein sequence.

<400> SEQUENCE: 286

Gly Trp Asn Tyr Val Phe Asp Tyr
 1               5

<210> SEQ ID NO 287
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 287

Glu Asp Asp Gly Met Asp Val
 1               5

<210> SEQ ID NO 288
<211> LENGTH: 14
<212> TYPE: PRT
<213> ORGANISM: Artificial Sequence
<220> FEATURE:
<223> OTHER INFORMATION: Artificially synthesized protein sequence.

<400> SEQUENCE: 288

Asp Gly Asp Val Asp Thr Ala Met Val Asp Ala Phe Asp Ile
 1               5                   10

<210> SEQ ID NO 289
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 289

Gly Asp Tyr Asp Phe Trp Ser Gly Glu Phe Asp Tyr
 1               5                   10

<210> SEQ ID NO 290
<211> LENGTH: 19
<212> TYPE: PRT
<213> ORGANISM: Artificial Sequence
<220> FEATURE:
<223> OTHER INFORMATION: Artificially synthesized protein sequence.

<400> SEQUENCE: 290

Asp Gln Gly Gln Asp Gly Tyr Ser Tyr Gly Tyr Gly Tyr Tyr Gly
 1               5                   10                  15

Met Asp Val

<210> SEQ ID NO 291
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 291

Ala Asp Tyr Asp Phe Trp Ser Gly Tyr Phe Asp Phe
 1               5                   10
```

<210> SEQ ID NO 292
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 292

Ala Asp Tyr Asp Phe Trp Ser Gly Tyr Phe Asp Ser
1               5                   10

<210> SEQ ID NO 293
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 293

Asp Arg Leu Cys Thr Asn Gly Val Cys Tyr Glu Asp Tyr Gly Met Asp
1               5                   10                  15

Val

<210> SEQ ID NO 294
<211> LENGTH: 13
<212> TYPE: PRT
<213> ORGANISM: Artificial Sequence
<220> FEATURE:
<223> OTHER INFORMATION: Artificially synthesized protein sequence.

<400> SEQUENCE: 294

Asp Val Gln Asp Tyr Gly Asp Tyr Asp Tyr Phe Asp Tyr
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 295

Ala Asp Tyr Asp Phe Trp Ser Gly His Phe Asp Cys
1               5                   10

<210> SEQ ID NO 296
<211> LENGTH: 14
<212> TYPE: PRT
<213> ORGANISM: Artificial Sequence
<220> FEATURE:
<223> OTHER INFORMATION: Artificially synthesized protein sequence.

<400> SEQUENCE: 296

Glu Arg Tyr Ser Gly Tyr Asp Asp Pro Asp Gly Phe Asp Ile
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 297

Ala Asp Tyr Asp Phe Trp Ser Gly His Phe Asp Tyr

```
<210> SEQ ID NO 298
<211> LENGTH: 13
<212> TYPE: PRT
<213> ORGANISM: Artificial Sequence
<220> FEATURE:
<223> OTHER INFORMATION: Artificially synthesized protein sequence.

<400> SEQUENCE: 298

Asp Pro His Asp Tyr Ser Asn Tyr Glu Ala Phe Asp Phe
1               5                   10

<210> SEQ ID NO 299
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 299

Arg Asp Glu Val Arg Gly Phe Asp Tyr
1               5

<210> SEQ ID NO 300
<211> LENGTH: 6
<212> TYPE: PRT
<213> ORGANISM: Artificial Sequence
<220> FEATURE:
<223> OTHER INFORMATION: Artificially synthesized protein sequence.

<400> SEQUENCE: 300

Gly Gln Trp Leu Asp Val
1               5

<210> SEQ ID NO 301
<211> LENGTH: 15
<212> TYPE: PRT
<213> ORGANISM: Artificial Sequence
<220> FEATURE:
<223> OTHER INFORMATION: Artificially synthesized protein sequence.

<400> SEQUENCE: 301

Asp Arg Glu Leu Glu Leu Tyr Tyr Tyr Tyr Tyr Gly Met Asp Val
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Artificially synthesized protein sequence.

<400> SEQUENCE: 302

Asp Arg Glu Leu Glu Gly Tyr Ser Asn Tyr Tyr Gly Val Asp Val
1               5                   10                  15

<210> SEQ ID NO 303
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 303

His Glu Asn Tyr Gly Asp Tyr Asn Tyr
1               5
```

<210> SEQ ID NO 304
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 304

Asp Arg Glu Arg Glu Trp Asp Asp Tyr Gly Asp Pro Gln Gly Met Asp
1               5                   10                  15
Val

<210> SEQ ID NO 305
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 305

Phe Gly Asp Leu Pro Tyr Asp Tyr Ser Tyr Tyr Glu Trp Phe Asp Pro
1               5                   10                  15

<210> SEQ ID NO 306
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 306

Asp Leu Tyr Asp Phe Trp Ser Gly Tyr Pro Tyr Tyr Tyr Gly Met Asp
1               5                   10                  15
Val

<210> SEQ ID NO 307
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 307

Asp Tyr Tyr Gly Ser Gly Ser Phe Tyr Tyr Tyr Gly Met Asp Val
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 308

Glu Ala Ile Phe Gly Val Gly Pro Tyr Tyr Tyr Tyr Gly Met Asp Val
1               5                   10                  15

<210> SEQ ID NO 309
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 309

```
Gly Gly Arg Tyr Ser Ser Trp Ser Tyr Tyr Tyr Gly Met Asp
1               5                   10                  15

Val
```

<210> SEQ ID NO 310
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 310

```
Gly Gly Asp Ser Asn Tyr Glu Asp Tyr Tyr Tyr Tyr Gly Met Asp
1               5                   10                  15

Val
```

<210> SEQ ID NO 311
<211> LENGTH: 19
<212> TYPE: PRT
<213> ORGANISM: Artificial Sequence
<220> FEATURE:
<223> OTHER INFORMATION: Artificially synthesized protein sequence.

<400> SEQUENCE: 311

```
Asp Ser Ser Tyr Tyr Asp Ser Ser Gly Tyr Tyr Leu Tyr Tyr Ala
1               5                   10                  15

Met Asp Val
```

<210> SEQ ID NO 312
<211> LENGTH: 15
<212> TYPE: PRT
<213> ORGANISM: Artificial Sequence
<220> FEATURE:
<223> OTHER INFORMATION: Artificially synthesized protein sequence.

<400> SEQUENCE: 312

```
Gly Gly Thr Gly Thr Asn Tyr Tyr Tyr Tyr Tyr Gly Met Asp Val
1               5                   10                  15
```

<210> SEQ ID NO 313
<211> LENGTH: 10
<212> TYPE: PRT
<213> ORGANISM: Artificial Sequence
<220> FEATURE:
<223> OTHER INFORMATION: Artificially synthesized protein sequence.

<400> SEQUENCE: 313

```
Asp Arg Gly Asp Phe Asp Ala Phe Asp Ile
1               5                   10
```

<210> SEQ ID NO 314
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 314

```
Ala Ala Arg Leu Asp Tyr Tyr Tyr Gly Met Asp Val
1               5                   10
```

<210> SEQ ID NO 315
<211> LENGTH: 9
<212> TYPE: PRT

<213> ORGANISM: Artificial Sequence
<220> FEATURE:
<223> OTHER INFORMATION: Artificially synthesized protein sequence.

<400> SEQUENCE: 315

Asp Lys Trp Thr Trp Tyr Phe Asp Leu
1               5

<210> SEQ ID NO 316
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 316

Asp Ser Glu Ser Glu Tyr Ser Ser Ser Ser Asn Tyr Gly Met Asp Val
1               5                   10                  15

<210> SEQ ID NO 317
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 317

Gln Met Ala Gly Asn Tyr Tyr Tyr Gly Met Asp Val
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 318

Arg Ala Ser Gln Gly Ile Arg Asn Asp Leu Gly
1               5                   10

<210> SEQ ID NO 319
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 319

Lys Ser Ser Gln Ser Val Leu Tyr Ser Ser Asn Asn Lys Asn Tyr Leu
1               5                   10                  15

Ala

<210> SEQ ID NO 320
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 320

Arg Ala Ser Gln Asp Ile Arg Asn Asp Leu Gly
1               5                   10

<210> SEQ ID NO 321
<211> LENGTH: 16

```
<212> TYPE: PRT
<213> ORGANISM: Artificial Sequence
<220> FEATURE:
<223> OTHER INFORMATION: Artificially synthesized protein sequence.

<400> SEQUENCE: 321

Arg Ser Ser Gln Ser Leu Leu His Ser Asn Gly Tyr Asn Tyr Leu Asp
 1               5                  10                  15

<210> SEQ ID NO 322
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 322

Arg Ser Ser Gln Ser Leu Leu His Ser Asn Gly Tyr Asn Tyr Leu Glu
 1               5                  10                  15

<210> SEQ ID NO 323
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 323

Arg Ala Ser Gln Ser Leu Ser Gly Asn Tyr Leu Ala
 1               5                  10

<210> SEQ ID NO 324
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 324

Gln Ala Ser Gln Asp Ile Ser Asn Tyr Leu Asn
 1               5                  10

<210> SEQ ID NO 325
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 325

Arg Ala Gly Gln Gly Ile Arg Asn Asp Leu Gly
 1               5                  10

<210> SEQ ID NO 326
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 326

Arg Ala Ser Gln Ser Ile Ser Ser Tyr Leu Asn
 1               5                  10

<210> SEQ ID NO 327
<211> LENGTH: 11
<212> TYPE: PRT
```

<213> ORGANISM: Artificial Sequence
<220> FEATURE:
<223> OTHER INFORMATION: Artificially synthesized protein sequence.

<400> SEQUENCE: 327

Arg Ala Ser Gln Gly Ile Arg Asp Asp Leu Gly
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 328

Gln Ala Ser Gln Asp Ile Ser Asn Tyr Leu Ser
1               5                   10

<210> SEQ ID NO 329
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 329

Arg Ser Ser Gln Ser Leu Val Tyr Ser Asp Gly Tyr Thr Tyr Leu His
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 330

Arg Ser Ser Gln Ser Leu Leu Tyr Ser Asn Gly Tyr Asn Tyr Leu Asp
1               5                   10                  15

<210> SEQ ID NO 331
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 331

Arg Ala Ser Gln Ala Ile Ser Asn Tyr Leu Asn
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 332

Arg Ala Ser Gln Ser Ile Arg Ser Tyr Leu Asn
1               5                   10

<210> SEQ ID NO 333
<211> LENGTH: 11
<212> TYPE: PRT
<213> ORGANISM: Artificial Sequence

```
<220> FEATURE:
<223> OTHER INFORMATION: Artificially synthesized protein sequence.

<400> SEQUENCE: 333

Arg Ala Ser Gln Ser Ile Ser Ser Tyr Leu His
1               5                   10

<210> SEQ ID NO 334
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 334

Lys Ser Ser Gln Ser Leu Leu Leu Ser Asp Gly Gly Thr Tyr Leu Tyr
1               5                   10                  15

<210> SEQ ID NO 335
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 335

Arg Ala Ser Gln Ser Ile Ser Ile Tyr Leu His
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 336

Arg Ala Ser Gln Ser Val Ser Ser Ser Tyr Leu Ala
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 337

Gln Ala Ser Gln Asp Ile Thr Asn Tyr Leu Asn
1               5                   10

<210> SEQ ID NO 338
<211> LENGTH: 16
<212> TYPE: PRT
<213> ORGANISM: Artificial Sequence
<220> FEATURE:
<223> OTHER INFORMATION: Artificially synthesized protein sequence.

<400> SEQUENCE: 338

Arg Ser Ser Gln Ser Leu Leu Tyr Ser Asn Gly Tyr Lys Tyr Leu Asp
1               5                   10                  15

<210> SEQ ID NO 339
<211> LENGTH: 11
<212> TYPE: PRT
<213> ORGANISM: Artificial Sequence
<220> FEATURE:
```

```
<223> OTHER INFORMATION: Artificially synthesized protein sequence.

<400> SEQUENCE: 339

Arg Ala Ser Gln Ser Ile Asn Ser Tyr Leu Asn
 1               5                  10

<210> SEQ ID NO 340
<211> LENGTH: 17
<212> TYPE: PRT
<213> ORGANISM: Artificial Sequence
<220> FEATURE:
<223> OTHER INFORMATION: Artificially synthesized protein sequence.

<400> SEQUENCE: 340

Arg Ser Ser Gln Ser Val Leu Tyr Ser Ser Asn Arg Asn Tyr Leu
 1               5                  10                  15

Ala

<210> SEQ ID NO 341
<211> LENGTH: 11
<212> TYPE: PRT
<213> ORGANISM: Artificial Sequence
<220> FEATURE:
<223> OTHER INFORMATION: Artificially synthesized protein sequence.

<400> SEQUENCE: 341

Arg Ala Ser Gln Thr Ile Ser Ser Tyr Leu Asn
 1               5                  10

<210> SEQ ID NO 342
<211> LENGTH: 12
<212> TYPE: PRT
<213> ORGANISM: Artificial Sequence
<220> FEATURE:
<223> OTHER INFORMATION: Artificially synthesized protein sequence.

<400> SEQUENCE: 342

Arg Ala Ser Gln Ser Val Ile Ser Ile Tyr Leu Ala
 1               5                  10

<210> SEQ ID NO 343
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 343

Ala Ala Ser Ser Leu Gln Ser
 1               5

<210> SEQ ID NO 344
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 344

Trp Ala Ser Thr Arg Glu Ser
 1               5

<210> SEQ ID NO 345
<211> LENGTH: 7
<212> TYPE: PRT
<213> ORGANISM: Artificial Sequence
```

-continued

```
<220> FEATURE:
<223> OTHER INFORMATION: Artificially synthesized protein sequence.

<400> SEQUENCE: 345

Leu Asp Ser His Arg Ala Ser
1               5

<210> SEQ ID NO 346
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 346

Leu Gly Ser Asn Arg Ala Ser
1               5

<210> SEQ ID NO 347
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 347

Gly Ala Ser Ser Arg Ala Thr
1               5

<210> SEQ ID NO 348
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 348

Val Ala Ser Asn Leu Glu Thr
1               5

<210> SEQ ID NO 349
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 349

Ala Ala Ser Arg Leu Gln Ser
1               5

<210> SEQ ID NO 350
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 350

Ala Ala Ser Ser Leu Gln Asn
1               5

<210> SEQ ID NO 351
<211> LENGTH: 7
<212> TYPE: PRT
<213> ORGANISM: Artificial Sequence
<220> FEATURE:
```

```
<223> OTHER INFORMATION: Artificially synthesized protein sequence.

<400> SEQUENCE: 351

Asp Ala Ser Asn Leu Glu Thr
1               5

<210> SEQ ID NO 352
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 352

Ala Glu Ser Ser Leu Gln Ser
1               5

<210> SEQ ID NO 353
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 353

Lys Val Ser Asn Trp Asp Ser
1               5

<210> SEQ ID NO 354
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 354

Leu Gly Phe His Arg Ala Ser
1               5

<210> SEQ ID NO 355
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 355

Ala Ala Ser Asn Leu Gln Ser
1               5

<210> SEQ ID NO 356
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 356

Glu Val Ser Asn Arg Phe Ser
1               5

<210> SEQ ID NO 357
<211> LENGTH: 7
<212> TYPE: PRT
<213> ORGANISM: Artificial Sequence
<220> FEATURE:
<223> OTHER INFORMATION: Artificially synthesized protein sequence.
```

```
<400> SEQUENCE: 357

Gly Ala Ser Ser Trp Ala Thr
1               5

<210> SEQ ID NO 358
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 358

Gly Ala Ser Gly Leu Gln Ser
1               5

<210> SEQ ID NO 359
<211> LENGTH: 7
<212> TYPE: PRT
<213> ORGANISM: Artificial Sequence
<220> FEATURE:
<223> OTHER INFORMATION: Artificially synthesized protein sequence.

<400> SEQUENCE: 359

Ala Ala Ser Ser Leu Gln Gly
1               5

<210> SEQ ID NO 360
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 360

Leu Gln His Asn Ser Tyr Pro Trp Thr
1               5

<210> SEQ ID NO 361
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 361

Leu Gln His Asn Gly Tyr Pro Trp Thr
1               5

<210> SEQ ID NO 362
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 362

Gln Gln Tyr Tyr Ser Thr Pro Leu Thr
1               5

<210> SEQ ID NO 363
<211> LENGTH: 9
<212> TYPE: PRT
<213> ORGANISM: Artificial Sequence
<220> FEATURE:
<223> OTHER INFORMATION: Artificially synthesized protein sequence.
```

```
<400> SEQUENCE: 363

Leu Gln His Asn Asn Tyr Pro Trp Thr
 1               5

<210> SEQ ID NO 364
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 364

Leu Gln His Asn Thr Tyr Pro Trp Thr
 1               5

<210> SEQ ID NO 365
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 365

Met Gln Ala Leu Gln Thr Pro Leu Thr
 1               5

<210> SEQ ID NO 366
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 366

Met Gln Ala Leu Gln Thr Pro Ile Thr
 1               5

<210> SEQ ID NO 367
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 367

Gln Gln Tyr Asp Arg Ser Pro Leu Thr
 1               5

<210> SEQ ID NO 368
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 368

Gln Gln Cys Asp Asn Leu Pro Leu Thr
 1               5

<210> SEQ ID NO 369
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 369
```

Gln His Tyr Asp Thr Leu Pro Leu Thr
1               5

<210> SEQ ID NO 370
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 370

Gln Gln Ser Tyr Ser Thr Pro Ile Thr
1               5

<210> SEQ ID NO 371
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 371

Leu Gln His His Ser Tyr Pro Trp Thr
1               5

<210> SEQ ID NO 372
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 372

Gln Gln Tyr Asp Asn Pro Pro Cys Ser
1               5

<210> SEQ ID NO 373
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 373

Met Gln Gly Ala His Trp Pro Ile Thr
1               5

<210> SEQ ID NO 374
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 374

Arg Gln Ala Leu Gln Thr Pro Leu Thr
1               5

<210> SEQ ID NO 375
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 375

```
Gln Gln Asn Asn Ser Leu Pro Ile Thr
 1               5
```

<210> SEQ ID NO 376
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 376

```
Gln Gln Ser Asn Gly Ser Pro Leu Thr
 1               5
```

<210> SEQ ID NO 377
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 377

```
Gln Gln Ser Tyr Ser Asn Pro Leu Thr
 1               5
```

<210> SEQ ID NO 378
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 378

```
Gln Gln Ser Ile Ser Ser Pro Leu Thr
 1               5
```

<210> SEQ ID NO 379
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 379

```
Gln Gln Ser Tyr Ser Thr Pro Leu Thr
 1               5
```

<210> SEQ ID NO 380
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 380

```
Gln Gln Ser Tyr Ser Thr Pro Arg Thr
 1               5
```

<210> SEQ ID NO 381
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 381

```
Met Gln Ser Met Gln Leu Pro Ile Thr
```

```
1               5
```

<210> SEQ ID NO 382
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 382

```
Gln Gln Ser Tyr Thr Ser Pro Ile Thr
1               5
```

<210> SEQ ID NO 383
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 383

```
Gln Gln Tyr Tyr Thr Thr Pro Leu Thr
1               5
```

<210> SEQ ID NO 384
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 384

```
Gln Gln Tyr Gly Ser Ser Pro Leu Thr
1               5
```

<210> SEQ ID NO 385
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 385

```
Gln Gln Cys Glu Asn Phe Pro Ile Thr
1               5
```

<210> SEQ ID NO 386
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 386

```
Gln Gln Ser Tyr Ser Ser Pro Leu Thr
1               5
```

<210> SEQ ID NO 387
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 387

```
Gln Gln Tyr Tyr Ser Thr Pro Arg Thr
1               5
```

<210> SEQ ID NO 388
<211> LENGTH: 9
<212> TYPE: PRT
<213> ORGANISM: Artificial Sequence
<220> FEATURE:
<223> OTHER INFORMATION: Artificially synthesized protein sequence.

<400> SEQUENCE: 388

Gln Gln Tyr Gly Ser Ser Pro Cys Ser
 1               5

<210> SEQ ID NO 389
<211> LENGTH: 5511
<212> TYPE: DNA
<213> ORGANISM: Homo sapiens
<220> FEATURE:
<221> NAME/KEY: CDS
<222> LOCATION: (194)...(4222)

<400> SEQUENCE: 389

```
acacacacac acccctcccc tgccatccct ccccggactc cggctccggc tccgattgca      60
atttgcaacc tccgctgccg tcgccgcagc agccaccaat tcgccagcgg ttcaggtggc     120
tcttgcctcg atgtcctagc ctaggggccc ccgggccgga cttggctggg ctcccttcac     180
cctctgcgga gtc atg agg gcg aac gac gct ctg cag gtg ctg ggc ttg        229
            Met Arg Ala Asn Asp Ala Leu Gln Val Leu Gly Leu
             1               5                  10 ctt ttc agc ctg gcc cgg ggc tcc gag gtg ggc aac tct cag gca gtg       277
Leu Phe Ser Leu Ala Arg Gly Ser Glu Val Gly Asn Ser Gln Ala Val
         15                  20                  25 tgt cct ggg act ctg aat ggc ctg agt gtg acc ggc gat gct gag aac       325
Cys Pro Gly Thr Leu Asn Gly Leu Ser Val Thr Gly Asp Ala Glu Asn
     30                  35                  40 caa tac cag aca ctg tac aag ctc tac gag agg tgt gag gtg gtg atg       373
Gln Tyr Gln Thr Leu Tyr Lys Leu Tyr Glu Arg Cys Glu Val Val Met
 45                  50                  55                  60 ggg aac ctt gag att gtg ctc acg gga cac aat gcc gac ctc tcc ttc       421
Gly Asn Leu Glu Ile Val Leu Thr Gly His Asn Ala Asp Leu Ser Phe
                 65                  70                  75 ctg cag tgg att cga gaa gtg aca ggc tat gtc ctc gtg gcc atg aat       469
Leu Gln Trp Ile Arg Glu Val Thr Gly Tyr Val Leu Val Ala Met Asn
             80                  85                  90 gaa ttc tct act cta cca ttg ccc aac ctc cgc gtg gtg cga ggg acc       517
Glu Phe Ser Thr Leu Pro Leu Pro Asn Leu Arg Val Val Arg Gly Thr
         95                 100                 105 cag gtc tac gat ggg aag ttt gcc atc ttc gtc atg ttg aac tat aac       565
Gln Val Tyr Asp Gly Lys Phe Ala Ile Phe Val Met Leu Asn Tyr Asn
    110                 115                 120 acc aac tcc agc cac gct ctg cgc cag ctc cgc ttg act cag ctc acc       613
Thr Asn Ser Ser His Ala Leu Arg Gln Leu Arg Leu Thr Gln Leu Thr
125                 130                 135                 140 gag att ctg tca ggg ggt gtt tat att gag aag aac gat aag ctt tgt       661
Glu Ile Leu Ser Gly Gly Val Tyr Ile Glu Lys Asn Asp Lys Leu Cys
                145                 150                 155 cac atg gac aca att gac tgg agg gac atc gtg agg gac cga gat gct       709
His Met Asp Thr Ile Asp Trp Arg Asp Ile Val Arg Asp Arg Asp Ala
            160                 165                 170 gag ata gtg gtg aag gac aat ggc aga agc tgt ccc ccc tgt cat gag       757
Glu Ile Val Val Lys Asp Asn Gly Arg Ser Cys Pro Pro Cys His Glu
        175                 180                 185
```

-continued

| | | |
|---|---|---|
| gtt tgc aag ggg cga tgc tgg ggt cct gga tca gaa gac tgc cag aca<br>Val Cys Lys Gly Arg Cys Trp Gly Pro Gly Ser Glu Asp Cys Gln Thr<br>190                         195                     200 | 805 |
| ttg acc aag acc atc tgt gct cct cag tgt aat ggt cac tgc ttt ggg<br>Leu Thr Lys Thr Ile Cys Ala Pro Gln Cys Asn Gly His Cys Phe Gly<br>205                   210                   215                   220 | 853 |
| ccc aac ccc aac cag tgc tgc cat gat gag tgt gcc ggg ggc tgc tca<br>Pro Asn Pro Asn Gln Cys Cys His Asp Glu Cys Ala Gly Gly Cys Ser<br>                          225                   230                   235 | 901 |
| ggc cct cag gac aca gac tgc ttt gcc tgc cgg cac ttc aat gac agt<br>Gly Pro Gln Asp Thr Asp Cys Phe Ala Cys Arg His Phe Asn Asp Ser<br>              240                   245                   250 | 949 |
| gga gcc tgt gta cct cgc tgt cca cag cct ctt gtc tac aac aag cta<br>Gly Ala Cys Val Pro Arg Cys Pro Gln Pro Leu Val Tyr Asn Lys Leu<br>          255                   260                   265 | 997 |
| act ttc cag ctg gaa ccc aat ccc cac acc aag tat cag tat gga gga<br>Thr Phe Gln Leu Glu Pro Asn Pro His Thr Lys Tyr Gln Tyr Gly Gly<br>270                   275                   280 | 1045 |
| gtt tgt gta gcc agc tgt ccc cat aac ttt gtg gtg gat caa aca tcc<br>Val Cys Val Ala Ser Cys Pro His Asn Phe Val Val Asp Gln Thr Ser<br>285                   290                   295                   300 | 1093 |
| tgt gtc agg gcc tgt cct cct gac aag atg gaa gta gat aaa aat ggg<br>Cys Val Arg Ala Cys Pro Pro Asp Lys Met Glu Val Asp Lys Asn Gly<br>                         305                   310                   315 | 1141 |
| ctc aag atg tgt gag cct tgt ggg gga cta tgt ccc aaa gcc tgt gag<br>Leu Lys Met Cys Glu Pro Cys Gly Gly Leu Cys Pro Lys Ala Cys Glu<br>              320                   325                   330 | 1189 |
| gga aca ggc tct ggg agc cgc ttc cag act gtg gac tcg agc aac att<br>Gly Thr Gly Ser Gly Ser Arg Phe Gln Thr Val Asp Ser Ser Asn Ile<br>               335                   340                   345 | 1237 |
| gat gga ttt gtg aac tgc acc aag atc ctg ggc aac ctg gac ttt ctg<br>Asp Gly Phe Val Asn Cys Thr Lys Ile Leu Gly Asn Leu Asp Phe Leu<br>350                   355                   360 | 1285 |
| atc acc ggc ctc aat gga gac ccc tgg cac aag atc cct gcc ctg gac<br>Ile Thr Gly Leu Asn Gly Asp Pro Trp His Lys Ile Pro Ala Leu Asp<br>365                   370                   375                   380 | 1333 |
| cca gag aag ctc aat gtc ttc cgg aca gta cgg gag atc aca ggt tac<br>Pro Glu Lys Leu Asn Val Phe Arg Thr Val Arg Glu Ile Thr Gly Tyr<br>                         385                   390                   395 | 1381 |
| ctg aac atc cag tcc tgg ccg ccc cac atg cac aac ttc agt gtt ttt<br>Leu Asn Ile Gln Ser Trp Pro Pro His Met His Asn Phe Ser Val Phe<br>              400                   405                   410 | 1429 |
| tcc aat ttg aca acc att gga ggc aga agc ctc tac aac cgg ggc ttc<br>Ser Asn Leu Thr Thr Ile Gly Gly Arg Ser Leu Tyr Asn Arg Gly Phe<br>         415                   420                   425 | 1477 |
| tca ttg ttg atc atg aag aac ttg aat gtc aca tct ctg ggc ttc cga<br>Ser Leu Leu Ile Met Lys Asn Leu Asn Val Thr Ser Leu Gly Phe Arg<br>430                   435                   440 | 1525 |
| tcc ctg aag gaa att agt gct ggg cgt atc tat ata agt gcc aat agg<br>Ser Leu Lys Glu Ile Ser Ala Gly Arg Ile Tyr Ile Ser Ala Asn Arg<br>445                   450                   455                   460 | 1573 |
| cag ctc tgc tac cac cac tct ttg aac tgg acc aag gtg ctt cgg ggg<br>Gln Leu Cys Tyr His His Ser Leu Asn Trp Thr Lys Val Leu Arg Gly<br>              465                   470                   475 | 1621 |
| cct acg gaa gag cga cta gac atc aag cat aat cgg ccg cgc aga gac<br>Pro Thr Glu Glu Arg Leu Asp Ile Lys His Asn Arg Pro Arg Arg Asp<br>              480                   485                   490 | 1669 |
| tgc gtg gca gag ggc aaa gtg tgt gac cca ctg tgc tcc tct ggg gga<br>Cys Val Ala Glu Gly Lys Val Cys Asp Pro Leu Cys Ser Ser Gly Gly<br>          495                   500                   505 | 1717 |

```
tgc tgg ggc cca ggc cct ggt cag tgc ttg tcc tgt cga aat tat agc      1765
Cys Trp Gly Pro Gly Pro Gly Gln Cys Leu Ser Cys Arg Asn Tyr Ser
510                 515                 520 cga gga ggt gtc tgt gtg acc cac tgc aac ttt ctg aat ggg gag cct      1813
Arg Gly Gly Val Cys Val Thr His Cys Asn Phe Leu Asn Gly Glu Pro
525                 530                 535                 540 cga gaa ttt gcc cat gag gcc gaa tgc ttc tcc tgc cac ccg gaa tgc      1861
Arg Glu Phe Ala His Glu Ala Glu Cys Phe Ser Cys His Pro Glu Cys
                545                 550                 555 caa ccc atg gag ggc act gcc aca tgc aat ggc tcg ggc tct gat act      1909
Gln Pro Met Glu Gly Thr Ala Thr Cys Asn Gly Ser Gly Ser Asp Thr
560                 565                 570 tgt gct caa tgt gcc cat ttt cga gat ggg ccc cac tgt gtg agc agc      1957
Cys Ala Gln Cys Ala His Phe Arg Asp Gly Pro His Cys Val Ser Ser
    575                 580                 585 tgc ccc cat gga gtc cta ggt gcc aag ggc cca atc tac aag tac cca      2005
Cys Pro His Gly Val Leu Gly Ala Lys Gly Pro Ile Tyr Lys Tyr Pro
590                 595                 600 gat gtt cag aat gaa tgt cgg ccc tgc cat gag aac tgc acc cag ggg      2053
Asp Val Gln Asn Glu Cys Arg Pro Cys His Glu Asn Cys Thr Gln Gly
605                 610                 615                 620 tgt aaa gga cca gag ctt caa gac tgt tta gga caa aca ctg gtg ctg      2101
Cys Lys Gly Pro Glu Leu Gln Asp Cys Leu Gly Gln Thr Leu Val Leu
                625                 630                 635 atc ggc aaa acc cat ctg aca atg gct ttg aca gta ata gca gga ttg      2149
Ile Gly Lys Thr His Leu Thr Met Ala Leu Thr Val Ile Ala Gly Leu
                640                 645                 650 gta gtg att ttc atg atg ctg ggc ggc act ttt ctc tac tgg cgt ggg      2197
Val Val Ile Phe Met Met Leu Gly Gly Thr Phe Leu Tyr Trp Arg Gly
            655                 660                 665 cgc cgg att cag aat aaa agg gct atg agg cga tac ttg gaa cgg ggt      2245
Arg Arg Ile Gln Asn Lys Arg Ala Met Arg Arg Tyr Leu Glu Arg Gly
670                 675                 680 gag agc ata gag cct ctg gac ccc agt gag aag gct aac aaa gtc ttg      2293
Glu Ser Ile Glu Pro Leu Asp Pro Ser Glu Lys Ala Asn Lys Val Leu
685                 690                 695                 700 gcc aga atc ttc aaa gag aca gag cta agg aag ctt aaa gtg ctt ggc      2341
Ala Arg Ile Phe Lys Glu Thr Glu Leu Arg Lys Leu Lys Val Leu Gly
                705                 710                 715 tcg ggt gtc ttt gga act gtg cac aaa gga gtg tgg atc cct gag ggt      2389
Ser Gly Val Phe Gly Thr Val His Lys Gly Val Trp Ile Pro Glu Gly
                720                 725                 730 gaa tca atc aag att cca gtc tgc att aaa gtc att gag gac aag agt      2437
Glu Ser Ile Lys Ile Pro Val Cys Ile Lys Val Ile Glu Asp Lys Ser
            735                 740                 745 gga cgg cag agt ttt caa gct gtg aca gat cat atg ctg gcc att ggc      2485
Gly Arg Gln Ser Phe Gln Ala Val Thr Asp His Met Leu Ala Ile Gly
750                 755                 760 agc ctg gac cat gcc cac att gta agg ctg ctg gga cta tgc cca ggg      2533
Ser Leu Asp His Ala His Ile Val Arg Leu Leu Gly Leu Cys Pro Gly
765                 770                 775                 780 tca tct ctg cag ctt gtc act caa tat ttg cct ctg ggt tct ctg ctg      2581
Ser Ser Leu Gln Leu Val Thr Gln Tyr Leu Pro Leu Gly Ser Leu Leu
                785                 790                 795 gat cat gtg aga caa cac cgg ggg gca ctg ggg cca cag ctg ctg ctc      2629
Asp His Val Arg Gln His Arg Gly Ala Leu Gly Pro Gln Leu Leu Leu
                800                 805                 810 aac tgg gga gta caa att gcc aag gga atg tac tac ctt gag gaa cat      2677
Asn Trp Gly Val Gln Ile Ala Lys Gly Met Tyr Tyr Leu Glu Glu His
```

-continued

```
                 815                 820                 825
ggt atg gtg cat aga aac ctg gct gcc cga aac gtg cta ctc aag tca      2725
Gly Met Val His Arg Asn Leu Ala Ala Arg Asn Val Leu Leu Lys Ser
            830                 835                 840 ccc agt cag gtt cag gtg gca gat ttt ggt gtg gct gac ctg ctg cct      2773
Pro Ser Gln Val Gln Val Ala Asp Phe Gly Val Ala Asp Leu Leu Pro
845                 850                 855                 860 cct gat gat aag cag ctg cta tac agt gag gcc aag act cca att aag      2821
Pro Asp Asp Lys Gln Leu Leu Tyr Ser Glu Ala Lys Thr Pro Ile Lys
                865                 870                 875 tgg atg gcc ctt gag agt atc cac ttt ggg aaa tac aca cac cag agt      2869
Trp Met Ala Leu Glu Ser Ile His Phe Gly Lys Tyr Thr His Gln Ser
            880                 885                 890 gat gtc tgg agc tat ggt gtg aca gtt tgg gag ttg atg acc ttc ggg      2917
Asp Val Trp Ser Tyr Gly Val Thr Val Trp Glu Leu Met Thr Phe Gly
        895                 900                 905 gca gag ccc tat gca ggg cta cga ttg gct gaa gta cca gac ctg cta      2965
Ala Glu Pro Tyr Ala Gly Leu Arg Leu Ala Glu Val Pro Asp Leu Leu
            910                 915                 920 gag aag ggg gag cgg ttg gca cag ccc cag atc tgc aca att gat gtc      3013
Glu Lys Gly Glu Arg Leu Ala Gln Pro Gln Ile Cys Thr Ile Asp Val
925                 930                 935                 940 tac atg gtg atg gtc aag tgt tgg atg att gat gag aac att cgc cca      3061
Tyr Met Val Met Val Lys Cys Trp Met Ile Asp Glu Asn Ile Arg Pro
                945                 950                 955 acc ttt aaa gaa cta gcc aat gag ttc acc agg atg gcc cga gac cca      3109
Thr Phe Lys Glu Leu Ala Asn Glu Phe Thr Arg Met Ala Arg Asp Pro
            960                 965                 970 cca cgg tat ctg gtc ata aag aga gag agt ggg cct gga ata gcc cct      3157
Pro Arg Tyr Leu Val Ile Lys Arg Glu Ser Gly Pro Gly Ile Ala Pro
        975                 980                 985 ggg cca gag ccc cat ggt ctg aca aac aag aag cta gag gaa gta gag      3205
Gly Pro Glu Pro His Gly Leu Thr Asn Lys Lys Leu Glu Glu Val Glu
            990                 995                 1000 ctg gag cca gaa cta gac cta gac cta gac ttg gaa gca gag gag gac      3253
Leu Glu Pro Glu Leu Asp Leu Asp Leu Asp Leu Glu Ala Glu Glu Asp
1005                1010                1015                1020 aac ctg gca acc acc aca ctg ggc tcc gcc ctc agc cta cca gtt gga      3301
Asn Leu Ala Thr Thr Thr Leu Gly Ser Ala Leu Ser Leu Pro Val Gly
                1025                1030                1035 aca ctt aat cgg cca cgt ggg agc cag agc ctt tta agt cca tca tct      3349
Thr Leu Asn Arg Pro Arg Gly Ser Gln Ser Leu Leu Ser Pro Ser Ser
            1040                1045                1050 gga tac atg ccc atg aac cag ggt aat ctt ggg gag tct tgc cag gag      3397
Gly Tyr Met Pro Met Asn Gln Gly Asn Leu Gly Glu Ser Cys Gln Glu
        1055                1060                1065 tct gca gtt tct ggg agc agt gaa cgg tgc ccc cgt cca gtc tct cta      3445
Ser Ala Val Ser Gly Ser Ser Glu Arg Cys Pro Arg Pro Val Ser Leu
            1070                1075                1080 cac cca atg cca cgg gga tgc ctg gca tca gag tca tca gag ggg cat      3493
His Pro Met Pro Arg Gly Cys Leu Ala Ser Glu Ser Ser Glu Gly His
1085                1090                1095                1100 gta aca ggc tct gag gct gag ctc cag gag aaa gtg tca atg tgt agg      3541
Val Thr Gly Ser Glu Ala Glu Leu Gln Glu Lys Val Ser Met Cys Arg
                1105                1110                1115 agc cgg agc agg agc cgg agc cca cgg cca cgc gga gat agc gcc tac      3589
Ser Arg Ser Arg Ser Arg Ser Pro Arg Pro Arg Gly Asp Ser Ala Tyr
            1120                1125                1130 cat tcc cag cgc cac agt ctg ctg act cct gtt acc cca ctc tcc cca      3637
```

```
His Ser Gln Arg His Ser Leu Leu Thr Pro Val Thr Pro Leu Ser Pro
        1135                1140                1145 ccc ggg tta gag gaa gag gat gtc aac ggt tat gtc atg cca gat aca      3685
Pro Gly Leu Glu Glu Glu Asp Val Asn Gly Tyr Val Met Pro Asp Thr
    1150                1155                1160 cac ctc aaa ggt act ccc tcc tcc cgg gaa ggc acc ctt tct tca gtg      3733
His Leu Lys Gly Thr Pro Ser Ser Arg Glu Gly Thr Leu Ser Ser Val
1165                1170                1175                1180 ggt ctc agt tct gtc ctg ggt act gaa gaa gaa gat gaa gat gag gag      3781
Gly Leu Ser Ser Val Leu Gly Thr Glu Glu Glu Asp Glu Asp Glu Glu
                1185                1190                1195 tat gaa tac atg aac cgg agg aga agg cac agt cca cct cat ccc cct      3829
Tyr Glu Tyr Met Asn Arg Arg Arg Arg His Ser Pro Pro His Pro Pro
        1200                1205                1210 agg cca agt tcc ctt gag gag ctg ggt tat gag tac atg gat gtg ggg      3877
Arg Pro Ser Ser Leu Glu Glu Leu Gly Tyr Glu Tyr Met Asp Val Gly
    1215                1220                1225 tca gac ctc agt gcc tct ctg ggc agc aca cag agt tgc cca ctc cac      3925
Ser Asp Leu Ser Ala Ser Leu Gly Ser Thr Gln Ser Cys Pro Leu His
1230                1235                1240 cct gta ccc atc atg ccc act gca ggc aca act cca gat gaa gac tat      3973
Pro Val Pro Ile Met Pro Thr Ala Gly Thr Thr Pro Asp Glu Asp Tyr
1245                1250                1255                1260 gaa tat atg aat cgg caa cga gat gga ggt ggt cct ggg ggt gat tat      4021
Glu Tyr Met Asn Arg Gln Arg Asp Gly Gly Gly Pro Gly Gly Asp Tyr
                1265                1270                1275 gca gcc atg ggg gcc tgc cca gca tct gag caa ggg tat gaa gag atg      4069
Ala Ala Met Gly Ala Cys Pro Ala Ser Glu Gln Gly Tyr Glu Glu Met
            1280                1285                1290 aga gct ttt cag ggg cct gga cat cag gcc ccc cat gtc cat tat gcc      4117
Arg Ala Phe Gln Gly Pro Gly His Gln Ala Pro His Val His Tyr Ala
        1295                1300                1305 cgc cta aaa act cta cgt agc tta gag gct aca gac tct gcc ttt gat      4165
Arg Leu Lys Thr Leu Arg Ser Leu Glu Ala Thr Asp Ser Ala Phe Asp
    1310                1315                1320 aac cct gat tac tgg cat agc agg ctt ttc ccc aag gct aat gcc cag      4213
Asn Pro Asp Tyr Trp His Ser Arg Leu Phe Pro Lys Ala Asn Ala Gln
1325                1330                1335                1340 aga acg taa ctcctgctcc ctgtggcact cagggagcat ttaatggcag              4262
Arg Thr * ctagtgcctt tagagggtac cgtcttctcc ctattccctc tctctcccag gtcccagccc    4322
cttttcccca gtcccagaca attccattca atctttggag gcttttaaac attttgacac    4382
aaaattctta tggtatgtag ccagctgtgc actttcttct ctttcccaac cccaggaaag    4442
gttttcctta ttttgtgtgc tttcccagtc ccattcctca gcttcttcac aggcactcct    4502
ggagatatga aggattactc tccatatccc ttcctctcag gctcttgact acttggaact    4562
aggctcttat gtgtgccttt gtttcccatc agactgtcaa gaagaggaaa gggaggaaac    4622
ctagcagagg aaagtgtaat tttggtttat gactcttaac cccctagaaa gacagaagct    4682
taaaatctgt gaagaaagag gttaggagta gatattgatt actatcataa ttcagcactt    4742
aactatgagc caggcatcat actaaacttc acctacatta tctcacttag tcctttatca    4802
tccttaaaac aattctgtga catacatatt atctcatttt acacaaaggg aagtcgggca    4862
tggtggctca tgcctgtaat ctcagcactt tgggaggctg aggcagaagg attacctgag    4922
gcaaggagtt tgagaccagc ttagccaaca tagtaagacc cccatctctt taaaaaaaaa    4982
aaaaaaaaaa aaaaaaaaac tttagaactg ggtgcagtgg ctcatgcctg taatcccagc    5042
```

```
cagcactttg ggaggctgag atgggaagat cacttgagcc cagaattaga gataagccta      5102
tggaaacata gcaagacact gtctctacag gggaaaaaaa aaaagaaac tgagccttaa       5162 agagatgaaa taattaagc agtagatcca ggatgcaaaa tcctcccaat tcctgtgcat       5222
gtgctcttat tgtaaggtgc caagaaaaac tgatttaagt tacagcccttt gtttaagggg    5282 cactgtttct tgttttttgca ctgaatcaag tctaacccca acagccacat cctcctatac    5342
ctagacatct catctcagga agtggtggtg ggggtagtca gaaggaaaaa taactggaca     5402
tctttgtgta aaccataatc cacatgtgcc gtaaatgatc ttcactcctt atccgagggc     5462
aaattcacaa ggatccccaa gatccacttt tagaagccat tctcatcca                 5511
```

<210> SEQ ID NO 390
<211> LENGTH: 1342
<212> TYPE: PRT
<213> ORGANISM: Homo sapiens

<400> SEQUENCE: 390

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
           100                 105                 110

Gly Lys Phe Ala Ile Phe Val Met Leu Asn Tyr Asn Thr Asn Ser Ser
       115                 120                 125

His Ala Leu Arg Gln Leu Arg Leu Thr Gln Leu Thr Glu Ile Leu Ser
   130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285
```

-continued

```
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
    450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
            500                 505                 510
Gly Pro Gly Gln Cys Leu Ser Cys Arg Asn Tyr Ser Arg Gly Gly Val
        515                 520                 525
Cys Val Thr His Cys Asn Phe Leu Asn Gly Glu Pro Arg Glu Phe Ala
    530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
            580                 585                 590
Val Leu Gly Ala Lys Gly Pro Ile Tyr Lys Tyr Pro Asp Val Gln Asn
        595                 600                 605
Glu Cys Arg Pro Cys His Glu Asn Cys Thr Gln Gly Cys Lys Gly Pro
    610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe Leu Tyr Trp Arg Gly Arg Arg Ile Gln
            660                 665                 670
Asn Lys Arg Ala Met Arg Arg Tyr Leu Glu Arg Gly Glu Ser Ile Glu
        675                 680                 685
Pro Leu Asp Pro Ser Glu Lys Ala Asn Lys Val Leu Ala Arg Ile Phe
    690                 695                 700
Lys Glu Thr Glu Leu Arg Lys Leu Lys Val Leu Gly Ser Gly Val Phe
```

-continued

```
            705                 710                 715                 720
Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
                740                 745                 750

Phe Gln Ala Val Thr Asp His Met Leu Ala Ile Gly Ser Leu Asp His
                755                 760                 765

Ala His Ile Val Arg Leu Leu Gly Leu Cys Pro Gly Ser Ser Leu Gln
        770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
        995                1000                1005

Leu Asp Leu Asp Leu Asp Leu Glu Ala Glu Glu Asp Asn Leu Ala Thr
    1010                1015                1020

Thr Thr Leu Gly Ser Ala Leu Ser Leu Pro Val Gly Thr Leu Asn Arg
1025                1030                1035                1040

Pro Arg Gly Ser Gln Ser Leu Leu Ser Pro Ser Ser Gly Tyr Met Pro
                1045                1050                1055

Met Asn Gln Gly Asn Leu Gly Glu Ser Cys Gln Glu Ser Ala Val Ser
                1060                1065                1070

Gly Ser Ser Glu Arg Cys Pro Arg Pro Val Ser Leu His Pro Met Pro
        1075                1080                1085

Arg Gly Cys Leu Ala Ser Glu Ser Ser Glu Gly His Val Thr Gly Ser
    1090                1095                1100

Glu Ala Glu Leu Gln Glu Lys Val Ser Met Cys Arg Ser Arg Ser Arg
1105                1110                1115                1120

Ser Arg Ser Pro Arg Pro Arg Gly Asp Ser Ala Tyr His Ser Gln Arg
                1125                1130                1135
```

```
                                            -continued

His Ser Leu Leu Thr Pro Val Thr Pro Leu Ser Pro Pro Gly Leu Glu
            1140                1145                1150

Glu Glu Asp Val Asn Gly Tyr Val Met Pro Asp Thr His Leu Lys Gly
        1155                1160                1165

Thr Pro Ser Ser Arg Glu Gly Thr Leu Ser Ser Val Gly Leu Ser Ser
    1170                1175                1180

Val Leu Gly Thr Glu Glu Asp Glu Asp Glu Glu Tyr Glu Tyr Met
1185                1190                1195                1200

Asn Arg Arg Arg His Ser Pro Pro His Pro Pro Arg Pro Ser Ser
            1205                1210                1215

Leu Glu Glu Leu Gly Tyr Glu Tyr Met Asp Val Gly Ser Asp Leu Ser
            1220                1225                1230

Ala Ser Leu Gly Ser Thr Gln Ser Cys Pro Leu His Pro Val Pro Ile
            1235                1240                1245

Met Pro Thr Ala Gly Thr Thr Pro Asp Glu Asp Tyr Glu Tyr Met Asn
    1250                1255                1260

Arg Gln Arg Asp Gly Gly Gly Pro Gly Gly Asp Tyr Ala Ala Met Gly
1265                1270                1275                1280

Ala Cys Pro Ala Ser Glu Gln Gly Tyr Glu Glu Met Arg Ala Phe Gln
                1285                1290                1295

Gly Pro Gly His Gln Ala Pro His Val His Tyr Ala Arg Leu Lys Thr
            1300                1305                1310

Leu Arg Ser Leu Glu Ala Thr Asp Ser Ala Phe Asp Asn Pro Asp Tyr
            1315                1320                1325

Trp His Ser Arg Leu Phe Pro Lys Ala Asn Ala Gln Arg Thr
            1330                1335                1340
```